US008445444B2

(12) United States Patent
Donald

(10) Patent No.: US 8,445,444 B2
(45) Date of Patent: *May 21, 2013

(54) COMPOSITIONS AND METHODS FOR DIAGNOSING, TREATING, AND PREVENTING PROSTATE CONDITIONS

(75) Inventor: Carlton D. Donald, Mount Pleasant, SC (US)

(73) Assignee: Phigenix, Inc., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/281,978

(22) Filed: Oct. 26, 2011

(65) Prior Publication Data

US 2012/0058130 A1 Mar. 8, 2012

Related U.S. Application Data

(63) Continuation of application No. 12/440,193, filed as application No. PCT/US2008/051168 on Jan. 16, 2008, now Pat. No. 8,088,603.

(60) Provisional application No. 60/885,142, filed on Jan. 16, 2007.

(51) Int. Cl.
| | |
|---|---|
| *A01N 61/00* | (2006.01) |
| *A61K 31/00* | (2006.01) |
| *A61K 35/14* | (2006.01) |
| *A61K 38/00* | (2006.01) |
| *A61K 38/16* | (2006.01) |
| *A61K 39/00* | (2006.01) |
| *A61K 39/395* | (2006.01) |
| *C07K 1/00* | (2006.01) |
| *C07K 14/00* | (2006.01) |
| *C07K 16/00* | (2006.01) |
| *C07K 17/00* | (2006.01) |
| *C12P 21/08* | (2006.01) |

(52) U.S. Cl.
USPC ............ 514/19.5; 514/1; 514/19.2; 514/19.3; 530/350; 530/380; 530/386; 530/387.1; 530/387.7; 424/130.1; 424/133.1; 424/138.1

(58) Field of Classification Search
USPC ................ 514/1, 19.2, 19.3, 19.5; 424/130.1, 424/133.1, 138.1; 530/350, 380, 386, 387.1, 530/387.7
See application file for complete search history.

(56) References Cited

U.S. PATENT DOCUMENTS

| | | |
|---|---|---|
| 5,869,045 A | 2/1999 | Hellstrom et al. |
| 2002/0142320 A1 | 10/2002 | Ogden et al. |
| 2003/0092657 A1 | 5/2003 | Goodyer et al. |
| 2003/0198970 A1 | 10/2003 | Roberts |
| 2004/0142389 A1 | 7/2004 | O'Mahony et al. |
| 2005/0287127 A1 | 12/2005 | Li et al. |
| 2007/0166728 A1 | 7/2007 | Abramson |

FOREIGN PATENT DOCUMENTS

WO 00/49175 A1 8/2000

OTHER PUBLICATIONS

Chamberlain et al. (Expert Opinion on Pharmacotherapy, 1(4): 603-614, 2000).*
Gura et al. (Science 278: 1041-1042, Nov. 7, 1997).*
Bodey et al. (Anticancer Research 20: 2665-2676, 2000).*
DeMarzo et al. Pathological and molecular aspects of prostate cancer. The Lancet. 361: 955-964, Mar. 15, 2003.*
Casey, G., The BRCA1 and BRCA2 Breast Cancer Genes. Current Opinion in Oncology, 9:88-93,1997.
Jatoi, I., Breast Cancer Screening. The American Journal of Surgery, 177:518-524, 1999.
Marcus et al., Hereditary Breast Cancer: Pathobiology, Prognosis, and BRCA1 and BRCA2 Gene Linkage; Cancer, 77:697-709,1996.
Miki et al., A Strong Candidate for the Breast and Ovarian Cancer Susceptibility Gene BRCA 1. Science, 266:66-71, 1994.
Morrison et al., Chimeric Human Antibody Molecules: Mouse Antigen-Binding Domains with Human Constant Region Domains. Proc. Natl. Acad. Sci. USA, 81:6851-6855,1984.
Stuart et al., Mammalian Pax Genes. Annu. Rev. Genet., 27:219-36,1993.
Wells, J. et al., Characterizing transcription factor binding sites using formaldehyde crosslinking and immunoprecipitation. Methods, 26:48-56., 2002.
Wilson, T. E. et al., Identification of the DNA binding site for NGFI-B by genetic selection in yeast. Science, 252: 1296-1300, 1991.
Xu, Rould, Jun, Desplan and Pabo (1995) Cell 80, 639-650.
Yang, D. et al., Multiple Roles of Antimicrobial Defensins, Cathelicidins, and Eosinophil-Derived Neurotoxin in Host Defense. Annual Review of Immunology 2004, 22, (1), 181-215.
Ylikoski A, et al., Simultaneous quantification of prostate-specific antigen and human glandular kallikrein 2 mRNA in bloodsamples from patients with prostate cancer and benign disease. Clin Chem 2002, 48:1265-1271.
Yuan SS, et al., Pax-2 interacts with RB and reverses its repression on the promoter of Rig-1, a Robo member. Biochem Biophys Res Commun 2002; 296(4):1019-1025.
Zucht HD, et al., Human beta-defensin-1: A urinary peptide present in variant molecular forms and 30 its putative functional implication. Eur J Med Res. Jul. 20, 1998;3(7):315-23.
European Search Report (Application No. 08727729.9 based on PCT application PCT/US08/51168, international filing date Jan. 16, 2008).
Khoubehi, et al., "Expression of the Development and Oncogenic PAX2 Gene in Human Prostate Cancer", Journal of Urology, vol. 165, pp. 2115-2120 (2001).
Donald, C. D., et al., "Cancer-Specific Loss of beta-Defensin 1 in Renal and Prostatic carcinomas", Laboratory Investigation, Vol.83, pp. 501-505 (2003).
Muratovska, a., et al., "Paired-box genes are frequently expressed in cancer and often required for cancer cell survival", Oncogene, Vol. 22, pp. 7989-7997 (2003).

(Continued)

*Primary Examiner* — Alana Harris Dent
(74) *Attorney, Agent, or Firm* — Ping Wang; Andrews Kurth, LLP

(57) ABSTRACT

Disclosed are compositions and methods for diagnosing, preventing, and treating prostate cancer and prostate intraepithelial neoplasia (PIN).

3 Claims, 41 Drawing Sheets
(13 of 41 Drawing Sheet(s) Filed in Color)

OTHER PUBLICATIONS

Notification of Transmittal of the International Search Report and The Written Opinion of the the International Searching Authority, or the Declaration, Form PCT/ISA/220 of Application No. PCT/US2009/054913, Sep. 17, 2010.

The International Preliminary Report on Patentability; (International Application No. PCT/US20081051168 filed Jan. 16, 2008).

Xiang, et al. AMP-activated protein kinase activators can inhibit the growth of prostate cancer cells by multiple mechanisms, Biochemical and Biophysical Research Communications, 321 (2004) 161-167.

Wallin et al., Dependence of BSAP Repressor and Activator Functions on BSAP Concentration, Science, vol. 279, (1998).

Vogelstein, et al., The multistep nature of Cancer, vol. 9, No. 4, (1993).

Uemura, et al., Angiotensin II Receptor Blocker: Possibility of Antitumor Agent for Prostate Cancer, Mini-Reviews in Medicinal Chemistry 6, (2006) pp. 835-844.

Uemura, et al., Renin-Angiotensin system is an Important factor in Hormone Refractory Prostate Cancer, The Prostate, 66, (2006) pp. 822-830.

Tepper, et al., Profiling of Gene Expression Changes Caused by p53 Gain-of-Function Mutant Alleles in Prostate Cancer Cells, The Prostate, 65 (2005) pp. 375-389.

Stuart, et al. Mammalian Pax genes, Annu. Rev. Genet., 27, (1993) pp. 219-236.

Stuart, et al., PAX and HOX in Neoplasia, Advances in Genetics, vol. 33, Academic Press (1995).

Stambolic, Negative Regulation of PKB/Akt-Dependent Cell Survival by the Tumor Suppressor PTEN, Cell, vol. 95, Cell Press (1998) pp. 29-39.

Seiden, et al., Detection of Circulating Tumor Cells in Men with localized Prostate Cancer, Journal of Clinical Oncology, vol. 12, No. 12 (1994) pp. 2634-2639.

Sherman, et al., Albumin and amino acids upregulate the expression of human beta-defensin 1, Molecular Immunology (2006) 1617-1623.

Schmidt, et al., Detection of Circulating Prostate Cells during Radical Prostatectomy by Standardized PSMA RT-PCR: Association with Positive Lymph Nodes and High Malignant Grade, Anticancer Research, 23 (2003) pp. 3991-4000.

Sanyanusin, et al., Genomic Structure of the Human PAX2 Gene, Genomics, Academic Press Inc., 35 (1996) pp. 258 (1995).

Saitoh, et al., Adenosine induces apoptosis in the human gastric cancer cells via an intrinsic pathway relevant to activation of AMP-activated protein kinase, Biochemical Pharmacology, 67 (2004) pp. 2005-2011.

Robson, et al., A Panorama of PAX genes in cancer and development, Nature Publishing Group, vol. 6 (2006).

Rieger, et al., Human blader carcinoma cell lines as indicators of oncogenic change relevant to urothelial neoplastic progression, British Journal of cancers, vol. 72 (1995) pp. 683-690.

Papo, et al., Vision and Reflections: Host defence peptides as new weapons in cancer treatment, Cellular and Molecular Life Sciences, 62 (2005) pp. 784-790.

Pantel, et al., Micrometastasis Detection and Treatment with Monoclonal Antibodies, Institute of Immunology, Ludwig-Maximilians University, 31.

Noguchi, et al., Detection of Breast Cancer Micrometastases in Axillary Lymph Nodes by Means of Reverse Transcriptase-Polymerase Chain Reaction, American Journal of Pathology, vol. 148, No. 2 (1996).

Nelson, et al., The Role of Inflammation in the Pathogenesis of Prostate Cancer, The Journal of Urology, American Urological Association (2004) vol. 172 (2004).

Meisse, et al., Sustained activation of AMP-activated protein kinase induces c-Jun N-terminal kinase activation and apoptosis in liver cells, FEBS Letters, 526 (2002) pp. 38-42.

McNamara, et al., Ocular Surface Epithelia Express mRNA for Human Beta Defensin-2, Exp. Eye Res., 69 (1999) pp. 483-490.

Maulbecker, et al., The oncogenic potential of PAX genes, The EMBO Journal, vol. 12, No. 6 (1993) pp. 2361-2367.

Matsumura, et al., Detection of α-Fetoprotein mRNA, an Indicator of Hematogenous Spreading Hepatocellular Carcinoma, in the Circulation: A Possible Predictor of Metastatic Hepatocellular Carcinoma, the American Association for the Study of Liver Diseases (1994).

McCray, et al., Human Epithelia Express a β-defensin, Am. J. Respir. Cell mol. Biol., vol. 16, (1997) pp. 343-349.

Mansouri, et al., Pax genes and their roles in cell differentiation and development, Current Opinion in Cell Biology, vol. 8 (1996) Current Biology Ltd., pp. 851-857.

Li, et al., AMPK-β1 submit is a p53-independent stress responsive protein that inhibits tumor cell growth upon forced expression, Carcinogenesis, vol. 24, No. 5 (2003) pp. 827-834.

Lehrer, et al., Defensins, Protegrins, and Other Cysteine-Rich Antimicrobial Peptides, Endogenous Vertebrate Antibiotics, pp. 228-239.

Lang, et al., PAX genes: Role in development, pathophysiology, and cancer, Biochemical Pharmacology, Elsevier Science Inc., vol. 73 (2007).

Kasahara, et al., Detection of genetic alterations in advances prostate cancer by comparative genomic hybridization, Cancer Genetics and Cytogenetics, Elsevier Science Inc., 137 (2002) pp. 59-63.

Jurevic, et al., Single-Nucleotide Polymorphisms and Haplotype Analysis in β-Defensin Genes in Different Ethnic Populations, Genetic Testing, Mary Liebert Inc., vol. 6, No. 4 (2002).

Jung, et al., 5-Aminoimidazole-4-carboxamide-ribonucleoside enhances oxidative stress-induced apoptosis through activation of nuclear factor-KB in mouse Neuro 2a neuroblastoma cells, Neuroscience Letters, Elsevier Science Inc., 354 (2004) pp. 197-200.

Jotsuka, et al., Persistent evidence of circulating tumor cells detected by means of RT-PCR for CEA mRNA predicts early relapse: A prospective study in node-negative breast cancer, Elsevier Inc. (2004).

Jia, et al., Discovery of new human β-defensins using a genomics-based approach, Gene, Elsevier Inc., 263 (2001) pp. 211-218.

Johnson, et al., The molecular detection of circulating tumour cells, British Journal of Cancer, Stockton Press, 72, (1995) pp. 268-276.

Hildebrandt, et al., Reverse transcriptase-polymerase chain reaction (RT-PCR)-controlled immunomagnetic purging of breast cancer cells using the magnetic cell separation (MACS) system: A sensitive method for monitoring purging efficiency, Experimental Hematology, International Society for Experimental Hematology, 25 (1997) pp. 57-65.

Harder, et al., Mapping of the gene Encoding Human β-Defensi-2 (DEFB2) to Chromosome region 8p22- p23.1, Genomics, Academic Press, 46 (1997) pp. 472-475.

Harder, et al., A peptide antibiotic from human skin, Nature, Macmillan Publishers Ltd. vol. 387 (1997).

Guseva, et al., Death Receptor-Induced Cell Death in Prostate Cancer, Journal of Cellular Biochemistry, vol. 91 (2004) pp. 70-99.

Gleason et al., Classification of Prostatic Carcinomas, Cancer Chemotherapy Reports, vol. 50, No. 3 (1996).

Gilbey, et al., The detection of circulating breast cancer cells in blood, J. Clin. Pathol., 57, vol. 57 (2004) pp. 903-911.

Gibson, et al., Inhibition of PAX2 expression results in alternate cell death pathways in prostate cancer cells differing in p53 status, Cancer Letters, Elsevier Science Inc., 248 (2007) pp. 251-261.

Goldman, et al., Human β-Defensin-1 is a Salt-Sensitive Antibiotic in lung That Is Inactivated in Cystic Fibrosis, Cell, vol. 88, Cell Press (1997) pp. 553-560.

Ghossein, et al., Detection of Circulating Tumor Cells in Patients With Localized and Metastatic Prostatic Carcinoma: Clinical Implications, Journal of Clinical Oncology, vol. 13, No. 5 (1995) pp. 1195-1200.

Gerhard, et al., Specific Detection of Carcinoembryonic Antigen-Expressing Tumor Cells in Bone Marrow Aspirates by polymerase Chain Reaction, Journal of Clinical Oncologym vol. 12, No. 5 (1994) pp. 725-729.

Ganz, et al., Antimicrobial Peptides of Phagocytes and Epithelia, Seminars In Hematology, vol. 34, No. 4 (1997) pp. 343-354.

Gann, et al., A Prosepective Evaluation of Plasma Prostate-Specific Antigen for Detection of Prostatic Cancer, JAMA, vol. 273 (1995).

Dunn, et al., Cancer immunoediting: from immuno-surveillance to tumor escape, Nature Imuunology, Nature, (2002) vol. 3, No. 11.

Dehbi, et al., The paired-box transcription factor, PAX2, positively modulates expression of the Wilms' tumor suppressor gene (WT1), Oncogene, Stockton Press, 13, (1996) pp. 447-453.

Dearnaley, et al., Increased Detection of Mammary Carcinoma Cells in Marrow Smears Using Antisera to Epithelial Membrane Antigen, Br. J. Cancer, vol. 44 (1981).

Dearnaley, et al., Increased Detection of Mammary Carcinoma Cells in Marrow Smears Using Antisera to Epithelial Membrane Antigen, Br. J. Cancer, 44, 85 (1981).

Caroll, et al., p53 Oncogene Mutations in Three Human Prostate Cancer Cell Lines, The Prostate, Wiley-Liss Inc., vol. 23 (1993) pp. 123-134.

van Bokhoven, et al., Molecular Characterization of Human Prostate Carcinoma Cell Lines, The Prostate, Wiley-Liss, Inc., 57 (2003) pp. 205-225.

Benson, et al., The staging and grading of prostatic cancer, The Prostate, pp. 261-272.

Ady, et al., Detection of HER-2/neu-positive circulating epithelial cells in prostate cancer patients, Br J Cancer 2004, 90:443-448.

Bals, et al., Mouse beta-defensin 1 is a salt-sensitive antimicrobial15 peptide present in epithelia of the lung and urogenital tract. Infect Immun. Mar. 1998;66(3): 1225-32.

Bensch, et al., hBD-1: a novel beta-defensin from human plasma. FEBS Lett. Jul. 17, 1995;368(2):331-5.

Bockmuhl, et al., Association of 8p23 deletions with poor survival in head and neck cancer. Otolaryngol Head Neck Surg 2001, 124, (4), 451-5.

Boyd, et al., Coexamination of site-specific transcription factor binding and promoter activity in living cells. Mol Cell Biol, 19: 8393-8399., 1999.

Braida, et al., 2004. A singlenucteotide polymorphism in the human beta-defensin 1 gene is associated with 35 HIV-1 infection in Italian children. Aids 18,1598-1600.

Buttiglieri, et al., Role of PAX2 in apoptosis resistance and proinvasive phenotype of Kaposi's sarcoma cells. J Biol Chem 2004,279, (6), 4136-43. 40.

Caroll, et al. p53 oncogene mutations in three human prostate cancer cell lines,Prostate 23 (2) (1993) 123-134.

Catalano, et al., Altered expression of androgen-receptor isoforms in human colon-cancer tissues. Int J Cancer 2000, 86, (3), 325-30.

Chaib, et al., Haploinsufficiency and reduced expression of genes localized to the 8p chromosomal region in human prostate tumors. Genes Chromosomes Cancer 2003, 37, (3), 306-13.

Coultas, et al. , The role of the Bcl-2 protein family in cancer. Semin Cancer Biol 2003,13,(2), 115-23.

Davies et al., Hum. Mol. Gen Jan. 15,13 (2); 235, 2004.

Discenza, et al., WT1 is a modifier of the PAX2 mutant phenotype: cooperation and interaction between WT1 and PAX2. Oncogene 2003,22, (50), 8145-55.

Donald, et al., Cancer-specific loss of beta-defensin in renal and prostatic carcinomas. Lab Invest 2003,83, (4), 501-5.

Dorfler, et al. C-terminal activating and inhibitory domains determine the transactivation potential of BSAP (PAX-5), PAX-2 and PAX-8, EMBO J. 15 (8)(1996)1971-1982.

Dressler, et al (1990) Development 109,787-795.

Dressler, et al., PAX2 in development and renal disease. Int J Dev Biol 1999;43(5):463-468.

Dressler, et al., Pax-2, kidney development, and oncogenesis. Med Pediatr Oncol 30 1996;27(5):440-444.

Eccles MR, He S, Legge M, Kumar R, Fox J, Zhou C, French M, Tsai RW. PAX genes in development and disease: the role of PAX2 in urogenital tract development, hit J Dev 35 Biol 2002;46(4):535-544.

Eccles MR, Wallis LJ, Fidler AE, Spurr NK, Goodfellow PJ, Reeve AE. Expression of the PAX2 gene in human fetal kidney and Wilms' tumor. Cell Growth Differ 1992;3(5):279-289.

Eccles, et al., 2002. PAX genes in development and disease: the role of PAX2 in urogenital tract development. Int. J. Dev. Biol. 46 (4), 535-544.

Ganz, 1999. Defensins and host defense. Science 286,420-421.

Ganz, T., 2002. Immunology. Versatile defensins. Science 298, 977-979. Ganz, T., 2004. Defensins: antimicrobial peptides of vertebrates. CRBiol. 327, 539-549.

Eccleset, et al., PAX genes in development and disease: the role of PAX2 in urogenital tract development, Int. J. Dev. Biol. 46 (4) (2002) 535-544.

Fong, et al., Dendritic Cell-Based Xenoantigen Vaccination for Prostate Cancer,Immunotherapy. J Immunol 2001,167, (12), 7150-7156.

Fonsato V. et al. Expression of Pax2 in human renal tumor-derived endothelial cells sustains apoptosis resistance and angiogenesis, Am J Pathol. Feb. 2006;168(2):706-1.

Fromont, G.; Joulin, V.; Chentrel-Groussard, K.; Vallancien, G.; Guillonneau, B.; Validire, P.; Latil, A.; Cussenot, O., Allelic losses in localized prostate cancer: association with prognostic factors. J Urol 2003,170, (4 Pt 1), 1394-7.

Fuji Y, Kageyama Y, Kawakami S, Kihara K, Oshima H: Detection of disseminated urothelial cancer cells in peripheral venous blood by a cytokeratin 20-specific nested reverse transcriptase-polymerase chain reaction. Jpn J Cancer Res 1999, 90:753-757.

Ganz, T., Defensins and host defense. Science 1999, 286, (5439), 420-1.

Ghossein RA, Bhattacharya S, Rosai J: Molecular detection of micrometastases and 20 circulating tumor cells in solid tumors. Clin Cancer Res 1999, 5:1950-1960.

Gnarra, J. R.; Dressier, G. R., Expression of Pax-2 in human renal cell carcinoma and growth inhibition by antisense oligonucieotides. Cancer Res 1995, 55, (18), 4092-8.

Gropp, R.; Frye, M.; Wagner, T. O.; Bargon, J., Epithelial defensins impair adenoviral infection: implication for adenovirus-mediated gene therapy. Hum Gene Ther 1999, 10, (6), 957-64.

Gunther, M.; Wagner, E.; Ogris, M., Specific targets in tumor tissue for the delivery of 40 therapeutic genes. Curr Med Chem Anti-Canc Agents 2005, 5, (2), 157-71.

Harder J, Barteis J, Christophers E, Schroder JM. Isolation and characterization of human beta-defensin-3, a novel human inducible peptide antibiotic. Biol Chem. Feb 23, 2001;276(8):5707-13.

Havik B, Ragnhildstveit E, Lorens JB, Saelemyr K, Fauske O, Knudsen LK, Fjose A. A novel paired domain DNA recognition motif can mediate PAX2 repression of gene transcription. Biochem Biophys Res Commun 1999;266(2):532-541.

Hoon DS, Sarantou T, Doi F, Chi DD, Kuo C, Conrad AJ, Schmid P, Turner R, Guiliano A: Detection of metastatic breast cancer by b-hCG polymerase chain reaction. Lit J 10 Cancer 1996, 69:369-374.

Hueber et al. PAX2 inactivation enhances cisplatin-induced apoptosis in renal carcinoma cells, Kidney Int. Apr. 2006;69(7):1139-45.

Hugel, A.; Wemert, N., Loss of heterozygosity (LOH), malignancy grade and clonality in microdissected prostate cancer. Br J Cancer 1999, 79, (3-4), 551-7.

Ino K, Shibata K, Kajiyama H, Yamamoto E, Kagasaka T, Nawa A, Nomura S, Kikkawa F. Angiotensin II type 1 receptor expression in ovarian cancer and its correlation with tumor angiogenesis and patient survival. Br J Cancer 2006;94(4):552-560.

Isaacs, W.B. et al. Wild-type p53 suppresses growth of human prostate cancer cells containing mutant p53 alleles, Cancer Res. 51(1991) 4716-4720.

Jackers, P., Szalai, G., and Watson, D. K. Ets-dependent regulation of target gene expression during megakaryopoiesls. in preparation, 2003. Jemal, A., Siegel, R.> Ward, E., Murray, T., Xu, J., Smigal, C, Thun, M.J., 2006. Cancer statistics, 2006. CA Cancer J. Clin. 56,106-130.

Jemal, A., Siegel, R.> Ward, E., Murray, T., Xu, J., Smigal, C, Thun, M.J., 2006. Cancer statistics, 2006. CA Cancer J. Clin. 56,106-130.

Jemal, A.; Tiwari, R. C; Murray, T.; Ghafoor, A.; Samuels, A.; Ward, E.; Feuer, E. J.; 25 Thun, M. J., Cancer statistics, 2004. CA Cancer J Clin 2004, 54, (1), 8-29.

Jia, et al., 30 A novel murine beta-defensin expressed in tongue, esophagus, and trachea. J Biol Chem. Oct. 27, 2000;275(43):33314-20.

Juin, et al., 2002. c-Myc functionally cooperates with Bax to induce apoptosis. Mol. Cell Biol. 40 22,6158-6169.

Kefas, et al. AMP-activated protein kinase can induce apoptosis of insulin-producing MIN6 cells through stimulation of c-Jun-N-terminal kinase. (2003) J. Mol. Endocrinol 30, 151-161.

Kelloff, et al. Progress in chemoprevention drug development: the promise of molecular biomarkers for prevention of intraepithelial neoplasia and cancer—a plan to move forward. Clin Cancer Res. Jun. 15, 2006;12(12):3661-97.

Khoubehi, et al. Expression of the developmental and oncogenic PAX2 gene in human prostate cancer. J Urol 2001:165(6Ptl:2115-2120.

Krisanaprakornkit S, Weinberg A, Perez CN, Dale BA. Expression of the peptide antibiotic human beta-defensin 1 in cultured gingival epithelial cells and gingival tissue.InfectImmun. Sep. 1998;66(9):4222-8.

Lin, et al., Differentially expressed genes in activin-induced apoptotic LKCaP cells. Biochem Biophys Res Commun 1999,257, (1), 187-92.

Linzmeier, et al., A 450-kb contig of defensin genes on human chromosome 8p23. Gene 1999,233, (1-2), 205-11.

Liu, et al. Identifying DNA-binding sites and analyzing DNA-binding domains using a yeast selection system. Methods: A companion to Methods in Enzymology, 5:125-137,1993.

Discenza MT, He S, Lee TH, Chu LL, Bolon B, Goodyer P, Eccles M, Pelletier J., 2003. WT1 is a modifier of the Pax2 mutant phenotype: cooperation and interaction between WT1 and Pax2. Oncogene 22 (50), 8145-8155.

Macoska, et al., Evolution of 8p loss in transformed human prostate epithelial cells. Cancer Genet Cytogenet 2004,154, (1), 36-43.

Mansouri, A. et al. Pax genes and their roles in cell differentiation and development, Cur. Opin. Cell Biol. 8 (1996) 851-857.

Margue, et al., Transcriptional modulation of the anti-apoptotic protein BCL-XL by the paired box transcription factors PAX3 and PAX3/FKHR. Oncogene 2000,19, (25), 2921-9.

Margue, CM. et al. Transcriptional modulation of the anti-apoptotic protein BCL-XL by the paired box transcription factors PAX3 and PAX3/FKHR, Oncogene 19 (25) (2003)2921-2929.

Margure, CM. et al. Transcriptional modulation of the anti-apoptotic protein BCL-XL by the paired box transcription factors PAX3 and PAX3/FKHR, Oncogene 19 (2000) 2921-2929.

Mathews, et al. Production of beta-defensin antimicrobial peptides by the oral mucosa and salivary glands. Infect Immun. Jun. 1999;67(6):2740-5.

Mazal, et al., Expression of aquaporins and PAX-2 compared to CD10 and cytokeratin 7 in renal neoplasms: a tissue microarray study. Mod Pathol 2005,18, (4), 535-40.

Mazzucchelli, et al., Molecular mechanisms in prostate cancer. A review. Anal Quant Cytol Histol 2004,26, (3), 127-10 33.

McConnell, et al., Differential regulation of the human Wilms tumor suppressor gene (WT1) promoter by two isoforms of PAX2. Oncogene 1997,14, (22), 2689-700.

McNeel, et al., 2005. Immune-based therapies for prostate cancer. Immunol. Lett. 96, 3-9.

Michalak, et al. A., Death squads enlisted by the tumor suppressor p53. Biochem Biophys Res Comrnun 2005,331, (3), 786-98.

Muratovska, et al. Paired-Box genes are frequently expressed in cancer and often required for cancer cell survival. Oncogene 2003;22(39):7989-7997.

Murer, et al., Expression of nuclear transcription factor PAX2 in renal biopsies of juvenile nephronophthisis. Nephron 2002, 91, (4), 588-93.

Nakamura, Y. Isolation of p53-target genes and their functional analysis, Cancer Sci. 95 (1) (2004) 7-11.

Nigro, et al., B. Human p53 and CDC2Hs genes combine to inhibit the proliferation of Saccharomyces cerevisiae. Mol Cell Biol, 12: 1357-1365., 1992.

Nishimura, M.; Abiko, Y.; Kurashige, Y.; Takeshima, M.; Yamazaki, M.; Kusano, K; Saitoh, M.; Nakashima, K.; Inoue, T.; Kaku, T., Effect of defensin peptides on eukaryotic cells: primary epithelial cells, fibroblasts and squamous cell carcinoma cell lines. Journal of Dermatological Science 2004,36, (2), 87.

O'Hara SM, Moreno JG, Zweitzig DR, Gross S, Gomella LG, Terstappen LW: Multigene reverse transcription-PCR profiling of circulating tumor cells in hormone-refractory prostate cancer. Clin Chem 2004, 50:826-835.

Ogata, T.; Muroya, K; Sasagawa, I.; Kosho, T.; Wakui, K.; Sakaznme, S.; Ito, K; Matsuo, N.; Ohashi, H.; Nagai, T., Genetic evidence for a novel gene(s) involved in urogenital development on 10q26. Kidney hit 2000, 58, (6), 2281-90.

O'Neil DA, Porter EM, Elewaut D, Anderson GM, Eckmann L, Ganz T, Kagnoff MF. Expression and regulation of the human beta-defensins hBD-1 and hBD-2 in intestinal epithelium. J Immunol. Dec. 15, 1999;163(12):6718-24.

Orlando, V. Mapping chromosomal proteins in vivo by formaldehyde-crosslinked-chromatin immunoprecipitation. Trends Biochem Sci, 25: 99-104., 2000.

Ostrom, L.; Tang, M. J.; Grass, P.; Dressier, G. R., Reduced PAX2 gene dosage increases apoptosis and slows the progression of renal cystic disease. Dev Biol 2000,219, (2), 250-8.

Palapattu, G.S., Sutciffe, S., Bastian, P.J., Platz, E.A., De Marzo, A.M., Isaacs, W.B., Nelson, W.G., 2005. Prostate carcinogenesis andinilammation: emerging insights. Carcinogenesis 26,1170-1181.

Perfettini, J. L.; Kroemer, R. T.; Kroemer, G., Fatal liaisons of p53 with Bax and Bak. Nat Cell Biol 2004, 6, (5), 386-8.

Perfettini, J. L.; Roumier, T.; Kroemer, G., Mitochondrial fusion and fission in the control of apoptosis. Trends Cell Biol 2005,15, (4), 179-83.

Perfettini, J.L. et al. Fatal liaisons of p53 with Bax and Bak, Nat. Cell Biol. 6 (5) (2004) 386-388.

Perfettini, J.L. et al. Mitochondrial fusion and fission in the control of apoptosis, Trends Cell Biol. 15 (4) (2005) 179-183.

Prasad, M.A., Trybus, T.M., Wojno, K.J., Macoska, J.A., 1998. Homozygous and frequent deletion of proximal 8p sequences in human prostate cancers: identification of a potential tumor suppressor gene site. Genes Chromosomes Cancer 23,255-262.

Raj GV, Moreno JG, Gomella LG: Utilization of polymerase chain reaction technology in the detection of solid tumors. Cancer 1998, 82:1419-1442.

Shariat SF, Kaftan MW, Song W, Bernard D, Gottenger E, Wheeler TM, Slawin KM: Early postoperative peripheral blood reverse transcription PCR assay for prostate-specific antigen is associated with prostate cancer progression in patients undergoing radical prostatectomy—Cancer Res 2003, 63:5874-5878.

Sikorski, R. S. and Hieter, P. A system of shuttle vectors and yeast host strains designed for efficient manipulation of DNA in Saccharomyces cerevisiae. Genetics, 122: 19-27., 1989.

Soeth E, Vogel I, Roder C, Juhl H, Marxsen J, Kruger U, Henne-Bruns D, Kremer B, Kalthoff H: Comparative analysis of bone marrow and venous blood isolates from gastrointestinal cancer patients for the detection of disseminated tumor cells using reverse transcription PCR. Cancer Res 1997, 57:3106-3110.

Strasser, A. The role of BH3-only proteins in the immune system, Nat. Rev. Immunol. 5 (3) (2005) 189-200.

Stuart ET, Heffher R, Oren M, Grass P. Loss of p53 function through PAX-mediated transcriptional repression. Embo J 1995 ;14(22):563 8-5645.

Tagge, E. P.; Hanson, P.; Re, G. G.; Othersen, H. B., Jr.; Smith, C. D.; Garvin, A. J., Paired box gene expression in Wilms' tumor. J Pediatr Surg 1994,29, (2), 134-41.

Takeuchi, S.; Iida, M.; Kobayashi, S.; Jin, K; Matsuda, T.; Kojima, H., Differential effects of phthalate esters on transcriptional activities via human estrogen receptors alpha and beta, and androgen receptor. Toxicology 2005,210, (2-3), 223-33.

Teixeira, M. R.; Ribeiro, F. R.; Eknaes, M.; Waehre, H,; Stenwig, A. E.; Giercksky, K. E.; Heim, S.; Lothe, R. A., Genomic analysis of prostate carcinoma specimens obtained via ultrasound-guided needle biopsy may be of use in preoperative decision-making. Cancer 2004,101, (8), 1786-93.

Tien, A.H., Xu, L.s Helgason, CD., 2005. Altered immunity accompanies disease progression in a mouse model of prostate dysplasia. Cancer Res. 65,2947-2955.

Tokino, T.; Nakamura, Y., The role of p53-target genes in human cancer. Crit Rev Oncol Hematol 2000, 33,(1), 1-6.

Torres, M. et al. PAX-2 controls multiple steps of urogenital development, Development 121(1995)4057-4065.

Valore EV, Park CH, Quayle AJ, Wiles KR, McCray PB Jr, Ganz T. Human beta-defensin-1: an antimicrobial peptide of urogenital tissues. J Clin Invest Apr. 15, 1998;101(8):1633-42.

Vecchione, A.; Ishii, H.; Baldassare, G.; Bassi, P.; Trapasso, F.; Alder, H.; Pagano, F.; Gomella, L. G.; Croce, C. M.; Baffa, R., FEZ1/LZTS1 is down-regulated in high-grade bladder cancer, and its restoration suppresses tumorigenicity in transitional cell carcinoma cells. Am J Pathol 2002,160, (4), 1345-52.

Wallin, JJ. et al. Dependence of BSAP repressor and activator functions on BSAP concentration, Science 279 (1998) 1961-1964.

Wang ZP, Eisenberger MA, Carducci MA, Partin AW, Scher HI, Ts'o PO: Identification and characterization of circulating prostate carcinoma cells. Cancer 2000, 88:2787-2795.

Wang, Z.; Lai, F. M., [Analysis of loss of heterozygosity on chromosome 8 in human prostate carcinoma and high grade prostatic intraepithelial neoplasia], Zhonghua Nan 10 Ke Xue 2004,10, (1), 26-8, 31.

U.S. Appl. No. 12/090,191, filed Oct. 16, 2006, Patented
U.S. Appl. No. 12/440,193, filed Mar. 13, 2009, Pending.
PCT/US08/51168, filed Jan. 16, 2008, Expired.
U.S. Appl. No. 12/546,292, filed Aug. 24, 2009, Pending.
PCT/US09/54913, filed Aug. 25, 2009, Pending.
U.S. Appl. No. 13/024,971, filed Feb. 10, 2011, Pending.

* cited by examiner

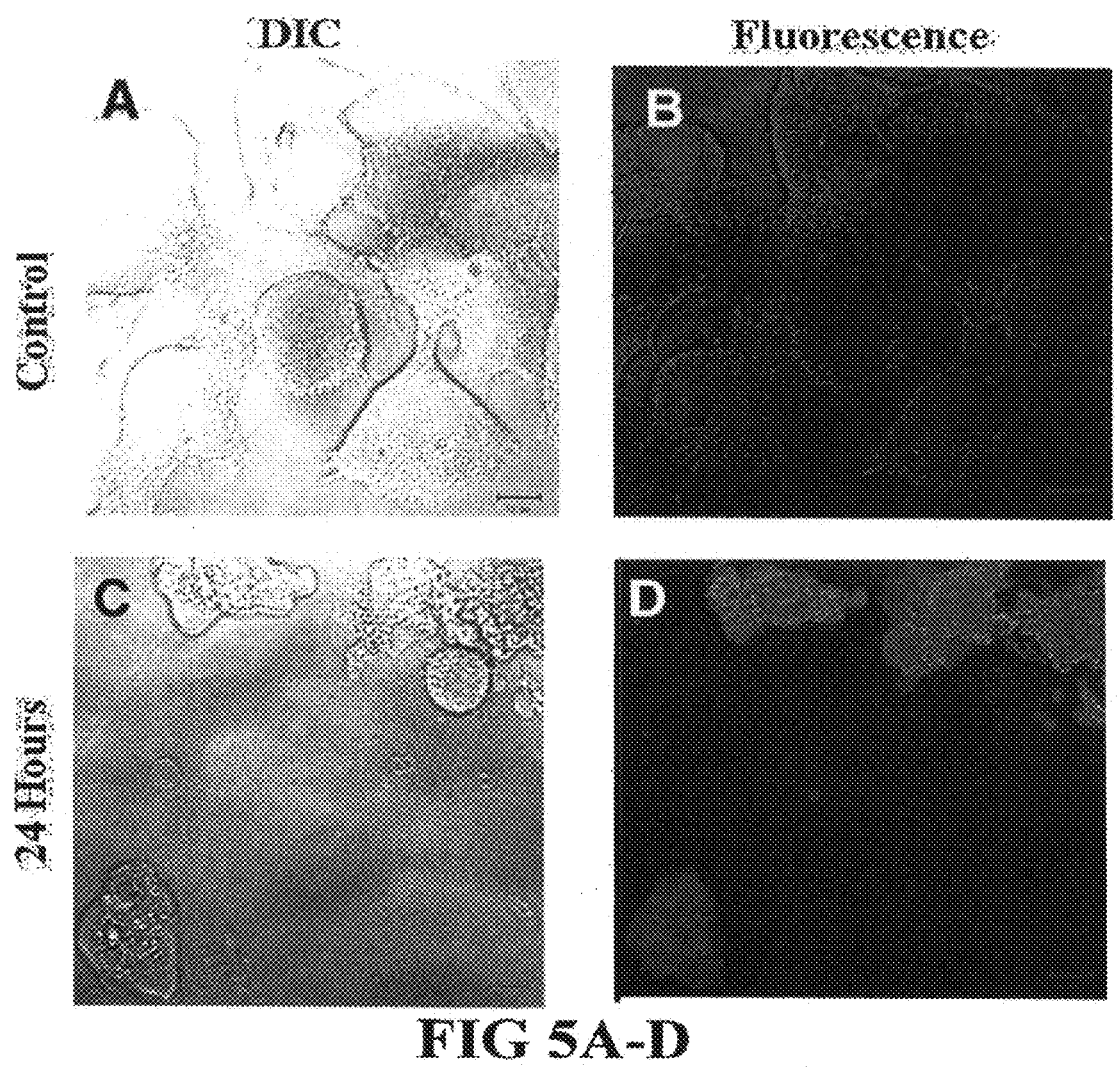
FIG 5A-D

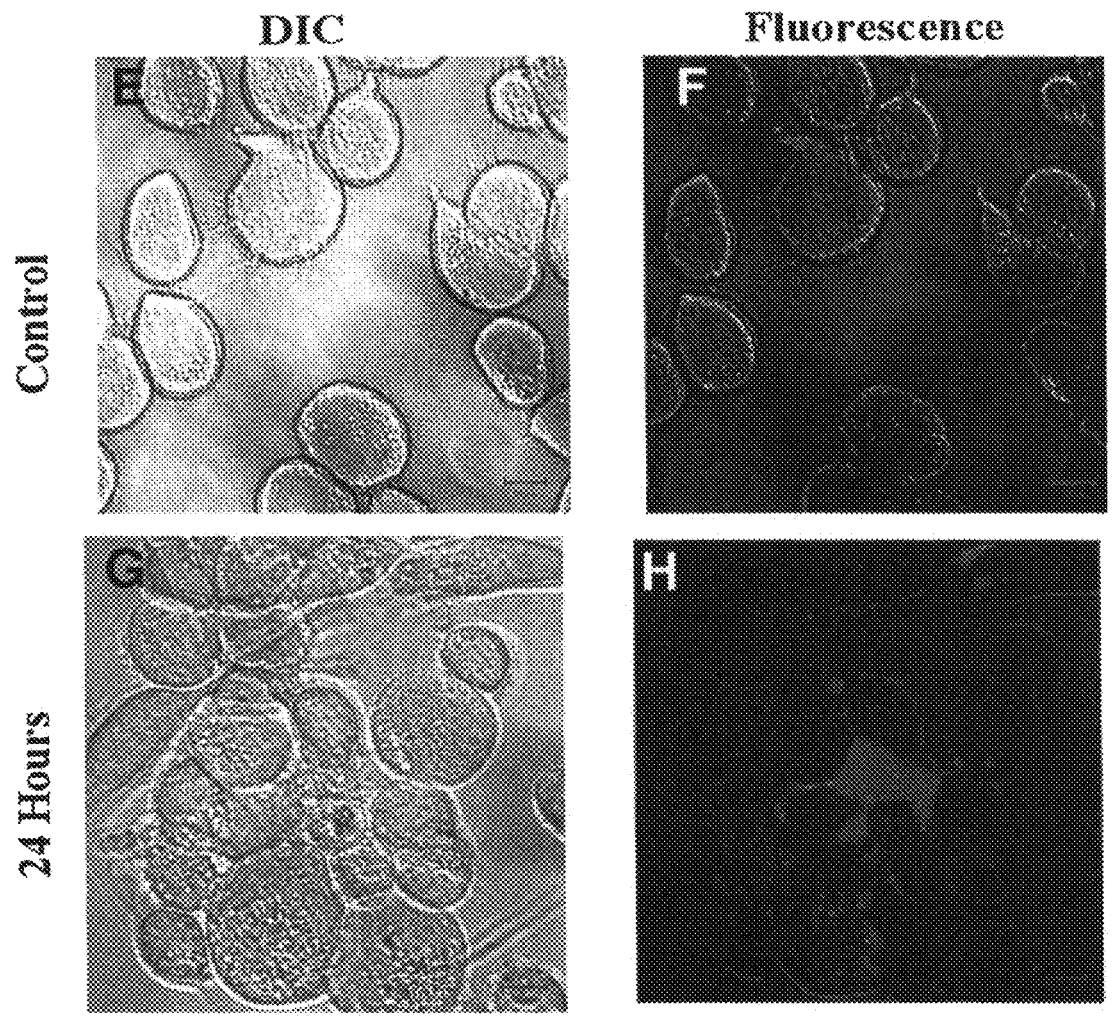
FIG 5E-H

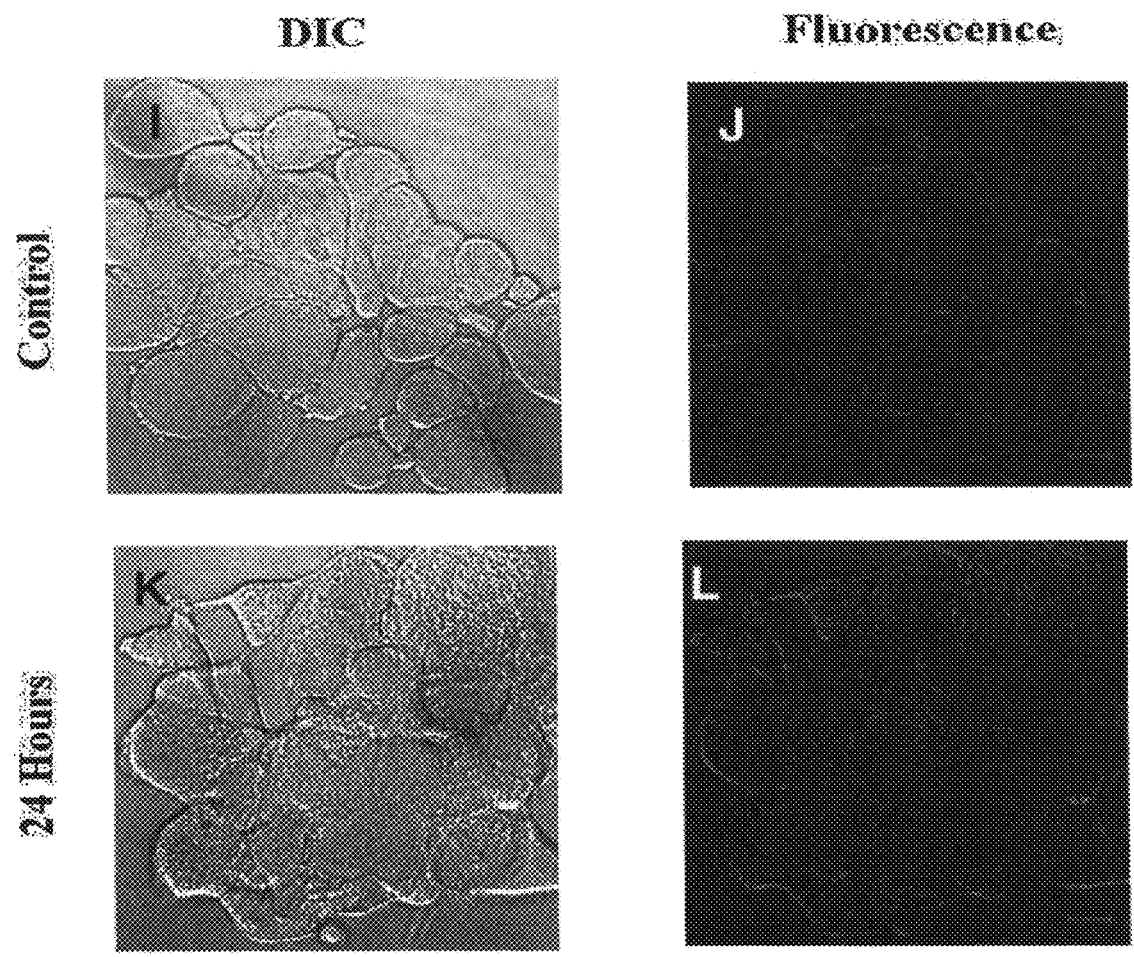
FIG 5I-L

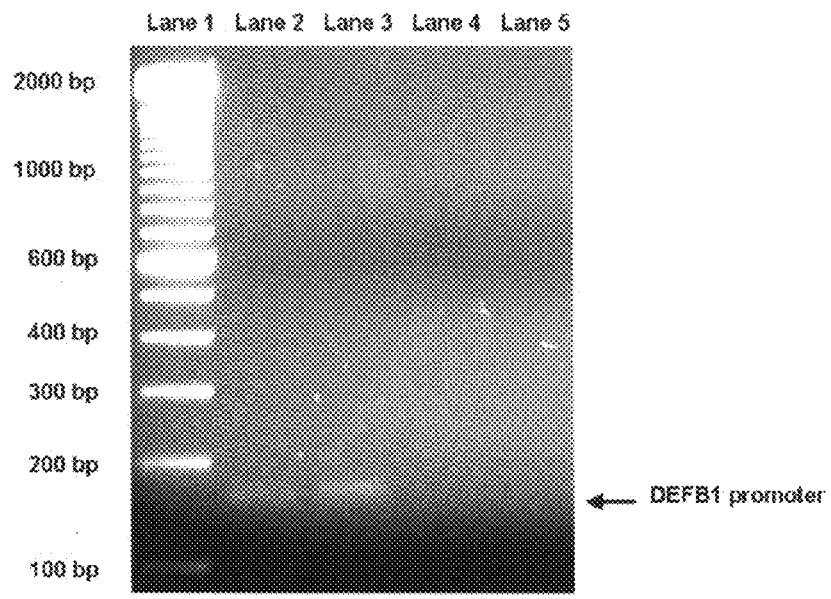
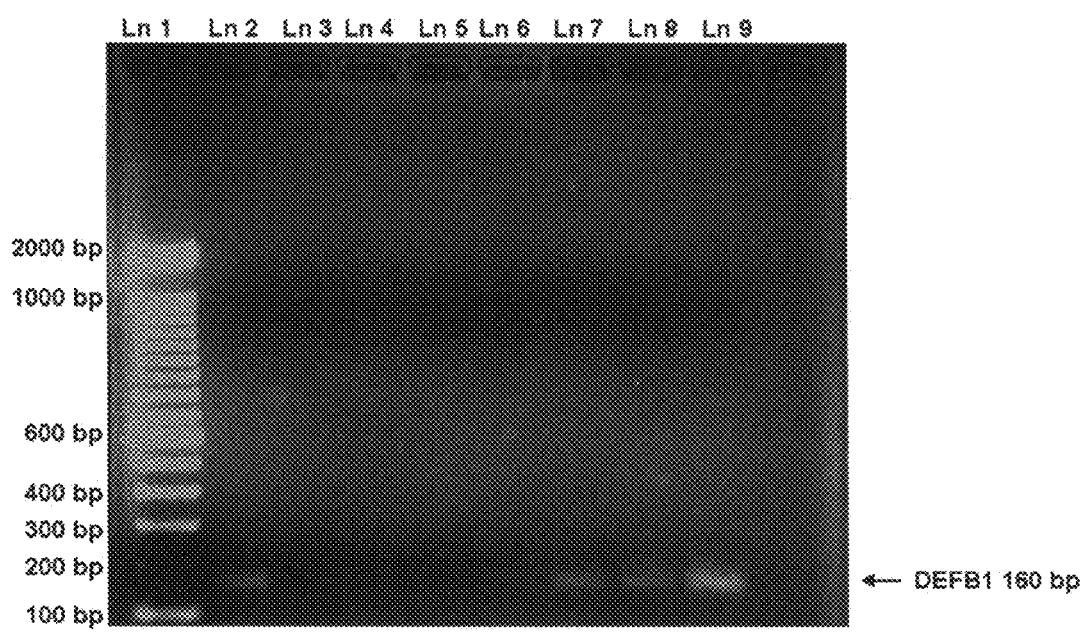
FIG. 15

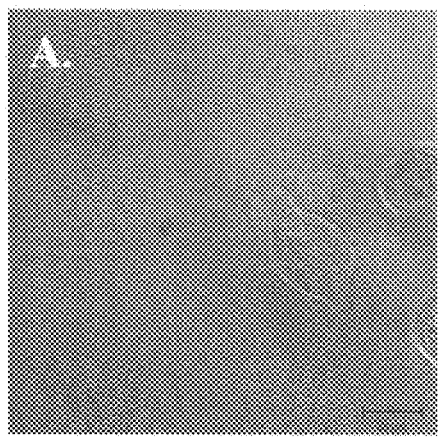
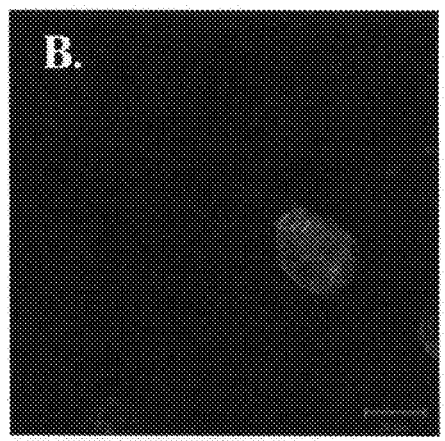
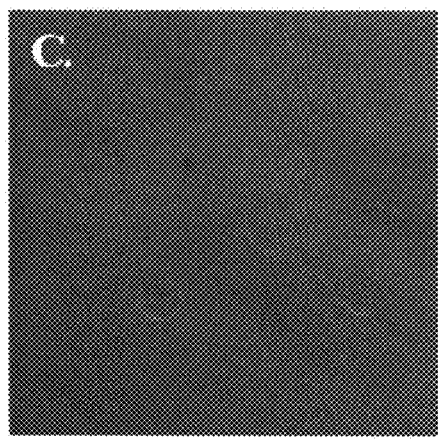
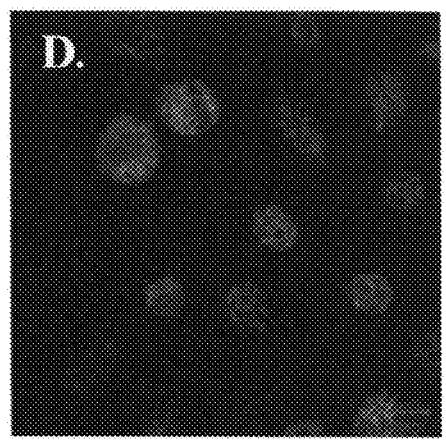
FIG. 32B

```
                        SEQUENCE LISTING

<160> NUMBER OF SEQ ID NOS: 79

<210> SEQ ID NO 1
<211> LENGTH: 5
<212> TYPE: DNA
<213> ORGANISM: Artificial Sequence
<220> FEATURE:
<223> OTHER INFORMATION: DEFB1 DNA core sequence of PAX2 protein
      binding site

<400> SEQUENCE: 1 ccttg                                                                       5

<210> SEQ ID NO 2
<211> LENGTH: 5
<212> TYPE: DNA
<213> ORGANISM: Artificial Sequence
<220> FEATURE:
<223> OTHER INFORMATION: A DNA recognition sequence of PAX2 protein

<400> SEQUENCE: 2 gttcc                                                                       5

<210> SEQ ID NO 3
<211> LENGTH: 21
<212> TYPE: RNA
<213> ORGANISM: Artificial Sequence
```

```
<220> FEATURE:
<223> OTHER INFORMATION: Synthetic construct

<400> SEQUENCE: 3
auagacucga cuugacuucu u                                              21

<210> SEQ ID NO 4
<211> LENGTH: 21
<212> TYPE: RNA
<213> ORGANISM: Artificial Sequence
<220> FEATURE:
<223> OTHER INFORMATION: Synthetic Construct

<400> SEQUENCE: 4
aucuucauca cguuccucu u                                               21

<210> SEQ ID NO 5
<211> LENGTH: 21
<212> TYPE: RNA
<213> ORGANISM: Artificial Sequence
<220> FEATURE:
<223> OTHER INFORMATION: Synthetic Construct

<400> SEQUENCE: 5
guauucagca aucuuguccu u                                              21

<210> SEQ ID NO 6
<211> LENGTH: 21
<212> TYPE: RNA
<213> ORGANISM: Artificial Sequence
<220> FEATURE:
<223> OTHER INFORMATION: Synthetic Construct

<400> SEQUENCE: 6
gauuugaugu gcucugaugu u                                              21

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7
acccgactat gttcgcctgg                                                20

<210> SEQ ID NO 8
<211> LENGTH: 21
<212> TYPE: DNA
<213> ORGANISM: Artificial Sequence
<220> FEATURE:
<223> OTHER INFORMATION: Synthetic Construct

<400> SEQUENCE: 8
aagctctgga tcgagtcttt g                                              21

<210> SEQ ID NO 9
<211> LENGTH: 20
<212> TYPE: DNA
<213> ORGANISM: Artificial Sequence
<220> FEATURE:
<223> OTHER INFORMATION: Synthetic Construct

<400> SEQUENCE: 9
atgtgtcagg cacacagacg                                                20
```

```
<210> SEQ ID NO 10
<211> LENGTH: 21
<212> TYPE: RNA
<213> ORGANISM: Artificial Sequence
<220> FEATURE:
<223> OTHER INFORMATION: Synthetic Construct

<400> SEQUENCE: 10
gucgagucua ucugcauccu u                                              21

<210> SEQ ID NO 11
<211> LENGTH: 21
<212> TYPE: RNA
<213> ORGANISM: Artificial Sequence
<220> FEATURE:
<223> OTHER INFORMATION: Synthetic Construct

<400> SEQUENCE: 11
ggaugcagau agacucgacu u                                              21

<210> SEQ ID NO 12
<211> LENGTH: 7
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(7)
<223> OTHER INFORMATION: v = is from 1 to 35 contiguous nucleotides
      flanking PAX2 DNA binding site; w = is from 1 to 35 contiguous
      nucleotides flanking PAX DNA binding site

<400> SEQUENCE: 12 vccttgw                                                               7

<210> SEQ ID NO 13
<211> LENGTH: 20
<212> TYPE: DNA
<213> ORGANISM: Artificial Sequence
<220> FEATURE:
<223> OTHER INFORMATION: Synthetic Construct

<400> SEQUENCE: 13
ctcccttcag ttccgtcgac                                                20

<210> SEQ ID NO 14
<211> LENGTH: 20
<212> TYPE: DNA
<213> ORGANISM: Artificial Sequence
<220> FEATURE:
<223> OTHER INFORMATION: Synthetic Construct

<400> SEQUENCE: 14
ctcccttcac cttggtcgac                                                20

<210> SEQ ID NO 15
<211> LENGTH: 40
<212> TYPE: DNA
<213> ORGANISM: Artificial Sequence
<220> FEATURE:
<223> OTHER INFORMATION: Synthetic Construct

<400> SEQUENCE: 15
actgtggcac ctcccttcag ttccgtcgac gaggttgtgc                          40
```

```
<210> SEQ ID NO 16
<211> LENGTH: 40
<212> TYPE: DNA
<213> ORGANISM: Artificial Sequence
<220> FEATURE:
<223> OTHER INFORMATION: Synthetic Construct

<400> SEQUENCE: 16
actgtggcac ctcccttcac cttggtcgac gaggttgtgc                            40

<210> SEQ ID NO 17
<211> LENGTH: 5
<212> TYPE: DNA
<213> ORGANISM: Artificial Sequence
<220> FEATURE:
<223> OTHER INFORMATION: A DNA scrambled sequence for oligonucleotide
      inhibitors of PAX2 binding site in DEFB1 promoter

<400> SEQUENCE: 17 ctctg                                                                   5

<210> SEQ ID NO 18
<211> LENGTH: 20
<212> TYPE: DNA
<213> ORGANISM: Artificial Sequence
<220> FEATURE:
<223> OTHER INFORMATION: Synthetic Construct

<400> SEQUENCE: 18
ctcccttcac tctggtcgac                                                  20

<210> SEQ ID NO 19
<211> LENGTH: 40
<212> TYPE: DNA
<213> ORGANISM: Artificial Sequence
<220> FEATURE:
<223> OTHER INFORMATION: Synthetic Construct

<400> SEQUENCE: 19
actgtggcac ctcccttcac tctggtcgac gaggttgtgc                            40

<210> SEQ ID NO 20
<211> LENGTH: 20
<212> TYPE: DNA
<213> ORGANISM: Artificial Sequence
<220> FEATURE:
<223> OTHER INFORMATION: Synthetic Construct

<400> SEQUENCE: 20
agaagttcac ccttgactgt                                                  20

<210> SEQ ID NO 21
<211> LENGTH: 20
<212> TYPE: DNA
<213> ORGANISM: Artificial Sequence
<220> FEATURE:
<223> OTHER INFORMATION: Synthetic Construct

<400> SEQUENCE: 21
agaagttcac gttccactgt                                                  20

<210> SEQ ID NO 22
<211> LENGTH: 20
<212> TYPE: DNA
<213> ORGANISM: Artificial Sequence
<220> FEATURE:
<223> OTHER INFORMATION: Synthetic Construct
```

```
<400> SEQUENCE: 22
agaagttcac gctctactgt                                                    20

<210> SEQ ID NO 23
<211> LENGTH: 39
<212> TYPE: DNA
<213> ORGANISM: Artificial Sequence
<220> FEATURE:
<223> OTHER INFORMATION: Synthetic Construct

<400> SEQUENCE: 23
ttagcgatta gaagttcacc cttgactgtg gcacctccc                               39

<210> SEQ ID NO 24
<211> LENGTH: 40
<212> TYPE: DNA
<213> ORGANISM: Artificial Sequence
<220> FEATURE:
<223> OTHER INFORMATION: Synthetic Construct

<400> SEQUENCE: 24
gttagcgatt agaagttcac gttccactgt ggcacctccc                              40

<210> SEQ ID NO 25
<211> LENGTH: 40
<212> TYPE: DNA
<213> ORGANISM: Artificial Sequence
<220> FEATURE:
<223> OTHER INFORMATION: Synthetic Construct

<400> SEQUENCE: 25
gttagcgatt agaagttcac gctctactgt ggcacctccc                              40

<210> SEQ ID NO 26
<211> LENGTH: 20
<212> TYPE: DNA
<213> ORGANISM: Artificial Sequence
<220> FEATURE:
<223> OTHER INFORMATION: Synthetic Construct

<400> SEQUENCE: 26
actgcccatt gcccaaacac                                                    20

<210> SEQ ID NO 27
<211> LENGTH: 21
<212> TYPE: DNA
<213> ORGANISM: Artificial Sequence
<220> FEATURE:
<223> OTHER INFORMATION: Synthetic Construct

<400> SEQUENCE: 27
aaaatcttgc cagctttccc c                                                  21

<210> SEQ ID NO 28
<211> LENGTH: 23
<212> TYPE: DNA
<213> ORGANISM: Artificial Sequence
<220> FEATURE:
<223> OTHER INFORMATION: Synthetic Construct

<400> SEQUENCE: 28
gtcggttacg gagcggaccg gag                                                23
```

```
<210> SEQ ID NO 29
<211> LENGTH: 24
<212> TYPE: DNA
<213> ORGANISM: Artificial Sequence
<220> FEATURE:
<223> OTHER INFORMATION: Synthetic Construct

<400> SEQUENCE: 29
taacatatag acaaacgcac accg                                              24

<210> SEQ ID NO 30
<211> LENGTH: 23
<212> TYPE: DNA
<213> ORGANISM: Artificial Sequence
<220> FEATURE:
<223> OTHER INFORMATION: Synthetic Construct

<400> SEQUENCE: 30
gcgcttgtgt cgccattgta ttc                                               23

<210> SEQ ID NO 31
<211> LENGTH: 24
<212> TYPE: DNA
<213> ORGANISM: Artificial Sequence
<220> FEATURE:
<223> OTHER INFORMATION: Synthetic Construct

<400> SEQUENCE: 31
gtcacaccac agaagtaagg ttcc                                              24

<210> SEQ ID NO 32
<211> LENGTH: 23
<212> TYPE: DNA
<213> ORGANISM: Artificial Sequence
<220> FEATURE:
<223> OTHER INFORMATION: Synthetic Construct

<400> SEQUENCE: 32
gtcggttacg gagcggaccg gag                                               23

<210> SEQ ID NO 33
<211> LENGTH: 25
<212> TYPE: DNA
<213> ORGANISM: Artificial Sequence
<220> FEATURE:
<223> OTHER INFORMATION: Synthetic Construct

<400> SEQUENCE: 33
cacagagcat tggcgatctc gatgc                                             25

<210> SEQ ID NO 34
<211> LENGTH: 18
<212> TYPE: DNA
<213> ORGANISM: Artificial Sequence
<220> FEATURE:
<223> OTHER INFORMATION: Synthetic Construct

<400> SEQUENCE: 34
cctggcaccc agcacaat                                                     18

<210> SEQ ID NO 35
<211> LENGTH: 32
<212> TYPE: DNA
<213> ORGANISM: Artificial Sequence
<220> FEATURE:
<223> OTHER INFORMATION: Synthetic Construct
```

<400> SEQUENCE: 35
gttgcctgcc agtcgccatg agaacttcct ac        32

<210> SEQ ID NO 36
<211> LENGTH: 20
<212> TYPE: DNA
<213> ORGANISM: Artificial Sequence
<220> FEATURE:
<223> OTHER INFORMATION: Synthetic Construct

<400> SEQUENCE: 36
gccgatccac acggagtact        20

<210> SEQ ID NO 37
<211> LENGTH: 32
<212> TYPE: DNA
<213> ORGANISM: Artificial Sequence
<220> FEATURE:
<223> OTHER INFORMATION: Synthetic Construct

<400> SEQUENCE: 37
tggccttccc tctgtaacag gtgccttgaa tt        32

<210> SEQ ID NO 38
<211> LENGTH: 21
<212> TYPE: RNA
<213> ORGANISM: Artificial Sequence
<220> FEATURE:
<223> OTHER INFORMATION: Synthetic Construct

<400> SEQUENCE: 38
gaagucaagu cgagucuauu u        21

<210> SEQ ID NO 39
<211> LENGTH: 21
<212> TYPE: RNA
<213> ORGANISM: Artificial Sequence
<220> FEATURE:
<223> OTHER INFORMATION: Synthetic Construct

<400> SEQUENCE: 39
gaggaaacgu gaugaagauu u        21

<210> SEQ ID NO 40
<211> LENGTH: 21
<212> TYPE: RNA
<213> ORGANISM: Artificial Sequence
<220> FEATURE:
<223> OTHER INFORMATION: Synthetic Construct

<400> SEQUENCE: 40
ggacaagauu gcugaauacu u        21

<210> SEQ ID NO 41
<211> LENGTH: 21
<212> TYPE: RNA
<213> ORGANISM: Artificial Sequence
<220> FEATURE:
<223> OTHER INFORMATION: Synthetic Construct

<400> SEQUENCE: 41
caucagagca caucaaaucu u        21

```
<210> SEQ ID NO 42
<211> LENGTH: 24
<212> TYPE: DNA
<213> ORGANISM: Artificial Sequence
<220> FEATURE:
<223> OTHER INFORMATION: Synthetic Construct

<400> SEQUENCE: 42
ccacccatgg caaattccat ggca                                              24

<210> SEQ ID NO 43
<211> LENGTH: 23
<212> TYPE: DNA
<213> ORGANISM: Artificial Sequence
<220> FEATURE:
<223> OTHER INFORMATION: Synthetic Construct

<400> SEQUENCE: 43
ctcaggccta tgcaaaaaga gga                                               23

<210> SEQ ID NO 44
<211> LENGTH: 23
<212> TYPE: DNA
<213> ORGANISM: Artificial Sequence
<220> FEATURE:
<223> OTHER INFORMATION: Synthetic Construct

<400> SEQUENCE: 44
aacctacgca cctacgtgag gag                                               23

<210> SEQ ID NO 45
<211> LENGTH: 20
<212> TYPE: DNA
<213> ORGANISM: Artificial Sequence
<220> FEATURE:
<223> OTHER INFORMATION: Synthetic Construct

<400> SEQUENCE: 45
gacacctgag ctgaccttgg                                                   20

<210> SEQ ID NO 46
<211> LENGTH: 24
<212> TYPE: DNA
<213> ORGANISM: Artificial Sequence
<220> FEATURE:
<223> OTHER INFORMATION: Synthetic Construct

<400> SEQUENCE: 46
tctagacggc aggtcaggtc aacc                                              24

<210> SEQ ID NO 47
<211> LENGTH: 20
<212> TYPE: DNA
<213> ORGANISM: Artificial Sequence
<220> FEATURE:
<223> OTHER INFORMATION: Synthetic Construct

<400> SEQUENCE: 47
gccctccctc caaaggagac                                                   20

<210> SEQ ID NO 48
<211> LENGTH: 22
<212> TYPE: DNA
<213> ORGANISM: Artificial Sequence
<220> FEATURE:
<223> OTHER INFORMATION: Synthetic Construct
```

```
<400> SEQUENCE: 48
cgttcagtcc atcccatttc tg                                    22

<210> SEQ ID NO 49
<211> LENGTH: 20
<212> TYPE: DNA
<213> ORGANISM: Artificial Sequence
<220> FEATURE:
<223> OTHER INFORMATION: Synthetic Construct

<400> SEQUENCE: 49
gaggaagtcc agtgtccagc                                       20

<210> SEQ ID NO 50
<211> LENGTH: 19
<212> TYPE: DNA
<213> ORGANISM: Artificial Sequence
<220> FEATURE:
<223> OTHER INFORMATION: Synthetic Construct

<400> SEQUENCE: 50
tcagcagtgg agggcaatg                                        19

<210> SEQ ID NO 51
<211> LENGTH: 23
<212> TYPE: DNA
<213> ORGANISM: Artificial Sequence
<220> FEATURE:
<223> OTHER INFORMATION: Synthetic Construct

<400> SEQUENCE: 51
cctctgtaac aggtgccttg aat                                   23

<210> SEQ ID NO 52
<211> LENGTH: 21
<212> TYPE: DNA
<213> ORGANISM: Artificial Sequence
<220> FEATURE:
<223> OTHER INFORMATION: Synthetic Construct

<400> SEQUENCE: 52
acagcaaacc tcctcacagc c                                     21

<210> SEQ ID NO 53
<211> LENGTH: 20
<212> TYPE: DNA
<213> ORGANISM: Artificial Sequence
<220> FEATURE:
<223> OTHER INFORMATION: Synthetic Construct

<400> SEQUENCE: 53
tggagacgtg gcacctcttg                                       20

<210> SEQ ID NO 54
<211> LENGTH: 24
<212> TYPE: DNA
<213> ORGANISM: Artificial Sequence
<220> FEATURE:
<223> OTHER INFORMATION: Synthetic Construct

<400> SEQUENCE: 54
tatgataccc gggagatcgt gatc                                  24
```

-continued

<210> SEQ ID NO 55
<211> LENGTH: 24
<212> TYPE: DNA
<213> ORGANISM: Artificial Sequence
<220> FEATURE:
<223> OTHER INFORMATION: Synthetic Construct

<400> SEQUENCE: 55
gtgcagatgc cggttcaggt actc                                              24

<210> SEQ ID NO 56
<211> LENGTH: 20
<212> TYPE: DNA
<213> ORGANISM: Artificial Sequence
<220> FEATURE:
<223> OTHER INFORMATION: Synthetic Construct

<400> SEQUENCE: 56
tcagccctgg actacctgca                                                   20

<210> SEQ ID NO 57
<211> LENGTH: 20
<212> TYPE: DNA
<213> ORGANISM: Artificial Sequence
<220> FEATURE:
<223> OTHER INFORMATION: Synthetic Construct

<400> SEQUENCE: 57
gaggtcccgg tacaccacgt                                                   20

<210> SEQ ID NO 58
<211> LENGTH: 135
<212> TYPE: PRT
<213> ORGANISM: Homo sapiens

<400> SEQUENCE: 58

Met Asp Met His Cys Lys Ala Asp Pro Phe Ser Ala Met His Arg His
1               5                   10                  15

Gly Gly Val Asn Gln Leu Gly Gly Val Phe Val Asn Gly Arg Pro Leu
            20                  25                  30

Pro Asp Val Val Arg Gln Arg Ile Val Glu Leu Ala His Gln Gly Val
        35                  40                  45

Arg Pro Cys Asp Ile Ser Arg Gln Leu Arg Val Ser His Gly Cys Val
    50                  55                  60

Ser Lys Ile Leu Gly Arg Tyr Tyr Glu Thr Gly Ser Ile Lys Pro Gly
65                  70                  75                  80

Val Ile Gly Gly Ser Lys Pro Lys Val Ala Thr Pro Lys Val Val Asp
                85                  90                  95

Lys Ile Ala Glu Tyr Lys Arg Gln Asn Pro Thr Met Phe Ala Trp Glu
            100                 105                 110

Ile Arg Asp Arg Leu Leu Ala Glu Gly Ile Cys Asp Asn Asp Thr Val
        115                 120                 125

Pro Ser Val Ser Ser Ile Asn
    130                 135

<210> SEQ ID NO 59
<211> LENGTH: 7331
<212> TYPE: DNA
<213> ORGANISM: Homo sapiens
<220> FEATURE:
<221> NAME/KEY: misc_feature
<222> LOCATION: (1)..(7331)
<223> OTHER INFORMATION: n= a, c, g, or t

<400> SEQUENCE: 59

```
ttccccctttt ccangagggc ctaatccgtt gcgcgcgcgc acgcggacac acacacacac    60
acacacacac acacacacac acacacggcc cccatagcca ccgcaactct cagcagcagn   120
ncctagctcc tctgacccga ggccccaaga cggcgggcac aggaacccct gggacgtcct   180
ggctccaggc tggacgtagg cggaggtggc aggagtggac aaacccaggc gggtcccacg   240
acgccccttt cctcgggtct ctccttgttt cagccagccg ctctcgcccc tggtcccctc   300
ttccctgcgt tagggtcctt tgtctccagc cacctcgcag cctgtccccg cctcggcggc   360
cctgcccttt gggcctccca gatctctctg gcgggtcccc ctgccttacc agctcccggc   420
tgtggcgcgc tcttcgcctg ctcctcacat ncacacagct gctgggagag gaggaaggaa   480
aggcggncgc gccgcggatg gatccgagac ggtagatttg gtgccggctc gcaaactctg   540
ggaaacttaa ngccggttct tccgcccctc tncaactatg nccagcgcgg cccggtcgcg   600
cgcgctcacc ccgcggggac ccttttcctt cctgtatttt cggctgcggc tgtttcgctt   660
cctctggtct cccagccttt ggagtggctt ccctggccct gcactccgtt cccttcggc    720
cgccccggc tgtcgcctgc ccccacccte cgcaggtccc acggtcgcgg cggcgatgac    780
tgtggaggta acgccgggga cgtcctgggt cagcctgcac cgtctccctc gaccacagcc   840
cgatgaggcc gcgggctccg ggccggctgc taagagagtt aatcattact cgcagcga     900
cactcagcct cccccttccga ctctctcgcc cggcctaggg gaggagggga ggggacagct  960
ggccaggtgg ggacttcggc ttcgcacaaa ccagcctctt caggcctccc agagacaggt  1020
ggtggcttct cagttccctc ggcaactctc taaggtcctc tttcttcccc tcctgtctct  1080
ccctccttcg agcctcctcc cagccaggcc tctccccacc gtctcctgtc cgctctggct  1140
ttgactgatt aactgcaggt cctggagaa ccaactttct ttgtttggaa ccggaccgga   1200
cgggatttcc ttccctaggt ctccgccaat gggccagctc ctcccgacgg ttttggcgga  1260
ctggctgaag aggaccgcgc ctgaggccac aattaacccg gctgttggtg gtggtggttg  1320
gggggtgggc agtgaggaat ttaaccgatc ctctagcagc tgcgctggtg cagttgggag  1380
gggggtgcag gaagtgggaa tggaggagtg gcaggaggta tagacagagg gaagaacgat  1440
aaacctggac aggtgtggca tagccaatag aaggggaaac aaaataaaac aggaaggcgg  1500
cgcggggagg aatccccagt aacctttata ggattgaagt tgggtggaaa acgccacctc  1560
ctgccctacc ttagcactca gatccctcct ttacctctttt gtgaaagggt aagagttcag  1620
aaagctggcc atttactcca taatctacta gagaaatgtc tgggtttgca aaatgcctat  1680
tgattagctc catggagtag acaagacagg cgtaattatc cccattttac aggtgagaaa  1740
actgagtctc aaagaagcaa agggactgtg tatgtagtgg ctgtcactttt tcctgtagg   1800
ctgtggggtg agtggcccct ttagctgtgc agaggtccat gggtatctag ggaggcggta  1860
caggctgtgt ccaggtctga gccagaagta ccagggcctc acgggctcc tagcccttt    1920
agcttgttct ctgttggaca ggaccttcac tcttactctc tagacctgct ggctgggttt  1980
ctcccagctt cgctatttt tcagttccct agtagagtgg cccatgggcg gtagccacct   2040
ggctggcccg tgccactaag aggcagcttt ggtggcaag tggcttgcat tgttgttgct   2100
cctcaaaggg cctgtgaagg gctgggcagg tcgcaaagac ctcttgtgag gggaaagcta  2160
gattaaaggg ggtaaggatc ctggaggata aaggccaagc acgtgcgcct ggactccaca  2220
ggaccaacag accgagcggg cggggccngc tgggagtcag gccccccggg cttcacgcag  2280
ggagcccaaa tattgggaac aaaagcagga aaagaagagt gagagcagga gggagggagg  2340
```

```
gagcgaggaa gcagaaatta gggggtctta gatgaaaaaa aaaagaaagt agctttaggg    2400
ggaatgtgct gtggagtgtg aaattgcagc ccatggtgct ccatattgta ccagaagctc    2460
ttccaaaaaa aaaaaaaaaa accatcctcc aacgtgacca gagggccagg caggggaag     2520 ggcgggagga gaatggggag gaggagggg aaggccggg caggagccgg tcaggccttt      2580
ctgcggaagg ggctggggtg taagtttcgg ctccctggga tctgacagcc gagggtatgc    2640
gccctggggt gcgccgggac ccagagggcg agtgagcctc ggttggtcgg ctctggagtt    2700
cggttgtcag aagaactttt atttttcttt ttggtggtga cttctaaaag tgggaataat    2760
ccagaaatga agctcagctg cggagctgca gctctgttct ccctctctcc cctgcctttc    2820
tgcttctctt cccttcggac tacttttctc cccttggttc taaatagctt tttccctct    2880 gaactttaat gcatttaatt tggtccgcgc tgtgggagc atttcctggg gagatgcatt     2940
taatttcgga atttctaatc ccctccctca gaccccggtc ctagctcccc tagccgctcc    3000
ccgggaagtg gaaggaggaa ggcaggtccc ggccacgggg gaggggcgcg gctgggatgc    3060
tcccgcggcc ccctccgtct caccaaggct cagccgcctt cccaagctac tggaggccgg    3120
gcgcctgggc cccgggtcag ggccctgcan gaagaagaga ggcaacccc gctttctgcc     3180 ttttcttcgc ctgggcaaga aaacgctggg ccagggaact ggaaaccgga aaacaggaga    3240 aagggttttnt ggaaggcanc gggagcgggt ggcagncggg gcancgggca ntggactagg   3300
tctacaccgg cacttcactt ttgcacaaca tgcccagaaa cgcatttgag agccctggag    3360
tcgcgcttgg cttggcttgg ggcgccggtg cgtgggtaca ctcgaggtcg gggtgcctat    3420
ccgccacccc gacacctaca cccagtgcag agcaggcgcg gcccagccag acaaccaggc    3480
cggcagtagc tcggcctgga gggcggaggc aaggttgggg gccgccaggc gcctgggcaa    3540
gcctggcagg gaagggagcc gagaaggcaa aggagccgag atccacaagg aagattnntt   3600
gggcagatca gatgcacaga ggcggctaat gaagcaaatc ccgagatggg tttcagagca    3660
actccccaaa agtttatttt gccttaaat ttccgcaggg aggcgggctc cttgtttgaa     3720
gtgtaaatgc ccctaggttg gggggtggaa gggccgcttt gaaaacacca gagagaaaag    3780
gttcatttag aggcggacgg gaaaagcaac caaccctgac aggtcggagc ccgggtagtg    3840
tttggggttg ggtngttttc tttctttctc tttcttttcc cctttcctct tctttcttcc    3900
cttttgtgnn ttttnnttgt tttttttntn ttnttttttnt ttaantggct ttcttgcttc   3960
cccccacccc tctactagac tctatagaag aaagagaaca gaaaggggg agtcagagga     4020 gcggccagtg actggatgaa ggccagccct tcatcctgga gccccaggag aaggcagagc    4080
tttggagaaa aggggttcct aatctccagg gagcattact ctttgactct ctagacccag    4140
gaatgggctg gacgctaatg gggaagcggc caggaacccg gcctggcgga agagtgagtg    4200
tccagctagt gcagtgctgg gaagacgatc ccaggagcag gggggactct caggggctac    4260
ctgggaatgg gactatcaga agggtcttta ctcctcanaa ggtgcatgtg aaggacaggt    4320
gtgtgaggac aacttccagc acacttggcg cattaagtcc ccttctctac aaaatggaaa    4380
atccttctcg cccaacatgt gaaaatgctt gttgtgggca cccacatttc atggtacttg    4440
taacatagga catgtctagc tggttctaga aaaatctgtg tctgtgtgga aggggggggg   4500
tttactcaca gctttcttcc ttcaatagtt cacacacccc gagacaaatt cctggatgac    4560
caacttggag agacctgggg caaaggttac tttagttctg agctcctcta aataaggacc    4620 cttttctcaac gttcctttca ccccagttct gggttaatta cttccagtta gtgcgtgttc   4680
gtggggttgt gaggccaaag caaacccggg agcgccatct gcaggcctca agaggaagag    4740
```

```
actgaccttagaggctaggccctgcgtcttcaacctctagcccaagggaaccaacctgcc    4800
tagccacccaagggaagtgggatagggctgggaggggcaggcggtgagg agtgttttcc    4860
tcccagactttaccccgcaggtggattaagcttattgggctctggaggatacaggaggga    4920
gggcaaatgccaggatcccagcggaccaggccccacaggagtgagaggctcagaacctc    4980
gtcccgctgagcctggcctgagctcctcctgaggaataagggcatcccaaaaacccgggt    5040
acaagacgcccagtagtagtagttaggctgagtcaggcaggtgcatctctccccatggta    5100
tctgccgcccaggctccggccagagggagggagcgcgagtccgcggcgcttccgcgggg    5160
cgcccggaactgcagacgggggctggaggaatctcggattcgggctgcaagagcgctgcg    5220
caagcttcgccgagccgccctttcgcagaccagggaagcggggggagggagcgaaggag    5280
ggagagagagttaaaacatcagcttgaaagtgcccaagatgattttattaagaccgaggg    5340
gaaaattatttcatgaaagattctccccggaatatttcttgtacttaaccagttagga    5400
agacaaagggcttctttctgcctggtgcgtgcgagcggaccccagcgagcaagggagct    5460
agtgccaaagagaactgcggaggctccggcaggagtggggacgtccccgtggttgcgcct    5520
cctgcgctcgccccggatccaccgagctagcagcgggcggcgctcagccgcgtccgcagc    5580
ctcctcttctccccagccggggagagccagcctcgtctcccacatcctctgccgccagcg    5640
acctgcagctccgcactgttccctcccctgtacccccttcccagtcaccccgagggttca    5700
gaaaccaagtccccggctctcccgccatccgctgggtccaccgaggcaggtgggtact    5760
cgccggaggcttcagctcgattctgaaccaagcgttctgactgccagacccggtggg    5820
caaggggactggggaggccctgcgcacagtcgcgtggaacgggaggggacaagacaaact    5880
gctggacactttccgtggaatgagaagtggggggtgcgtgggtgggaaggtacctccgg    5940
agggaaaggccaaagggaaggaccagaaagagaggaaggaagagccgggaaggaacggaa    6000
gggaactcagagccgaggtggtgggttgggctagggatgcgcactgggcccggggcc    6060
gcgcggccccaggcgggcactggccagtggatggcagggctgggcgagttagaactgagag    6120
cccggcttcacagcgcagcgcgctccgaggccctctgtcgttacctgaatattcattaga    6180
ctgaccgctctttatccttatctaacgttttatcttatcggcgagtttcgtttctcagtgt    6240
agttttaatcccgggctcccattccccctccccggtccgctccccctccctcttcc    6300
ttcgccggctgctccctccctccctccctccatttctccctccctgcctcccccttgc    6360
cggcaccggagtgacaggctcggggccctctcgccgaagctcggggctcagcgctggc    6420
gaatcacagagtggtggaatctattgccttgtgtctgacaagtcatccatctcccggcgcg    6480
gggaggggaggaggtctggaggggctttgcagcttttagagagacacacaccgggagc    6540
cgaggctccagtctccggccgagtcttctacagccgcaacccacctgggccagcccag    6600
agctgccagccgccgctcggctcctcccctccctcccggccttcggccgcggcggcgtgc    6660
gcctgccttttccgggggcggggcctggcccgcgcgctccctccccgcaggcgccacct    6720
cggacatccccggggttgctacttctctgccaacttcgccaactcgccagcacttggaga    6780
ggcccggctccctcccggcgccctctgacgcgccccgccccgcgcgctctccgaccacc    6840
gcctctcggatgaacaggttccaggggagctgagcgagtcgcctccccgcccagcttca    6900
gccctggctgcagctgcagcgcgagccatgcgcccccagtgcaccccggcccggcccacc    6960
gccccgggggcattctgctgaccgccagccccgagccccgacagtggcaagttgcggct    7020
actgcggttgcaagctccggccaacccggaggagcccagcggggagcgcagtgttgcgc    7080
ccccgccccgcgcgcgccgcagcagccgggcgttcactcatcctcccctcccccaccgt    7140
```

-continued

```
ccctcccttt tctcctcaag tcctgaagtt gagtttgaga ggcgacacgg cggcggcggc    7200
cgcgctgctc ccgctcctct gcctccccat ggatatgcac tgcaaagcag accccttctc    7260
cgcgatgcac cgtgagtacc cgcgcccggc tcctgtcccg gctcgggctc tccgtcccaa    7320
ccctgtccag t                                                         7331
```

<210> SEQ ID NO 60
<211> LENGTH: 416
<212> TYPE: PRT
<213> ORGANISM: Homo sapiens

<400> SEQUENCE: 60

| Met | Asp | Met | His | Cys | Lys | Ala | Asp | Pro | Phe | Ser | Ala | Met | His | Pro | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| His | Gly | Gly | Val | Asn | Gln | Leu | Gly | Gly | Val | Phe | Val | Asn | Gly | Arg | Pro |
|     |     |     | 20  |     |     |     |     | 25  |     |     |     |     | 30  |     |     |

| Leu | Pro | Asp | Val | Val | Arg | Gln | Arg | Ile | Val | Glu | Leu | Ala | His | Gln | Gly |
|     |     |     | 35  |     |     |     |     | 40  |     |     |     |     | 45  |     |     |

| Val | Arg | Pro | Cys | Asp | Ile | Ser | Arg | Gln | Leu | Arg | Val | Ser | His | Gly | Cys |
|     | 50  |     |     |     |     | 55  |     |     |     |     | 60  |     |     |     |     |

| Val | Ser | Lys | Ile | Leu | Gly | Arg | Tyr | Tyr | Glu | Thr | Gly | Ser | Ile | Lys | Pro |
| 65  |     |     |     |     | 70  |     |     |     |     | 75  |     |     |     |     | 80  |

| Gly | Val | Ile | Gly | Gly | Ser | Lys | Pro | Lys | Val | Ala | Thr | Pro | Lys | Val | Val |
|     |     |     |     | 85  |     |     |     |     | 90  |     |     |     |     | 95  |     |

| Asp | Lys | Ile | Ala | Glu | Tyr | Lys | Arg | Gln | Asn | Pro | Thr | Met | Phe | Ala | Trp |
|     |     |     | 100 |     |     |     |     | 105 |     |     |     |     | 110 |     |     |

| Glu | Ile | Arg | Asp | Arg | Leu | Leu | Ala | Glu | Gly | Ile | Cys | Asp | Asn | Asp | Thr |
|     |     |     | 115 |     |     |     |     | 120 |     |     |     |     | 125 |     |     |

| Val | Pro | Ser | Val | Ser | Ser | Ile | Asn | Arg | Ile | Ile | Arg | Thr | Lys | Val | Gln |
|     | 130 |     |     |     |     | 135 |     |     |     |     | 140 |     |     |     |     |

| Gln | Pro | Phe | His | Pro | Thr | Pro | Asp | Gly | Ala | Gly | Thr | Gly | Val | Thr | Ala |
| 145 |     |     |     |     | 150 |     |     |     |     | 155 |     |     |     |     | 160 |

| Pro | Gly | His | Thr | Ile | Val | Pro | Ser | Thr | Ala | Ser | Pro | Val | Ser | Ser |
|     |     |     |     | 165 |     |     |     |     | 170 |     |     |     |     | 175 |

| Ala | Ser | Asn | Asp | Pro | Val | Gly | Ser | Tyr | Ser | Ile | Asn | Gly | Ile | Leu | Gly |
|     |     |     | 180 |     |     |     |     | 185 |     |     |     |     | 190 |     |     |

| Ile | Pro | Arg | Ser | Asn | Gly | Glu | Lys | Arg | Lys | Arg | Asp | Glu | Val | Glu | Val |
|     |     |     | 195 |     |     |     |     | 200 |     |     |     |     | 205 |     |     |

| Tyr | Thr | Asp | Pro | Ala | His | Ile | Arg | Gly | Gly | Gly | Leu | His | Leu | Val |
|     |     |     | 210 |     |     |     |     | 215 |     |     |     |     | 220 |     |

| Trp | Thr | Leu | Arg | Asp | Val | Ser | Glu | Gly | Ser | Val | Pro | Asn | Gly | Asp | Ser |
| 225 |     |     |     |     | 230 |     |     |     |     | 235 |     |     |     |     | 240 |

| Gln | Ser | Gly | Val | Asp | Ser | Leu | Arg | Lys | His | Leu | Arg | Ala | Asp | Thr | Phe |
|     |     |     |     | 245 |     |     |     |     | 250 |     |     |     |     | 255 |     |

| Thr | Gln | Gln | Gln | Leu | Glu | Ala | Leu | Asp | Arg | Val | Phe | Glu | Arg | Pro | Ser |
|     |     |     | 260 |     |     |     |     | 265 |     |     |     |     | 270 |     |     |

| Tyr | Pro | Asp | Val | Phe | Gln | Ala | Ser | Glu | His | Ile | Lys | Ser | Glu | Gln | Gly |
|     |     |     | 275 |     |     |     |     | 280 |     |     |     |     | 285 |     |     |

| Asn | Glu | Tyr | Ser | Leu | Pro | Ala | Leu | Thr | Pro | Gly | Leu | Asp | Glu | Val | Lys |
|     |     |     | 290 |     |     |     |     | 295 |     |     |     |     | 300 |     |     |

| Ser | Ser | Leu | Ser | Ala | Ser | Thr | Asn | Pro | Glu | Leu | Gly | Ser | Asn | Val | Ser |
| 305 |     |     |     |     | 310 |     |     |     |     | 315 |     |     |     |     | 320 |

| Gly | Thr | Gln | Thr | Tyr | Pro | Val | Val | Thr | Gly | Arg | Asp | Met | Ala | Ser | Thr |
|     |     |     |     | 325 |     |     |     |     | 330 |     |     |     |     | 335 |     |

```
Thr Leu Pro Gly Tyr Pro Pro His Val Pro Pro Thr Gly Gln Gly Ser
                340                 345                 350

Tyr Pro Thr Ser Thr Leu Ala Gly Met Val Pro Gly Ser Glu Phe Ser
            355                 360                 365

Gly Asn Pro Tyr Ser His Pro Gln Tyr Thr Ala Tyr Asn Glu Ala Trp
        370                 375                 380

Arg Phe Ser Asn Pro Ala Leu Leu Ser Ser Pro Tyr Tyr Tyr Ser Ala
385                 390                 395                 400

Ala Pro Arg Ser Ala Pro Ala Ala Ala Ala Ala Tyr Asp Arg His
                405                 410                 415

<210> SEQ ID NO 61
<211> LENGTH: 4276
<212> TYPE: DNA
<213> ORGANISM: Homo sapiens

<400> SEQUENCE: 61
aggctccagt ctccggccga gtcttctcgc agccgcaacc cacctggggc cagcccagag      60
ctgccagcgc cgctcggctc cctccctccc tcccggccct tcggccgcgg cggcgtgcgc     120
ctgccttttc cggggcgggg gcctggcccc gcgcgctccc ctcccgcagg cgccacctcg     180
gacatccccg ggattgctac ttctctgcca acttcgccaa ctcgccagca cttggagagg     240
cccggctccc ctcccggcgc cctctgaccg ccccgcccc gcgcgctctc cgaccaccgc      300
ctctcggatg accaggttcc aggggagctg agcgagtcgc ctcccccgcc cagcttcagc     360
cctggctgca gctgcagcgc gagccatgcg ccccagtgc accccggccc ggcccaccgc      420
cccggggcca ttctgctgac cgcccagccc cgagccccga cagtggcaag ttgcggctac     480
tgcagttgca agctccggcc aacccggagg agccccagcg gggagcgcag tgttgcgccc     540 ccgcccccg cgcgcccgc agcagccggg cgttcactca tcctccctcc cccaccgtcc       600
ctcccttttc tcctcaagtc ctgaagttga gtttgagagg cgacacgcg gcggcggccg      660 cgctgctccc gctcctctgc ctcccatgg atatgcactg caaagcagac cccttctccg      720
cgatgcaccc agggcacggg ggtgtgaacc agctcggggg ggtgtttgtg aacggccggc     780
ccctacccga cgtggtgagg cagcgcatcg tggagctggc ccaccagggt gtgcggccct     840
gtgacatctc ccggcagctg cgggtcagcc acggctgtgt cagcaaaatc ctgggcaggt     900
actacgagac cggcagcatc aagccgggtg tgatcggtgg ctccaagccc aaagtggcga     960
cgcccaaagt ggtggacaag attgctgaat acaaacgaca gaacccgact atgttcgcct    1020
gggagattcg agaccggctc ctggccgagg gcatctgtga caatgacaca gtgcccagcg    1080
tctcttccat caacagaatc atccggacca aagttcagca gcctttccac ccaacgccgg    1140
atggggctgg gacaggagtg accgcccctg gccacaccat tgttcccagc acggcctccc    1200
ctcctgtttc cagcgcctcc aatgacccag tgggatccta ctccatcaat gggatcctgg    1260
ggattcctcg ctccaatggt gagaagagga acgtgatga gttgaggta tacactgatc     1320 ctgcccacat tagaggaggt ggaggtttgc atctggtctg gacttttaaga gatgtgtctg    1380 agggctcagt ccccaatgga gattcccaga gtggtgtgga cagtttgcgg aagcacttgc    1440
gagctgacac cttcacccag cagcagctgg aagctttgga tcgggtcttt gagcgtcctt    1500
cctaccctga cgtcttccag gcatcagagc acatcaaatc agaacagggg aacgagtact    1560
cccctcccag cctgacccct gggcttgatg aagtcaagtc gagtctatct gcatccacca    1620
accctgagct gggcagcaac gtgtcaggca cacagacata cccagttgtg actggtcgtg    1680
acatggcgag caccactctg cctggttacc cccctcacgt gcccccccact ggccagggaa    1740
```

```
gctaccccac ctccaccctg gcaggaatgg tgcctgggag cgagttctcc ggcaacccgt      1800
acagccaccc ccagtacacg gcctacaacg aggcttggag attcagcaac cccgccttac      1860
taagttcccc ttattattat agtgccgccc cccggtccgc ccctgccgct gctgccgctg      1920
cctatgaccg ccactagtta ccgcggggac cacatcaagc ttcaggccga cagcttcggc      1980
ctccacatcg tccccgtctg accccacccc ggagggaggg aggaccgacg cgacgcgatg      2040
cctcccggcc accgcccag cctcacccca tcccacgacc cccgcaaccc ttcacatcac       2100 cccctcgaa ggtcggacag gacgggtgga gccgtgggcg ggaccctcag gcccgggccc       2160
gccgccccca gccccgcctg ccgccctcc ccgcctgcct ggactgcgcg cgccgtgag        2220 ggggattcgg cccagctcgt cccggcctcc accaagccag cccgaagcc cgccagccac       2280 cctgccggac tcgggcgcga cctgctggcg cgcgccggat gtttctgtga cacacaatca      2340
gcgcggaccg cagcgcggcc cagccccggg cacccgcctc ggacgctcgg gcgccaggag      2400
gcttcgctgg aggggctggg ccaaggagat taagaagaaa acgactttct gcaggaggaa      2460
gagcccgctg ccgaatccct gggaaaaatt cttttccccc agtgccagcc ggactgccct      2520
cgccttccgg gtgtgccctg tcccagaaga tggaatgggg gtgtgggggt ccggctctag      2580
gaacgggctt tggggcgtc aggtctttcc aaggttggga cccaaggatc ggggggccca       2640
gcagcccgca ccgatcgagc cggactctcg gctcttcact gctcctcctg gcctgcctag      2700
ttccccaggg cccggcacct cctgctgcga gacccggctc tcagccctgc cttgccccta      2760
cctcagcgtc tcttccacct gctggcctcc cagtttcccc tcctgccagt ccttcgcctg      2820
tcccttgacg ccctgcatcc tcctccctga ctcgcagccc catcggacgc tctcccggga      2880
ccgccgcagg accagtttcc atagactgcg gactggggtc ttcctccagc agttacttga      2940 tgcccctcc cccgacacag actctcaatc tgccggtggt aagaaccggt tctgagctgg       3000
cgtctgagct gctgcggggt ggaagtgggg ggctgcccac tccactcctc ccatcccctc      3060
ccagcctcct cctccggcag gaactgaaca gaaccacaaa aagtctacat ttatttaata      3120
tgatggtctt tgcaaaaagg aacaaaacaa cacaaaagcc caccaggctg ctgctttgtg      3180
gaaagacggt gtgtgtcgtg tgaaggcgaa acccggtgta cataacccct cccccctccgc     3240 cccgccccgc ccggccccgt agagtccctg tcgcccgccg gccctgcctg tagatacgcc      3300
ccgctgtctg tgctgtgaga gtcgccgctc gctggggggg aagggggga cacagctaca      3360 cgcccattaa agcacagcac gtcctggggg aggggggcat tttttatgtt acaaaaaaaa      3420
attacgaaag aaaagaaatc tctatgcaaa atgacgaaca tggtcctgtg gactcctctg      3480
gcctgttttg ttggctcttt ctctgtaatt ccgtgttttc gcttttcct ccctgcccct       3540 ctctccctct gccctctct cctctccgct tctctccccc tctgtctctg tctctctccg       3600
tctctgtcgc tcttgtctgt ctgtctctgc tctttcctcg gcctctctcc ccagacctgg      3660
cccggccgcc ctgtctccgc aggctagatc cgaggtggca gctccagccc ccgggctcgc      3720
cccctcgcgc gcgtgcccg cgcgcccgg gcggccgaag gccgggccgc ccgtcccgc         3780 cccgtagttg ctctttcggt agtggcgatg cgccctgcat gtctcctcac ccgtggatcg      3840
tgacgactcg aaataacaga acaaagtca ataaagtgaa aataaataaa aatccttgaa       3900
caaatccgaa aaggcttgga gtcctcgccc agatctctct cccctgcgag ccctttttat      3960
ttgagaagga aaaagagaaa agagaatcgt ttaagggaac ccggcgccca gccaggctcc      4020 agtgcccga acgggcggc gagggcggcg agggcgccga ggtccggccc atcccagtcc        4080
tgtggggctg gccgggcaga gaccccggac ccaggcccag gcctaacctg ctaaatgtcc      4140
```

```
ccggacggtt ctggtctcct cggccacttt cagtgcgtcg gttcgttttg attctttttc    4200
ttttgtgcac ataagaaata aataataata ataaataaag aataaaattt tgtatgtcaa    4260
aaaaaaaaaa aaaaaa                                                     4276
```

<210> SEQ ID NO 62
<211> LENGTH: 393
<212> TYPE: PRT
<213> ORGANISM: Homo sapiens

<400> SEQUENCE: 62

```
Met Asp Met His Cys Lys Ala Asp Pro Phe Ser Ala Met His Pro Gly
1               5                   10                  15

His Gly Gly Val Asn Gln Leu Gly Gly Val Phe Val Asn Gly Arg Pro
                20                  25                  30

Leu Pro Asp Val Val Arg Gln Arg Ile Val Glu Leu Ala His Gln Gly
            35                  40                  45

Val Arg Pro Cys Asp Ile Ser Arg Gln Leu Arg Val Ser His Gly Cys
        50                  55                  60

Val Ser Lys Ile Leu Gly Arg Tyr Tyr Glu Thr Gly Ser Ile Lys Pro
65                  70                  75                  80

Gly Val Ile Gly Gly Ser Lys Pro Lys Val Ala Thr Pro Lys Val Val
                85                  90                  95

Asp Lys Ile Ala Glu Tyr Lys Arg Gln Asn Pro Thr Met Phe Ala Trp
            100                 105                 110

Glu Ile Arg Asp Arg Leu Leu Ala Glu Gly Ile Cys Asp Asn Asp Thr
        115                 120                 125

Val Pro Ser Val Ser Ser Ile Asn Arg Ile Ile Arg Thr Lys Val Gln
130                 135                 140

Gln Pro Phe His Pro Thr Pro Asp Gly Ala Gly Thr Gly Val Thr Ala
145                 150                 155                 160

Pro Gly His Thr Ile Val Pro Ser Thr Ala Ser Pro Val Ser Ser
                165                 170                 175

Ala Ser Asn Asp Pro Val Gly Ser Tyr Ser Ile Asn Gly Ile Leu Gly
            180                 185                 190

Ile Pro Arg Ser Asn Gly Glu Lys Arg Lys Arg Asp Glu Asp Val Ser
        195                 200                 205

Glu Gly Ser Val Pro Asn Gly Asp Ser Gln Ser Gly Val Asp Ser Leu
210                 215                 220

Arg Lys His Leu Arg Ala Asp Thr Phe Thr Gln Gln Gln Leu Glu Ala
225                 230                 235                 240

Leu Asp Arg Val Phe Glu Arg Pro Ser Tyr Pro Asp Val Phe Gln Ala
                245                 250                 255

Ser Glu His Ile Lys Ser Glu Gln Gly Asn Glu Tyr Ser Leu Pro Ala
            260                 265                 270

Leu Thr Pro Gly Leu Asp Glu Val Lys Ser Ser Leu Ser Ala Ser Thr
        275                 280                 285

Asn Pro Glu Leu Gly Ser Asn Val Ser Gly Thr Gln Thr Tyr Pro Val
290                 295                 300

Val Thr Gly Arg Asp Met Ala Ser Thr Thr Leu Pro Gly Tyr Pro Pro
305                 310                 315                 320

His Val Pro Pro Thr Gly Gln Gly Ser Tyr Pro Thr Ser Thr Leu Ala
                325                 330                 335

Gly Met Val Pro Gly Ser Glu Phe Ser Gly Asn Pro Tyr Ser His Pro
            340                 345                 350
```

```
Gln Tyr Thr Ala Tyr Asn Glu Ala Trp Arg Phe Ser Asn Pro Ala Leu
        355                 360                 365
Leu Ser Ser Pro Tyr Tyr Tyr Ser Ala Ala Pro Arg Ser Ala Pro Ala
    370                 375                 380
Ala Ala Ala Ala Ala Tyr Asp Arg His
385                 390

<210> SEQ ID NO 63
<211> LENGTH: 4207
<212> TYPE: DNA
<213> ORGANISM: Homo sapiens

<400> SEQUENCE: 63
aggctccagt ctccggccga gtcttctcgc agccgcaacc cacctggggc cagcccagag       60
ctgccagcgc cgctcggctc cctccctccc tcccggccct tcggccgcgg cggcgtgcgc      120
ctgccttttc cggggcggg ggcctggccc gcgcgctccc ctcccgcagg cgccacctcg       180
gacatccccg ggattgctac ttctctgcca acttcgccaa ctcgcagca cttggagagg       240 cccggctccc ctcccggcgc cctctgaccg ccccgcccc gcgcgctctc cgaccaccgc       300
ctctcggatg accaggttcc aggggagctg agcgagtcgc ctccccgcc cagcttcagc       360 cctggctgca gctgcagcgc gagccatgcg ccccagtgc accccggccc ggcccaccgc       420
cccggggcca ttctgctgac cgcccagccc cgagccccga cagtggcaag ttgcggctac       480
tgcagttgca agctccggcc aacccggagg agccccagcg gggagcgcag tgttgcgccc      540
cccgcccccg cgcgccccgc agcagccggg cgttcactca tcctccctcc cccaccgtcc      600 ctccctttc tcctcaagtc ctgaagttga gtttgagagg cgacacggcg gcggcggccg      660
cgctgctccc gctcctctgc ctcccatgg atatgcactg caaagcagac ccttctcccg      720
cgatgcaccc agggcacggg ggtgtgaacc agctcggggg ggtgtttgtg aacggccggc      780
ccctacccga cgtggtgagg cagcgcatcg tggagctggc ccaccagggt gtgcggccct      840
gtgacatctc ccggcagctg cgggtcagcc acggctgtgt cagcaaaatc ctgggcaggt      900
actacgagac cggcagcatc aagccgggtg tgatcggtgg ctccaagccc aaagtggcga      960
cgcccaaagt ggtggacaag attgctgaat acaaacgaca gaacccgact atgttcgcct     1020
gggagattcg agaccggctc ctggccgagg gcatctgtga caatgacaca gtgcccagcg     1080
tctcttccat caacagaatc atccggacca agttcagca gcctttccac ccaacgccgg     1140
atggggctgg gacaggagtg accgcccctg gccacaccat tgttcccagc acggcctccc     1200
ctcctgtttc cagcgcctcc aatgacccag tgggatccta ctccatcaat gggatcctgg     1260
ggattcctcg ctccaatggt gagaagagga acgtgatga agatgtgtct gagggctcag     1320
tccccaatgg agattcccag agtggtgtgg acagtttgcg gaagcacttg cgagctgaca     1380 ccttcacccca gcagcagctg gaagctttgg atcgggtctt tgagcgtcct tcctaccctg     1440
acgtcttcca ggcatcagag cacatcaaat cagaacaggg gaacgagtac tccctcccag     1500
ccctgacccc tgggcttgat gaagtcaagt cgagtctatc tgcatccacc aaccctgagc     1560
tgggcagcaa cgtgtcaggc acacagacat acccagttgt gactggtcgt gacatggcga     1620
gcaccactct gcctggttac ccccctcacg tgccccccac tggccaggga agctacccca     1680 cctcaccct ggcaggaatg gtgcctggga gcgagttctc cggcaacccg tacagccacc     1740
cccagtacac ggcctacaac gaggcttgga gattcagcaa ccccgcctta ctaagttccc     1800
cttattatta tagtgccgcc cccggtccg ccctgccgc tgctgccgct gcctatgacc     1860
gccactagtt accgcgggga ccacatcaag cttcaggccg acagcttcgg cctccacatc     1920
```

```
gtccccgtct gaccccaccc cggagggagg gaggaccgac gcgacgcgat gcctcccggc    1980
caccgcccca gcctcacccc atcccacgac ccccgcaacc cttcacatca ccccccctcga   2040
aggtcggaca ggacgggtgg agccgtgggc gggaccctca ggcccgggcc cgccgccccc    2100
agccccgcct gccgcccctc cccgcctgcc tggactgcgc ggcgccgtga gggggattcg    2160
gcccagctcg tcccggcctc caccaagcca gccccgaagc ccgccagcca ccctgccgga    2220
ctcgggcgcg acctgctggc gcgcgccgga tgtttctgtg acacacaatc agcgcggacc    2280
gcagcgcggc ccagccccgg gcacccgcct cggacgctcg ggcgccagga ggcttcgctg    2340
gaggggctgg gccaaggaga ttaagaagaa aacgactttc tgcaggagga agagcccgct    2400
gccgaatccc tgggaaaaat tcttttcccc cagtgccagc cggactgccc tcgccttccg    2460
ggtgtgccct gtcccagaag atggaatggg ggtgtggggg tccggctcta ggaacgggct    2520
ttgggggcgt caggtctttc caaggttggg acccaaggat cgggggcccc agcagcccgc    2580
accgatcgag ccggactctc ggctcttcac tgctcctcct ggcctgccta gttccccagg    2640
gcccggcacc tcctgctgcg agacccggct ctcagccctg ccttgcccct acctcagcgt    2700
ctcttccacc tgctggcctc ccagtttccc ctcctgccag tccttcgcct gtcccttgac    2760
gccctgcatc ctcctccctg actcgcagcc ccatcggacg ctctcccggg accgccgcag    2820
gaccagtttc catagactgc ggactggggt cttcctccag cagttacttg atgcccctc     2880
ccccgacaca gactctcaat ctgccggtgg taagaaccgg ttctgagctg gcgtctgagc    2940
tgctgcgggg tggaagtggg gggctgccca ctccactcct cccatcccct cccagcctcc    3000
tcctccggca ggaactgaac agaaccacaa aaagtctaca tttatttaat atgatggtct    3060
ttgcaaaaag gaacaaaaca acacaaaagc ccaccaggct gctgctttgt ggaaagacgg    3120
tgtgtgtcgt gtgaaggcga aacccggtgt acataacccc tcccccctccg ccccgccccg    3180
cccggccccg tagagtccct gtcgcccgcc ggccctgcct gtagatacgc cccgctgtct    3240
gtgctgtgag agtcgccgct cgctgggggg gaagggggg acacagctac acgcccatta    3300
aagcacagca cgtcctgggg gaggggggca ttttttatgt tacaaaaaaa aattacgaaa    3360
gaaaagaaat ctctatgcaa aatgacgaac atggtcctgt ggactcctct ggcctgtttt    3420
gttggctctt tctctgtaat tccgtgtttt cgcttttttcc tccctgcccc tctctccctc   3480
tgcccctctc tcctctccgc ttctctcccc ctctgtctct gtctctctcc gtctctgtcg    3540
ctcttgtctg tctgtctctg ctctttcctc ggcctctctc cccagacctg gcccggccgc    3600
cctgtctccg caggctagat ccgaggtggc agctccagcc cccgggctcg ccccctcgcg    3660
ggcgtgcccc gcgcgcccg gcggccgaa ggccgggccg cccgtcccg ccccgtagtt       3720
gctctttcgg tagtggcgat gcgccctgca tgtctcctca cccgtggatc gtgacgactc    3780
gaaataacag aaacaaagtc aataaagtga aaataaataa aaatccttga acaaatccga    3840
aaaggcttgg agtcctcgcc cagatctctc tcccctgcga gcccttttta tttgagaagg    3900
aaaaagagaa aagagaatcg tttaagggaa cccggcgccc agccaggctc cagtggcccg    3960
aacggggcgc cgaggcggc gagggcgccg aggtccggcc catcccagtc ctgtgggct      4020
ggccgggcag agaccccgga cccaggccca ggcctaacct gctaaatgtc cccggacggt    4080
tctggtctcc tcggccactt tcagtgcgtc ggttcgtttt gattcttttt cttttgtgca    4140
cataagaaat aaataataat aataaataaa gaataaaatt ttgtatgtca aaaaaaaaa    4200
aaaaaaa                                                              4207
```

```
<210> SEQ ID NO 64
<211> LENGTH: 396
<212> TYPE: PRT
<213> ORGANISM: Homo sapiens

<400> SEQUENCE: 64

Met Asp Met His Cys Lys Ala Asp Pro Phe Ser Ala Met His Pro Gly
1               5                   10                  15

His Gly Gly Val Asn Gln Leu Gly Gly Val Phe Val Asn Gly Arg Pro
            20                  25                  30

Leu Pro Asp Val Val Arg Gln Arg Ile Val Glu Leu Ala His Gln Gly
        35                  40                  45

Val Arg Pro Cys Asp Ile Ser Arg Gln Leu Arg Val Ser His Gly Cys
50                  55                  60

Val Ser Lys Ile Leu Gly Arg Tyr Tyr Glu Thr Gly Ser Ile Lys Pro
65                  70                  75                  80

Gly Val Ile Gly Gly Ser Lys Pro Lys Val Ala Thr Pro Lys Val Val
                85                  90                  95

Asp Lys Ile Ala Glu Tyr Lys Arg Gln Asn Pro Thr Met Phe Ala Trp
            100                 105                 110

Glu Ile Arg Asp Arg Leu Leu Ala Glu Gly Ile Cys Asp Asn Asp Thr
        115                 120                 125

Val Pro Ser Val Ser Ser Ile Asn Arg Ile Ile Arg Thr Lys Val Gln
130                 135                 140

Gln Pro Phe His Pro Thr Pro Asp Gly Ala Gly Thr Gly Val Thr Ala
145                 150                 155                 160

Pro Gly His Thr Ile Val Pro Ser Thr Ala Ser Pro Pro Val Ser Ser
                165                 170                 175

Ala Ser Asn Asp Pro Val Gly Ser Tyr Ser Ile Asn Gly Ile Leu Gly
            180                 185                 190

Ile Pro Arg Ser Asn Gly Glu Lys Arg Lys Arg Asp Glu Asp Val Ser
        195                 200                 205

Glu Gly Ser Val Pro Asn Gly Asp Ser Gln Ser Gly Val Asp Ser Leu
210                 215                 220

Arg Lys His Leu Arg Ala Asp Thr Phe Thr Gln Gln Gln Leu Glu Ala
225                 230                 235                 240

Leu Asp Arg Val Phe Glu Arg Pro Ser Tyr Pro Asp Val Phe Gln Ala
                245                 250                 255

Ser Glu His Ile Lys Ser Glu Gln Gly Asn Glu Tyr Ser Leu Pro Ala
            260                 265                 270

Leu Thr Pro Gly Leu Asp Glu Val Lys Ser Ser Leu Ser Ala Ser Thr
        275                 280                 285

Asn Pro Glu Leu Gly Ser Asn Val Ser Gly Thr Gln Thr Tyr Pro Val
290                 295                 300

Val Thr Gly Arg Asp Met Ala Ser Thr Thr Leu Pro Gly Tyr Pro Pro
305                 310                 315                 320

His Val Pro Pro Thr Gly Gln Gly Ser Tyr Pro Thr Ser Thr Leu Ala
                325                 330                 335

Gly Met Val Pro Glu Ala Ala Val Gly Pro Ser Ser Ser Leu Met Ser
            340                 345                 350

Lys Pro Gly Arg Lys Leu Ala Glu Val Pro Pro Cys Val Gln Pro Thr
        355                 360                 365
```

Gly Ala Ser Ser Pro Ala Thr Arg Thr Ala Thr Pro Ser Thr Arg Pro
        370                 375                 380

Thr Thr Arg Leu Gly Asp Ser Ala Thr Pro Pro Tyr
385                 390                 395

<210> SEQ ID NO 65
<211> LENGTH: 4290
<212> TYPE: DNA
<213> ORGANISM: Homo sapiens

<400> SEQUENCE: 65

| | | | | | |
|---|---|---|---|---|---|
| aggctccagt | ctccggccga | gtcttctcgc | agccgcaacc | cacctggggc | cagcccagag | 60 |
| ctgccagcgc | cgctcggctc | cctccctccc | tcccggccct | tcggccgcgg | cggcgtgcgc | 120 |
| ctgccttttc | cggggcggg | ggcctggccc | gcgcgctccc | ctcccgcagg | cgccacctcg | 180 |
| gacatccccg | ggattgctac | ttctctgcca | acttcgccaa | ctcgccagca | cttggagagg | 240 |
| cccggctccc | ctcccggcgc | cctctgaccg | ccccgcccc | gcgcgctctc | cgaccaccgc | 300 |
| ctctcggatg | accaggttcc | aggggagctg | agcgagtcgc | ctccccgcc | cagcttcagc | 360 |
| cctggctgca | gctgcagcgc | gagccatgcg | ccccagtgc | accccggccc | ggcccaccgc | 420 |
| cccggggcca | ttctgctgac | cgcccagccc | cgagccccga | cagtggcaag | ttgcggctac | 480 |
| tgcagttgca | agctccggcc | aacccggagg | agccccagcg | gggagcgcag | tgttgcgccc | 540 |
| cccgccccg | cgcgcccgc | agcagccggg | cgttcactca | tcctccctcc | cccaccgtcc | 600 |
| ctcccttttc | tcctcaagtc | ctgaagttga | gtttgagagg | cgacacgcg | gcggcggccg | 660 |
| cgctgctccc | gctcctctgc | ctccccatgg | atatgcactg | caaagcagac | cccttctccg | 720 |
| cgatgcaccc | agggcacggg | ggtgtgaacc | agctcggggg | ggtgtttgtg | aacggccggc | 780 |
| ccctacccga | cgtggtgagg | cagcgcatcg | tggagctggc | ccaccaggt | gtgcggcct | 840 |
| gtgacatctc | ccggcagctg | cgggtcagcc | acggctgtgt | cagcaaaatc | ctgggcaggt | 900 |
| actacgagac | cggcagcatc | aagccgggtg | tgatcggtgg | ctccaagccc | aaagtggcga | 960 |
| cgcccaaagt | ggtggacaag | attgctgaat | acaaacgaca | gaacccgact | atgttcgcct | 1020 |
| gggagattcg | agaccggctc | ctggccgagg | gcatctgtga | caatgacaca | gtgcccagcg | 1080 |
| tctcttccat | caacagaatc | atccggacca | agttcagca | gccttccac | ccaacgccgg | 1140 |
| atggggctgg | acaggagtg | accgcccctg | gccacaccat | tgttcccagc | acggcctccc | 1200 |
| ctcctgtttc | cagcgcctcc | aatgacccag | tgggatccta | ctccatcaat | gggatcctgg | 1260 |
| ggattcctcg | ctccaatggt | gagaagagga | acgtgatga | agatgtgtct | gagggctcag | 1320 |
| tccccaatgg | agattcccag | agtggtgtgg | acagtttgcg | gaagcacttg | cgagctgaca | 1380 |
| ccttcacccca | gcagcagctg | gaagctttgg | atcgggtctt | tgagcgtcct | tcctaccctg | 1440 |
| acgtcttcca | ggcatcagag | cacatcaaat | cagaacaggg | gaacgagtac | tccctcccag | 1500 |
| ccctgacccc | tgggcttgat | gaagtcaagt | cgagtctatc | tgcatccacc | aaccctgagc | 1560 |
| tgggcagcaa | cgtgtcaggc | acacagacat | acccagttgt | gactggtcgt | gacatggcga | 1620 |
| gcaccactct | gcctggttac | ccccctcacg | tgccccccac | tggccaggga | agctaccca | 1680 |
| cctccaccct | gcaggaatg | gtgcctgagg | ctgcagttgg | tccctcatcc | tccctcatga | 1740 |
| gcaagccggg | gaggaagctt | gcagaagtgc | cccttgtgt | gcaacccact | ggagcgagtt | 1800 |
| ctccggcaac | ccgtacagcc | accccagta | cacggcctac | aacgaggctt | ggagattcag | 1860 |
| caaccccgc | ttactaagtt | ccccttatta | ttatagtgcc | gccccggt | ccgccctgc | 1920 |
| cgctgctgcc | gctgcctatg | accgccacta | gttaccgcgg | ggaccacatc | aagcttcagg | 1980 |

```
ccgacagctt cggcctccac atcgtccccg tctgacccca ccccggaggg agggaggacc    2040
gacgcgacgc gatgcctccc ggccaccgcc ccagcctcac cccatcccac gaccccgca     2100
accettcaca tcaccccct  cgaaggtcgg acaggacggg tggagccgtg ggcgggaccc   2160
tcaggcccgg gcccgccgcc cccagcccg  cctgccgccc ctccccgcct gcctggactg    2220
cgcggcgccg tgaggggat  tcggcccagc tcgtcccggc ctccaccaag ccagccccga   2280
agcccgccag ccaccctgcc ggactcgggc gcgacctgct ggcgcgcgcc ggatgtttct    2340
gtgacacaca atcagcgcgg accgcagcgc ggcccagccc cgggcacccg cctcggacgc    2400
tcgggcgcca ggaggcttcg ctggaggggc tgggccaagg agattaagaa gaaaacgact    2460
ttctgcagga ggaagagccc gctgccgaat ccctgggaaa aattctttc  ccccagtgcc   2520
agccggactg ccctcgcctt ccgggtgtgc cctgtcccag aagatggaat gggggtgtgg    2580
gggtccggct ctaggaacgg gctttggggg cgtcaggtct ttccaaggtt gggacccaag    2640
gatcgggggg cccagcagcc cgcaccgatc gagccggact ctcggctctt cactgctcct    2700
cctggcctgc ctagttcccc agggcccggc acctcctgct gcgagacccg gctctcagcc    2760
ctgccttgcc cctacctcag cgtctcttcc acctgctggc ctcccagttt ccctcctgc     2820
cagtccttcg cctgtccctt gacgcccgc  atcctcctcc ctgactcgca gccccatcgg    2880
acgctctccc gggaccgccg caggaccagt ttccatagac tgcggactgg ggtcttcctc    2940
cagcagttac ttgatgcccc ctcccccgac acagactctc aatctgccgg tggtaagaac    3000
cggttctgag ctggcgtctg agctgctgcg gggtggaagt ggggggctgc ccactccact    3060
cctcccatcc cctcccagcc tcctcctccg gcaggaactg aacagaacca caaaaagtct    3120
acatttattt aatatgatgg tctttgcaaa aaggaacaaa acaacacaaa agcccaccag    3180
gctgctgctt tgtggaaaga cggtgtgtgt cgtgtgaagg cgaaacccgg tgtacataac    3240
ccctccccct ccgccccgcc ccgcccgcc  ccgtagagtc cctgtcgccc gccggccctg    3300
cctgtagata cgccccgctg tctgtgctgt gagagtcgcc gctcgctggg ggggaagggg    3360
gggacacagc tacacgccca ttaaagcaca gcacgtcctg ggggaggggg gcatttttta    3420
tgttacaaaa aaaaattacg aaagaaaaga aatctctatg caaaatgacg aacatggtcc    3480
tgtggactcc tctggcctgt tttgttggct cttttctctgt aattccgtgt tttcgctttt    3540
tcctccctgc ccctctctcc ctctgccct  ctctcctctc cgcttctctc ccctctgtc    3600
tctgtctctc tccgtctctg tcgctcttgt ctgtctgtct ctgctctttc ctcggcctct    3660
ctccccagac ctggcccggc cgccctgtct ccgcaggcta gatccgaggt ggcagctcca    3720
gcccccgggc tcgccccctc gcgggcgtgc ccgcgcgcc  ccgggcggcc gaaggccggg    3780
ccgccccgtc ccgccccgta gttgctctt  cggtagtggc gatgcgccct gcatgtctcc    3840
tcacccgtgg atcgtgacga ctcgaaataa cagaaacaaa gtcaataaag tgaaaataaa    3900
taaaaatcct tgaacaaatc cgaaaaggct tggagtcctc gcccagatct ctctcccctg    3960
cgagcccttt ttatttgaga aggaaaaaga gaaagagaa  tcgtttaagg gaacccggcg    4020
cccagccagg ctccagtggc ccgaacgggg cggcgagggc ggcgagggcg ccgaggtccg    4080
gcccatccca gtcctgtggg gctggccggg cagagacccc ggacccaggc ccaggcctaa    4140
cctgctaaat gtccccggac ggttctggtc tcctcggcca cttcagtgc  gtcggttcgt    4200
tttgattctt tttcttttgt gcacataaga aataaataat aataataaat aaagaataaa    4260
attttgtatg tcaaaaaaaa aaaaaaaaaa                                     4290
```

```
<210> SEQ ID NO 66
<211> LENGTH: 408
<212> TYPE: PRT
<213> ORGANISM: Homo sapiens

<400> SEQUENCE: 66

Met Asp Met His Cys Lys Ala Asp Pro Phe Ser Ala Met His Pro Gly
1               5                   10                  15

His Gly Gly Val Asn Gln Leu Gly Gly Val Phe Val Asn Gly Arg Pro
            20                  25                  30

Leu Pro Asp Val Val Arg Gln Arg Ile Val Glu Leu Ala His Gln Gly
        35                  40                  45

Val Arg Pro Cys Asp Ile Ser Arg Gln Leu Arg Val Ser His Gly Cys
    50                  55                  60

Val Ser Lys Ile Leu Gly Arg Tyr Tyr Glu Thr Gly Ser Ile Lys Pro
65                  70                  75                  80

Gly Val Ile Gly Gly Ser Lys Pro Lys Val Ala Thr Pro Lys Val Val
                85                  90                  95

Asp Lys Ile Ala Glu Tyr Lys Arg Gln Asn Pro Thr Met Phe Ala Trp
            100                 105                 110

Glu Ile Arg Asp Arg Leu Leu Ala Glu Gly Ile Cys Asp Asn Asp Thr
        115                 120                 125

Val Pro Ser Val Ser Ser Ile Asn Arg Ile Ile Arg Thr Lys Val Gln
130                 135                 140

Gln Pro Phe His Pro Thr Pro Asp Gly Ala Gly Thr Gly Val Thr Ala
145                 150                 155                 160

Pro Gly His Thr Ile Val Pro Ser Thr Ala Ser Pro Val Ser Ser
                165                 170                 175

Ala Ser Asn Asp Pro Val Gly Ser Tyr Ser Ile Asn Gly Ile Leu Gly
            180                 185                 190

Ile Pro Arg Ser Asn Gly Glu Lys Arg Lys Arg Asp Glu Asp Val Ser
        195                 200                 205

Glu Gly Ser Val Pro Asn Gly Asp Ser Gln Ser Gly Val Asp Ser Leu
210                 215                 220

Arg Lys His Leu Arg Ala Asp Thr Phe Thr Gln Gln Gln Leu Glu Ala
225                 230                 235                 240

Leu Asp Arg Val Phe Glu Arg Pro Ser Tyr Pro Asp Val Phe Gln Ala
                245                 250                 255

Ser Glu His Ile Lys Ser Glu Gln Gly Asn Glu Tyr Ser Leu Pro Ala
            260                 265                 270

Leu Thr Pro Gly Leu Asp Glu Val Lys Ser Ser Leu Ser Ala Ser Thr
        275                 280                 285

Asn Pro Glu Leu Gly Ser Asn Val Ser Gly Thr Gln Thr Tyr Pro Val
290                 295                 300

Val Thr Gly Arg Asp Met Ala Ser Thr Thr Leu Pro Gly Tyr Pro Pro
305                 310                 315                 320

His Val Pro Pro Thr Gly Gln Gly Ser Tyr Pro Thr Ser Thr Leu Ala
                325                 330                 335

Gly Met Val Pro Gly Ser Glu Phe Ser Gly Asn Pro Tyr Ser His Pro
            340                 345                 350

Gln Tyr Thr Ala Tyr Asn Glu Ala Trp Arg Phe Ser Asn Pro Ala Leu
        355                 360                 365

Leu Met Pro Pro Pro Gly Pro Pro Leu Pro Leu Leu Pro Leu Pro Met
370                 375                 380
```

```
Thr Ala Thr Ser Tyr Arg Gly Asp His Ile Lys Leu Gln Ala Asp Ser
385                 390                 395                 400

Phe Gly Leu His Ile Val Pro Val
            405
```

<210> SEQ ID NO 67
<211> LENGTH: 4188
<212> TYPE: DNA
<213> ORGANISM: Homo sapiens

<400> SEQUENCE: 67

```
aggctccagt ctccggccga gtcttctcgc agccgcaacc cacctggggc cagcccagag     60
ctgccagcgc cgctcggctc cctccctccc tccggccct  tcggccgcgg cggcgtgcgc    120
ctgccttttc cggggcggg  ggcctggccc gcgcgctccc ctcccgcagg cgccacctcg    180
gacatccccg ggattgctac ttctctgcca acttcgccaa ctcgccagca cttggagagg    240
cccggctccc ctcccggcgc cctctgaccg ccccgcccc  gcgcgctctc cgaccaccgc    300
ctctcggatg accaggttcc aggggagctg agcgagtcgc ctccccgcc  cagcttcagc    360
cctggctgca gctgcagcgc gagccatgcg ccccagtgc  accccggccc ggcccaccgc    420
cccggggcca ttctgctgac cgcccagccc cgagccccga cagtggcaag ttgcggctac    480
tgcagttgca agctccggcc aacccggagg agccccagcg gggagcgcag tgttgcgccc    540
ccgcccccg  cgcgccccgc agcagccggg cgttcactca tcctccctcc cccaccgtcc    600
ctcccttttc tcctcaagtc ctgaagttga gtttgagagg cgacacgcg  gcggcggccg    660
cgctgctccc gctcctctgc ctccccatgg atatgcactg caaagcagac cccttctccg    720
cgatgcaccc agggcacggg ggtgtgaacc agctcggggg ggtgtttgtg aacggccggc    780
ccctacccga cgtggtgagg cagcgcatcg tggagctggc caccagggt  gtgcggccct    840
gtgacatctc ccggcagctg cgggtcagcc acggctgtgt cagcaaaatc ctgggcaggt    900
actacgagac cggcagcatc aagccgggtg tgatcggtgg ctccaagccc aaagtggcga    960
cgcccaaagt ggtggacaag attgctgaat acaaacgaca gaacccgact atgttcgcct   1020
gggagattcg agaccggctc ctggccgagg gcatctgtga caatgacaca gtgcccagcg   1080
tctcttccat caacagaatc atccggacca agttcagca  gcctttccac ccaacgccgg   1140
atggggctgg acaggagtg  accgcccctg gccacaccat tgttcccagc acggcctccc   1200
ctcctgtttc cagcgcctcc aatgacccag tgggatccta ctccatcaat gggatcctgg   1260
ggattcctcg ctccaatggt gagaagagga acgtgatga  agatgtgtct gagggctcag   1320
tccccaatgg agattcccag agtggtgtgg acagtttgcg gaagcacttg cgagctgaca   1380
ccttcacccc agcagcagctg gaagctttgg atcgggtctt tgagcgtcct tcctaccctg   1440
acgtcttcca ggcatcagag cacatcaaat cagaacaggg gaacgagtac tccctcccag   1500
ccctgacccc tgggcttgat gaagtcaagt cgagtctatc tgcatccacc aaccctgagc   1560
tgggcagcaa cgtgtcaggc acacagacat acccagttgt gactggtcgt gacatggcga   1620
gcaccactct gcctggttac ccccctcacg tgcccccac  tggccagggg agctaccccca   1680
cctccaccct ggcaggaatg gtgcctggga gcgagttctc cggcaacccg tacagccacc   1740
cccagtacac ggcctacaac gaggcttgga gattcagcaa ccccgcctta ctaatgccgc   1800
ccccggtcc  gccctgccg  ctgctgccgc tgcctatgac cgccactagt taccgcgggg   1860
accacatcaa gcttcaggcc gacagcttcg gcctccacat cgtcccgtc  tgaccccacc   1920
ccggagggag ggaggaccga cgcgacgcga tgcctcccgg ccaccgcccc agcctcaccc   1980
```

| | |
|---|---|
| catcccacga cccccgcaac ccttcacatc acccccctcg aaggtcggac aggacgggtg | 2040 |
| gagccgtggg cgggacccte aggcccgggc ccgccgcccc cagccccgcc tgccgcccct | 2100 |
| ccccgcctgc ctggactgcg cggcgccgtg agggggattc ggcccagctc gtcccggcct | 2160 |
| ccaccaagcc agccccgaag cccgccagcc accctgccgg actcgggcgc gacctgctgg | 2220 |
| cgcgcgccgg atgtttctgt gacacacaat cagcgcggac cgcagcgcgg cccagccccg | 2280 |
| ggcacccgcc tcgacgctc gggcgccagg aggcttcgct ggaggggctg ggccaaggag | 2340 |
| attaagaaga aaacgacttt ctgcaggagg aagagcccgc tgccgaatcc ctgggaaaaa | 2400 |
| ttcttttccc ccagtgccag ccggactgcc ctcgccttcc gggtgtgccc tgtcccagaa | 2460 |
| gatggaatgg gggtgtgggg gtccggctct aggaacgggc tttggggggcg tcaggtcttt | 2520 |
| ccaaggttgg gacccaagga tcgggggggcc cagcagcccg caccgatcga gccggactct | 2580 |
| cggctcttca ctgctcctcc tggcctgcct agttccccag ggcccggcac ctcctgctgc | 2640 |
| gagacccggc tctcagccct gccttgcccc tacctcagcg tctcttccac ctgctggcct | 2700 |
| cccagtttcc cctcctgcca gtccttcgcc tgtcccttga cgccctgcat cctcctcct | 2760 |
| gactcgcagc cccatcggac gctctcccgg gaccgccgca ggaccagttt ccatagactg | 2820 |
| cggactgggg tcttcctcca gcagttactt gatgccccct ccccgacac agactctcaa | 2880 |
| tctgccggtg gtaagaaccg gttctgagct ggcgtctgag ctgctgcggg gtggaagtgg | 2940 |
| ggggctgccc actccactcc tcccatcccc tcccagcctc ctcctccggc aggaactgaa | 3000 |
| cagaaccaca aaaagtctac atttatttaa tatgatggtc tttgcaaaaa ggaacaaaac | 3060 |
| aacacaaaag cccaccaggc tgctgctttg tggaaagacg gtgtgtgtcg tgtgaaggcg | 3120 |
| aaacccggtg tacataaccc ctcccccctcc gccccgcccc gccggcccc gtagagtccc | 3180 |
| tgtcgcccgc cggccctgcc tgtagatacg ccccgctgtc tgtgctgtga gagtcgccgc | 3240 |
| tcgctggggg ggaagggggg gacacagcta cacgcccatt aaagcacagc acgtcctggg | 3300 |
| ggagggggc attttttatg ttacaaaaaa aaattacgaa agaaaagaaa tctctatgca | 3360 |
| aaatgacgaa catggtcctg tggactcctc tggcctgttt tgttggctct ttctctgtaa | 3420 |
| ttccgtgttt tcgcttttc ctccctgccc ctctctccct ctgcccctct ctcctctccg | 3480 |
| cttctctccc cctctgtctc tgtctctctc cgtctctgtc gctcttgtct gtctgtctct | 3540 |
| gctctttcct cggcctctct cccagacct ggccggccg ccctgtctcc gcaggctaga | 3600 |
| tccgaggtgg cagctccagc cccgggctc gccccctcgc gggcgtgccc cgcgcgcccc | 3660 |
| gggcggccga aggccgggcc gccccgtccc gccccgtagt tgctcttcg gtagtggcga | 3720 |
| tgccgccctgc atgtctcctc acccgtggat cgtgacgact cgaaataaca gaaacaaagt | 3780 |
| caataaagtg aaaataaata aaaatccttg aacaaatccg aaaaggcttg gagtcctcgc | 3840 |
| ccagatctct ctcccctgcg agccctttt atttgagaag gaaaaagaga aaagagaatc | 3900 |
| gtttaaggga acccggcgcc cagccaggct ccagtggccc gaacggggcg gcgagggcgg | 3960 |
| cgagggcgcc gaggtccggc ccatcccagt cctgtggggc tggccgggca gagacccgg | 4020 |
| acccaggccc aggcctaacc tgctaaatgt ccccggacgg ttctggtctc ctcggccact | 4080 |
| ttcagtgcgt cggttcgttt tgattctttt tcttttgtgc acataagaaa taataataa | 4140 |
| taataaataa agaataaaat tttgtatgtc aaaaaaaaaa aaaaaaa | 4188 |

<210> SEQ ID NO 68
<211> LENGTH: 431
<212> TYPE: PRT
<213> ORGANISM: Homo sapiens

<400> SEQUENCE: 68

```
Met Asp Met His Cys Lys Ala Asp Pro Phe Ser Ala Met His Pro Gly
1               5                   10                  15

His Gly Gly Val Asn Gln Leu Gly Gly Val Phe Val Asn Gly Arg Pro
            20                  25                  30

Leu Pro Asp Val Val Arg Gln Arg Ile Val Glu Leu Ala His Gln Gly
        35                  40                  45

Val Arg Pro Cys Asp Ile Ser Arg Gln Leu Arg Val Ser His Gly Cys
    50                  55                  60

Val Ser Lys Ile Leu Gly Arg Tyr Tyr Glu Thr Gly Ser Ile Lys Pro
65                  70                  75                  80

Gly Val Ile Gly Gly Ser Lys Pro Lys Val Ala Thr Pro Lys Val Val
                85                  90                  95

Asp Lys Ile Ala Glu Tyr Lys Arg Gln Asn Pro Thr Met Phe Ala Trp
            100                 105                 110

Glu Ile Arg Asp Arg Leu Leu Ala Glu Gly Ile Cys Asp Asn Asp Thr
        115                 120                 125

Val Pro Ser Val Ser Ser Ile Asn Arg Ile Ile Arg Thr Lys Val Gln
    130                 135                 140

Gln Pro Phe His Pro Thr Pro Asp Gly Ala Gly Thr Gly Val Thr Ala
145                 150                 155                 160

Pro Gly His Thr Ile Val Pro Ser Thr Ala Ser Pro Pro Val Ser Ser
                165                 170                 175

Ala Ser Asn Asp Pro Val Gly Ser Tyr Ser Ile Asn Gly Ile Leu Gly
            180                 185                 190

Ile Pro Arg Ser Asn Gly Glu Lys Arg Lys Arg Asp Glu Val Glu Val
        195                 200                 205

Tyr Thr Asp Pro Ala His Ile Arg Gly Gly Gly Leu His Leu Val
    210                 215                 220

Trp Thr Leu Arg Asp Val Ser Glu Gly Ser Val Pro Asn Gly Asp Ser
225                 230                 235                 240

Gln Ser Gly Val Asp Ser Leu Arg Lys His Leu Arg Ala Asp Thr Phe
                245                 250                 255

Thr Gln Gln Gln Leu Glu Ala Leu Asp Arg Val Phe Glu Arg Pro Ser
            260                 265                 270

Tyr Pro Asp Val Phe Gln Ala Ser Glu His Ile Lys Ser Glu Gln Gly
        275                 280                 285

Asn Glu Tyr Ser Leu Pro Ala Leu Thr Pro Gly Leu Asp Glu Val Lys
    290                 295                 300

Ser Ser Leu Ser Ala Ser Thr Asn Pro Glu Leu Gly Ser Asn Val Ser
305                 310                 315                 320

Gly Thr Gln Thr Tyr Pro Val Val Thr Gly Arg Asp Met Ala Ser Thr
                325                 330                 335

Thr Leu Pro Gly Tyr Pro Pro His Val Pro Pro Thr Gly Gln Gly Ser
            340                 345                 350

Tyr Pro Thr Ser Thr Leu Ala Gly Met Val Pro Gly Ser Glu Phe Ser
        355                 360                 365

Gly Asn Pro Tyr Ser His Pro Gln Tyr Thr Ala Tyr Asn Glu Ala Trp
    370                 375                 380

Arg Phe Ser Asn Pro Ala Leu Leu Met Pro Pro Pro Gly Pro Pro Leu
385                 390                 395                 400
```

```
Pro Leu Leu Pro Leu Pro Met Thr Ala Thr Ser Tyr Arg Gly Asp His
            405                 410                 415

Ile Lys Leu Gln Ala Asp Ser Phe Gly Leu His Ile Val Pro Val
        420                 425                 430

<210> SEQ ID NO 69
<211> LENGTH: 4257
<212> TYPE: DNA
<213> ORGANISM: Homo sapiens

<400> SEQUENCE: 69
aggctccagt ctccggccga gtcttctcgc agccgcaacc cacctggggc cagcccagag     60
ctgccagcgc cgctcggctc cctccctccc tcccggccct tcggccgcgg cggcgtgcgc    120
ctgccttttc cggggcggg ggcctggccc gcgcgctccc ctcccgcagg cgccacctcg     180
gacatccccg ggattgctac ttctctgcca acttcgccaa ctcgccagca cttggagagg    240
cccggctccc ctcccggcgc cctctgaccg ccccgcccc gcgcgctctc cgaccaccgc     300
ctctcggatg accaggttcc aggggagctg agcgagtcgc ctccccgcc cagcttcagc     360 cctggctgca gctgcagcgc gagccatgcg ccccagtgc accccggccc ggcccaccgc     420
cccggggcca ttctgctgac cgcccagccc cgagccccga cagtggcaag ttgcggctac    480
tgcagttgca agctccggcc aacccggagg agcccagcg gggagcgcag tgttgcgccc     540 cccgccccg cgcgccccgc agcagccggg cgttcactca tcctccctcc cccaccgtcc     600 ctccctttc tcctcaagtc ctgaagttga gtttgagagg cgacacggcg gcggcggccg    660
cgctgctccc gctcctctgc ctccccatgg atatgcactg caaagcagac cccttctccg     720
cgatgcaccc agggcacggg ggtgtgaacc agctcggggg ggtgtttgtg aacggccggc    780
ccctacccga cgtggtgagg cagcgcatcg tggagctggc caccagggt gtgcggccct     840 gtgacatctc ccggcagctg cgggtcagcc acggctgtgt cagcaaaatc ctgggcaggt    900
actacgagac cggcagcatc aagccgggtg tgatcggtgg ctccaagccc aaagtggcga    960
cgcccaaagt ggtggacaag attgctgaat acaaacgaca gaacccgact atgttcgcct   1020
gggagattcg agaccggctc ctggccgagg gcatctgtga caatgacaca gtgcccagcg   1080
tctcttccat caacagaatc atccggacca agttcagca gcctttccac ccaacgccgg    1140
atggggctgg gacaggagtg accgcccctg gccacaccat tgttcccagc acggcctccc   1200 ctcctgttc cagcgcctcc aatgacccag tgggatccta ctccatcaat gggatcctgg    1260
ggattcctcg ctccaatggt gagaagagga aacgtgatga agttgaggta tacactgatc    1320
ctgcccacat tagaggaggt ggaggtttgc atctggtctg gactttaaga gatgtgtctg    1380
agggctcagt ccccaatgga gattcccaga gtggtgtgga cagtttgcgg aagcacttgc    1440
gagctgacac cttcacccag cagcagctgg aagctttgga tcgggtcttt gagcgtcctt   1500
cctaccctga cgtcttccag gcatcagagc acatcaaatc agaacagggg aacgagtact   1560 cctccagc cctgacccct gggcttgatg aagtcaagtc gagtctatct gcatccacca     1620
accctgagct gggcagcaac gtgtcaggca cacagacata cccagttgtg actggtcgtg    1680
acatggcgag caccactctg cctggttacc ccctcacgt gcccccact ggccagggaa     1740 gctaccccac ctcacccctg gcaggaatgg tgcctgggag cgagttctcc ggcaacccgt    1800
acagccaccc ccagtacacg gcctacaacg aggcttggga attcagcaac cccgccttac   1860
taatgccgcc ccccggtccg ccctgccgc tgctgccgct gcctatgacc gccactagtt    1920
```

```
accgcgggga ccacatcaag cttcaggccg acagcttcgg cctccacatc gtccccgtct    1980
gaccccaccc cggagggagg gaggaccgac gcgacgcgat gcctcccggc caccgcccca    2040
gcctcacccc atcccacgac ccccgcaacc cttcacatca ccccccctcga aggtcggaca   2100 ggacgggtgg agccgtgggc gggaccctca ggcccgggcc cgccgccccc agcccagcct    2160
gccgcccctc cccgcctgcc tggactgcgc ggcgccgtga gggggattcg gcccagctcg    2220
tcccggcctc caccaagcca gccccgaagc ccgccagcca ccctgccgga ctcgggcgcg    2280
acctgctggc gcgcgccgga tgtttctgtg acacacaatc agcgcggacc gcagcgcggc    2340 ccagcccgg gcaccgcct cggacgctcg ggcgccagga ggcttcgctg gaggggctgg      2400
gccaaggaga ttaagaagaa aacgactttc tgcaggagga agagcccgct gccgaatccc    2460
tgggaaaaat tcttttcccc cagtgccagc cggactgccc tcgccttccg ggtgtgccct    2520
gtcccagaag atggaatggg ggtgtggggg tccggctcta ggaacgggct ttgggggcgt    2580
caggtctttc caaggttggg acccaaggat cggggggccc agcagcccgc accgatcgag    2640
ccggactctc ggctcttcac tgctcctcct ggcctgccta gttccccagg gcccggcacc    2700
tcctgctgcg agacccggct ctcagccctg ccttgcccct acctcagcgt ctcttccacc    2760
tgctggcctc ccagtttccc ctcctgccag tccttcgcct gtcccttgac gccctgcatc    2820
ctcctccctg actcgcagcc ccatcggacg ctctcccggg accgccgcag gaccagtttc    2880
catagactgc ggactggggt cttcctccag cagttacttg atgccccctc ccccgacaca    2940
gactctcaat ctgccggtgg taagaaccgg ttctgagctg gcgtctgagc tgctgcgggg    3000
tggaagtggg gggctgccca ctccactcct cccatcccct cccagcctcc tcctccggca    3060
ggaactgaac agaaccacaa aaagtctaca tttatttaat atgatggtct ttgcaaaaag    3120
gaacaaaaca acacaaaagc ccaccaggct gctgctttgt ggaaagacgg tgtgtgtcgt    3180
gtgaaggcga aacccggtgt acataacccc tccccctccg ccccgccccg ccggccccg    3240 tagagtccct gtcgcccgcc ggccctgcct gtagatacgc cccgctgtct gtgctgtgag   3300
agtcgccgct cgctggggg gaagggggg acacagctac acgcccatta aagcacagca     3360
cgtcctgggg gaggggggca ttttttatgt tacaaaaaaa aattacgaaa gaaagaaat    3420 ctctatgcaa aatgacgaac atggtcctgt ggactcctct ggcctgtttt gttggctctt    3480
tctctgtaat tccgtgtttt cgcttttttcc tccctgcccc tctctccctc tgcccctctc   3540
tcctctccgc ttctctcccc ctctgtctct gtctctctcc gtctctgtcg ctcttgtctg    3600
tctgtctctg ctcttttcctc ggcctctctc cccagacctg gccggccgc cctgtctccg    3660 caggctagat ccgaggtggc agctccagcc cccgggctcg cccctcgcg ggcgtgcccc     3720 gcgcgccccg ggcggccgaa ggccgggccg cccccgtcccg ccccgtagtt gctctttcgg   3780
tagtggcgat gcgccctgca tgtctcctca cccgtggatc gtgacgactc gaaataacag    3840
aaacaaagtc aataaagtga aaataaataa aaatccttga acaaatccga aaaggcttgg    3900
agtcctcgcc cagatctctc tcccctgcga gccctttttta tttgagaagg aaaaagagaa    3960
aagagaatcg tttaagggaa cccggcgccc agccaggctc cagtgcccg aacgggcgg      4020 cgagggcggc gagggcgccg aggtccggcc catcccagtc ctgtggggct ggccgggcag    4080
agaccccgga cccaggccca ggcctaacct gctaaatgtc cccggacggt tctggtctcc    4140
tcggccactt tcagtgcgtc ggttcgtttt gattcttttt cttttgtgca cataagaaat    4200
aaataataat aataaataaa gaataaaatt ttgtatgtca aaaaaaaaaa aaaaaa        4257
```

```
<210> SEQ ID NO 70
<211> LENGTH: 104
<212> TYPE: DNA
<213> ORGANISM: Artificial Sequence
<220> FEATURE:
<223> OTHER INFORMATION: Synthetic Construct

<400> SEQUENCE: 70
ttcacccttg actgtggcac ctcccttcag ttccgtcgac gaggttgtgc aatccaccag      60
tcttataaat acagtgacgc tccagcctct ggaagcctct gtca                     104

<210> SEQ ID NO 71
<211> LENGTH: 17
<212> TYPE: DNA
<213> ORGANISM: Artificial Sequence
<220> FEATURE:
<223> OTHER INFORMATION: Synthetic Construct

<400> SEQUENCE: 71
tcaagcgtga ctaattg                                                     17

<210> SEQ ID NO 72
<211> LENGTH: 12
<212> TYPE: DNA
<213> ORGANISM: Artificial Sequence
<220> FEATURE:
<223> OTHER INFORMATION: Consensus Sequence

<400> SEQUENCE: 72
cggcacggtt ga                                                          12

<210> SEQ ID NO 73
<211> LENGTH: 13
<212> TYPE: DNA
<213> ORGANISM: Artificial Sequence
<220> FEATURE:
<221> NAME/KEY: misc_feature
<222> LOCATION: (1)..(13)
<223> OTHER INFORMATION: n is a, g, c or t in consensus binding site
      sequence

<400> SEQUENCE: 73
nntnnygcgt gar                                                         13

<210> SEQ ID NO 74
<211> LENGTH: 13
<212> TYPE: DNA
<213> ORGANISM: Artificial Sequence
<220> FEATURE:
<221> NAME/KEY: misc_feature
<222> LOCATION: (1)..(13)
<223> OTHER INFORMATION: n is a, g, c or t in consensus binding site
      sequence

<400> SEQUENCE: 74
tngtcaygcr tga                                                         13

<210> SEQ ID NO 75
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: n is a, g, c or t in consensus binding site
      sequence
```

-continued

```
<400> SEQUENCE: 75
rncantgnng cgkracsr                                                18

<210> SEQ ID NO 76
<211> LENGTH: 18
<212> TYPE: DNA
<213> ORGANISM: Artificial Sequence
<220> FEATURE:
<223> OTHER INFORMATION: Consensus Sequence

<400> SEQUENCE: 76
atatctagag cggaacgg                                                18

<210> SEQ ID NO 77
<211> LENGTH: 11
<212> TYPE: DNA
<213> ORGANISM: Artificial Sequence
<220> FEATURE:
<223> OTHER INFORMATION: Consensus Sequence

<400> SEQUENCE: 77
ttcacgcwts a                                                       11

<210> SEQ ID NO 78
<211> LENGTH: 13
<212> TYPE: DNA
<213> ORGANISM: Artificial Sequence
<220> FEATURE:
<221> NAME/KEY: misc_feature
<222> LOCATION: (1)..(13)
<223> OTHER INFORMATION: n is a, g, c or t in consensus binding site
      sequence

<400> SEQUENCE: 78
tcgtcacrcn yna                                                     13

<210> SEQ ID NO 79
<211> LENGTH: 12
<212> TYPE: DNA
<213> ORGANISM: Artificial Sequence
<220> FEATURE:
<223> OTHER INFORMATION: Consensus Sequence

<400> SEQUENCE: 79
cgtcacgstt sr                                                      12
```

COMPOSITIONS AND METHODS FOR DIAGNOSING, TREATING, AND PREVENTING PROSTATE CONDITIONS

The present application is a continuation application of U.S. patent application Ser. No. 12/440,193, filed on Mar. 13, 2009 as a national stage application of PCT/US2008/051168, which claims priority to U.S. Provisional Application No. 60/885,142, filed Jan. 16, 2007. The entirety of all of the aforementioned applications is incorporated herein by reference.

BACKGROUND

Current anticancer chemotherapies that are based on alkylating agents, anti-metabolites and natural products are heterogeneous in their mechanism of action. Consequently, most of them also act against normal cells resulting in severe side effects and toxicity to the patient.

The accumulation of mutations and the loss of cellular control functions cause progressive phenotypic changes from normal histology to early pre-cancer such as intraepithelial neoplasia (IEN) to increasingly severe IEN to superficial cancer and finally to invasive disease. Although this process can be relatively aggressive in some cases, it generally occurs relatively slowly over years and even decades. Oncogene addiction is the physiologic dependence of cancer cells on the continued activation or overexpression of single oncogenes for maintaining the malignant phenotype. This dependence occurs in the milieu of the other changes that mark neoplastic progression.

Cancer chemoprevention is defined as the prevention of cancer or treatment at the pre-cancer state or even earlier. The long period of progression to invasive cancer is a major scientific opportunity but also an economic obstacle to showing the clinical benefit of candidate chemopreventive drugs. Therefore, an important component of chemopreventive agent development research in recent years has been to identify earlier (pre-cancer) end points or biomarkers that accurately predict an agent's clinical benefit or cancer incidence-reducing effect. In many cancers, IEN is an early end point such as in prostate.

SUMMARY

In accordance with the purpose of this invention, as embodied and broadly described herein, this invention relates to compositions and methods for diagnosing, preventing, and treating prostate cancer and prostate intraepithelial neoplasia (PIN).

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The file of this patent contains at least one drawing executed in color. Copies of this patent with color drawings will be provided by the Patent and Trademark Office upon request and payment of the necessary fee.

The accompanying drawings, which are incorporated in and constitute a part of this specification, illustrate several embodiments of the disclosed method and compositions and together with the description, serve to explain the principles of the disclosed method and compositions.

FIG. 1 shows quantitative RT-PCR (QRT-PCR) analysis of beta-defensin-1 (DEFB1) expression. In order to verify induction of DEFB1 expression, QRT-PCR was performed.

FIG. 5 shows pan-caspase analysis following DEFB1 induction. DU145 and PC3 cells were stained with FAM-VAD-FMK-labeled fluoromethyl ketone to detect caspase activity. Cells were visible under DIC for each condition. Confocal microscopic analysis revealed no caspase staining in control DU145 (B), PC3 cells (F) and LNCaP (J). Cells treated with PonA for 24 hours to induce DEFB1 revealed caspase activity in DU145 (D) and PC3 (H). No caspase activity was detected in LNCaP (L).

FIG. 6A shows Western blot analysis of PC3 and DU145 cells transfected with PAX2 siRNA duplex at day zero (lane 1), day two (lane 2), and day four (lane 3). FIG. 6B shows Western blot analysis of PC3 and DU145 cells transfected with PAX2 siRNA duplex at day zero (lane 1), day two (lane 2), day four (lane 3) and day 6 (lane 4). PAX2 protein was undetectable as early as after four days of treatment (lane 3) in DU145 cells and after six days of treatment in PC3. Blots were stripped and re-probed for β-actin as an internal control.

FIG. 10 shows analysis of apoptotic factors following PAX2 siRNA treatment. Changes in expression of pro-apoptotic factors were compared in untreated control cells and in cells treated for six days with PAX2 siRNA.

FIG. 15 shows ChIP analysis of PAX2 binding to DEFB1 promoter. ChIP analysis was performed on DU145 and PC3 cells. Following immunoprecipitation with an anti-PAX2 antibody, PCR was performed to detect the DEFB1 promoter region containing the GTTCC (SEQ ID NO: 2) PAX2 recognition site. This demonstrates that the PAX2 transcriptional repressor is bound to the DEFB1 promoter in prostate cancer cell lines.

FIG. 23 shows effect of Los and MAP Kinase inhibitors on PAX2 expression in DU145 cells.

FIG. 24 shows effect of Los and MEK kinase inhibitors on PAX2 activation in DU145 cells.

FIG. 27A shows PAX2 expression is regulated by the AT1R signaling pathway. Inhibition of PAX2 expression results in the re-expression of DEFB1 and cancer cell death. FIG. 27B shows compounds which block the AT1R, downstream kinases or directly suppresses PAX2 offer a novel approach to treating prostate cancer.

FIG. 31 shows analysis of hBD-1 expression in human prostate tissue. hBD-1 relative expression levels were compared in normal clinical samples from patients that underwent radical prostatectomies. The dashed line serves as a point of reference to compare values obtained between gross and LCM-derived specimen, and corresponding Gleason scores are indicated above each bar.

FIG. 32 shows analysis of hBD-1 expression in prostate cell lines. FIG. 32B shows ectopic hBD-1 expression verified in the prostate cancer cell line DU145 by immunocytochemistry. hPrEC cells were stained for hBD-1 as a positive control (a: DIC and b: fluorescence). DU145 cells were transfected with hBD-1 and induced for 18 h (c: DIC and d: fluorescence). Sizebar=20 µM.

FIG. 35A shows comparison of hBD-1 expression levels in normal, PIN and tumor sections. FIG. 35B shows comparison of cMYC expression level in normal, PIN and tumor sections.

FIG. 37A shows PAX2 expression examined by Western blot analysis in HPrEC prostate primary cells (lane 1) and in DU145 (lane 2), PC3 (lane 3) and LNCaP (lane 4) prostate cancer cells. Blots were stripped and re-probed for-actin as an internal control to ensure equal loading. FIG. 37B shows Western blot analysis of DU145, PC3 and LNCaP all confirmed knockdown of PAX2 expression following transfection with PAX2 siRNA duplex. Again, blots were stripped and re-probed for β-actin as an internal control.

FIG. 41A shows BAD expression increased in DU145, PC3 and LNCaP following PAX2 knockdown. FIG. 41B shows BID expression levels increased in LNCaP and DU145, but not in PC3 cells. FIG. 41C shows AKT expression decreased in LNCaP and DU145. However, there was no change in AKT expression in PC3 cells following PAX2 knockdown. Results represent mean±SD, n=9. Asterisks represents statistical differences ($p<0.05$).

DETAILED DESCRIPTION

Figure 1A:
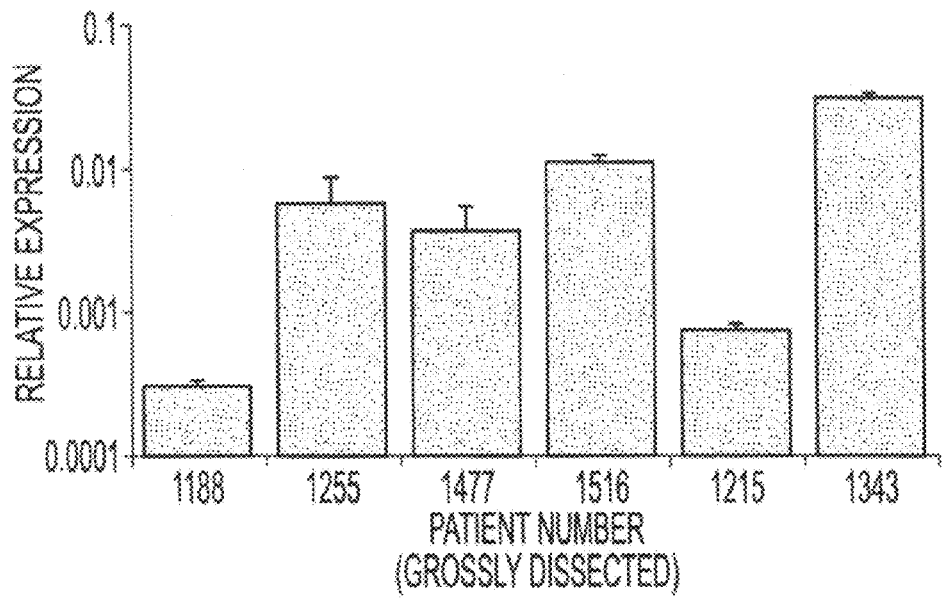
FIG. 1A shows DEFB1 relative expression levels compared in clinical samples from 6 patients that underwent radical prostatectomies.

The disclosed method and compositions may be understood more readily by reference to the following detailed description of particular embodiments and the Example included therein and to the Figures and their previous and following description.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a peptide is disclosed and discussed and a number of modifications that can be made to a number of molecules including the peptide are discussed, each and every combination and permutation of peptide and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Those skilled in the art will recognize, or be able to ascertain using no more than routine experimentation, many equivalents to the specific embodiments of the method and compositions described herein. Such equivalents are intended to be encompassed by the following claims.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

A. Diagnosing, Treating and Preventing Prostate Cancer

Disclosed herein are compositions and methods of diagnosing, preventing, and treating prostate cancer and prostate intraepithelial neoplasia (PIN).

1. Prostate Cancer

Carcinoma of the prostate has become a significant disease in many countries and it is the most commonly diagnosed malignancy in men in the western world, its occurrence increasing significantly with age. This increase and the recent deaths of many public figures from prostate cancer have served to highlight the need to do something about this cancer. It has been suggested that the wider availability of screening may limit mortality from prostate cancer.

Prostate cancer screening currently consists of a rectal examination and measurement of prostate specific antigen (PSA) levels. These methods lack specificity as digital rectal examination has considerable inter-examiner variability and PSA levels may be elevated in benign prostatic hyperplasia (BPH), prostatic inflammation and other conditions. The comparative failure of PSA as a diagnostic test was shown in 366 men who developed prostate cancer while being included in the Physicians Health Study, a prospective study of over 22,000 men. PSA levels were measured in serum, which was stored at the start of the study, and elevated levels were found in only 47% of men developing prostate cancer within the subsequent four years (Gann et al, 1995).

Prostate cancers can be scored using the Gleason system, as well known to those skilled in the art (Gleason, et al. 1966). This uses tissue architecture rather than cytological features. A grade of 1 to 5 (well to poorly differentiated) is used, and the combined score of the most frequent and more severe areas of the lesion are combined. Gleason scores provide prognostic information that may be valuable in addition to the assessment of the stage of the tumor (staging). Gleason scores of 2 to 4 and 8 to 10 have good predictive value, but about three quarters of tumors have intermediate values.

Two principal systems are used for staging prostate cancer: TNM and the Jewett system (Benson & Olsson, et al. 1989). Staging takes in to account any metastatic spread of the tumor and is difficult, because it is difficult to assess either local lymph node involvement or local invasion. Tumor size is also difficult to measure as tumor tissue cannot be distinguished macroscopically from normal prostate tissue, and because the prostate gland lacks a distinct capsule and is surrounded by a layer of fibrous fatty tissue.

Four categories describe the prostate tumor's (T) stage, ranging from T1 to T4. For T1, the cancer is microscopic, unilateral and non palpable. The doctor can't feel the tumor or see it with imaging such as transrectal ultrasound. Treatment for BPH may have disclosed the disease, or it was confirmed through the use of a needle biopsy done because of an elevated PSA. For T2, the doctor can feel the cancer with a DRE. It appears the disease is confined to the prostate gland on one or both sides of the gland. For T3, the cancer has advanced to tissue immediately outside the gland. For T4, the cancer has spread to other parts of the body.

Present screening methods are therefore unsatisfactory; there is no reliable method for diagnosing the cancer, or predicting or preventing its possible metastatic spread, which is the main cause of death for most patients.

2. PAX2

PAX genes are a family of nine developmental control genes coding for nuclear transcription factors. They play an important role in embryogenesis and are expressed in a very ordered temporal and spatial pattern. They all contain a "paired box" region of 384 base pairs encoding a DNA binding domain which is highly conserved throughout evolution (Stuart, E T, et al. 1994). The influence of Pax genes on developmental processes has been demonstrated by the numerous natural mouse and human syndromes that can be attributed directly to even a heterozygous insufficiency in a Pax gene. A PAX2 sequence is given in Dressler, et al. 1990. Examples of cancers in which PAX2 expression has been detected are listed in Table 1.

TABLE 1

PAX2-expressing cancers

| PAX2 Expressing Cancers | Estimated New Cases in US | Estimated Deaths in US | Estimated New Cases Global | Estimated Deaths Global |
|---|---|---|---|---|
| Prostate | 234,460 | 27,350 | 679,023 | 221,002 |
| Breast | 214,600 | 41,430 | 1,151,298 | 410,712 |
| Ovarian | 20,180 | 15,310 | 204,500 | 124,860 |
| Renal | 38,890 | 12,840 | 208,479 | 101,895 |
| Brain | 12,820 | 18,820 | 189,485 | 141,650 |
| Cervical | 9,710 | 3,700 | 493,243 | 273,505 |
| Bladder | 61,420 | 13,060 | 356,556 | 145,009 |
| Leukemia | 35,020 | 22,280 | 300,522 | 222,506 |
| Kaposi Sarcoma | Data Not Available | Data Not Available | Data Not Available | Data Not Available |
| TOTAL(approx.) | 627,100 | 154,790 | 3,583,106 | 1,641,139 |

3. DEFB1

Beta-defensins are cationic peptides with broad-spectrum antimicrobial activity that are products of epithelia and leukocytes (Ganz and Weiss, 1997). These two exon, single gene products are expressed at epithelial surfaces and secreted at sites including the skin (Harder et al., 1997), cornea (McNamara et al., 1999), tongue (Mathews et al., 1999, Jia et al., 2000), gingiva (Mathews et al., 1999; Krisanaprakornkit et al., 1998), salivary glands (Mathews et al., 1999), esophagus (Jia et al., 2000), intestine (O'Neil et al., 1999), kidney (Valore et al., 1998; Zucht et al., 1998), urogenital tract (Valore et al., 1998), and the respiratory epithelium (Bals et al., 1998; Goldman et al., 1997; McCray and Bentley. 1997). To date, five beta-defensin genes of epithelial origin have been identified and characterized in humans: DEFB1 (Bensch et al., 1995), DEFB 2 (Harder et al., 1997), DEFB3 (Harder et al., 2001; Jia et al., 2001), DEFB4, and HE2/EP2.

The primary structure of each beta-defensin gene product is characterized by small size, a six cysteine motif, high cationic charge and exquisite diversity beyond these features. The most characteristic feature of defensin proteins is their six-cysteine motif that forms a network of three disulfide bonds. The three disulfide bonds in the beta-defensin proteins are between C1-C5, C2-C4 and C3-C6. The most common spacing between adjacent cysteine residues is 6, 4, 9, 6, 0. The spacing between the cysteines in the beta-defensin proteins can vary by one or two amino acids except for C5 and C6, located nearest the carboxy terminus. In all known vertebrate beta-defensin genes, these two cysteine residues are adjacent to each other.

A second feature of the beta-defensin proteins is their small size. Each beta-defensin gene encodes a preproprotein that ranges in size from 59 to 80 amino acids with an average size of 65 amino acids. This gene product is then cleaved by an unknown mechanism to create the mature peptide that ranges in size from 36 to 47 amino acids with an average size of 45 amino acids. The exceptions to these ranges are the EP2/HE2 gene products that contain the beta-defensin motif and are expressed in the epididymis.

A third feature of beta-defensin proteins is the high concentration of cationic residues. The number of positively charged residues (arginine, lysine, histidine) in the mature peptide ranges from 6 to 14 with an average of 9.

The final feature of the beta-defensin gene products is their diverse primary structure but apparent conservation of tertiary structure. Beyond the six cysteines, no single amino acid at a given position is conserved in all known members of this protein family. However, there are positions that are conserved that appear to be important for secondary and tertiary structures and function.

Despite the great diversity of the primary amino acid sequence of the beta-defensin proteins, the limited data suggests that the tertiary structure of this protein family is conserved. The structural core is a triple-stranded, antiparallel beta-sheet, as exemplified for the proteins encoded by BNBD-12 and DEFB2. The three beta-strands are connected by a beta-turn, and an alpha-hairpin loop, and the second beta-strand also contains a beta-bulge. When these structures are folded into their proper tertiary structure, the apparently random sequence of cationic and hydrophobic residues are concentrated into two faces of a globular protein. One face is hydrophilic and contains many of the positively charged side chains and the other is hydrophobic. In solution, the BBD-2 protein encoded by the DEFB2 gene exhibited an alpha-helical segment near the N-terminus not previously ascribed to solution structures of alpha-defensins or to the beta-defensin BNBD-12. The amino acids whose side chains are directed toward the surface of the protein are less conserved between beta.defensin proteins while the amino acid residues in the three beta-strands of the core beta-sheet are more highly conserved.

Beta-defensin peptides are produced as pre-pro-peptides and then cleaved to release a C-terminal active peptide fragment, however the pathways for the intracellular processing, storage and release of the human beta-defensin peptides in airway epithelia are unknown.

4. Diagnosing

A key advantage of the present teaching is that the herein disclosed methods afford a more rapid and simplified process to identify from a tissue or bodily fluid a subject having or at risk for prostate cancer.

Thus, the herein disclosed methods can comprise the detection, including measurement, of PAX2 and/or DEFB1 in a tissue of the subject, such as a biopsy sample of the prostate. Prostate biopsy is a procedure in which small samples are removed from a man's prostate gland to be tested for the presence of cancer. It is typically performed when the scores from a PSA blood test rise to a level that is associated with the possible presence of prostate cancer.

The herein disclosed methods can comprise the detection, including measurement, of PAX2 and/or DEFB1 in a cell of the subject, such as a cell from the prostate of the subject.

In addition, the herein disclosed methods can comprise the detection, including measurement, of PAX2 and/or DEFB1 in bodily fluid of the subject, such as blood, urine, plasma, serum, tears, lymph, bile, cerebrospinal fluid, interstitial fluid, aqueous or vitreous humor, colostrum, sputum, amniotic fluid, saliva, anal and vaginal secretions, perspiration, semen, transudate, exudate, and synovial fluid. Blood plasma is the liquid component of blood, in which the blood cells are suspended. Plasma is the largest single component of blood, making up about 55% of total blood volume. Serum refers to blood plasma in which clotting factors (such as fibrin) have been removed. Blood plasma contains many vital proteins including fibrinogen, globulins and human serum albumin. Sometimes blood plasma can contain viral impurities which must be extracted through viral processing.

Identification of blood protein markers that provide more accurate or earlier diagnosis of cancer can have a positive impact on cancer treatment and management. As disclosed herein, aberrant PAX2 expression occurs early in the progression of cancer and can be an initiating event in tumorigenesis. Therefore, samples from patients collected to screen for the presence of PAX2 protein or antigens can be used for the early detection of cancer.

Furthermore, the incorporation of PAX2 screening can provide clinicians with a prognosticator for initiated or pre-cancerous tissue. Candidates for this test include patients at high risk (based on age, race) for cancer. As a diagnostic, a positive PAX2 test can then be followed by additional screening with biomarker to determine cancer site. In addition, these patients can be candidates for PAX2 inhibitors for chemoprevention for their cancers. Alternatively, this test can be used on patients as a measure of the effectiveness of their cancer therapy or to monitor cancer recurrence.

As another example, patients who present with potential indicators of cancer such as the detection of nodules in the prostate during a digital rectal exam by the clinician, or those who experience a sudden rise in PSA often are in the "Watchful Waiting" state. It is often difficult to ascertain whether these patients have or will develop cancer. The detection of PAX2 in samples, such as plasma/serum, from these patients can be used to assist the decision to obtain a biopsy in men with suspected prostate cancer, which can lead to a reduction in the number of unnecessary prostatic biopsies and earlier intervention for their disease.

Also provided herein is a method of diagnosing prostate cancer in a subject, comprising detecting in cells from the prostate of the subject levels of PAX2 and beta defensin-1 (DEFB1), wherein the ratio of PAX2 to DEFB1 is at least about 100:1.

Also provided herein is a method of diagnosing prostate intraepithelial neoplasia (PIN) in a subject, comprising detecting in cells from the prostate of the subject levels of PAX2 and beta defensin-1 (DEFB1), wherein the ratio of PAX2 to DEFB1 is at least about 40:1 and less than about 100:1.

Also provided herein is a method of identifying a subject as having a normal prostate, comprising detecting in cells from the prostate of the subject levels of PAX2 and beta defensin-1 (DEFB1), wherein the ratio of PAX2 to DEFB1 is less than about 40:1.

Also provided herein is a method of distinguishing among normal, pre-cancerous and cancerous prostate conditions in a subject, comprising detecting in cells from the prostate of the subject levels of PAX2 and beta defensin-1 (DEFB1). In some aspects, wherein the ratio of PAX2 to DEFB1 is less than about 40:1, a normal prostate condition is detected. In some aspects, wherein the ratio of PAX2 to DEFB1 is at least about 40:1 and less than about 100:1, a precancerous condition is detected. In some aspects, wherein the ratio of PAX2 to DEFB1 is at least about 100:1, a cancerous prostate is detected.

5. Diagnosing and Treating

Also provided herein is a method of diagnosing and treating prostate cancer in a subject, comprising detecting in cells from the prostate of the subject levels of PAX2 and beta defensin-1 (DEFB1), wherein the ratio of PAX2 to DEFB1 is at least about 100:1, further comprising treating said subject.

Also provided herein is a method of diagnosing and treating prostate intraepithelial neoplasia (PIN) in a subject, comprising detecting in cells from the prostate of the subject levels of PAX2 and beta defensin-1 (DEFB1), wherein the ratio of PAX2 to DEFB1 is at least about 40:1 and less than about 100:1, further comprising treating said subject.

As used in the disclosed methods, treatment for prostate cancer can involve watchful waiting, surgery, radiation therapy, High Intensity Focused Ultrasound (HIFU), chemotherapy, cryosurgery, hormonal therapy, or some combination. Which option is best depends on the stage of the disease, the Gleason score, and the PSA level. Other important factors are the man's age, his general health, and his feelings about potential treatments and their possible side effects.

If the cancer has spread beyond the prostate, treatment options significantly change, so most doctors who treat prostate cancer use a variety of nomograms to predict the probability of spread. Treatment by watchful waiting, HIFU, radiation therapy, cryosurgery, and surgery are generally offered to men whose cancer remains within the prostate. Hormonal therapy and chemotherapy are often reserved for disease which has spread beyond the prostate. However, there are exceptions: radiation therapy may be used for some advanced tumors, and hormonal therapy is used for some early stage tumors. Cryotherapy, hormonal therapy, and chemotherapy may also be offered if initial treatment fails and the cancer progresses.

Watchful waiting, also called "active surveillance," refers to observation and regular monitoring without invasive treatment. Watchful waiting is often used when an early stage, slow-growing prostate cancer is found in an older man. Watchful waiting may also be suggested when the risks of surgery, radiation therapy, or hormonal therapy outweigh the possible benefits. Other treatments can be started if symptoms develop, or if there are signs that the cancer growth is accelerating (e.g., rapidly rising PSA, increase in Gleason score on repeat biopsy, etc.). Most men who choose watchful waiting for early stage tumors eventually have signs of tumor progression, and they may need to begin treatment within three years.

Surgical removal of the prostate, or prostatectomy, is a common treatment either for early stage prostate cancer, or for cancer which has failed to respond to radiation therapy. The most common type is radical retropubic prostatectomy, when the surgeon removes the prostate through an abdominal incision. Another type is radical perineal prostatectomy, when the surgeon removes the prostate through an incision in the perineum, the skin between the scrotum and anus. Radical prostatectomy can also be performed laparoscopically, through a series of small (1 cm) incisions in the abdomen, with or without the assistance of a surgical robot.

Radical prostatectomy is highly effective for tumors which have not spread beyond the prostate; cure rates depend on risk factors such as PSA level and Gleason grade. However, it may cause nerve damage that significantly alters the quality of life of the prostate cancer survivor. Medications such as sildenafil (Viagra), tadalafil (Clalis), or vardenafil (Levitra) may be used to restore some degree of potency. For most men with organ-confined disease, a more limited "nerve-sparing" technique may help avoid urinary incontinence and impotence.

Radical prostatectomy has traditionally been used alone when the cancer is small. In the event of positive margins or locally advanced disease found on pathology, adjuvant radiation therapy may offer improved survival. Surgery may also be offered when a cancer is not responding to radiation therapy. However, because radiation therapy causes tissue changes, prostatectomy after radiation has a higher risk of complications.

Transurethral resection of the prostate, commonly called a "TURP," is a surgical procedure performed when the tube from the bladder to the penis (urethra) is blocked by prostate enlargement. TURP is generally for benign disease and is not meant as definitive treatment for prostate cancer. During a TURP, a small tube (cystoscope) is placed into the penis and the blocking prostate is cut away.

In metastatic disease, where cancer has spread beyond the prostate, removal of the testicles (called orchiectomy) may be done to decrease testosterone levels and control cancer growth.

Brachytherapy for prostate cancer is administered using "seeds," small radioactive rods implanted directly into the tumor. Radiation therapy, also known as radiotherapy, uses Gamma-rays to kill prostate cancer cells. Two different kinds of radiation therapy are used in prostate cancer treatment: external beam radiation therapy and brachytherapy.

External beam radiation therapy uses a linear accelerator to produce high-energy Gamma-rays which are directed in a beam towards the prostate. A technique called Intensity Modulated Radiation Therapy (IMRT) may be used to adjust the radiation beam to conform with the shape of the tumor, allowing higher doses to be given to the prostate and seminal vesicles with less damage to the bladder and rectum. External beam radiation therapy is generally given over several weeks, with daily visits to a radiation therapy center.

External beam radiation therapy for prostate cancer is delivered by a linear accelerator, such as this one. Brachytherapy involves the placement of about 100 small "seeds" containing radioactive material (such as iodine-125 or palladium-103) with a needle through the skin of the perineum directly into the tumor. These seeds emit lower-energy X-rays which are only able to travel a short distance. Brachytherapy seeds will stay in the prostate permanently, but men with implanted seeds are not at risk of exposing others to radiation.

Radiation therapy is commonly used in prostate cancer treatment. It may be used instead of surgery for early cancers, and it may also be used in advanced stages of prostate cancer to treat painful bone metastases. Radiation treatments also can be combined with hormonal therapy for intermediate risk disease, when radiation therapy alone is less likely to cure the cancer. External beam radiation can be combined with brachytherapy for intermediate to high risk situations. Also considered is a "triple modality" combination of external beam radiation therapy, brachytherapy, and hormonal therapy.

Radiation therapy is often offered to men whose medical problems make surgery more risky. Radiation therapy appears to cure small tumors that are confined to the prostate just about as well as surgery. However, as of 2006 some issues remain unresolved, such as whether radiation should be given to the rest of the pelvis, how much the absorbed dose should be, and whether hormonal therapy should be given at the same time.

Cryosurgery is another method of treating prostate cancer. It is less invasive than radical prostatectomy, and general anesthesia is less commonly used. Under ultrasound guidance, metal rods are inserted through the skin of the perineum into the prostate. Liquid nitrogen is used to cool the rods, freezing the surrounding tissue at −196° C. (−320° F.). As the water within the prostate cells freeze, the cells die. The urethra is protected from freezing by a catheter filled with warm liquid. Cryosurgery generally causes fewer problems with urinary control than other treatments, but impotence occurs up to ninety percent of the time.

Hormonal therapy uses medications or surgery to block prostate cancer cells from getting dihydrotestosterone (DHT), a hormone produced in the prostate and required for the growth and spread of most prostate cancer cells. Blocking DHT often causes prostate cancer to stop growing and even shrink. However, hormonal therapy rarely cures prostate cancer because cancers which initially respond to hormonal therapy typically become resistant after one to two years. Hormonal therapy is therefore usually used when cancer has spread from the prostate. It can also be given to men undergoing radiation therapy or surgery to help prevent return of their cancer.

Hormonal therapy for prostate cancer targets the pathways the body uses to produce DHT. A feedback loop involving the testicles, the hypothalamus, and the pituitary, adrenal, and prostate glands controls the blood levels of DHT. First, low blood levels of DHT stimulate the hypothalamus to produce gonadotropin releasing hormone (GnRH). GnRH then stimulates the pituitary gland to produce luteinizing hormone (LH), and LH stimulates the testicles to produce testosterone. Finally, testosterone from the testicles and dehydroepiandrosterone from the adrenal glands stimulate the prostate to produce more DHT. Hormonal therapy can decrease levels of DHT by interrupting this pathway at any point.

Orchiectomy is surgery to remove the testicles. Because the testicles make most of the body's testosterone, after orchiectomy testosterone levels drop. Now the prostate not only lacks the testosterone stimulus to produce DHT, but also it does not have enough testosterone to transform into DHT.

Antiandrogens are medications such as flutamide, bicalutamide, nilutamide, and cyproterone acetate which directly block the actions of testosterone and DHT within prostate cancer cells.

Medications which block the production of adrenal androgens such as DHEA include ketoconazole and aminoglutethimide. Because the adrenal glands only make about 5% of the body's androgens, these medications are generally used only in combination with other methods that can block the 95% of androgens made by the testicles. These combined methods are called total androgen blockade (TAB). TAB can also be achieved using antiandrogens.

GnRH action can be interrupted in one of two ways. GnRH antagonists suppress the production of GnRH directly, while GnRH agonists suppress GnRH through the process of down-regulation after an initial stimulation effect. Abarelix is an example of a GnRH antagonist, while the GnRH agonists include leuprolide, goserelin, triptorelin, and buserelin. Initially, these medications increase the production of LH. However, because the constant supply of the medication does not match the body's natural production rhythm, production of both LH and GnRH decreases after a few weeks.

6. Treating/Preventing

Also provided herein is a method of preventing prostate cancer in a subject, comprising administering to a subject diagnosed with prostate intraepithelial neoplasia (PIN) a composition comprising an inhibitor of PAX2 expression or activity. "Activities" of a protein include, for example, transcription, translation, intracellular translocation, secretion, phosphorylation by kinases, cleavage by proteases, homophilic and heterophilic binding to other proteins, ubiquitination. In some aspects, "PAX2 activity" refers specifically to the binding of PAX2 to the DEFB-1 promoter. Also provided herein is a method of preventing prostate cancer in a subject, comprising diagnosing a subject with prostate intraepithelial neoplasia (PIN) and administering to the subject a composition comprising an inhibitor of PAX2 expression or activity. The subject can be diagnosed with PIN by detecting in cells from the prostate of the subject levels of PAX2 and beta defensin-1 (DEFB1), wherein the ratio of PAX2 to DEFB1 is at least about 40:1 and less than about 100:1.

In some aspects, PAX2 is upregulated at the atrophy stage prior to PIN. Thus, also provided is a method of preventing prostate cancer in a subject, comprising detecting in cells from the prostate of the subject levels of PAX2 and beta defensin-1 (DEFB1), wherein the ratio of PAX2 to DEFB1 is at least about 40:1 and less than about 100:1, and administering to the subject a composition comprising an inhibitor of PAX2 expression or activity.

Also provided herein is a method of treating prostate intraepithelial neoplasia (PIN) in a subject, comprising diagnosing a subject with PIN and administering to the subject a composition comprising an inhibitor of PAX2 expression or activity. The subject can be diagnosed with PIN by detecting in cells from the prostate of the subject levels of PAX2 and beta defensin-1 (DEFB1), wherein the ratio of PAX2 to DEFB1 is at least about 40:1 and less than about 100:1.

Also provided is a method of treating or preventing prostate intraepithelial neoplasia (PIN) in a subject, comprising detecting in cells from the prostate of the subject levels of PAX2 and beta defensin-1 (DEFB1), wherein the ratio of PAX2 to DEFB1 is at least about 40:1 and less than about 100:1, and administering to the subject a composition comprising an inhibitor of PAX2 expression or activity.

Also provided herein is a method of treating prostate cancer in a subject, comprising diagnosing a subject with prostate cancer and administering to the subject a composition comprising an inhibitor of PAX2 expression or activity. The subject can be diagnosed with prostate cancer by detecting in cells from the prostate of the subject levels of PAX2 and beta defensin-1 (DEFB1), wherein the ratio of PAX2 to DEFB1 is at least about 100:1.

The inhibitor of the disclosed methods can be a selective antagonist of angiotensin II. The inhibitor of the disclosed methods can be a selective antagonist of angiotensin-converting enzyme (ACE). For example, the inhibitor can be enalapril. The inhibitor can be can be a selective antagonist of angiotensin II type 1 receptor (AT1R). For example, the inhibitor can be valsartan, olmesartan, or telmisartan. The inhibitor can be a selective antagonist of MEK. The inhibitor can be a selective antagonist of ERK1,2. The inhibitor can be a selective antagonist of STAT3. The inhibitor can be a selective antagonist of PAX2. The inhibitor can block the binding of PAX2 to the beta defensin-1 (DEFB1) promoter. In some aspects, the disclosed inhibitor of PAX2 expression or activity is not an AT1R receptor antagonist.

By "selective antagonist" is meant something that directly binds and inhibits the activity of the target. "Activities" of a protein include, for example, transcription, translation, intracellular translocation, secretion, phosphorylation by kinases, cleavage by proteases, homophilic and heterophilic binding to other proteins, ubiquitination. Thus, for example, a selective antagonist of a kinase can bind the kinase and inhibit the phosphorylation of the target of the kinase. Thus, for example, a selective antagonist of a kinase can bind the kinase and prevent the binding of the kinase to its substrate.

Also provided herein is a method of treating or preventing prostate cancer in a subject, comprising administering to said subject a composition comprising a selective antagonist of MEK and/or ERK1,2. This can also be a method of inhibiting expression of PAX2. The subject in this method can first be diagnosed with a pre-cancerous condition (e.g., PIN) or with cancer.

The selective antagonist of MEK and/or ERK1,2 can be U0126. U0126 is a chemically synthesized organic compound that was initially recognized as a cellular AP-1 antagonist, and found to be a very selective and highly potent inhibitor of Mitogen-Activated Protein Kinase (MAPK) cascade by inhibiting its immediate upstream activators, Mitogen Activated Protein Kinase Kinase 1 and 2 (also known as MEK1 and MEK2, IC50: 70 and 60 nM respectively). U0126 inhibits both active and inactive MEK1,2, unlike PD098059 which only inhibits activation of inactive MEK. Blockade of MEK activation would prevent downstream phosphorylation of a number of factors including p62TCF (Elk-1), an upstream inducer of c-Fos and c-Jun, components of the AP-1 complex. Inhibition of MEK/ERK pathway by U0126 also prevents all effects of oncogenic H-Ras and K-Ras, inhibits part of the effects triggered by growth factors and blocks the production of inflammatory cytokines and matrix metalloproteinases.

The selective antagonist of MEK and/or ERK1,2 can be PD98059. PD98059 (MEK1 Inhibitor) has been shown to act in vivo as a highly selective inhibitor of MEK1 activation and the MAP kinase cascade. PD98059 binds to the inactive forms of MEK1 and prevents activation by upstream activators such as c-Raf. PD98059 inhibits activation of MEK1 and MEK2 with IC50 values of 4 µM and 50 µM, respectively.

Also provided herein is a method of treating or preventing prostate cancer in a subject, comprising administering to said subject a composition comprising a selective antagonist of STAT3. This is also a method of inhibiting expression of PAX2. The subject in this method can first be diagnosed with a pre-cancerous condition (e.g., PIN) or with cancer.

As shown herein, PAX2 inhibits expression of DEFB1, and DEFB1 is shown to have tumor cell killing activity. Thus, provided is a method of treating cancer in a subject by inhibiting expression of PAX2. An example of a cancer treated by the present method is prostate cancer. The present methods are particularly effective for treatment of late stage prostate cancer.

In the cancer treatment methods disclosed, the method of inhibiting expression of PAX 2 can be by administration of a nucleic acid encoding a siRNA for PAX 2. Dharmachon is a commercial source for such siRNAs.

For example, the siRNA for use in the methods can be comprise:
AUAGACUCGACUUGACUUCUU (SEQ ID NO: 3),
AUCUUCAUCACGUUUCCUCUU (SEQ ID NO: 4),
GUAUUCAGCAAUCUUGUCCUU (SEQ ID NO: 5),
GAUUUGAUGUGCUCUGAUGUU (SEQ ID NO: 6), or
  combinations thereof, including fragments of at least 10
  nucleic acids and conservative variants thereof.

Further examples of target sequences for molecules that inhibit PAX2 include:
1 ACCCGACTATGTTCGCCTGG (SEQ ID NO: 7),
2 AAGCTCTGGATCGAGTCTTTG (SEQ ID NO: 8),
and #4 ATGTGTCAGGCACACAGACG (SEQ ID NO: 9).
  #4 was shown to inhibit PAX2 (Davies et al., Hum. Mol.
  Gen January 15, 13 (2); 235).
  Another paper (Muratovska et al., Paired-Box genes are
  frequently expressed in cancer and often required for cancer
  cell survival Oncogene (2003) 22, 7989-7997) discloses the
  following siRNAs: GUCGAGUCUAUCUGCAUCCUU
  (SEQ ID NO: 10) and GGAUGCAGAUAGACUCGACUU
  (SEQ ID NO: 11).

To down-regulate Pax2 expression, Fonsato et al. transfected tumor-derived endothelial cells with an anti-sense PAX2 vector. See Fonsato V. et al. Am J Pathol. 2006; 168 (2):706-1, which is incorporated herein by reference for its description of this molecule. Similarly, Hueber et al. teach that PAX2 antisense cDNA and PAX2-small interfering RNA (100 nM) reduce endogenous PAX2 protein. See Hueber et al. Kidney Int. 2006, which is incorporated herein for its teaching of PAX2 antisense and PAX2 siRNA.

Additional inhibitors of PAX2 expression or the binding of PAX2 to the DEFB1 promoter are provided to increase DEFB1 expression in the presently disclosed methods. For example, small molecules and antibodies can be designed based on the present studies to interfere with or inhibit the binding of PAX2 to the DEFB1 promoter.

As shown herein, PAX2 inhibits expression of DEFB1, and DEFB1 is shown to have tumor cell killing activity. Thus, a method of treating cancer in a subject by administering DEFB1 is also provided. An example of a cancer treated by the present method is prostate cancer.

Similarly, provided is a method of treating cancer in a subject by increasing expression of DEFB1 in the subject. The present methods of administering or increasing the expression of DEFB1 are particularly effective for treatment of late stage prostate cancer.

In one embodiment of the methods of the invention for treating cancer by administering DEFB1 or increasing DEFB1 expression (e.g., by inhibiting expression or binding of PAX2), the subject is a subject diagnosed with prostate cancer. In a further embodiment of the methods of the invention for treating cancer by administering DEFB1 or increasing DEFB1 expression (e.g., by inhibiting expression or binding of PAX2), the subject is a subject diagnosed with advanced (late stage) prostate cancer.

In the method wherein the expression of DEFB1 is increased, it can be increased by blocking the binding of PAX2 to the DEFB1 promoter. The blocking of binding of PAX2 to the DEFB1 promoter can be by administration of an oligonucleotide containing the PAX2 DNA binding site of DEFB1. This oligonucleotide can be complementary to the sequence of PAX2 that binds to the DEFB1 promoter. Alternatively, the oligonucleotide can interact with the PAX2 in a way that inhibits binding to DEFB1. This interaction can be based on three-dimensional structure rather than primary nucleotide sequence.

PAX proteins are a family of transcription factors conserved during evolution and able to bind specific DNA sequences through a domains called a "paired domain" and a "homeodomain". The paired domain (PD) is a consensus sequence shared by certain PAX proteins (e.g., PAX2 and PAX6). The PD directs DNA binding of amino acids located in the α3-helix forming a DNA-Protein complex. For PAX2, the amino acids in the HD recognize and interact specifically with a CCTTG (SEQ ID NO:1) DNA core sequence. Oligonucleotides up to and exceeding 64 bases in length, which include this sequence or its complement are expected to be inhibitors.

The DNA-binding specificity of the PAX-8 paired domain was investigated. Site selection experiments indicate that PAX-8 binds to a consensus sequence similar to those bound by PAX-2 and PAX-5. When consensus sequences of various paired domains are observed in light of recent structural studies describing paired-domain-DNA interaction (Xu, et al. 1995), it appears that base-pairs contacted in the minor groove are conserved, while most of the base-pairs contacted in the major groove are not. Therefore a network of specific minor groove contacts is a common characteristic of paired-domain-DNA interactions. The functional importance of such a network can be successfully tested by analyzing the effect of consensus-based mutations on the PAX2 binding site of the DEFB1 promoter.

The PAX2 DNA binding site of DEFB1 can comprise SEQ ID NO: 1 (CCTTG).

The oligonucleotide comprising to the PAX2 DNA binding site of DEFB1 is selected from the group consisting of V-CCTTG-W (SEQ ID NO: 12), wherein V is from 1 to 35 contiguous flanking nucleotides of DEFB1 and W is from 1 to 35 nucleotides. The nucleotides can be contiguous nucleotides that normally flank the PAX2 DNA binding site of DEFB1. Alternatively, they can be unrelated to DEFB1, and selected routinely to avoid interference with the recognition sequence.

For example, the inhibitory oligonucleotides can be selected from the group consisting of:

```
                                          (SEQ ID NO: 13)
CTCCCTTCAGTTCCGTCGAC (SEQ ID NO: 14)
CTCCCTTCACCTTGGTCGAC (SEQ ID NO: 15)
ACTGTGGCACCTCCCTTCAGTTCCGTCGACGAGGTTGTGC (SEQ ID NO: 16)
ACTGTGGCACCTCCCTTCACCTTGGTCGACGAGGTTGTGC
```

The disclosed compositions can be used to treat any disease where uncontrolled cellular proliferation occurs such as cancers. A non-limiting list of different types of cancers is as follows: lymphomas (Hodgkins and non-Hodgkins), leukemias, carcinomas, carcinomas of solid tissues, squamous cell carcinomas, adenocarcinomas, sarcomas, gliomas, high grade gliomas, blastomas, neuroblastomas, plasmacytomas, histiocytomas, melanomas, adenomas, hypoxic tumors, myelomas, AIDS-related lymphomas or sarcomas, metastatic cancers, or cancers in general.

A representative but non-limiting list of cancers that the disclosed compositions can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, or pancreatic cancer. Compounds disclosed herein may also be used for the treatment of pre-cancer conditions such as cervical and anal dysplasias, other dysplasias, severe dysplasias, hyperplasias, atypical hyperplasias, and neoplasias. Further, a number of diseases stemming from chronic inflammation, e.g., prostatitis and Benign Prostatic Hypertrophy (BPH), as well as various cancers of the prostate, can be impacted by the present methods and compounds.

DEFB1's gene locus (8p23.3) is a hotspot for deletions and has been linked to patients with poorer prognosis. Thus, DEFB1 (and perhaps PAX2) can be used as a biomarker, e.g., in a screening for the early detection of prostate cancer. Furthermore, data presented here indicate that its loss may occur as early as PIN (or even before), and may be a major contributing factor to the onset of prostate cancer.

B. Compositions

1. Immunoassays

There are numerous methods for detecting analytes, such as proteins, such as PAX2 and/or DEFB1, known or newly discovered in the art, which can be used in the disclosed methods. For example, PAX2 and/or DEFB1 can be detected using standard immunodetection methods. The steps of various useful immunodetection methods have been described in the scientific literature, such as, e.g., Maggio et al., Enzyme-Immunoassay, (1987) and Nakamura, et al., Enzyme Immunoassays: Heterogeneous and Homogeneous Systems, Handbook of Experimental Immunology, Vol. 1: Immunochemistry, 27.1-27.20 (1986), each of which is incorporated herein by reference in its entirety and specifically for its teaching regarding immunodetection methods. Immunoassays, in their most simple and direct sense, are binding assays involving binding between antibodies and antigen. Many types and formats of immunoassays are known and all are suitable for detecting the disclosed biomarkers. Examples of immunoassays are enzyme linked immunosorbent assays (ELISAs), radioimmunoassays (RIA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), and fluorescence recovery/localization after photobleaching (FRAP/FLAP).

In general, immunoassays involve contacting a sample suspected of containing a molecule of interest (such as the disclosed biomarkers) with an antibody to the molecule of interest or contacting an antibody to a molecule of interest (such as antibodies to the disclosed biomarkers) with a molecule that can be bound by the antibody, as the case may be, under conditions effective to allow the formation of immunocomplexes. Contacting a sample with the antibody to the molecule of interest or with the molecule that can be bound by an antibody to the molecule of interest under conditions effective and for a period of time sufficient to allow the formation of immune complexes (primary immune complexes) is generally a matter of simply bringing into contact the molecule or antibody and the sample and incubating the mixture for a period of time long enough for the antibodies to form immune complexes with, i.e., to bind to, any molecules (e.g., antigens) present to which the antibodies can bind. In many forms of immunoassay, the sample-antibody composition, such as a tissue section, ELISA plate, dot blot or Western blot, can then be washed to remove any non-specifically bound antibody species, allowing only those antibodies specifically bound within the primary immune complexes to be detected.

Immunoassays can include methods for detecting or quantifying the amount of a molecule of interest (such as the disclosed biomarkers or their antibodies) in a sample, which methods generally involve the detection or quantitation of any immune complexes formed during the binding process. In general, the detection of immunocomplex formation is well known in the art and can be achieved through the application of numerous approaches. These methods are generally based upon the detection of a label or marker, such as any radioactive, fluorescent, biological or enzymatic tags or any other known label. See, for example, U.S. Pat. Nos. 3,817,837; 3,850,752; 3,939,350; 3,996,345; 4,277,437; 4,275,149 and 4,366,241, each of which is incorporated herein by reference in its entirety and specifically for teachings regarding immunodetection methods and labels.

As used herein, a label can include a fluorescent dye, a member of a binding pair, such as biotin/streptavidin, a metal (e.g., gold), or an epitope tag that can specifically interact with a molecule that can be detected, such as by producing a colored substrate or fluorescence. Substances suitable for detectably labeling proteins include fluorescent dyes (also known herein as fluorochromes and fluorophores) and enzymes that react with colorometric substrates (e.g., horseradish peroxidase). The use of fluorescent dyes is generally preferred in the practice of the invention as they can be detected at very low amounts. Furthermore, in the case where multiple antigens are reacted with a single array, each antigen can be labeled with a distinct fluorescent compound for simultaneous detection. Labeled spots on the array are detected using a fluorimeter, the presence of a signal indicating an antigen bound to a specific antibody.

Fluorophores are compounds or molecules that luminesce. Typically fluorophores absorb electromagnetic energy at one wavelength and emit electromagnetic energy at a second wavelength. Representative fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-Hydroxy Tryptamine (5-HAT); 5-ROX (carboxy-X-rhodamine); 6-Carboxyrhodamine 6G; 6-CR 6G; 6-JOE; 7-Amino-4-methylcoumarin; 7-Aminoactinomycin D (7-AAD); 7-Hydroxy-4-I methylcoumarin; 9-Amino-6-chloro-2-methoxyacridine (ACMA); ABQ; Acid Fuchsin; Acridine Orange; Acridine Red; Acridine Yellow; Acriflavin; Acriflavin Feulgen SITSA; Aequorin (Photoprotein); AFPs—AutoFluorescent Protein—(Quantum Biotechnologies) see sgGFP, sgBFP; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; Aminomethylcoumarin (AMCA); AMCA-X; Aminoactinomycin D; Aminocoumarin; Anilin Blue; Anthrocyl stearate; APC-Cy7; APTRA-BTC; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); Blue Fluorescent Protein; BFP/GFP FRET; Bimane; Bisbenzemide; Bisbenzimide (Hoechst); bis-BTC; Blancophor FFG; Blancophor SV; BOBO™-1; BOBO™-3; Bodipy492/515; Bodipy493/503; Bodipy500/510; Bodipy; 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; BTC; BTC-5N; Calcein; Calcein Blue; Calcium Crimson-; Calcium Green; Calcium Green-1 Ca2+ Dye; Calcium Green-2 Ca2+; Calcium Green-5N Ca2+; Calcium Green-C18 Ca2+; Calcium Orange; Calcofluor White; Carboxy-X-rhodamine (5-ROX); Cascade Blue™; Cascade Yellow; Catecholamine; CCF2 (GeneBlazer); CFDA; CFP (Cyan Fluorescent Protein); CFP/YFP FRET; Chlorophyll; Chromomycin A; Chromomycin A; CL-NERF; CMFDA; Coelenterazine; Coelenterazine cp; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM I Methylcoumarin; CTC; CTC Formazan; Cy2™; Cy3.1 8; Cy3.5™; Cy3™; Cy5.1 8; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3'DCFDA; DCFH (Dichlorodihydrofluorescein Diacetate); DDAO; DHR (Dihydrorhodamine 123); Di-4-ANEPPS; Di-8-

ANEPPS (non-ratio); DiA (4-Di 16-ASP); Dichlorodihydrofluorescein Diacetate (DCFH); DiD-Lipophilic Tracer; DiD (DilC18(5)); DIDS; Dihydrorhodamine 123 (DHR); Dil (DilC18(3)); 1Dinitrophenol; DiO (DiOC18(3)); DiR; DiR (DilC18(7)); DM-NERF (high pH); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (111) chloride; EYFP; Fast Blue; FDA; Feulgen (Pararosaniline); FIF (Formaldehyd Induced Fluorescence); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; Fluor X; FM 1-43™; FM 4-46; Fura Red™ (high pH); Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer; (CCF2); GFP(S65T); GFP red shifted (rs-GFP); GFP wild type' non-UV excitation (wtGFP); GFP wild type, UV excitation (wtGFP); GFPuv; Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1 low calcium; Indodicarbocyanine (DiD); Indotricarbocyanine (DiR); Intrawhite Cf; JC-1; JO JO-1; JO-PRO-1; LaserPro; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-1ndo-1; Magnesium Green; Magnesium Orange; Malachite Green; Marina Blue; I Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxedidole; Noradrenaline; Nuclear Fast Red; i Nuclear Yellow; Nylosan Brilliant lavin E8G; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26 (Sigma); PKH67; PMIA; Pontochrome Blue Black; POPO-1; POPO-3; PO-PRO-1; PO-I PRO-3; Primuline; Procion Yellow; Propidium 1odid (P1); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine: Phalloidine; Rhodamine Red; Rhodamine WT; Rose Bengal; R-phycocyanine; R-phycoerythrin (PE); rsGFP; S65A; S65C; S65L; S65T; Sapphire GFP; SBFI; Serotonin; Sevron Brilliant Red 2B; Sevron Brilliant Red 4G; Sevron I Brilliant Red B; Sevron Orange; Sevron Yellow L; sgBFP™ (super glow BFP); sgGFP™ (super glow GFP); SITS (Primuline; Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3 sulfopropyl)quinolinium); Stilbene; Sulphorhodamine B and C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TON; Thiolyte; Thiozole Orange; Tinopol CBS (Calcofluor White); TIER; TO-PRO-1; TO-PRO-3; TO-PRO-5; TOTO-1; TOTO-3; TriColor (PE-Cy5); TRITC TetramethylRodamineIsoThioCyanate; True Blue; Tru Red; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO3; YOYO-1;YOYO-3; Sybr Green; Thiazole orange (interchelating dyes); semiconductor nanoparticles such as quantum dots; or caged fluorophore (which can be activated with light or other electromagnetic energy source), or a combination thereof.

Labeling can be either direct or indirect. In direct labeling, the detecting antibody (the antibody for the molecule of interest) or detecting molecule (the molecule that can be bound by an antibody to the molecule of interest) include a label. Detection of the label indicates the presence of the detecting antibody or detecting molecule, which in turn indicates the presence of the molecule of interest or of an antibody to the molecule of interest, respectively. In indirect labeling, an additional molecule or moiety is brought into contact with, or generated at the site of, the immunocomplex. For example, a signal-generating molecule or moiety such as an enzyme can be attached to or associated with the detecting antibody or detecting molecule. The signal-generating molecule can then generate a detectable signal at the site of the immunocomplex. For example, an enzyme, when supplied with suitable substrate, can produce a visible or detectable product at the site of the immunocomplex. ELISAs use this type of indirect labeling.

As another example of indirect labeling, an additional molecule (which can be referred to as a binding agent) that can bind to either the molecule of interest or to the antibody (primary antibody) to the molecule of interest, such as a second antibody to the primary antibody, can be contacted with the immunocomplex. The additional molecule can have a label or signal-generating molecule or moiety. The additional molecule can be an antibody, which can thus be termed a secondary antibody. Binding of a secondary antibody to the primary antibody can form a so-called sandwich with the first (or primary) antibody and the molecule of interest. The immune complexes can be contacted with the labeled, secondary antibody under conditions effective and for a period of time sufficient to allow the formation of secondary immune complexes. The secondary immune complexes can then be generally washed to remove any non-specifically bound labeled secondary antibodies, and the remaining label in the secondary immune complexes can then be detected. The additional molecule can also be or include one of a pair of molecules or moieties that can bind to each other, such as the biotin/avadin pair. In this mode, the detecting antibody or detecting molecule should include the other member of the pair.

Other modes of indirect labeling include the detection of primary immune complexes by a two step approach. For example, a molecule (which can be referred to as a first binding agent), such as an antibody, that has binding affinity for the molecule of interest or corresponding antibody can be used to form secondary immune complexes, as described above. After washing, the secondary immune complexes can be contacted with another molecule (which can be referred to as a second binding agent) that has binding affinity for the first binding agent, again under conditions effective and for a period of time sufficient to allow the formation of immune complexes (thus forming tertiary immune complexes). The second binding agent can be linked to a detectable label or signal-generating molecule or moiety, allowing detection of the tertiary immune complexes thus formed. This system can provide for signal amplification.

Immunoassays that involve the detection of as substance, such as a protein or an antibody to a specific protein, include label-free assays, protein separation methods (i.e., electrophoresis), solid support capture assays, or in vivo detection. Label-free assays are generally diagnostic means of determining the presence or absence of a specific protein, or an antibody to a specific protein, in a sample. Protein separation methods are additionally useful for evaluating physical properties of the protein, such as size or net charge. Capture assays are generally more useful for quantitatively evaluating the concentration of a specific protein, or antibody to a specific protein, in a sample. Finally, in vivo detection is useful for evaluating the spatial expression patterns of the substance, i.e., where the substance can be found in a subject, tissue or cell.

Provided that the concentrations are sufficient, the molecular complexes ([Ab-Ag]n) generated by antibody-antigen interaction are visible to the naked eye, but smaller amounts may also be detected and measured due to their ability to scatter a beam of light. The formation of complexes indicates that both reactants are present, and in immunoprecipitation assays a constant concentration of a reagent antibody is used to measure specific antigen ([Ab-Ag]n), and reagent antigens are used to detect specific antibody ([Ab-Ag]n). If the reagent species is previously coated onto cells (as in hemagglutination assay) or very small particles (as in latex agglutination assay), "clumping" of the coated particles is visible at much lower concentrations. A variety of assays based on these elementary principles are in common use, including Ouchterlony immunodiffusion assay, rocket immunoelectrophoresis, and immunoturbidometric and nephelometric assays. The main limitations of such assays are restricted sensitivity (lower detection limits) in comparison to assays employing labels and, in some cases, the fact that very high concentrations of analyte can actually inhibit complex formation, necessitating safeguards that make the procedures more complex. Some of these Group I assays date right back to the discovery of antibodies and none of them have an actual "label" (e.g. Ag-enz). Other kinds of immunoassays that are label free depend on immunosensors, and a variety of instruments that can directly detect antibody-antigen interactions are now commercially available. Most depend on generating an evanescent wave on a sensor surface with immobilized ligand, which allows continuous monitoring of binding to the ligand. Immunosensors allow the easy investigation of kinetic interactions and, with the advent of lower-cost specialized instruments, may in the future find wide application in immunoanalysis.

The use of immunoassays to detect a specific protein can involve the separation of the proteins by electophoresis. Electrophoresis is the migration of charged molecules in solution in response to an electric field. Their rate of migration depends on the strength of the field; on the net charge, size and shape of the molecules and also on the ionic strength, viscosity and temperature of the medium in which the molecules are moving. As an analytical tool, electrophoresis is simple, rapid and highly sensitive. It is used analytically to study the properties of a single charged species, and as a separation technique.

Generally the sample is run in a support matrix such as paper, cellulose acetate, starch gel, agarose or polyacrylamide gel. The matrix inhibits convective mixing caused by heating and provides a record of the electrophoretic run: at the end of the run, the matrix can be stained and used for scanning, autoradiography or storage. In addition, the most commonly used support matrices—agarose and polyacrylamide—provide a means of separating molecules by size, in that they are porous gels. A porous gel may act as a sieve by retarding, or in some cases completely obstructing, the movement of large macromolecules while allowing smaller molecules to migrate freely. Because dilute agarose gels are generally more rigid and easy to handle than polyacrylamide of the same concentration, agarose is used to separate larger macromolecules such as nucleic acids, large proteins and protein complexes. Polyacrylamide, which is easy to handle and to make at higher concentrations, is used to separate most proteins and small oligonucleotides that require a small gel pore size for retardation.

Proteins are amphoteric compounds; their net charge therefore is determined by the pH of the medium in which they are suspended. In a solution with a pH above its isoelectric point, a protein has a net negative charge and migrates towards the anode in an electrical field. Below its isoelectric point, the protein is positively charged and migrates towards the cathode. The net charge carried by a protein is in addition independent of its size—i.e., the charge carried per unit mass (or length, given proteins and nucleic acids are linear macromolecules) of molecule differs from protein to protein. At a given pH therefore, and under non-denaturing conditions, the electrophoretic separation of proteins is determined by both size and charge of the molecules.

Sodium dodecyl sulphate (SDS) is an anionic detergent which denatures proteins by "wrapping around" the polypeptide backbone—and SDS binds to proteins fairly specifically in a mass ratio of 1.4:1. In so doing, SDS confers a negative charge to the polypeptide in proportion to its length. Further, it is usually necessary to reduce disulphide bridges in proteins (denature) before they adopt the random-coil configuration necessary for separation by size; this is done with 2-mercaptoethanol or dithiothreitol (DTT). In denaturing SDS-PAGE separations therefore, migration is determined not by intrinsic electrical charge of the polypeptide, but by molecular weight.

Determination of molecular weight is done by SDS-PAGE of proteins of known molecular weight along with the protein to be characterized. A linear relationship exists between the logarithm of the molecular weight of an SDS-denatured polypeptide, or native nucleic acid, and its Rf. The Rf is calculated as the ratio of the distance migrated by the molecule to that migrated by a marker dye-front. A simple way of determining relative molecular weight by electrophoresis (Mr) is to plot a standard curve of distance migrated vs. log 10 MW for known samples, and read off the log Mr of the sample after measuring distance migrated on the same gel.

In two-dimensional electrophoresis, proteins are fractionated first on the basis of one physical property, and, in a second step, on the basis of another. For example, isoelectric focusing can be used for the first dimension, conveniently carried out in a tube gel, and SDS electrophoresis in a slab gel can be used for the second dimension. One example of a procedure is that of O'Farrell, P. H., High Resolution Two-dimensional Electrophoresis of Proteins, J. Biol. Chem. 250: 4007-4021 (1975), herein incorporated by reference in its entirety for its teaching regarding two-dimensional electrophoresis methods. Other examples include but are not limited to, those found in Anderson, L and Anderson, N G, High resolution two-dimensional electrophoresis of human plasma proteins, Proc. Natl. Acad. Sci. 74:5421-5425 (1977), Ornstein, L., Disc electrophoresis, L. Ann. N.Y. Acad. Sci. 121:321349 (1964), each of which is herein incorporated by reference in its entirety for teachings regarding electrophoresis methods.

Laemmli, U. K., Cleavage of structural proteins during the assembly of the head of bacteriophage 14, Nature 227:680 (1970), which is herein incorporated by reference in its entirety for teachings regarding electrophoresis methods, discloses a discontinuous system for resolving proteins denatured with SDS. The leading ion in the Laemmli buffer system is chloride, and the trailing ion is glycine. Accordingly, the resolving gel and the stacking gel are made up in Tris-HCl buffers (of different concentration and pH), while the tank buffer is Tris-glycine. All buffers contain 0.1% SDS.

One example of an immunoassay that uses electrophoresis that is contemplated in the current methods is Western blot analysis. Western blotting or immunoblotting allows the determination of the molecular mass of a protein and the measurement of relative amounts of the protein present in different samples. Detection methods include chemiluminescence and chromagenic detection. Standard methods for Western blot analysis can be found in, for example, D. M. Bollag et al., Protein Methods (2d edition 1996) and E. Harlow & D. Lane, Antibodies, a Laboratory Manual (1988), U.S. Pat. No. 4,452,901, each of which is herein incorporated by reference in their entirety for teachings regarding Western blot methods. Generally, proteins are separated by gel electrophoresis, usually SDS-PAGE. The proteins are transferred to a sheet of special blotting paper, e.g., nitrocellulose, though other types of paper, or membranes, can be used. The proteins retain the same pattern of separation they had on the gel. The blot is incubated with a generic protein (such as milk proteins) to bind to any remaining sticky places on the nitrocellulose. An antibody is then added to the solution which is able to bind to its specific protein.

The attachment of specific antibodies to specific immobilized antigens can be readily visualized by indirect enzyme immunoassay techniques, usually using a chromogenic substrate (e.g. alkaline phosphatase or horseradish peroxidase) or chemiluminescent substrates. Other possibilities for probing include the use of fluorescent or radioisotope labels (e.g., fluorescein, 125I). Probes for the detection of antibody binding can be conjugated anti-immunoglobulins, conjugated staphylococcal Protein A (binds IgG), or probes to biotinylated primary antibodies (e.g., conjugated avidin/streptavidin).

The power of the technique lies in the simultaneous detection of a specific protein by means of its antigenicity, and its molecular mass. Proteins are first separated by mass in the SDS-PAGE, then specifically detected in the immunoassay step. Thus, protein standards (ladders) can be run simultaneously in order to approximate molecular mass of the protein of interest in a heterogeneous sample.

The gel shift assay or electrophoretic mobility shift assay (EMSA) can be used to detect the interactions between DNA binding proteins and their cognate DNA recognition sequences, in both a qualitative and quantitative manner. Exemplary techniques are described in Ornstein L., Disc electrophoresis—I: Background and theory, Ann. NY Acad. Sci. 121:321-349 (1964), and Matsudiara, P T and D R Burgess, SDS microslab linear gradient polyacrylamide gel electrophoresis, Anal. Biochem. 87:386-396 (1987), each of which is herein incorporated by reference in its entirety for teachings regarding gel-shift assays.

In a general gel-shift assay, purified proteins or crude cell extracts can be incubated with a labeled (e.g., 32P-radiolabeled) DNA or RNA probe, followed by separation of the complexes from the free probe through a nondenaturing polyacrylamide gel. The complexes migrate more slowly through the gel than unbound probe. Depending on the activity of the binding protein, a labeled probe can be either double-stranded or single-stranded. For the detection of DNA binding proteins such as transcription factors, either purified or partially purified proteins, or nuclear cell extracts can be used. For detection of RNA binding proteins, either purified or partially purified proteins, or nuclear or cytoplasmic cell extracts can be used. The specificity of the DNA or RNA binding protein for the putative binding site is established by competition experiments using DNA or RNA fragments or oligonucleotides containing a binding site for the protein of interest, or other unrelated sequence. The differences in the nature and intensity of the complex formed in the presence of specific and nonspecific competitor allows identification of specific interactions. Refer to Promega, Gel Shift Assay FAQ, available at <http://www.promega.com/faq/gelshfaq.html> (last visited Mar. 25, 2005), which is herein incorporated by reference in its entirety for teachings regarding gel shift methods.

Gel shift methods can include using, for example, colloidal forms of COOMASSIE (Imperial Chemicals Industries, Ltd) blue stain to detect proteins in gels such as polyacrylamide electrophoresis gels. Such methods are described, for example, in Neuhoff et al., Electrophoresis 6:427-448 (1985), and Neuhoff et al., Electrophoresis 9:255-262 (1988), each of which is herein incorporated by reference in its entirety for teachings regarding gel shift methods. In addition to the conventional protein assay methods referenced above, a combination cleaning and protein staining composition is described in U.S. Pat. No. 5,424,000, herein incorporated by reference in its entirety for its teaching regarding gel shift methods. The solutions can include phosphoric, sulfuric, and nitric acids, and Acid Violet dye.

Radioimmune Precipitation Assay (RIPA) is a sensitive assay using radiolabeled antigens to detect specific antibodies in serum. The antigens are allowed to react with the serum and then precipitated using a special reagent such as, for example, protein A sepharose beads. The bound radiolabeled immunoprecipitate is then commonly analyzed by gel electrophoresis. Radioimmunoprecipitation assay (RIPA) is often used as a confirmatory test for diagnosing the presence of HIV antibodies. RIPA is also referred to in the art as Farr Assay, Precipitin Assay, Radioimmune Precipitin Assay; Radioimmunoprecipitation Analysis; Radioimmunoprecipitation Analysis, and Radioimmunoprecipitation Analysis.

While the above immunoassays that utilize electrophoresis to separate and detect the specific proteins of interest allow for evaluation of protein size, they are not very sensitive for evaluating protein concentration. However, also contemplated are immunoassays wherein the protein or antibody specific for the protein is bound to a solid support (e.g., tube, well, bead, or cell) to capture the antibody or protein of interest, respectively, from a sample, combined with a method of detecting the protein or antibody specific for the protein on the support. Examples of such immunoassays include Radioimmunoassay (RIA), Enzyme-Linked Immunosorbent Assay (ELISA), Flow cytometry, protein array, multiplexed bead assay, and magnetic capture.

Radioimmunoassay (RIA) is a classic quantitative assay for detection of antigen-antibody reactions using a radioactively labeled substance (radioligand), either directly or indirectly, to measure the binding of the unlabeled substance to a specific antibody or other receptor system. Radioimmunoassay is used, for example, to test hormone levels in the blood without the need to use a bioassay. Non-immunogenic substances (e.g., haptens) can also be measured if coupled to larger carrier proteins (e.g., bovine gamma-globulin or human serum albumin) capable of inducing antibody formation. RIA involves mixing a radioactive antigen (because of the ease with which iodine atoms can be introduced into tyrosine residues in a protein, the radioactive isotopes 125I or 131I are often used) with antibody to that antigen. The antibody is generally linked to a solid support, such as a tube or beads. Unlabeled or "cold" antigen is then adding in known quantities and measuring the amount of labeled antigen displaced. Initially, the radioactive antigen is bound to the antibodies. When cold antigen is added, the two compete for antibody binding sites—and at higher concentrations of cold antigen, more binds to the antibody, displacing the radioactive variant. The bound antigens are separated from the unbound ones in solution and the radioactivity of each used to plot a binding curve. The technique is both extremely sensitive, and specific.

Enzyme-Linked Immunosorbent Assay (ELISA), or more generically termed EIA (Enzyme ImmunoAssay), is an immunoassay that can detect an antibody specific for a protein. In such an assay, a detectable label bound to either an antibody-binding or antigen-binding reagent is an enzyme. When exposed to its substrate, this enzyme reacts in such a manner as to produce a chemical moiety which can be detected, for example, by spectrophotometric, fluorometric or visual means. Enzymes which can be used to detectably label reagents useful for detection include, but are not limited to, horseradish peroxidase, alkaline phosphatase, glucose oxidase, β-galactosidase, ribonuclease, urease, catalase, malate dehydrogenase, staphylococcal nuclease, asparaginase, yeast alcohol dehydrogenase, alpha.-glycerophosphate dehydrogenase, triose phosphate isomerase, glucose-6-phosphate dehydrogenase, glucoamylase and acetylcholinesterase. For descriptions of ELISA procedures, see Voller, A. et al., J. Clin. Pathol. 31:507-520 (1978); Butler, J. E., Meth. Enzymol. 73:482-523 (1981); Maggio, E. (ed.), Enzyme Immunoassay, CRC Press, Boca Raton, 1980; Butler, J. E., In: Structure of Antigens, Vol. 1 (Van Regenmortel, M., CRC Press, Boca Raton, 1992, pp. 209-259; Butler, J. E., In: van Oss, C. J. et al., (eds), Immunochemistry, Marcel Dekker, Inc., New York, 1994, pp. 759-803; Butler, J. E. (ed.), Immunochemistry of Solid-Phase Immunoassay, CRC Press, Boca Raton, 1991); Crowther, "ELISA: Theory and Practice," In: Methods in Molecule Biology, Vol. 42, Humana Press; New Jersey, 1995; U.S. Pat. No. 4,376,110, each of which is incorporated herein by reference in its entirety and specifically for teachings regarding ELISA methods.

Variations of ELISA techniques are know to those of skill in the art. In one variation, antibodies that can bind to proteins can be immobilized onto a selected surface exhibiting protein affinity, such as a well in a polystyrene microtiter plate. Then, a test composition suspected of containing a marker antigen can be added to the wells. After binding and washing to remove non-specifically bound immunocomplexes, the bound antigen can be detected. Detection can be achieved by the addition of a second antibody specific for the target protein, which is linked to a detectable label. This type of ELISA is a simple "sandwich ELISA." Detection also can be achieved by the addition of a second antibody, followed by the addition of a third antibody that has binding affinity for the second antibody, with the third antibody being linked to a detectable label.

Another variation is a competition ELISA. In competition ELISA's, test samples compete for binding with known amounts of labeled antigens or antibodies. The amount of reactive species in the sample can be determined by mixing the sample with the known labeled species before or during incubation with coated wells. The presence of reactive species in the sample acts to reduce the amount of labeled species available for binding to the well and thus reduces the ultimate signal.

Regardless of the format employed, ELISAs have certain features in common, such as coating, incubating or binding, washing to remove non-specifically bound species, and detecting the bound immunecomplexes. Antigen or antibodies can be linked to a solid support, such as in the form of plate, beads, dipstick, membrane or column matrix, and the sample to be analyzed applied to the immobilized antigen or antibody. In coating a plate with either antigen or antibody, one will generally incubate the wells of the plate with a solution of the antigen or antibody, either overnight or for a specified period of hours. The wells of the plate can then be washed to remove incompletely adsorbed material. Any remaining available surfaces of the wells can then be "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, a secondary or tertiary detection means rather than a direct procedure can also be used. Thus, after binding of a protein or antibody to the well, coating with a non-reactive material to reduce background, and washing to remove unbound material, the immobilizing surface is contacted with the control clinical or biological sample to be tested under conditions effective to allow immunecomplex (antigen/antibody) formation. Detection of the immunecomplex then requires a labeled secondary binding agent or a secondary binding agent in conjunction with a labeled third binding agent.

"Under conditions effective to allow immunecomplex (antigen/antibody) formation" means that the conditions include diluting the antigens and antibodies with solutions such as BSA, bovine gamma globulin (BGG) and phosphate buffered saline (PBS)/Tween so as to reduce non-specific binding and to promote a reasonable signal to noise ratio.

The suitable conditions also mean that the incubation is at a temperature and for a period of time sufficient to allow effective binding. Incubation steps can typically be from about 1 minute to twelve hours, at temperatures of about 20° to 30° C., or can be incubated overnight at about 0° C. to about 10° C.

Following all incubation steps in an ELISA, the contacted surface can be washed so as to remove non-complexed material. A washing procedure can include washing with a solution such as PBS/Tween or borate buffer. Following the formation of specific immunecomplexes between the test sample and the originally bound material, and subsequent washing, the occurrence of even minute amounts of immunecomplexes can be determined.

To provide a detecting means, the second or third antibody can have an associated label to allow detection, as described above. This can be an enzyme that can generate color development upon incubating with an appropriate chromogenic substrate. Thus, for example, one can contact and incubate the first or second immunecomplex with a labeled antibody for a period of time and under conditions that favor the development of further immunecomplex formation (e.g., incubation for 2 hours at room temperature in a PBS-containing solution such as PBS-Tween).

After incubation with the labeled antibody, and subsequent to washing to remove unbound material, the amount of label can be quantified, e.g., by incubation with a chromogenic substrate such as urea and bromocresol purple or 2,2'-azido-di-(3-ethyl-benzthiazoline-6-sulfonic acid [ABTS] and H2O2, in the case of peroxidase as the enzyme label. Quantitation can then be achieved by measuring the degree of color generation, e.g., using a visible spectra spectrophotometer.

Protein arrays are solid-phase ligand binding assay systems using immobilized proteins on surfaces which include glass, membranes, microtiter wells, mass spectrometer plates, and beads or other particles. The assays are highly parallel (multiplexed) and often miniaturized (microarrays, protein, chips). Their advantages include being rapid and automatable, capable of high sensitivity, economical on reagents, and giving an abundance of data for a single experiment. Bioinformatics support is important; the data handling demands sophisticated software and data comparison analysis. However, the software can be adapted from that used for DNA arrays, as can much of the hardware and detection systems.

One of the chief formats is the capture array, in which ligand-binding reagents, which are usually antibodies but can also be alternative protein scaffolds, peptides or nucleic acid aptamers, are used to detect target molecules in mixtures such as plasma or tissue extracts. In diagnostics, capture arrays can be used to carry out multiple immunoassays in parallel, both testing for several analytes in individual sera for example and testing many serum samples simultaneously. In proteomics, capture arrays are used to quantitate and compare the levels of proteins in different samples in health and disease, i.e. protein expression profiling. Proteins other than specific ligand binders are used in the array format for in vitro functional interaction screens such as protein-protein, protein-DNA, protein-drug, receptor-ligand, enzyme-substrate, etc. The capture reagents themselves are selected and screened against many proteins, which can also be done in a multiplex array format against multiple protein targets.

For construction of arrays, sources of proteins include cell-based expression systems for recombinant proteins, purification from natural sources, production in vitro by cell-free translation systems, and synthetic methods for peptides. Many of these methods can be automated for high throughput production. For capture arrays and protein function analysis, it is important that proteins should be correctly folded and functional; this is not always the case, e.g. where recombinant proteins are extracted from bacteria under denaturing conditions. Nevertheless, arrays of denatured proteins are useful in screening antibodies for cross-reactivity, identifying autoantibodies and selecting ligand binding proteins.

Protein arrays have been designed as a miniaturization of familiar immunoassay methods such as ELISA and dot blotting, often utilizing fluorescent readout, and facilitated by robotics and high throughput detection systems to enable multiple assays to be carried out in parallel. Commonly used physical supports include glass slides, silicon, microwells, nitrocellulose or PVDF membranes, and magnetic and other microbeads. While microdrops of protein delivered onto planar surfaces are the most familiar format, alternative architectures include CD centrifugation devices based on developments in microfluidics (Gyros, Monmouth Junction, N.J.) and specialised chip designs, such as engineered microchannels in a plate (e.g., The Living Chip™, Biotrove, Woburn, Mass.) and tiny 3D posts on a silicon surface (Zyomyx, Hayward Calif.). Particles in suspension can also be used as the basis of arrays, providing they are coded for identification; systems include colour coding for microbeads (Luminex, Austin, Tex.; Bio-Rad Laboratories) and semiconductor nanocrystals (e.g., QDots™, Quantum Dot, Hayward, Calif.), and barcoding for beads (UltraPlex™, SmartBead Technologies Ltd, Babraham, Cambridge, UK) and multimetal microrods (e.g., Nanobarcodes™ particles, Nanoplex Technologies, Mountain View, Calif.). Beads can also be assembled into planar arrays on semiconductor chips (LEAPS technology, BioArray Solutions, Warren, N.J.).

Immobilization of proteins involves both the coupling reagent and the nature of the surface being coupled to. A good protein array support surface is chemically stable before and after the coupling procedures, allows good spot morphology, displays minimal nonspecific binding, does not contribute a background in detection systems, and is compatible with different detection systems. The immobilization method used are reproducible, applicable to proteins of different properties (size, hydrophilic, hydrophobic), amenable to high throughput and automation, and compatible with retention of fully functional protein activity. Orientation of the surface-bound protein is recognized as an important factor in presenting it to ligand or substrate in an active state; for capture arrays the most efficient binding results are obtained with orientated capture reagents, which generally require site-specific labeling of the protein.

Both covalent and noncovalent methods of protein immobilization are used and have various pros and cons. Passive adsorption to surfaces is methodologically simple, but allows little quantitative or orientational control; it may or may not alter the functional properties of the protein, and reproducibility and efficiency are variable. Covalent coupling methods provide a stable linkage, can be applied to a range of proteins and have good reproducibility; however, orientation may be variable, chemical derivatization may alter the function of the protein and requires a stable interactive surface. Biological capture methods utilizing a tag on the protein provide a stable linkage and bind the protein specifically and in reproducible orientation, but the biological reagent must first be immobilized adequately and the array may require special handling and have variable stability.

Several immobilization chemistries and tags have been described for fabrication of protein arrays. Substrates for covalent attachment include glass slides coated with amino- or aldehyde-containing silane reagents. In the Versalinx™ system (Prolinx, Bothell, Wash.) reversible covalent coupling is achieved by interaction between the protein derivatised with phenyldiboronic acid, and salicylhydroxamic acid immobilized on the support surface. This also has low background binding and low intrinsic fluorescence and allows the immobilized proteins to retain function. Noncovalent binding of unmodified protein occurs within porous structures such as HydroGel™ (PerkinElmer, Wellesley, Mass.), based on a 3-dimensional polyacrylamide gel; this substrate is reported to give a particularly low background on glass microarrays, with a high capacity and retention of protein function. Widely used biological coupling methods are through biotin/streptavidin or hexahistidine/Ni interactions, having modified the protein appropriately. Biotin may be conjugated to a polylysine backbone immobilised on a surface such as titanium dioxide (Zyomyx) or tantalum pentoxide (Zeptosens, Witterswil, Switzerland).

Array fabrication methods include robotic contact printing, ink-jetting, piezoelectric spotting and photolithography.

A number of commercial arrayers are available [e.g. Packard Biosciences] as well as manual equipment [V & P Scientific]. Bacterial colonies can be robotically gridded onto PVDF membranes for induction of protein expression in situ.

At the limit of spot size and density are nanoarrays, with spots on the nanometer spatial scale, enabling thousands of reactions to be performed on a single chip less than 1 mm square. BioForce Laboratories have developed nanoarrays with 1521 protein spots in 85 sq microns, equivalent to 25 million spots per sq cm, at the limit for optical detection; their readout methods are fluorescence and atomic force microscopy (AFM).

Fluorescence labeling and detection methods are widely used. The same instrumentation as used for reading DNA microarrays is applicable to protein arrays. For differential display, capture (e.g., antibody) arrays can be probed with fluorescently labeled proteins from two different cell states, in which cell lysates are directly conjugated with different fluorophores (e.g. Cy-3, Cy-5) and mixed, such that the color acts as a readout for changes in target abundance. Fluorescent readout sensitivity can be amplified 10-100 fold by tyramide signal amplification (TSA) (PerkinElmer Lifesciences). Planar waveguide technology (Zeptosens) enables ultrasensitive fluorescence detection, with the additional advantage of no intervening washing procedures. High sensitivity can also be achieved with suspension beads and particles, using phycoerythrin as label (Luminex) or the properties of semiconductor nanocrystals (Quantum Dot). A number of novel alternative readouts have been developed, especially in the commercial biotech arena. These include adaptations of surface plasmon resonance (HTS Biosystems, Intrinsic Bioprobes, Tempe, Ariz.), rolling circle DNA amplification (Molecular Staging, New Haven Conn.), mass spectrometry (Intrinsic Bioprobes; Ciphergen, Fremont, Calif.), resonance light scattering (Genicon Sciences, San Diego, Calif.) and atomic force microscopy [BioForce Laboratories].

Capture arrays form the basis of diagnostic chips and arrays for expression profiling. They employ high affinity capture reagents, such as conventional antibodies, single domains, engineered scaffolds, peptides or nucleic acid aptamers, to bind and detect specific target ligands in high throughput manner.

Antibody arrays have the required properties of specificity and acceptable background, and some are available commercially (BD Biosciences, San Jose, Calif.; Clontech, Mountain View, Calif.; BioRad; Sigma, St. Louis, Mo.). Antibodies for capture arrays are made either by conventional immunization (polyclonal sera and hybridomas), or as recombinant fragments, usually expressed in *E. coli*, after selection from phage or ribosome display libraries (Cambridge Antibody Technology, Cambridge, UK; BioInvent, Lund, Sweden; Affitech, Walnut Creek, Calif.; Biosite, San Diego, Calif.). In addition to the conventional antibodies, Fab and scFv fragments, single V-domains from camelids or engineered human equivalents (Domantis, Waltham, Mass.) may also be useful in arrays.

The term "scaffold" refers to ligand-binding domains of proteins, which are engineered into multiple variants capable of binding diverse target molecules with antibody-like properties of specificity and affinity. The variants can be produced in a genetic library format and selected against individual targets by phage, bacterial or ribosome display. Such ligand-binding scaffolds or frameworks include 'Affibodies' based on *Staph. aureus* protein A (Affibody, Bromma, Sweden), 'Trinectins' based on fibronectins (Phylos, Lexington, Mass.) and 'Anticalins' based on the lipocalin structure (Pieris Proteolab, Freising-Weihenstephan, Germany). These can be used on capture arrays in a similar fashion to antibodies and may have advantages of robustness and ease of production.

Nonprotein capture molecules, notably the single-stranded nucleic acid aptamers which bind high protein ligands with high specificity and affinity, are also used in arrays (SomaLogic, Boulder, Colo.). Aptamers are selected from libraries of oligonucleotides by the Selex™ procedure and their interaction with protein can be enhanced by covalent attachment, through incorporation of brominated deoxyuridine and UV-activated crosslinking (photoaptamers). Photocrosslinking to ligand reduces the crossreactivity of aptamers due to the specific steric requirements. Aptamers have the advantages of ease of production by automated oligonucleotide synthesis and the stability and robustness of DNA; on photoaptamer arrays, universal fluorescent protein stains can be used to detect binding.

Protein analytes binding to antibody arrays may be detected directly or via a secondary antibody in a sandwich assay. Direct labelling is used for comparison of different samples with different colours. Where pairs of antibodies directed at the same protein ligand are available, sandwich immunoassays provide high specificity and sensitivity and are therefore the method of choice for low abundance proteins such as cytokines; they also give the possibility of detection of protein modifications. Label-free detection methods, including mass spectrometry, surface plasmon resonance and atomic force microscopy, avoid alteration of ligand. What is required from any method is optimal sensitivity and specificity, with low background to give high signal to noise. Since analyte concentrations cover a wide range, sensitivity has to be tailored appropriately; serial dilution of the sample or use of antibodies of different affinities are solutions to this problem. Proteins of interest are frequently those in low concentration in body fluids and extracts, requiring detection in the pg range or lower, such as cytokines or the low expression products in cells.

An alternative to an array of capture molecules is one made through 'molecular imprinting' technology, in which peptides (e.g., from the C-terminal regions of proteins) are used as templates to generate structurally complementary, sequence-specific cavities in a polymerizable matrix; the cavities can then specifically capture (denatured) proteins that have the appropriate primary amino acid sequence (ProteinPrint™, Aspira Biosystems, Burlingame, Calif.).

Another methodology which can be used diagnostically and in expression profiling is the ProteinChip® array (Ciphergen, Fremont, Calif.), in which solid phase chromatographic surfaces bind proteins with similar characteristics of charge or hydrophobicity from mixtures such as plasma or tumor extracts, and SELDI-TOF mass spectrometry is used to detection the retained proteins.

Large-scale functional chips have been constructed by immobilizing large numbers of purified proteins and used to assay a wide range of biochemical functions, such as protein interactions with other proteins, drug-target interactions, enzyme-substrates, etc. Generally they require an expression library, cloned into *E. coli*, yeast or similar from which the expressed proteins are then purified, e.g. via a His tag, and immobilized. Cell free protein transcription/translation is a viable alternative for synthesis of proteins which do not express well in bacterial or other in vivo systems.

For detecting protein-protein interactions, protein arrays can be in vitro alternatives to the cell-based yeast two-hybrid system and may be useful where the latter is deficient, such as interactions involving secreted proteins or proteins with disulphide bridges. High-throughput analysis of biochemical activities on arrays has been described for yeast protein kinases and for various functions (protein-protein and protein-lipid interactions) of the yeast proteome, where a large proportion of all yeast open-reading frames was expressed and immobilised on a microarray. Large-scale 'proteome chips' promise to be very useful in identification of functional interactions, drug screening, etc. (Proteometrix, Branford, Conn.).

As a two-dimensional display of individual elements, a protein array can be used to screen phage or ribosome display libraries, in order to select specific binding partners, including antibodies, synthetic scaffolds, peptides and aptamers. In this way, 'library against library' screening can be carried out. Screening of drug candidates in combinatorial chemical libraries against an array of protein targets identified from genome projects is another application of the approach.

A multiplexed bead assay, such as, for example, the BD™ Cytometric Bead Array, is a series of spectrally discrete particles that can be used to capture and quantitate soluble analytes. The analyte is then measured by detection of a fluorescence-based emission and flow cytometric analysis. Multiplexed bead assay generates data that is comparable to ELISA based assays, but in a "multiplexed" or simultaneous fashion. Concentration of unknowns is calculated for the cytometric bead array as with any sandwich format assay, i.e. through the use of known standards and plotting unknowns against a standard curve. Further, multiplexed bead assay allows quantification of soluble analytes in samples never previously considered due to sample volume limitations. In addition to the quantitative data, powerful visual images can be generated revealing unique profiles or signatures that provide the user with additional information at a glance.

2. Antibodies

Disclosed herein are antibodies that specifically bind PAX2 or DEFB1 that can be used to detect PAX2 or DEFB1 in a sample in the herein disclosed diagnostic methods or can be used to inhibit the interaction between PAX2 and DEFB1 in the herein disclosed methods of treating or preventing prostate cancer or PIN.

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with, for example, PAX2 or DEFB1, such that PAX2 is inhibited from interacting with DEFB1. Antibodies that bind the disclosed regions of PAX2 or DEFB1 involved in the interaction between PAX2 and DEFB1 are also disclosed. The antibodies can be tested for their desired activity using the in vitro assays described herein, or by analogous methods, after which their in vivo therapeutic and/or prophylactic activities are tested according to known clinical testing methods.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., Proc. Natl. Acad. Sci. USA, 81:6851-6855 (1984)).

The disclosed monoclonal antibodies can be made using any procedure which produces mono clonal antibodies. For example, disclosed monoclonal antibodies can be prepared using hybridoma methods, such as those described by Kohler and Milstein, Nature, 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro, e.g., using the HIV Env-CD4-co-receptor complexes described herein.

The monoclonal antibodies may also be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al. In vitro methods are also suitable for preparing monovalent antibodies. Digestion of antibodies to produce fragments thereof; particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. Curr. Opin. Biotechnol. 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

The disclosed human antibodies can be prepared using any technique. Examples of techniques for human monoclonal antibody production include those described by Cole et al. (Monoclonal Antibodies and Cancer Therapy, Alan R. Liss, p. 77, 1985) and by Boerner et al. (J. Immunol., 147(1):86-95, 1991). Human antibodies (and fragments thereof) can also be produced using phage display libraries (Hoogenboom et al., J. Mol. Biol., 227:381, 1991; Marks et al., J. Mol. Biol., 222: 581, 1991).

The disclosed human antibodies can also be obtained from transgenic animals. For example, transgenic, mutant mice that are capable of producing a full repertoire of human antibodies, in response to immunization, have been described (see, e.g., Jakobovits et al., Proc. Natl. Acad. Sci. USA, 90:2551-255 (1993); Jakobovits et al., Nature, 362:255-258 (1993); Bruggermann et al., Year in Immunol., 7:33 (1993)). Specifically, the homozygous deletion of the antibody heavy chain joining region (J(H)) gene in these chimeric and germline mutant mice results in complete inhibition of endogenous antibody production, and the successful transfer of the human germ-line antibody gene array into such germ-line mutant mice results in the production of human antibodies upon antigen challenge. Antibodies having the desired activity are selected using Env-CD4-co-receptor complexes as described herein.

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fv, Fab, Fab', or other antigen-binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies may also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones et al., Nature, 321:522-525 (1986), Reichmann et al., Nature, 332:323-327 (1988), and Presta, Curr. Opin. Struct. Biol., 2:593-596 (1992)).

Methods for humanizing non-human antibodies are well known in the art. For example, humanized antibodies can be generated according to the methods of Winter and co-workers (Jones et al., Nature, 321:522-525 (1986), Riechmann et al., Nature, 332:323-327 (1988), Verhoeyen et al., Science, 239: 1534-1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.).

Administration of the antibodies can be done as disclosed herein. Nucleic acid approaches for antibody delivery also exist. The broadly neutralizing anti PAX2 or DEFB1 antibodies and antibody fragments can also be administered to patients or subjects as a nucleic acid preparation (e.g., DNA or RNA) that encodes the antibody or antibody fragment, such that the patient's or subject's own cells take up the nucleic acid and produce and secrete the encoded antibody or antibody fragment. The delivery of the nucleic acid can be by any means, as disclosed herein, for example.

3. Sequence Similarities

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

4. Hybridization/Selective Hybridization

The term hybridization typically means a sequence driven interaction between at least two nucleic acid molecules, such as a primer or a probe and a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization may involve hybridization in high ionic strength solution (6×SSC or 6×SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook et al., Molecular Cloning: A Laboratory Manual, 2nd Ed., Cold Spring Harbor Laboratory, Cold Spring Harbor, N.Y., 1989; Kunkel et al. Methods Enzymol. 1987:154:367, 1987 which is herein incorporated by reference for material at least related to hybridization of nucleic acids). A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in for example, 10 or 100 or 1000 fold excess. This type of assay can be performed at under conditions where both the limiting and non-limiting primer are for example, 10 fold or 100 fold or 1000 fold below their kd, or where only one of the nucleic acid molecules is 10 fold or 100 fold or 1000 fold or where one or both nucleic acid molecules are above their kd.

Another way to define selective hybridization is by looking at the percentage of primer that gets enzymatically manipulated under conditions where hybridization is required to promote the desired enzymatic manipulation. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation, for example if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions may provide different percentages of hybridization between two nucleic acid molecules, but unless otherwise indicated meeting the parameters of any of the methods would be sufficient. For example if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein.

5. Nucleic Acids

There are a variety of molecules disclosed herein that are nucleic acid based. The disclosed nucleic acids are made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

i. Nucleotides and Related Molecules

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. An non-limiting example of a nucleotide would be 3'-AMP (3'-adenosine monophosphate) or 5'-GMP (5'-guanosine monophosphate). There are many varieties of these types of molecules available in the art and available herein.

A nucleotide analog is a nucleotide which contains some type of modification to either the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties. There are many varieties of these types of molecules available in the art and available herein.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid. There are many varieties of these types of molecules available in the art and available herein.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety. (Letsinger et al., Proc. Natl. Acad. Sci. USA, 1989,86, 6553-6556). There are many varieties of these types of molecules available in the art and available herein.

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

ii. Sequences

There are a variety of sequences related to the protein molecules involved in the signaling pathways disclosed herein, for example PAX2, or any of the nucleic acids disclosed herein for making PAX2, all of which are encoded by nucleic acids or are nucleic acids. The sequences for the human analogs of these genes, as well as other analogs, and alleles of these genes, and splice variants and other types of variants, are available in a variety of protein and gene databases, including Genbank. Those sequences available at the time of filing this application at Genbank are herein incorporated by reference in their entireties as well as for individual subsequences contained therein. Genbank can be accessed at http://www.ncbi.nih.gov/entrez/query.fcgi. Those of skill in the art understand how to resolve sequence discrepancies and differences and to adjust the compositions and methods relating to a particular sequence to other related sequences. Primers and/or probes can be designed for any given sequence given the information disclosed herein and known in the art.

iii. Functional Nucleic Acids

The PAX2 inhibitor of the provided method can be a functional nucleic acid. Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, RNAi, and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA of PAX2 or the genomic DNA of PAX2 or they can interact with the polypeptide PAX2. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant (Kd) less than or equal to 10-6, 10-8, 10-10, or 10-12. A representative sample of methods and techniques which aid in the design and use of antisense molecules can be found in U.S. Pat. Nos. 5,135,917, 5,294,533, 5,627,158, 5,641,754, 5,691,317, 5,780,607, 5,786,138, 5,849,903, 5,856,103, 5,919,772, 5,955,590, 5,990,088, 5,994,320, 5,998,602, 6,005,095, 6,007,995, 6,013,522, 6,017,898, 6,018,042, 6,025,198, 6,033,910, 6,040,296, 6,046,004, 6,046,319, and 6,057,437.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Aptamers can bind very tightly with Kd's from the target molecule of less than 10-12 M. It is preferred that the aptamers bind the target molecule with a Kd less than 10-6, 10-8, 10-10, or 10-12. Aptamers can bind the target molecule with a very high degree of specificity. For example, aptamers have been isolated that have greater than a 10,000 fold difference in binding affinities between the target molecule and another molecule that differ at only a single position on the molecule (U.S. Pat. No. 5,543,293). It is preferred that the aptamer have a Kd with the target molecule at least 10, 100, 1000, 10,000, or 100,000 fold lower than the Kd with a background binding molecule. It is preferred when doing the comparison for a polypeptide for example, that the background molecule be a different polypeptide. Representative examples of how to make and use aptamers to bind a variety of different target molecules can be found in U.S. Pat. Nos. 5,476,766, 5,503,978, 5,631,146, 5,731,424, 5,780,228, 5,792,613, 5,795,721, 5,846,713, 5,858,660, 5,861,254, 5,864,026, 5,869,641, 5,958,691, 6,001,988, 6,011,020, 6,013,443, 6,020,130, 6,028,186, 6,030,776, and 6,051,698.

Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes, (U.S. Pat. Nos. 5,334,711, 5,436,330, 5,616,466, 5,633,133, 5,646,020, 5,652,094, 5,712,384, 5,770,715, 5,856,463, 5,861,288, 5,891,683, 5,891,684, 5,985,621, 5,989,908, 5,998,193, 5,998,203; International Patent Application Nos. WO 9858058 by Ludwig and Sproat, WO 9858057 by Ludwig and Sproat, and WO 9718312 by Ludwig and Sproat) hairpin ribozymes (for example, U.S. Pat. Nos. 5,631,115, 5,646,031, 5,683,902, 5,712,384, 5,856,188, 5,866,701, 5,869,339, and 6,022,962), and tetrahymena ribozymes (for example, U.S. Pat. Nos. 5,595,873 and 5,652,107). There are also a number of ribozymes that are not found in natural systems, but which have been engineered to catalyze specific reactions de novo (for example, U.S. Pat. Nos. 5,580,967, 5,688,670, 5,807, 718, and 5,910,408). Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Representative examples of how to make and use ribozymes to catalyze a variety of different reactions can be found in U.S. Pat. Nos. 5,646,042, 5,693,535, 5,731,295, 5,811,300, 5,837, 855, 5,869,253, 5,877,021, 5,877,022, 5,972,699, 5,972,704, 5,989,906, and 6,017,756.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependant on both Watson-Crick and Hoogsteen base-pairing. Triplex molecules are preferred because they can bind target regions with high affinity and specificity. It is preferred that the triplex forming molecules bind the target molecule with a Kd less than 10-6, 10-8, 10-10, or 10-12. Representative examples of how to make and use triplex forming molecules to bind a variety of different target molecules can be found in U.S. Pat. Nos. 5,176,996, 5,645,985, 5,650,316, 5,683,874, 5,693,773, 5,834,185, 5,869,246, 5,874,566, and 5,962,426.

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. (WO 92/03566 by Yale, and Forster and Altman, Science 238:407-409 (1990)).

Similarly, eukaryotic EGS/RNAse P-directed cleavage of RNA can be utilized to cleave desired targets within eukarotic cells. (Yuan et al., Proc. Natl. Acad. Sci. USA 89:8006-8010 (1992); WO 93/22434 by Yale; WO 95/24489 by Yale; Yuan and Altman, EMBO J. 14:159-168 (1995), and Carrara et al., Proc. Natl. Acad. Sci. (USA) 92:2627-2631 (1995)). Representative examples of how to make and use EGS molecules to facilitate cleavage of a variety of different target molecules be found in U.S. Pat. Nos. 5,168,053, 5,624,824, 5,683,873, 5,728,521, 5,869,248, and 5,877,162.

Gene expression can also be effectively silenced in a highly specific manner through RNA interference (RNAi). This silencing was originally observed with the addition of double stranded RNA (dsRNA) (Fire, A., et al. (1998) Nature, 391: 806-11; Napoli, C., et al. (1990) Plant Cell 2:279-89; Hannon, G. J. (2002) Nature, 418:244-51). Once dsRNA enters a cell, it is cleaved by an RNase III-like enzyme, Dicer, into double stranded small interfering RNAs (siRNA) 21-23 nucleotides in length that contains 2 nucleotide overhangs on the 3' ends (Elbashir, S. M., et al. (2001) Genes Dev., 15:188-200; Bernstein, E., et al. (2001) Nature, 409:363-6; Hammond, S. M., et al. (2000) Nature, 404:293-6). In an ATP dependent step, the siRNAs become integrated into a multi-subunit protein complex, commonly known as the RNAi induced silencing complex (RISC), which guides the siRNAs to the target RNA sequence (Nykanen, A., et al. (2001) Cell, 107:309-21). At some point the siRNA duplex unwinds, and it appears that the antisense strand remains bound to RISC and directs degradation of the complementary mRNA sequence by a combination of endo and exonucleases (Martinez, J., et al. (2002) Cell, 110:563-74). However, the effect of iRNA or siRNA or their use is not limited to any type of mechanism.

Short Interfering RNA (siRNA) is a double-stranded RNA that can induce sequence-specific post-transcriptional gene silencing, thereby decreasing or even inhibiting gene expression. In one example, an siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends, herein incorporated by reference for the method of making these siRNAs. Sequence specific gene silencing can be achieved in mammalian cells using synthetic, short double-stranded RNAs that mimic the siRNAs produced by the enzyme dicer (Elbashir, S. M., et al. (2001) Nature, 411:494 498) (Ui-Tei, K., et al. (2000) FEBS Lett 479:79-82). siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's SILENCER® siRNA Construction Kit. Disclosed herein are any siRNA designed as described above based on the sequences for PAX2.

The production of siRNA from a vector is more commonly done through the transcription of a short hairpin RNAs (shRNAs). Kits for the production of vectors comprising shRNA are available, such as, for example, Imgenex's GENESUPPRESSOR™ Construction Kits and Invitrogen's BLOCK-ITT™ inducible RNAi plasmid and lentivirus vectors. Disclosed herein are any shRNA designed as described above based on the sequences for the herein disclosed inflammatory mediators.

6. Cell Delivery Systems

There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991) Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

i. Nucleic Acid Based Delivery Systems

Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)).

As used herein, plasmid or viral vectors are agents that transport the disclosed nucleic acids, such as PAX2 siRNA into the cell without degradation and include a promoter yielding expression of the gene in the cells into which it is delivered. In some embodiments the vectors are derived from either a virus or a retrovirus. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors can have higher transaction (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

a. Retroviral Vectors

A retrovirus is an animal virus belonging to the virus family of Retroviridae, including any types, subfamilies, genus, or tropisms. Retroviral vectors, in general, are described by Verma, I. M., Retroviral vectors for gene transfer. In Microbiology-1985, American Society for Microbiology, pp. 229-232, Washington, (1985), which is incorporated by reference herein. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

b. Adenoviral Vectors

The construction of replication-defective adenoviruses has been described (Berkner et al., J. Virology 61:1213-1220 (1987); Massie et al., Mol. Cell. Biol. 6:2872-2883 (1986); Haj-Ahmad et al., J. Virology 57:267-274 (1986); Davidson et al., J. Virology 61:1226-1239 (1987); Zhang "Generation and identification of recombinant adenovirus by liposome-mediated transfection and PCR analysis" BioTechniques 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, J. Clin. Invest. 92:1580-1586 (1993); Kirshenbaum, J. Clin. Invest. 92:381-387 (1993); Roessler, J. Clin. Invest. 92:1085-1092 (1993); Moullier, Nature Genetics 4:154-159 (1993); La Salle, Science 259:988-990 (1993); Gomez-Foix, J. Biol. Chem. 267:25129-25134 (1992); Rich, Human Gene Therapy 4:461-476 (1993); Zabner, Nature Genetics 6:75-83 (1994); Guzman, Circulation Research 73:1201-1207 (1993); Bout, Human Gene Therapy 5:3-10 (1994); Zabner, Cell 75:207-216 (1993); Caillaud, Eur. J. Neuroscience 5:1287-1291 (1993); and Ragot, J. Gen. Virology 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, Virology 40:462-477 (1970); Brown and Burlingham, J. Virology 12:386-396 (1973); Svensson and Persson, J. Virology 55:442-449 (1985); Seth, et al., J. Virol. 51:650-655 (1984); Seth, et al., Mol. Cell. Biol. 4:1528-1533 (1984); Varga et al., J. Virology 65:6061-6070 (1991); Wickham et al., Cell 73:309-319 (1993)).

A viral vector can be one based on an adenovirus which has had the E1 gene removed and these virons are generated in a cell line such as the human 293 cell line. In another preferred embodiment both the E1 and E3 genes are removed from the adenovirus genome.

c. Adeno-Associated Viral Vectors

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorproated by reference for material related to the AAV vector.

The disclosed vectors thus provide DNA molecules which are capable of integration into a mammalian chromosome without substantial toxicity.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

d. Large Payload Viral Vectors

Molecular genetic experiments with large human herpesviruses have provided a means whereby large heterologous DNA fragments can be cloned, propagated and established in cells permissive for infection with herpesviruses (Sun et al., Nature genetics 8: 33-41, 1994; Cotter and Robertson, Curr Opin Mol Ther 5: 633-644, 1999). These large DNA viruses (herpes simplex virus (HSV) and Epstein-Barr virus (EBV), have the potential to deliver fragments of human heterologous DNA>150 kb to specific cells. EBV recombinants can maintain large pieces of DNA in the infected B-cells as episomal DNA. Individual clones carried human genomic inserts up to 330 kb appeared genetically stable The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA>220 kb and to infect cells that can stably maintain DNA as episomes.

Other useful systems include, for example, replicating and host-restricted non-replicating vaccinia virus vectors.

ii. Non-Nucleic Acid Based Systems

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. Am. J. Resp. Cell. Mol. Biol. 1:95-100 (1989); Feigner et al. Proc. Natl. Acad. Sci. USA 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., Bioconjugate Chem., 2:447-451, (1991); Bagshawe, K. D., Br. J. Cancer, 60:275-281, (1989); Bagshawe, et al., Br. J. Cancer, 58:700-703, (1988); Senter, et al., Bioconjugate Chem., 4:3-9, (1993); Battelli, et al., Cancer Immunol. Immunother., 35:421-425, (1992); Pietersz and McKenzie, Immunolog. Reviews, 129: 57-80, (1992); and Roffler, et al., Biochem. Pharmacol, 42:2062-2065, (1991)). These techniques can be used for a variety of other specific cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., Cancer Research, 49:6214-6220, (1989); and Litzinger and Huang, Biochimica et Biophysica Acta, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

Nucleic acids that are delivered to cells which are to be integrated into the host cell genome, typically contain integration sequences. These sequences are often viral related sequences, particularly when viral based systems are used. These viral intergration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

iii. In Vivo/Ex Vivo

As described above, the compositions can be administered in a pharmaceutically acceptable carrier and can be delivered to the subject=s cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

7. Kits

The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits for detecting, treating, or preventing prostate cancer or PIN, the kit comprising peptides or antibodies that specifically bind PAX2 and DEFB1.

8. Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

i. Viral Promoters and Enhancers

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., Nature, 273: 113 (1978)). The immediate early promoter of the human cytomegalovirus is conveniently obtained as a HindIII E restriction fragment (Greenway, P. J. et al., Gene 18: 355-360 (1982)). Of course, promoters from the host cell or related species also are useful herein.

Enhancer generally refers to a sequence of DNA that functions at no fixed distance from the transcription start site and can be either 5' (Laimins, L. et al., Proc. Natl. Acad. Sci. 78: 993 (1981)) or 3' (Lusky, M. L., et al., Mol. Cell Bio. 3: 1108 (1983)) to the transcription unit. Furthermore, enhancers can be within an intron (Banerji, J. L. et al., Cell 33: 729 (1983)) as well as within the coding sequence itself (Osborne, T. F., et al., Mol. Cell Bio. 4: 1293 (1984)). They are usually between 10 and 300 by in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, -fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contain a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

ii. Markers

The viral vectors can include nucleic acid sequence encoding a marker product. This marker product is used to determine if the gene has been delivered to the cell and once delivered is being expressed. Preferred marker genes are the E. Coli lacZ gene, which encodes β-galactosidase, and green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., J. Molec. Appl. Genet. 1: 327 (1982)), mycophenolic acid, (Mulligan, R. C. and Berg, P. Science 209: 1422 (1980)) or hygromycin, (Sugden, B. et al., Mol. Cell. Biol. 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

9. Pharmaceutical Carriers

The disclosed compositions can be used therapeutically in combination with a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Suitable carriers and their formulations are described in Remington: The Science and Practice of Pharmacy (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., Bioconjugate Chem., 2:447-451, (1991); Bagshawe, K. D., Br. J. Cancer, 60:275-281, (1989); Bagshawe, et al., Br. J. Cancer, 58:700-703, (1988); Senter, et al., Bioconjugate Chem., 4:3-9, (1993); Battelli, et al., Cancer Immunol. Immunother., 35:421-425, (1992); Pietersz and McKenzie, Immunolog. Reviews, 129: 57-80, (1992); and Roffler, et al., Biochem. Pharmacol, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., Cancer Research, 49:6214-6220, (1989); and Litzinger and Huang, Biochimica et Biophysica Acta, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

10. Combinatorial Chemistry

The disclosed compositions can be used as targets for any combinatorial technique to identify molecules or macromolecular molecules that interact with the disclosed compositions in a desired way. Also disclosed are the compositions that are identified through combinatorial techniques or screening techniques in which the compositions disclosed as the PAX2 sequence or portions thereof (e.g., PAX2 DNA-binding domain), are used as the target in a combinatorial or screening protocol.

It is understood that when using the disclosed compositions in combinatorial techniques or screening methods, molecules, such as macromolecular molecules, will be identified that have particular desired properties such as inhibition or stimulation or the target molecule's function. The molecules identified and isolated when using the disclosed compositions, such as, DEFB1 or PAX2, are also disclosed. Thus, the products produced using the combinatorial or screening approaches that involve the disclosed compositions are also considered herein disclosed.

It is understood that the disclosed methods for identifying molecules that inhibit the interactions between, for example, DEFB1 promoter and PAX2 can be performed using high through put means. For example, putative inhibitors can be identified using Fluorescence Resonance Energy Transfer (FRET) to quickly identify interactions. The underlying theory of the techniques is that when two molecules are close in space, ie, interacting at a level beyond background, a signal is produced or a signal can be quenched. Then, a variety of experiments can be performed, including, for example, adding in a putative inhibitor. If the inhibitor competes with the interaction between the two signaling molecules, the signals will be removed from each other in space, and this will cause a decrease or an increase in the signal, depending on the type of signal used. This decrease or increasing signal can be correlated to the presence or absence of the putative inhibitor. Any signaling means can be used. For example, disclosed are methods of identifying an inhibitor of the interaction between any two of the disclosed molecules comprising, contacting a first molecule and a second molecule together in the presence of a putative inhibitor, wherein the first molecule or second molecule comprises a fluorescence donor, wherein the first or second molecule, typically the molecule not comprising the donor, comprises a fluorescence acceptor; and measuring Fluorescence Resonance Energy Transfer (FRET), in the presence of the putative inhibitor and the in absence of the putative inhibitor, wherein a decrease in FRET in the presence of the putative inhibitor as compared to FRET measurement in its absence indicates the putative inhibitor inhibits binding between the two molecules. This type of method can be performed with a cell system as well.

Combinatorial chemistry includes but is not limited to all methods for isolating small molecules or macromolecules that are capable of binding either a small molecule or another macromolecule, typically in an iterative process. Proteins, oligonucleotides, and sugars are examples of macromolecules. For example, oligonucleotide molecules with a given function, catalytic or ligand-binding, can be isolated from a complex mixture of random oligonucleotides in what has been referred to as "in vitro genetics" (Szostak, TIBS 19:89, 1992). One synthesizes a large pool of molecules bearing random and defined sequences and subjects that complex mixture, for example, approximately 1015 individual sequences in 100 μg of a 100 nucleotide RNA, to some selection and enrichment process. Through repeated cycles of affinity chromatography and PCR amplification of the molecules bound to the ligand on the column, Ellington and Szostak (1990) estimated that 1 in 1010 RNA molecules folded in such a way as to bind a small molecule dyes. DNA molecules with such ligand-binding behavior have been isolated as well (Ellington and Szostak, 1992; Bock et al, 1992). Techniques aimed at similar goals exist for small organic molecules, proteins, antibodies and other macromolecules known to those of skill in the art. Screening sets of molecules for a desired activity whether based on small organic libraries, oligonucleotides, or antibodies is broadly referred to as combinatorial chemistry. Combinatorial techniques are particularly suited for defining binding interactions between molecules and for isolating molecules that have a specific binding activity, often called aptamers when the macromolecules are nucleic acids.

There are a number of methods for isolating proteins which either have de novo activity or a modified activity. For example, phage display libraries have been used to isolate numerous peptides that interact with a specific target. (See for example, U.S. Pat. Nos. 6,031,071; 5,824,520; 5,596,079; and 5,565,332 which are herein incorporated by reference at least for their material related to phage display and methods relate to combinatorial chemistry)

A preferred method for isolating proteins that have a given function is described by Roberts and Szostak (Roberts R. W. and Szostak J. W. Proc. Natl. Acad. Sci. USA, 94(23)12997-302 (1997). This combinatorial chemistry method couples the functional power of proteins and the genetic power of nucleic acids. An RNA molecule is generated in which a puromycin molecule is covalently attached to the 3'-end of the RNA molecule. An in vitro translation of this modified RNA molecule causes the correct protein, encoded by the RNA to be translated. In addition, because of the attachment of the puromycin, a peptidyl acceptor which cannot be extended, the growing peptide chain is attached to the puromycin which is attached to the RNA. Thus, the protein molecule is attached to the genetic material that encodes it. Normal in vitro selection procedures can now be done to isolate functional peptides. Once the selection procedure for peptide function is complete traditional nucleic acid manipulation procedures are performed to amplify the nucleic acid that codes for the selected functional peptides. After amplification of the genetic material, new RNA is transcribed with puromycin at the 3'-end, new peptide is translated and another functional round of selection is performed. Thus, protein selection can be performed in an iterative manner just like nucleic acid selection techniques. The peptide which is translated is controlled by the sequence of the RNA attached to the puromycin. This sequence can be anything from a random sequence engineered for optimum translation (i.e. no stop codons etc.) or it can be a degenerate sequence of a known RNA molecule to look for improved or altered function of a known peptide. The conditions for nucleic acid amplification and in vitro translation are well known to those of ordinary skill in the art and are preferably performed as in Roberts and Szostak (Roberts R. W. and Szostak J. W. Proc. Natl. Acad. Sci. USA, 94(23) 12997-302 (1997)).

Another preferred method for combinatorial methods designed to isolate peptides is described in Cohen et al. (Cohen B. A., et al., Proc. Natl. Acad. Sci. USA 95(24):14272-7 (1998)). This method utilizes and modifies two-hybrid technology. Yeast two-hybrid systems are useful for the detection and analysis of protein:protein interactions. The two-hybrid system, initially described in the yeast *Saccharomyces cerevisiae*, is a powerful molecular genetic technique for identifying new regulatory molecules, specific to the protein of interest (Fields and Song, Nature 340:245-6 (1989)). Cohen et al., modified this technology so that novel interactions between synthetic or engineered peptide sequences could be identified which bind a molecule of choice. The benefit of this type of technology is that the selection is done in an intracellular environment. The method utilizes a library of peptide molecules that attached to an acidic activation domain.

Using methodology well known to those of skill in the art, in combination with various combinatorial libraries, one can isolate and characterize those small molecules or macromolecules, which bind to or interact with the desired target. The relative binding affinity of these compounds can be compared and optimum compounds identified using competitive binding studies, which are well known to those of skill in the art.

Techniques for making combinatorial libraries and screening combinatorial libraries to isolate molecules which bind a desired target are well known to those of skill in the art. Representative techniques and methods can be found in but are not limited to U.S. Pat. Nos. 5,084,824, 5,288,514, 5,449, 754, 5,506,337, 5,539,083, 5,545,568, 5,556,762, 5,565,324, 5,565,332, 5,573,905, 5,618,825, 5,619,680, 5,627,210, 5,646,285, 5,663,046, 5,670,326, 5,677,195, 5,683,899, 5,688,696, 5,688,997, 5,698,685, 5,712,146, 5,721,099, 5,723,598, 5,741,713, 5,792,431, 5,807,683, 5,807,754, 5,821,130, 5,831,014, 5,834,195, 5,834,318, 5,834,588, 5,840,500, 5,847,150, 5,856,107, 5,856,496, 5,859,190, 5,864,010, 5,874,443, 5,877,214, 5,880,972, 5,886,126, 5,886,127, 5,891,737, 5,916,899, 5,919,955, 5,925,527, 5,939,268, 5,942,387, 5,945,070, 5,948,696, 5,958,702, 5,958,792, 5,962,337, 5,965,719, 5,972,719, 5,976,894, 5,980,704, 5,985,356, 5,999,086, 6,001,579, 6,004,617, 6,008,321, 6,017,768, 6,025,371, 6,030,917, 6,040,193, 6,045,671, 6,045,755, 6,060,596, and 6,061,636.

Combinatorial libraries can be made from a wide array of molecules using a number of different synthetic techniques. For example, libraries containing fused 2,4-pyrimidinediones (U.S. Pat. No. 6,025,371) dihydrobenzopyrans (U.S. Pat. Nos. 6,017,768 and 5,821,130), amide alcohols (U.S. Pat. No. 5,976,894), hydroxy-amino acid amides (U.S. Pat. No. 5,972, 719) carbohydrates (U.S. Pat. No. 5,965,719), 1,4-benzodiazepin-2,5-diones (U.S. Pat. No. 5,962,337), cyclics (U.S. Pat. No. 5,958,792), biaryl amino acid amides (U.S. Pat. No. 5,948,696), thiophenes (U.S. Pat. No. 5,942,387), tricyclic Tetrahydroquinolines (U.S. Pat. No. 5,925,527), benzofurans (U.S. Pat. No. 5,919,955), isoquinolines (U.S. Pat. No. 5,916, 899), hydantoin and thiohydantoin (U.S. Pat. No. 5,859,190), indoles (U.S. Pat. No. 5,856,496), imidazol-pyrido-indole and imidazol-pyrido-benzothiophenes (U.S. Pat. No. 5,856, 107) substituted 2-methylene-2,3-dihydrothiazoles (U.S. Pat. No. 5,847,150), quinolines (U.S. Pat. No. 5,840,500), PNA (U.S. Pat. No. 5,831,014), containing tags (U.S. Pat. No. 5,721,099), polyketides (U.S. Pat. No. 5,712,146), morpholino-subunits (U.S. Pat. Nos. 5,698,685 and 5,506,337), sulfamides (U.S. Pat. No. 5,618,825), and benzodiazepines (U.S. Pat. No. 5,288,514).

Screening molecules similar to the disclosed siRNA molecules for inhibition of PAX2 suppression of DEFB1 expression is a method of isolating desired compounds.

Molecules isolated which can either be competitive inhibitors or non-competitive inhibitors.

In another embodiment the inhibitors are non-competitive inhibitors. One type of non-competitive inhibitor will cause allosteric rearrangements.

As used herein combinatorial methods and libraries included traditional screening methods and libraries as well as methods and libraries used in iterative processes.

11. Computer Assisted Drug Design

The disclosed compositions can be used as targets for any molecular modeling technique to identify either the structure of the disclosed compositions or to identify potential or actual molecules, such as small molecules, which interact in a desired way with the disclosed compositions. The nucleic acids, peptides, and related molecules disclosed herein can be used as targets in any molecular modeling program or approach.

It is understood that when using the disclosed compositions in modeling techniques, molecules, such as macromolecular molecules, will be identified that have particular desired properties such as inhibition or stimulation of the target molecule's function. The molecules identified and isolated when using the disclosed compositions, such as, SEQ ID NO:1, are also disclosed. Thus, the products produced using the molecular modeling approaches that involve the disclosed compositions, such as, SEQ ID NO:1, are also considered herein disclosed.

Thus, one way to isolate molecules that bind a molecule of choice is through rational design. This is achieved through structural information and computer modeling. Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 Acta Pharmaceutica Fennica 97, 159-166; Ripka, New Scientist 54-57 (Jun. 16, 1988); McKinaly and Rossmann, 1989 Annu. Rev. Pharmacol. Toxiciol. 29, 111-122; Perry and Davies, QSAR: Quantitative Structure-Activity Relationships in Drug Design pp. 189-193 (Alan R. Liss, Inc. 1989); Lewis and Dean, 1989 Proc. R. Soc. Lond. 236, 125-140 and 141-162; and, with respect to a model enzyme for nucleic acid components, Askew, et al., 1989 J. Am. Chem. Soc. 111, 1082-1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of molecules specifically interacting with specific regions of DNA or RNA, once that region is identified.

Although described above with reference to design and generation of compounds which could alter binding, one could also screen libraries of known compounds, including natural products or synthetic chemicals, and biologically active materials, including proteins, for compounds which alter substrate binding or enzymatic activity.

12. Computer Readable Mediums

It is understood that the disclosed nucleic acids and proteins can be represented as a sequence consisting of the nucleotides of amino acids. There are a variety of ways to display these sequences, for example the nucleotide guanosine can be represented by G or g. Likewise the amino acid valine can be represented by Val or V. Those of skill in the art understand how to display and express any nucleic acid or protein sequence in any of the variety of ways that exist, each of which is considered herein disclosed. Specifically contemplated herein is the display of these sequences on computer readable mediums, such as, commercially available floppy disks, tapes, chips, hard drives, compact disks, and video disks, or other computer readable mediums. Also disclosed are the binary code representations of the disclosed sequences. Those of skill in the art understand what computer readable mediums. Thus, computer readable mediums on which the nucleic acids or protein sequences are recorded, stored, or saved.

Disclosed are computer readable mediums comprising the sequences and information regarding the sequences set forth herein. Also disclosed are computer readable mediums comprising the sequences and information regarding the sequences set forth.

C. Methods

1. Administration

A composition disclosed herein may be administered in a number of ways depending on whether local or systemic treatment is desired, and on the area to be treated. For example, the compositions may be administered orally, parenterally (e.g., intravenous, subcutaneous, intraperitoneal, or intramuscular injection), by inhalation, extracorporeally, topically (including transdermally, ophthalmically, vaginally, rectally, intranasally) or the like.

As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. Thus, effective dosages and schedules for administering the compositions may be determined empirically, and making such determinations is within the skill in the art. The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be deter mined by one of skill in the art. The dosage can be adjusted by the individual physician in the event of any counter indications. Dosage can vary, and can be administered in one or more dose administrations daily, for one or several days. Guidance can be found in the literature for appropriate dosages for given classes of pharmaceutical products.

For example, a typical daily dosage of the disclosed composition used alone might range from about 1 µg/kg to up to 100 mg/kg of body weight or more per day, depending on the factors mentioned above.

Following administration of a disclosed composition for treating, inhibiting, or preventing prostate cancer or PIN, the efficacy of the therapeutic can be assessed in various ways well known to the skilled practitioner. For instance, one of ordinary skill in the art will understand that a composition disclosed herein is efficacious in treating or inhibiting prostate cancer in a subject by observing that the composition reduces PSA antigen or prevents a further increase in size of prostate tumor. PSA antigen can be measured by methods that are known in the art, for example, using antibody assays to detect the presence of PSA protein in a sample (e.g., but not limited to, blood) from a subject or patient, or by measuring the level of circulating PSA levels in the patient.

The compositions that inhibit the interactions disclosed herein may be administered prophylactically to patients or subjects who are at risk for prostate cancer or who have been newly diagnosed with PIN or prostate cancer.

Other molecules that interact with PSA or DEFB1 to inhibit the interactions which do not have a specific pharmaceutical function, but which may be used for tracking changes within cellular chromosomes or for the delivery of diagnostic tools for example can be delivered in ways similar to those described for the pharmaceutical products.

2. Making

The compositions disclosed herein and the compositions necessary to perform the disclosed methods can be made using any method known to those of skill in the art for that particular reagent or compound unless otherwise specifically noted.

i. Nucleic Acid Synthesis

For example, the nucleic acids, such as, the oligonucleotides to be used as primers can be made using standard chemical synthesis methods or can be produced using enzymatic methods or any other known method. Such methods can range from standard enzymatic digestion followed by nucleotide fragment isolation (see for example, Sambrook et al., Molecular Cloning: A Laboratory Manual, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1 Plus DNA synthesizer (for example, Model 8700 automated synthesizer of Milligen-Biosearch, Burlington, Mass. or ABI Model 380B). Synthetic methods useful for making oligonucleotides are also described by Ikuta et al., Ann. Rev. Biochem. 53:323-356 (1984), (phosphotriester and phosphite-triester methods), and Narang et al., Methods Enzymol., 65:610-620 (1980), (phosphotriester method). Protein nucleic acid molecules can be made using known methods such as those described by Nielsen et al., Bioconjug. Chem. 5:3-7 (1994).

ii. Peptide Synthesis

One method of producing the disclosed proteins, such as SEQ ID NO: 49, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

D. Definitions

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents.

It must be noted that as used herein and in the appended claims, the singular forms "a," "an," and "the" include plural reference unless the context clearly dictates otherwise. Thus, for example, reference to "a peptide" includes a plurality of such peptides, reference to "the peptide" is a reference to one or more peptides and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Throughout the description and claims of this specification, the word "comprise" and variations of the word, such as "comprising" and "comprises," means "including but not limited to," and is not intended to exclude, for example, other additives, components, integers or steps.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

E. Examples

1. Example 1

Human Beta Defensin-1 is Cytotoxic to Late-Stage Prostate Cancer and Plays a Role in Prostate Cancer Tumor Immunity Abstract DEFB1 was cloned into an inducible expression system to examine what effect it had on normal prostate epithelial cells, as well as androgen receptor positive (AR+) and androgen receptor negative (AR−) prostate cancer cell lines. Induction of DEFB1 expression resulted in a decrease in cellular growth in AR− cells DU145 and PC3, but had no effect on the growth of the AR+ prostate cancer cells LNCaP. DEFB1 also caused rapid induction of caspase-mediated apoptosis. Data presented here are the first to provide evidence of its role in innate tumor immunity and indicate that its loss contributes to tumor progression in prostate cancer.

Materials and Methods

Cell Lines: The cell lines DU145 were cultured in DMEM medium, PC3 were grown in F12 medium, and LNCaP were grown in RPMI medium (Life Technologies, Inc., Grand Island, N.Y.). Growth media for all three lines was supplemented with 10% (v/v) fetal bovine serum (Life Technologies). The hPrEC cells were cultured in prostate epithelium basal media (Cambrex Bio Science, Inc., Walkersville, Md.). All cell lines were maintained at 37° C. and 5% CO2.

Tissue Samples and Laser Capture Microdissection: Prostate tissues obtained from consented patients that underwent radical prostatectomy were acquired through the Hollings Cancer Center tumor bank in accordance with an Institutional Review Board-approved protocol. This included guidelines for the processing, sectioning, histological characterization, RNA purification and PCR amplification of samples. Following pathologic examination of frozen tissue sections, laser capture microdissection (LCM) was performed to ensure that the tissue samples assayed consisted of pure populations of benign prostate cells. For each tissue section analyzed, LCM was performed at three different regions containing benign tissue and the cells collected were then pooled.

Cloning of DEFB1 Gene: DEFB1 cDNA was generated from RNA by reverse transcription-PCR. The PCR primers were designed to contain ClaI and KpnI restriction sites. DEFB1 PCR products were restriction digested with ClaI and KpnI and ligated into a TA cloning vector. The TA/DEFB1 vector was then transfected into E. coli by heat shock and individual clones were selected and expanded. Plasmids were isolated by Cell Culture DNA Midiprep (Qiagen, Valencia, Calif.) and sequence integrity verified by automated sequencing. The DEFB1 gene fragment was then ligated into the pTRE2 digested with ClaI and KpnI, which served as an intermediate vector for orientation purposes. Then the pTRE2/DEFB1 construct was digested with ApaI and KpnI to excise the DEFB1 insert, which was ligated into pIND vector of the Ecdysone Inducible Expression System (Invitrogen, Carlsbad, Calif.) also double digested with ApaI and KpnI. The construct was again transfected into *E. coli* and individual clones were selected and expanded. Plasmids were isolated and sequence integrity of pIND/DEFB1 was again verified by automated sequencing.

Transfection: Cells ($1 \times 10^6$) were seeded onto 100-mm Petri dishes and grown overnight. Then the cells were co-transfected using Lipofectamine 2000 (Invitrogen, Carlsbad, Calif.) with 1 ps of pVgRXR plasmid, which expresses the heterodimeric ecdysone receptor, and 1 µg of the pIND/DEFB1 vector construct or empty pIND control vector in Opti-MEM media (Life Technologies, Inc., Grand Island, N.Y.).

RNA Isolation and Quantitative RT-PCR: In order to verify DEFB1 protein expression in the cells transfected with DEFB1 construct, RNA was collected after a 24 hour induction period with Ponasterone A (Pon A). Briefly, total RNA was isolated using the SV Total RNA Isolation System (Promega, Madison, Wis.) from approximately $1 \times 10^6$ cells harvested by trypsinizing. Here, cells were lysed and total RNA was isolated by centrifugation through spin columns. For cells collected by LCM, total RNA was isolated using the PicoPure RNA Isolation Kit (Arcturus Biosciences, Mt. View, Calif.) following the manufacturer's protocol. Total RNA (0.5 µg per reaction) from both sources was reverse transcribed into cDNA utilizing random primers (Promega). AMV Reverse Transcriptase II enzyme (500 units per reaction; Promega) was used for first strand synthesis and Tfl DNA Polymerase for second strand synthesis (500 units per reaction; Promega) as per the manufacturer's protocol. In each case, 50 pg of cDNA was used per ensuing PCR reaction. Two-step QRT-PCR was performed on cDNA generated using the MultiScribe Reverse Transcripatase from the TaqMan Reverse Transcription System and the SYBR Green PCR Master Mix (Applied Biosystems).

The primer pair for DEFB1 (Table 2) was generated from the published DEFB1 sequence (GenBank Accession No. U50930). Forty cycles of PCR were performed under standard conditions using an annealing temperature of 56° C. In addition, β-actin (Table 2) was amplified as a housekeeping gene to normalize the initial content of total cDNA. DEFB1 expression was calculated as the relative expression ratio between DEFB1 and β-actin and was compared in cells lines induced and uninduced for DEFB1 expression, as well as LCM benign prostatic tissue. As a negative control, QRT-PCR reactions without cDNA template were also performed. All reactions were run three times in triplicate.

MTT Cell Viability Assay: To examine the effects of DEFB1 on cell growth, metabolic 3-[4,5-dimethylthiazol-2-yl]-2,5 diphenyl tetrazolium bromide (MTT) assays were performed. PC3, DU145 and LNCaP cells co-transfected with pVgRXR plasmid and pIND/DEFB1 construct or empty pIND vector were seeded onto a 96-well plate at $1-5 \times 10^3$ cells per well. Twenty-four hours after seeding, fresh growth medium was added containing 10 µM Ponasterone A daily to induce DEFB1 expression for 24-, 48- and 72 hours after which the MTT assay was performed according to the manufacturer's instructions (Promega). Reactions were performed three times in triplicate.

Flow Cytometry: PC3 and DU145 cells co-transfected with the DEFB1 expression system were grown in 60-mm dishes and induced for 12, 24, and 48 hours with 10 µM Ponasterone A. Following each incubation period, the medium was collected from the plates (to retain any detached cells) and combined with PBS used to wash the plates. The remaining attached cells were harvested by trypsinization and combined with the detached cells and PBS. The cells were then pelleted at 4° C. (500×g) for 5 min, washed twice in PBS, and resuspended in 100 ul of 1× Annexin binding buffer (0.1 M Hepes/NaOH at pH 7.4, 1.4 M NaCl, 25 mM $CaCl_2$) containing 5 µl of Annexin V-FITC and 5 µl of PI. The cells were incubated at RT for 15 min in the dark, then diluted with 400 µl of 1× Annexin binding buffer and analyzed by FACscan (Becton Dickinson, San Jose, Calif.). All reactions were performed three times.

Microscopic Analysis: Cell morphology was analyzed by phase contrast microscopy. DU145, PC3 and LNCaP cells containing no vector, empty plasmid or DEFB1 plasmid were seeded onto 6 well culture plates (BD Falcon, USA). The following day plasmid-containing cells were induced for a period of 48 h with media containing 10 µM Ponasterone A, while control cells received fresh media. The cells were then viewed under an inverted Zeiss IM 35 microscope (Carl Zeiss, Germany). Phase contrast pictures of a field of cells were obtained using the SPOT Insight Mosaic 4.2 camera (Diagnostic Instruments, USA). Cells were examined by phase contrast microscopy under 32× magnification and digital images were stored as uncompressed TIFF files and exported into Photoshop CS software (Adobe Systems, San Jose, Calif.) for image processing and hard copy presentation.

Caspase Detection

Detection of caspase activity in the prostate cancer cell lines was performed using APO LOGIX™ Carboxyfluorescin Caspase detection kit (Cell Technology, Mountain View, Calif.). Active caspases were detected through the use of a FAM-VAD-FMK inhibitor that irreversibly binds to active caspases. Briefly, DU 145 and PC3 cells ($1.5-3 \times 10^5$) containing the DEFB1 expression system were plated in 35 mm glass bottom microwell dishes (Matek, Ashland, Mass.) and treated for 24 hours with media only or with media containing PonA as previously described. Next, 10 µl of a 30× working dilution of carboxyfluorescein labeled peptide fluoromethyl ketone (FAM-VAD-FMK) was added to 300 µl of media and added to each 35 mm dish. Cells were then incubated for 1 hour at 37° C. under 5% CO2. Then, the medium was aspirated and the cells were washed twice with 2 ml of a 1× Working dilution Wash Buffer. Cells were viewed under differential interference contrast (DIC) or under laser excitation at 488 nm. The fluorescent signal was analyzed using a confocal microscope (Zeiss LSM 5 Pascal) and a 63×DIC oil lens with a Vario 2 RGB Laser Scanning Module.

Statistical Analysis

Statistical differences were evaluated using the Student's t-test for unpaired values. P values were determined by a two-sided calculation, and a P value of less than 0.05 was considered statistically significant.

Results

Figure 1B:
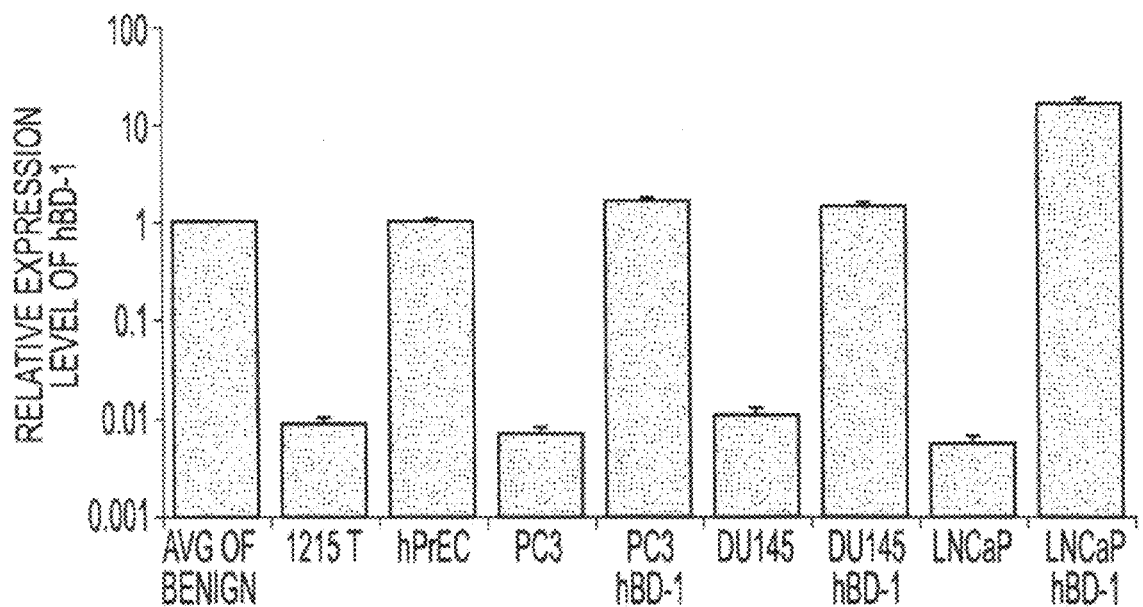
FIG. 1B shows DEFB1 relative expression levels compared in benign and malignant prostatic clinical samples, hPrEC cells and in prostate cancer cell lines before and after DEFB1 induction.

DEFB1 Expression in Prostate Tissue and Cell Lines: DEFB1 expression levels were measured by QRT-PCR in benign and malignant prostatic tissue, hPrEC prostate epithelial cells and DU145, PC3 and LNCaP prostate cancer cells. DEFB1 expression was detected in all of the benign clinical samples. The average amount of DEFB1 relative expression was 0.0073. In addition, DEFB1 relative expression in hPrEC cells was 0.0089. There was no statistical difference in DEFB1 expression detected in the benign prostatic tissue samples and hPrEC (FIG. 1A). Analysis of the relative DEFB1 expression levels in the prostate cancer cell lines revealed significantly lower levels in DU145, PC3 and LNCaP. As a further point of reference, relative DEFB1 expression was measured in the adjacent malignant section of prostatic tissue from patient #1215. There were no significant differences in the level of DEFB1 expression observed in the three prostate cancer lines compared to malignant prostatic tissue from patient #1215 (FIG. 1B). In addition, expression levels in all four samples were close to the no template negative controls which confirmed little to no endogenous DEFB1 expression (data not shown). QRT-PCR was also performed on the prostate cancer cell lines transfected with the DEFB1 expression system. Following a 24 hour induction period, relative expression levels were 0.01360 in DU145, 0.01503 in PC3 and 0.138 in LNCaP. Amplification products were verified by gel electrophoresis.

Figure 1C:
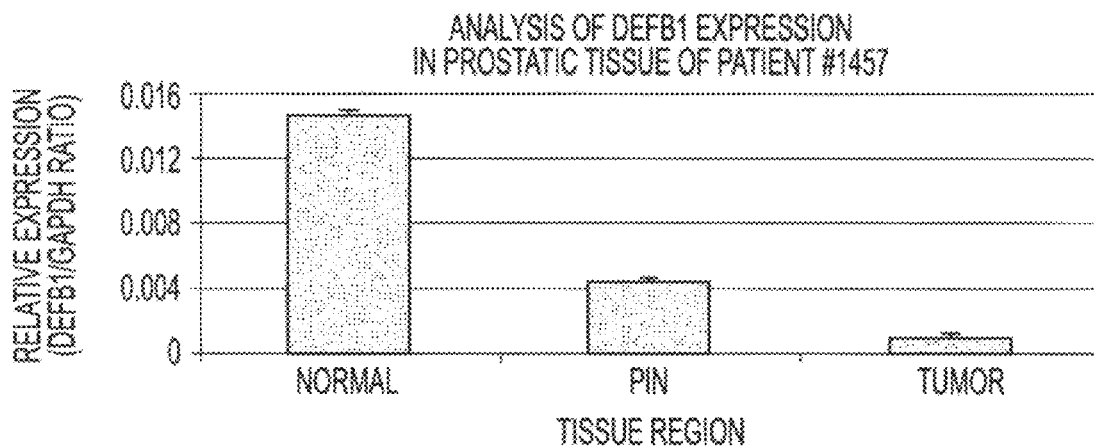
FIG. 1C shows DEFB1 relative expression levels analyzed in benign tissue, malignant tissue and prostate intraepithelial neoplasia (PIN) in a single tissue section.
Figure 1D:
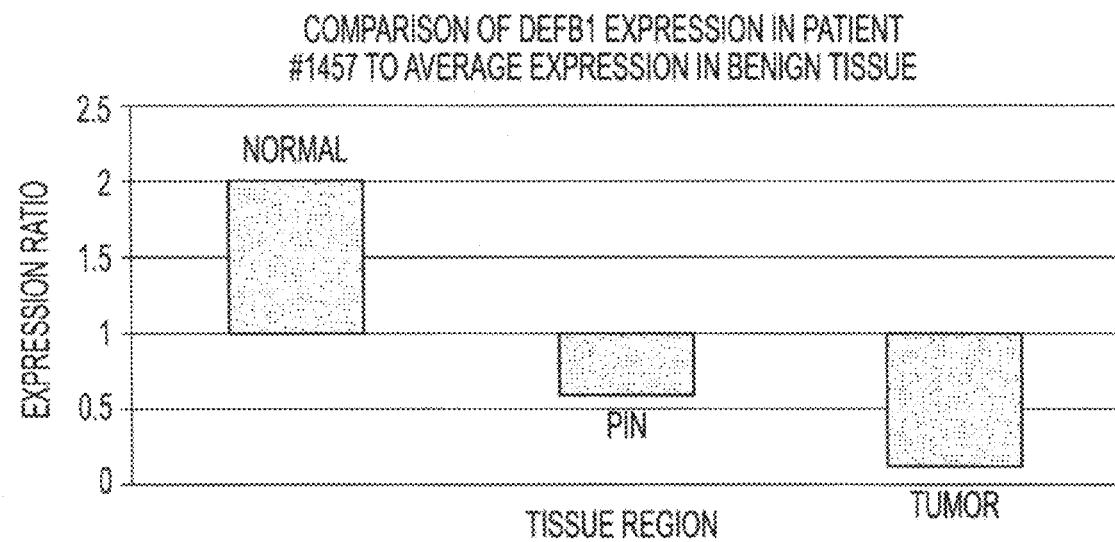
FIG. 1D shows DEFB1 expression in benign tissue, malignant tissue and PIN in one patient compared to the average DEFB1 expression level found in benign tissue.

QRT-PCR was performed on LCM tissues regions containing benign, PIN and cancer. DEFB1 relative expression was 0.0146 in the benign region compared to 0.0009 in the malignant region (FIG. 1C.). This represents a 94% decrease which again demonstrates a significant down-regulation of expression. Furthermore, analysis of PIN revealed that DEFB1 expression level was 0.044 which was a 70% decrease. Comparing expression in patient #1457 to the average expression level found in benign regions of six other patients (FIG. 1A.) revealed a ratio of 1.997 representing almost twice as much expression (FIG. 1D.). However, the expression ratio was 0.0595 in PIN and was 0.125 in malignant tissue compared to average expression levels in benign tissue.

Figure 2:
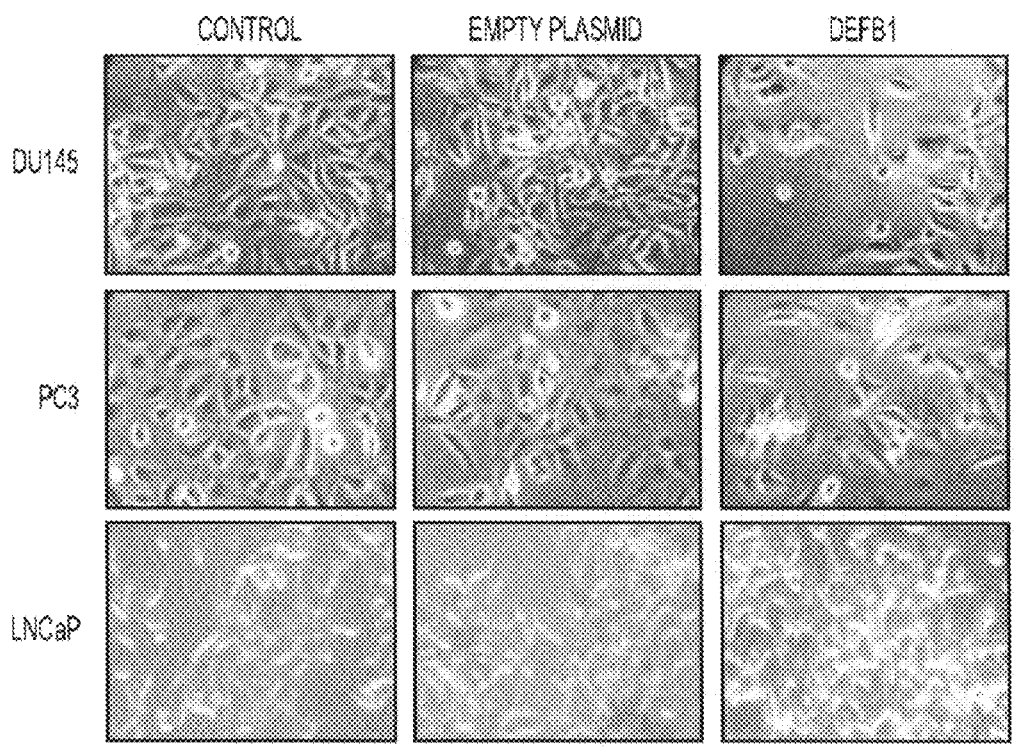
FIG. 2 shows microscopic analysis of DEFB1 induced changes in membrane integrity and cell morphology. Cell morphology of DU145, PC3 and LNCaP was analyzed by phase contrast microscopy after 48 hours of DEFB1 induction. Membrane ruffling is indicated by black arrows and apoptotic bodies are indicated white arrows.

DEFB1 Causes Cell Membrane Permeability and Ruffling: Induction of DEFB1 in the prostate cancer cell lines resulted in a significant reduction in cell number in DU145 and PC3, but had no effect on cell proliferation in LNCaP (FIG. 2). As a negative control, cell proliferation was monitored in all three lines containing empty plasmid. There were no observable changes in cell morphology in DU145, PC3 or LNCaP cells following the addition of PonA. In addition, DEFB1 induction resulted in morphological changes in both DU145 and PC3. Here cells appeared more rounded and exhibited membrane ruffling indicative of cell death. Apoptotic bodies were also present in both lines.

Figure 3:
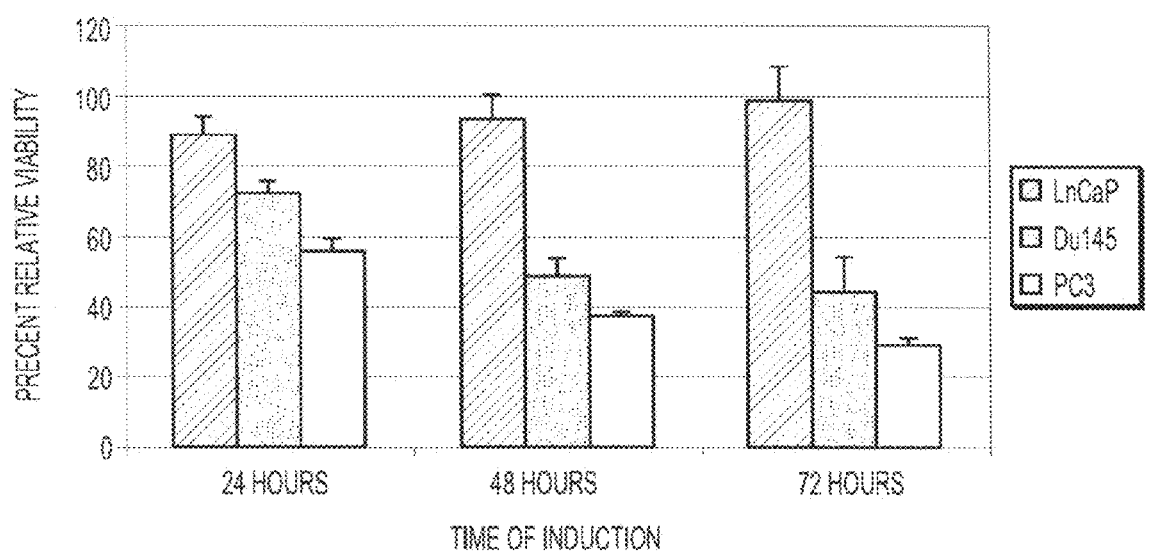
FIG. 3 shows analysis of DEFB1 Cytotoxicity in Prostate Cancer Cells. The prostate cell lines DU145, PC3 and LNCaP were treated with PonA to induce DEFB1 expression for 1-3 days after which MTT assay was performed to determine cell viability. Results represent mean±s.d., n=9.

Expression of DEFB1 Results in Decreased Cell Viability: The MTT assay showed a reduction in cell viability by DEFB1 in PC3 and DU145 cells, but no significant effect on LNCaP cells (FIG. 3). After 24 hours, relative cell viability was 72% in DU145 and 56% in PC3. Analysis 48 hours after induction revealed 49% cell viability in DU145 and 37% cell viability in PC3. After 72 hours of DEFB1 expression resulted in 44% and 29% relative cell viability in DU145 and PC3 cells, respectively.

Figure 4A:
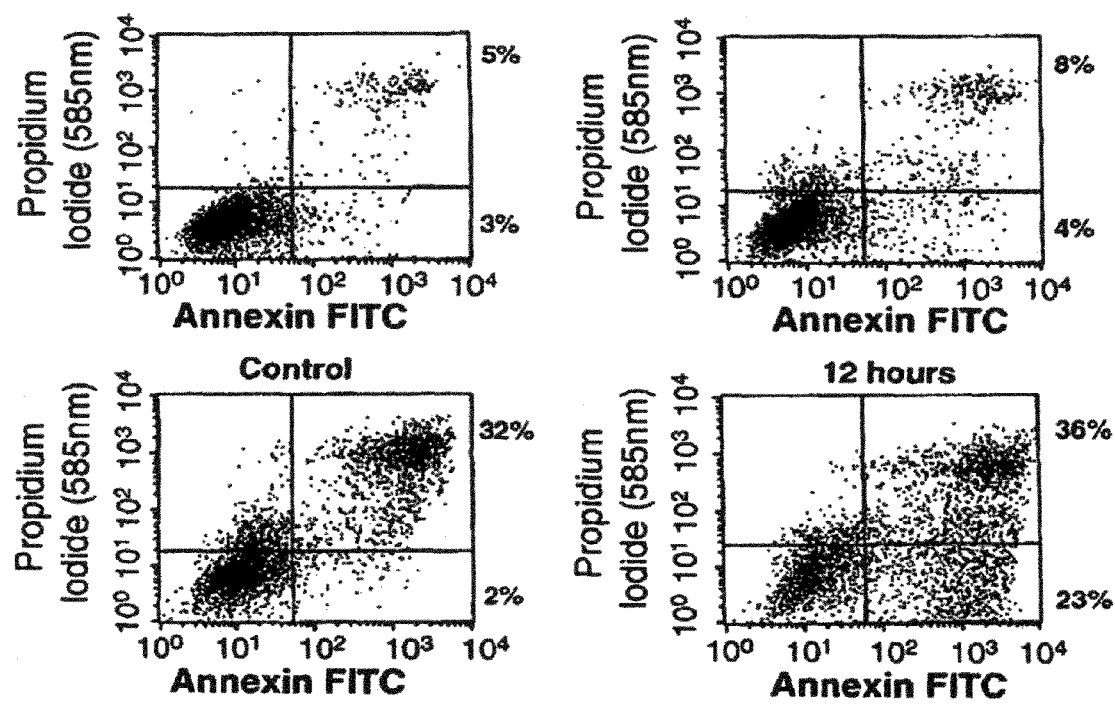
FIG. 4 shows induction of cell death in DU145 and PC3 cells by DEFB1. DEFB1 expression was induced in prostate cancer cell lines DU145 (A) and PC3 (B) and then subjected to annexin V/FITC/propidium iodide staining and flow cytometric analysis. Cells positive for propidium iodide and annexin V were considered apoptotic. Times of induction are shown under each panel. Numbers next to the boxes for each time point represent the percentages of propidium iodide (PI)$^-$ annexin V$^+$ cells (lower right quadrant), and PI$^+$ annexin V$^+$ cells (upper right quadrant). The data are from a single experiment that is representative of three separate experiments.
Figure 4B:
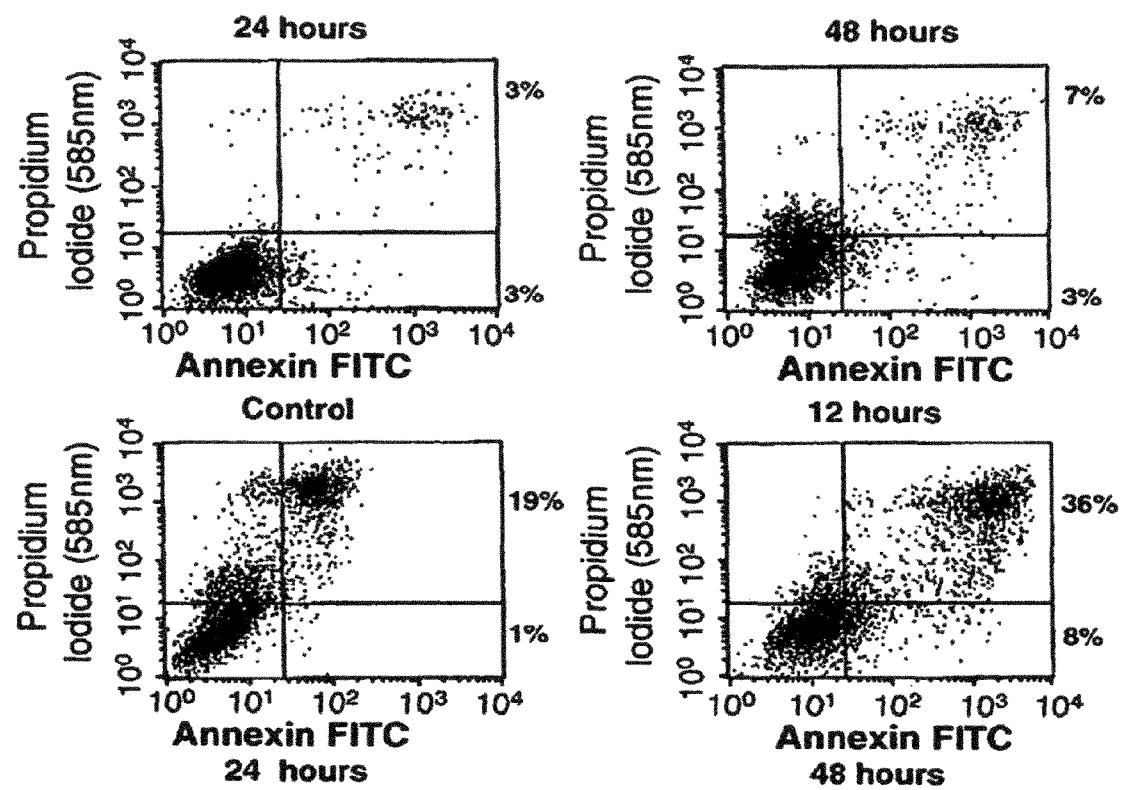

DEFB1 Causes Rapid Caspase-mediated Apoptosis in Late-stage Prostate Cancer Cells: In order to determine whether the effects of DEFB1 on PC3 and DU145 were cytostatic or cytotoxic, FACS analysis was performed. Under normal growth conditions, more than 90% of PC3 and DU145 cultures were viable and non-apoptotic (lower left quadrant) and did not stain with annexin V or PI (FIG. 4). After inducing DEFB1 expression in PC3 cells, the number of apoptotic cells (lower and upper right quadrants) totaled 10% at 12 hours, 20% at 24 hours, and 44% at 48 hours. For DU145 cells, the number of apoptotic cells totaled 12% after 12 hours, 34% at 24 hours, and 59% after 48 hours of induction. There was no increase in apoptosis observed in cells containing empty plasmid following induction with PonA (data not shown).

Caspase activity was determined by confocal laser microscopic analysis (FIG. 5). DU145 and PC3 cell were induced for DEFB1 expression and activity was monitored based on the binding of green fluoresing FAM-VAD-FMK to caspases in cells actively undergoing apoptosis. Analysis of cells under DIC showed the presence of viable control DU145 (A), PC3 (E) and LNCaP (I) cells at 0 hours. Excitation by the confocal laser at 488 nm produced no detectable green staining which indicates no caspase activity in DU145 (B), PC3 (F) or LNCaP (J). Following induction for 24 hours, DU145 (C), PC3 (G) and LNCaP (K) cells were again visible under DIC. Confocal analysis under fluorescence revealed green staining in DU145 (D) and PC3 (H) cell indicating caspase activity. However, there was no green staining in LNCaP (L), indicating no induction of apoptosis by DEFB1.

Conclusion

To assess its functional role, the DEFB1 gene was cloned into the ecdysone inducible expression system and its effect on prostate cancer cells examined. The present data demonstrate DEFB1 cytotoxic activity against late-stage androgen receptor negative hormone refractory prostate cancer cells. In conclusion, this study provides the functional role of DEFB1 in prostate cancer. Furthermore, these findings show that DEFB1 is part of an innate immune system involved in tumor immunity. Data presented here demonstrate that DEFB1 expressed at physiological levels is cytotoxic to AR− hormone refractory prostate cancer cells, but not to AR+ hormone sensitive prostate cancer cell nor to normal prostate epithelial cells. Given that DEFB1 is constitutively expressed in normal prostate cells without cytotoxicity, it may be that late-stage AR− prostate cancer cells possess distinct phenotypic characteristics that render them sensitive to DEFB1 cytotoxicity. Thus, DEFB1 is a viable therapeutic agent for the treatment of late-stage prostate cancer.

2. Example 2 siRNA Mediated Knockdown of PAX2 Expression Results in Prostate Cancer Cell Death Independent of p53 Status Abstract This example examines the effects of inhibiting PAX2 expression by RNA interference in prostate cancer cells which differ in p53 gene status. These results demonstrate that the inhibition of PAX2 results in cell death irrespective of p53 status, indicating that there are additional tumor suppressor genes or cell death pathways inhibited by PAX2 in prostate cancer.

Materials and Methods

Cell Lines: The cell lines PC3, DU145 and LNCaP were obtained from the American Type Culture Collection (Rockville, Md., USA). PC3 cell were grown in F-12 media, DU145 in DMEM, and LNCaP in RPMI all supplemented with 10% (v/v) fetal bovine serum. Cell were maintained at 37° C. in 5% $CO_2$.

siRNA Silencing of PAX2: In order to achieve efficient gene silencing, a pool of four complementary short interfering ribonucleotides (siRNAs) targeting human PAX2 mRNA (Accession No. NM_003989.1), were synthesized (Dharmacon Research, Lafayette, Colo., USA). A second pool of four siRNAs were used as an internal control to test for the specificity of PAX2 siRNAs. Two of the sequences synthesized target the GL2 luciferase mRNA (Accession No. X65324), and two were non-sequence-specific (Table 3). For annealing of siRNAs, 35 M of single strands were incubated in annealing buffer (100 mM potassium acetate, 30 mM HEPES-KOH at pH 7.4, 2 mM magnesium acetate) for 1 min at 90° C. followed by 1 h incubation at 37° C.

Western Analysis: Briefly, cells were harvested by trypsinization and washed twice with PBS. Lysis buffer was prepared according to the manufacturer's instructions (Sigma), and was then added to the cells. Following a 15 minute incubation period at 4° C. on an orbital shaker, cell lysate were then collected and centrifuged for 10 minutes at 12000×g to pellet cellular debris. The protein-containing supernatant were then collected and quantitated. Next, 25 μg protein extract was loaded onto an 8-16% gradient SDS-PAGE (Novex). Following electrophoresis, proteins were transferred to PVDF membranes, and then blocked with 5% nonfat dry milk in TTBS (0.05% Tween 20 and 100 mM Tris-Cl) for 1 hour. Blots were then probed with rabbit anti-PAX2 primary antibody (Zymed, San Francisco, Calif.) at a 1:2000 dilution. After washing, the membranes were incubated with anti-rabbit antibody conjugated to horseradish peroxidase (HRP) (dilution 1:5000; Sigma), and signal detection was visualized using chemilluminescence reagents (Pierce) on an Alpha Innotech Fluorchem 8900. As a control, blots were stripped and reprobed with mouse anti-β-actin primary antibody (1:5000; Sigma-Aldrich) and HRP-conjugated anti-mouse secondary antibody (1:5000; Sigma-Aldrich) and signal detection was again visualized.

Phase Contrast Microscopy: The effect of PAX2 knockdown on cell growth was analyzed by phase contrast microscopy. Here, 1-2×10$^4$ cells were seeded onto 6 well culture plates (BD Falcon, USA). The following day cells were treated with media only, negative control non-specific siRNA or PAX2 siRNA and allowed to incubate for six days. The cells were then viewed under an inverted Zeiss IM 35 microscope (Carl Zeiss, Germany) at 32× magnification. Phase contrast pictures of a field of cells were obtained using the SPOT Insight Mosaic 4.2 camera (Diagnostic Instruments, USA).

MTT Cytotoxicity Assay: DU145, PC3 and LNCaP cells (1×105) were transfected with 0.5 μg of the PAX2 siRNA pool or control siRNA pool using Codebreaker transfection reagent according to the manufacturer's protocol (Promega). Next, cell suspensions were diluted and seeded onto a 96-well plate at 1-5×10$^3$ cells per well and allowed to grow for 2-, 4- or 6 days. After culture, cell viability was determined by measuring the conversion of 3-[4,5-dimethylthiazol-2-yl]-2,5 diphenyl tetrazolium bromide, MTT (Promega), to a colored formazan product. Absorbance was read at 540 nm on a scanning multiwell spectrophotometer.

Pan-Caspase Detection: Detection of caspase activity in the prostate cancer cell lines was performed using APO LOGIX™ Carboxyfluorescin Caspase detection kit (Cell Technology, Mountain View, Calif.). Active caspases were detected through the use of a FAM-VAD-FMK inhibitor that irreversibly binds to active caspases. Briefly, cells (1-2×104) onto 35 mm glass bottom microwell dishes (Matek, Ashland, Mass.) and treated with media only or PAX2 siRNA as previously described. Next, 10 μl of a 30× working dilution of carboxyfluorescein labeled peptide fluoromethyl ketone (FAM-VAD-FMK) was added to 300 μl of media and added to each 35 mm dish. Cells were then incubated for 1 hour at 37° C. under 5% CO2. Then, the medium was aspirated and the cells were washed twice with 2 ml of a 1× Working dilution Wash Buffer. Cells were viewed under differential interference contrast (DIC) or under laser excitation at 488 nm. The fluorescent signal was analyzed using a confocal microscope (Zeiss LSM 5 Pascal) and a 63×DIC oil lens with a Vario 2 RGB Laser Scanning Module.

Quantitative Real-time RT-PCR: Quantitative real-time RT-PCR was performed in order to verify gene expression after PAX2 siRNA treatment in PC3, DU145 and LNCaP cell lines. Total RNA was isolated using the SV Total RNA Isolation System (Promega). Briefly, approximately 1×10$^6$ cells were harvested by trypsinizing, and rinsed in PBS. Cells were then lysed and total RNA was isolated by centrifugation through spin columns. Total RNA (0.5 μg per reaction) was reverse transcribed into cDNA utilizing Oligo (dT) 15 primer (Promega) and AMV Reverse Transcriptase II enzyme (500 units per reaction; Promega) for first strand synthesis and Tfl DNA Polymerase for second strand synthesis (500 units per reaction; Promega) as per the manufacturers' protocol, with identical control samples treated without RT enzyme. Typically, 50 pg of each cDNA was used per ensuing PCR reaction Two-step QRT-PCR was performed on cDNA generated using the MultiScribe Reverse Transcripatase from the TaqMan Reverse Transcription System and the SYBR Green PCR Master Mix (PE Biosystems). The primer pairs for BAX, BID and BAD were generated from the published sequences (Table 3). Reactions were performed in MicroAmp Optical 96-well Reaction Plate (PE Biosystems). Forty cycles of PCR were performed under standard conditions using an annealing temperature of 60° C. Quantification was determined by the cycle number where exponential amplification began (threshold value) and averaged from the values obtained from the triplicate repeats. There was an inverse relationship between message level and threshold value. In addition, GAPDH was used as a housekeeping gene to normalize the initial content of total cDNA. Gene expression was calculated as the relative expression ratio between the pro-apoptotic genes and GAPDH. All reactions were carried out in triplicate.

Figure 6:
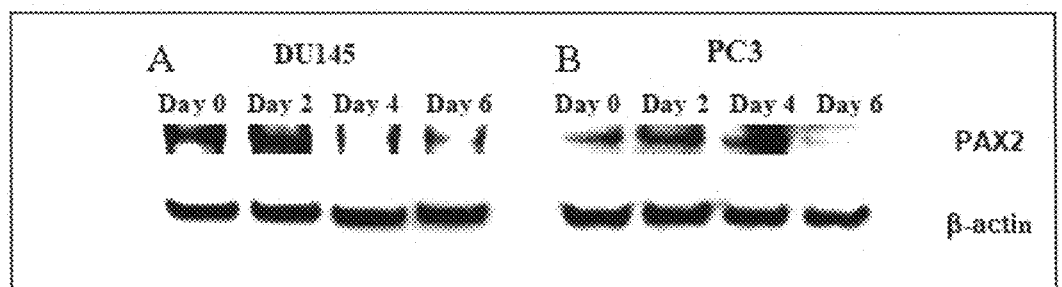
FIG. 6 shows silencing of paired box homeotic gene 2 (PAX2) protein expression following PAX2 siRNA Treatment.

Results siRNA Inhibition of PAX2 Protein: In order to confirm that the siRNA effective targeted the PAX2 mRNA, Western Analysis was performed to monitor PAX2 protein expression levels over a six day treatment period. Cells were given a single round of transfection with the pool of PAX2 siRNA. The results confirmed specific targeting of PAX2 mRNA by showing knock-down of PAX2 protein by day four in DU145 (FIG. 6a) and by day six in PC3 (FIG. 6b).

Figure 7:
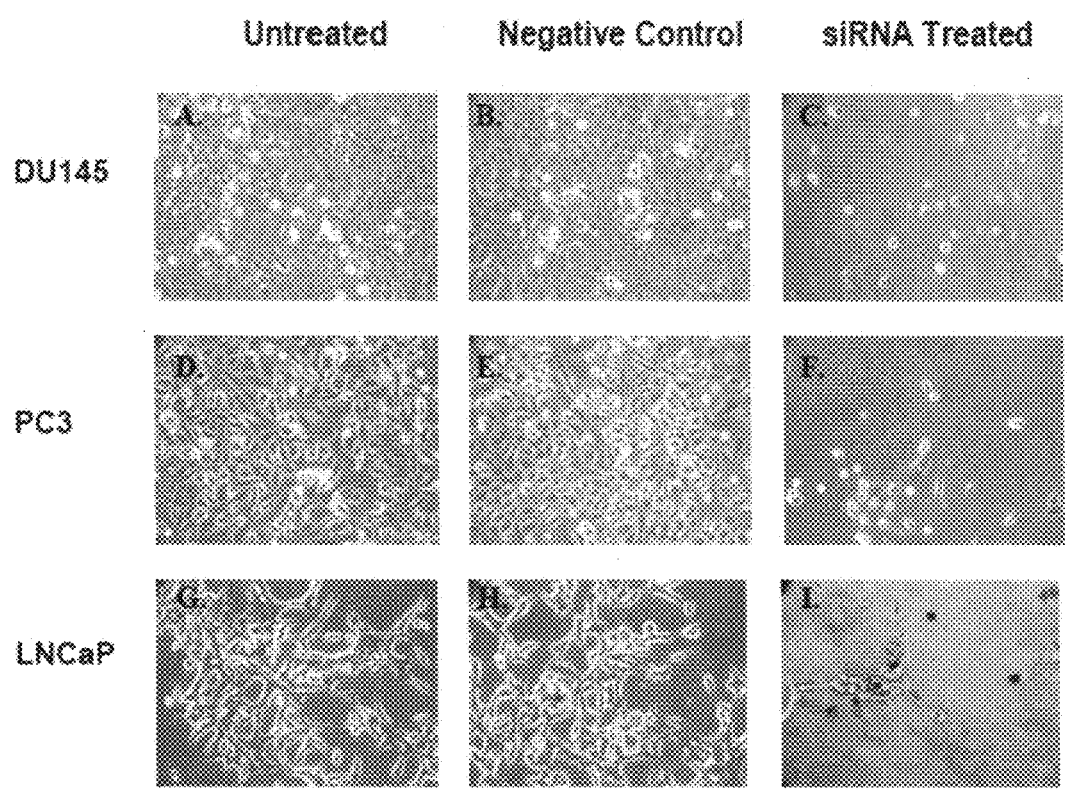
FIG. 7 shows analysis of prostate cancer cells growth after treatment with PAX2 siRNA. Phase contrast microscopic analysis of DU145, PC3 and LNCaP at 6 days in the presence of normal growth media. Treatment with negative control siRNA had no effect on the cells. However, there was a significant reduction in cell number in all three lines following treatment with PAX2 siRNA.

Knock-down of PAX2 inhibit Prostate Cancer Cell Growth: Cells were analyzed following a six day treatment period with media only, negative control non-specific siRNA or PAX2 siRNA (FIG. 7). DU145 (a), PC3 (d) and LNCaP (g) cells all reached at least 90% confluency in the culture dishes containing media only. Treatment of DU145 (b), PC3 (e) and LNCaP (h) with negative control non-specific siRNA had no effect on cell growth, and cells again reached confluency after six days. However, treatment with PAX2 siRNA resulted in a significant decrease in cell number. DU145 cells were approximately 15% confluent (c) and PC3 cells were only 10% confluent (f). LNCaP cell were 5% confluent following siRNA treatment.

Figure 8:
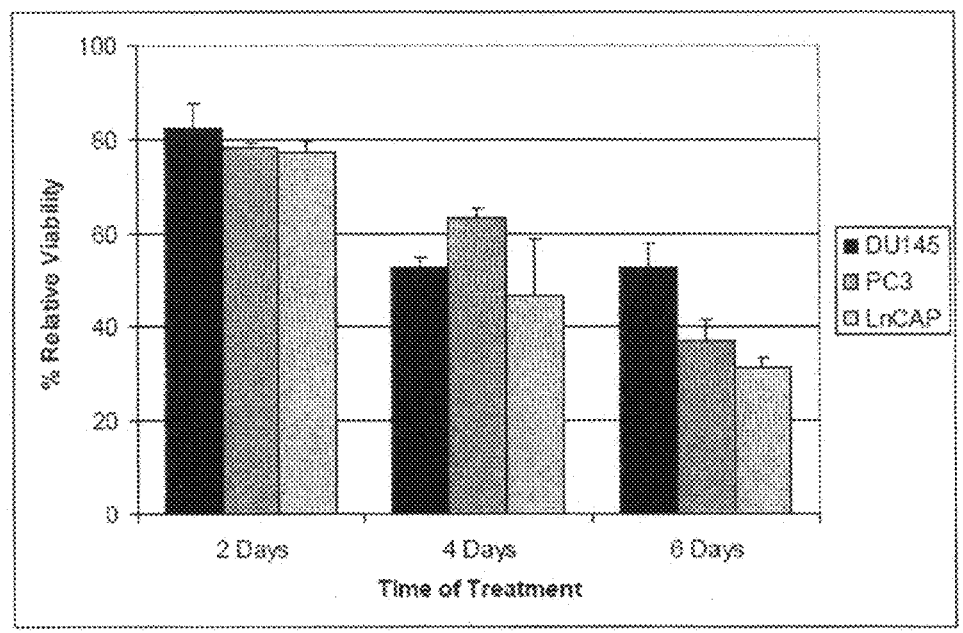
FIG. 8 shows analysis of cell death following siRNA silencing of PAX2. Prostate cancer cell lines PC3, DU145, and LNCaP were treated with 0.5 μg of a pool of four PAX2 siRNA's or four non-specific control siRNA's for 2, 4 or 6 days after which MTT assay was done to determine cell viability. Results represent mean±s.d., n=9.

Cytotoxicity Assays: Cell viability was measured after two-, four-, and six-day exposure times, and is expressed as a ratio of the 570-630 nm absorbance of treated cells divided by that of the untreated control cells (FIG. 8). Relative cell viability following 2 days of treatment was 77% in LNCaP, 82% in DU145 and 78% in PC3. After four days, relative cell viability was 46% in LNCaP, 53% in DU145 and 63% in PC3. After six days of treatment, relative cell viability decreased to 31% in LNCaP, 37% in PC3, and was 53% in DU145. As negative controls, cell viability was measured in after a six day treatment period with negative control non-specific siRNA or transfection reagent alone. For both conditions, there was no statistically significant change in cell viability compared to normal growth media.

Figure 9:
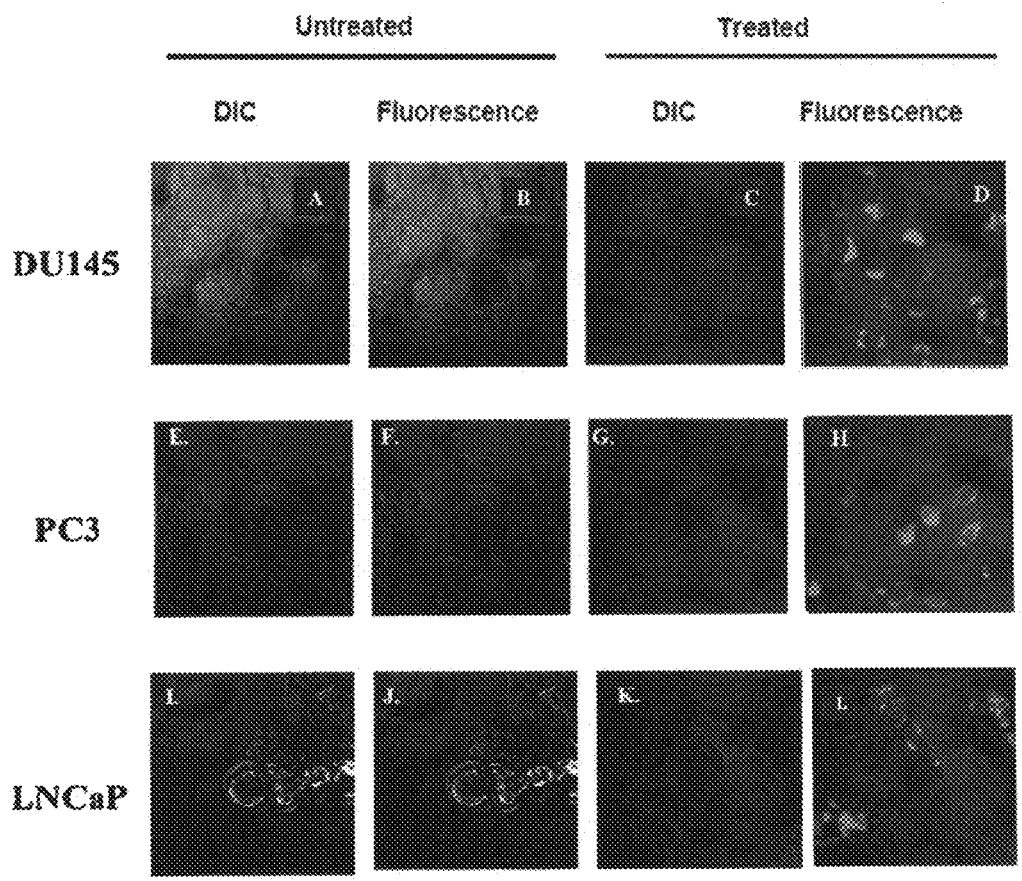
FIG. 9 shows analysis of caspase activity. DU145, PC3 and LNCaP cells were stained with carboxyfluorescein-labeled fluoromethyl ketone to detected caspase activity following treatment with PAX2 siRNA. Confocal microscopic analysis of untreated and treated cells show cells were visible with DIC. Analysis under fluorescence revealed no caspase staining in control DU145 (B), PC3 cells (F) and LNCaP cells (J). However, cell treated with PAX2 siRNA induced caspase activity in DU145 (D), PC3 (H) and LNCaP (L).

Pan-Caspase Detection: Caspase activity was detected by confocal laser microscopic analysis. DU145, PC3 and LNCaP cells were treated with PAX2 siRNA and activity was monitored based on the binding of FAM-labeled peptide to caspases in cells actively undergoing apoptosis which will fluoresce green. Analysis of cells with media only under DIC shows the presence of viable DU145 (A), PC3 (E) and LNCaP (I) cells at 0 hours (FIG. 9). Excitation by the confocal laser at 488 nm produced no detectable green staining which indicates no caspase activity in untreated DU145 (B), PC3 (F) or LNCaP (J). Following four days of treatment with PAX2 siRNA, DU145 (C), PC3 (G) and LNCaP (K) cells were again visible under DIC. Under fluorescence, the treated DU145 (D), PC3 (H) and LNCaP (L) cells presented green staining indicating caspase activity.

Effect of PAX2 Inhibition on Pro-Apoptotic Factors

Figure 10A:
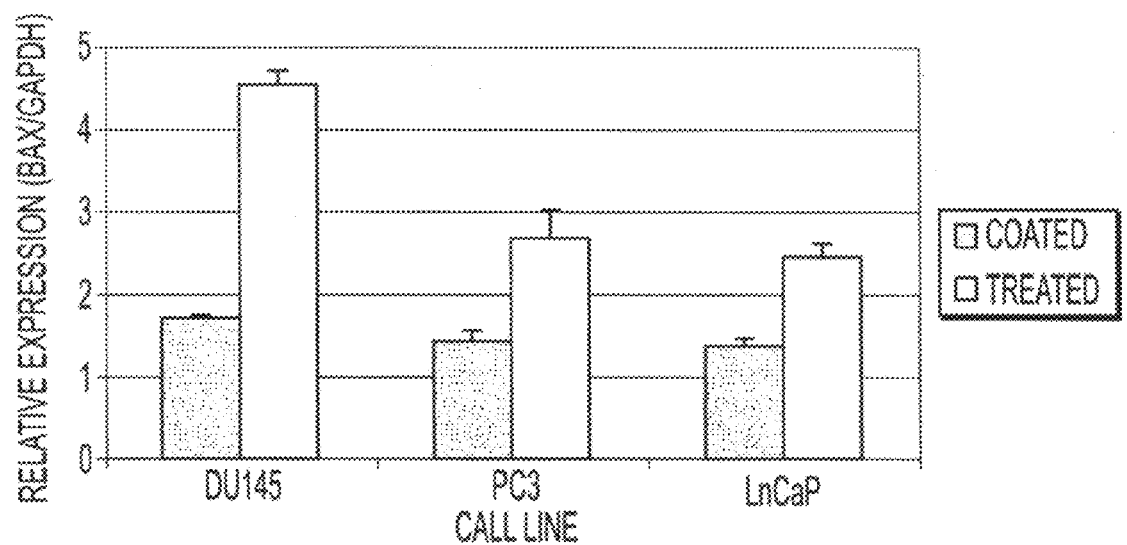
FIG. 10A shows Bcl-2-associated X protein (BAX) expression levels increased in DU145, PC3 and LNCaP.
Figure 10B:
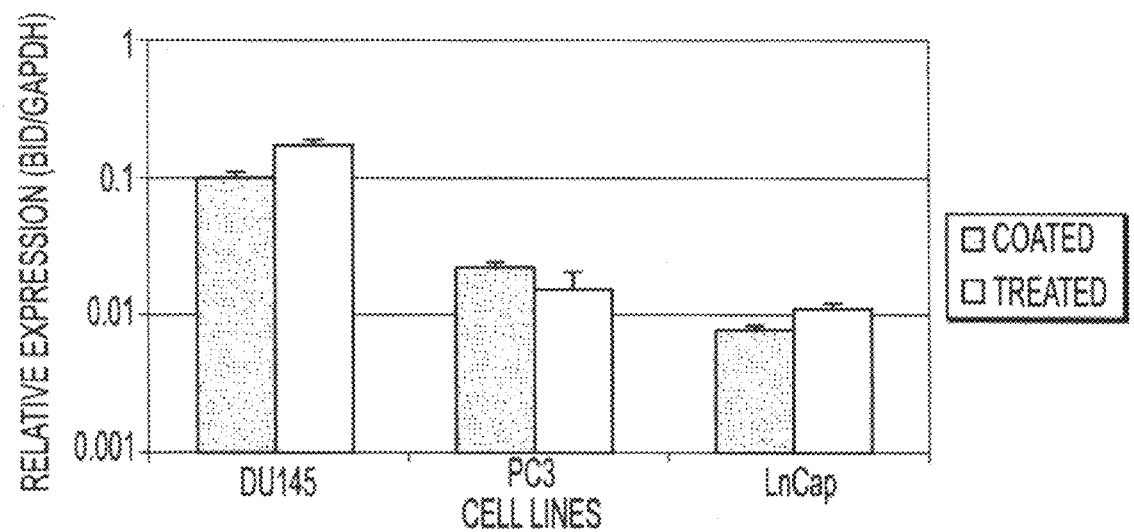
FIG. 10B shows BH3 interacting domain death agonist (BID) expression increased in DU145 and LNCaP, but change in PC3.
Figure 10C:
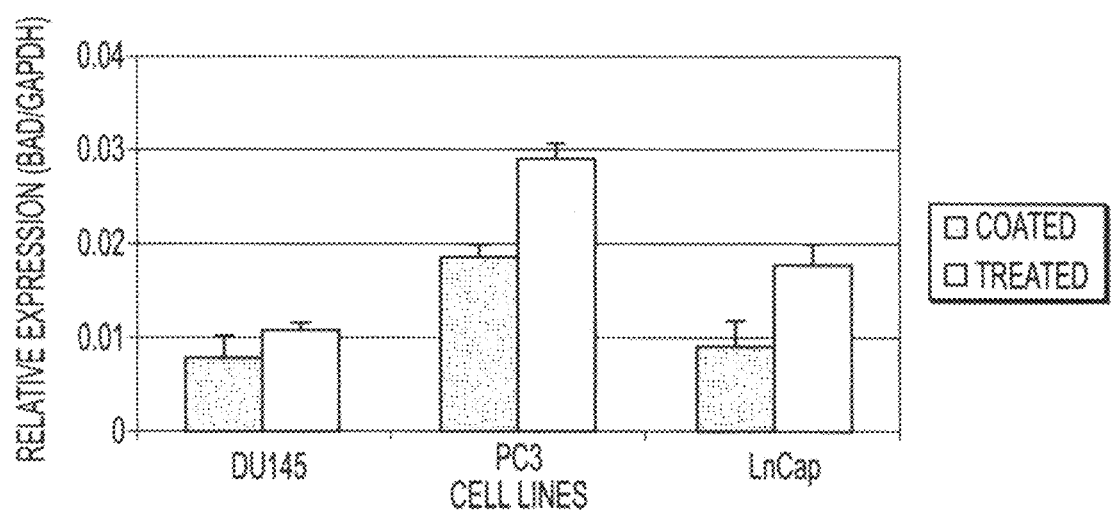
FIG. 10C shows Bcl-2-associated death promoter (BAD) expression levels increased in all three cell lines.
Figure 11:
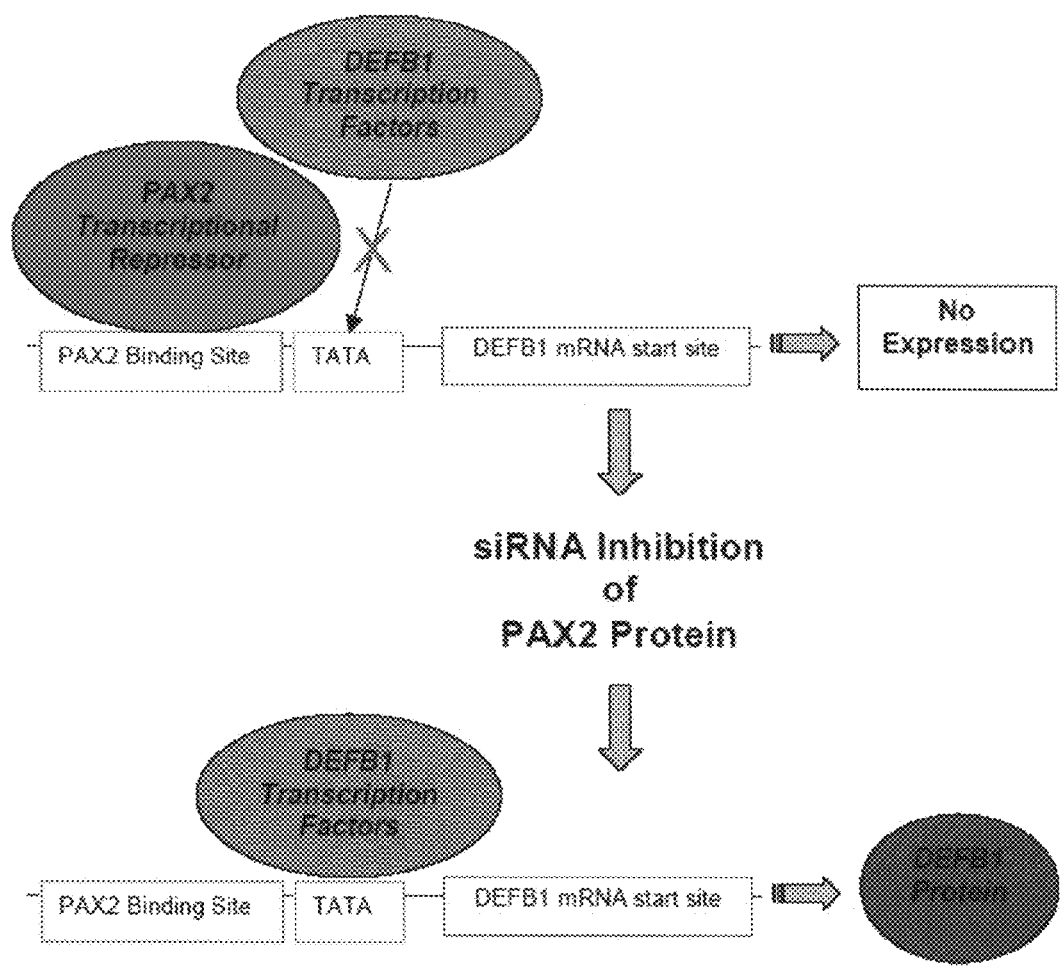
FIG. 11 shows model of PAX2 binding to DNA recognition sequence. The PAX2 transcriptional repressor binds to a CCTTG (SEQ ID NO: 1) recognition site immediately adjacent to the DEFB1 TATA box preventing transcription and DEFB1 protein expression. Inhibition of PAX2 protein expression allows normal DEFB1 expression.
Figure 12:
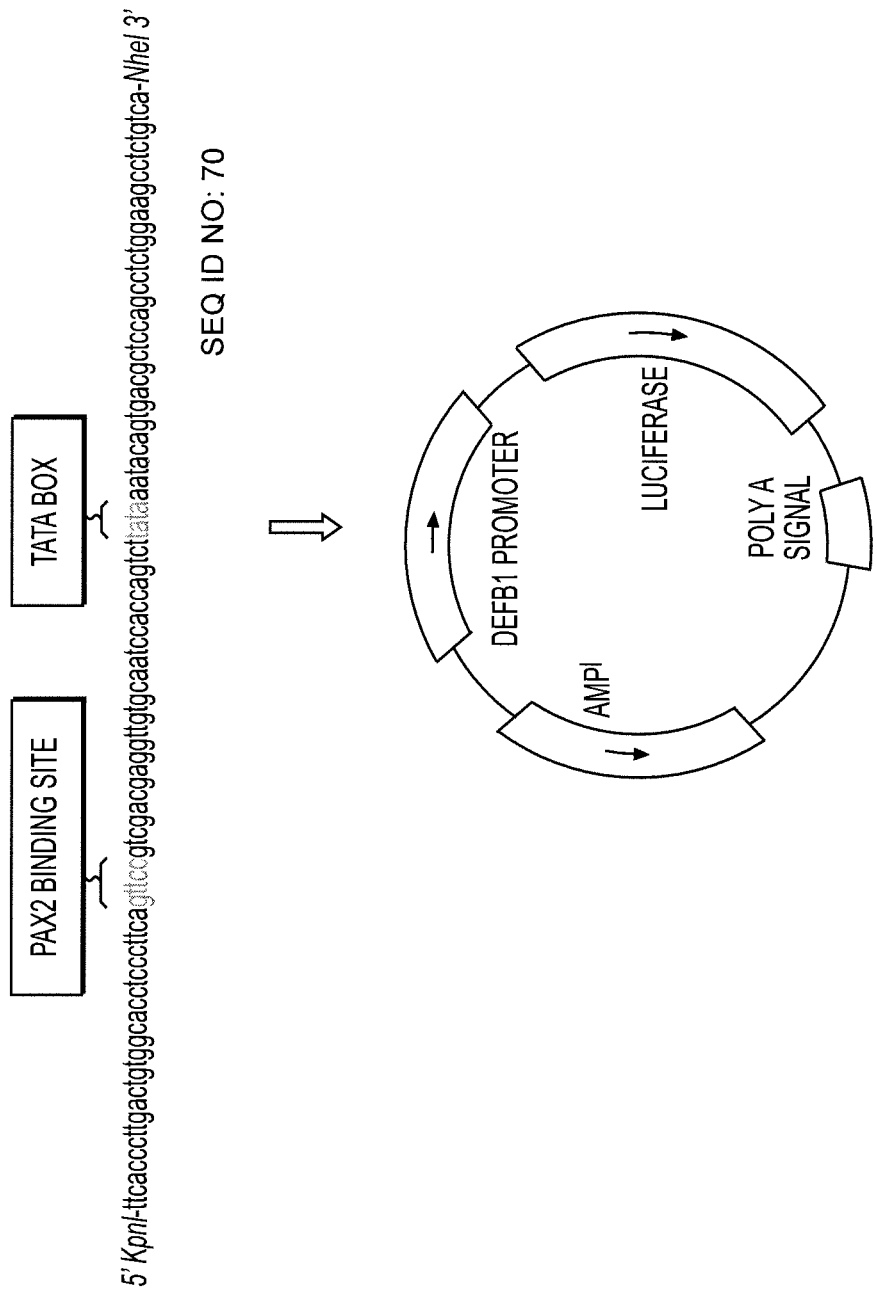
FIG. 12 illustrates the DEFB1 Reporter Construct. The DEFB1 promoter consisting of the first 160 bases upstream of the mRNA start site was PCR amplified from DU145 cell and ligated into the pGL3 luciferase reporter plasmid. SEQ ID NO:70 depicts the KpnI-NheI fragment of the DEFB1 promoter.

DU145, PC3 and LNCaP cells were treated with siRNA against PAX2 for six days and expression of pro-apoptotic genes dependent and independent of p53 transcription regulation were measured to monitor cell death pathways. For BAX, there was a 1.81-fold increase in LNCaP, a 2.73-fold increase in DU145, and a 1.87-fold increase in PC3 (FIG. 10a). Expression levels of BID increased by 1.38-fold in LNCaP and 1.77-fold in DU145 (FIG. 10b). However, BID expression levels decreased by 1.44-fold in PC3 following treatment (FIG. 10c). Analysis of BAD revealed a 2.0-fold increase in expression in LNCaP, a 1.38-fold increase in DU145, and a 1.58-fold increase in PC3.

Conclusion

Despite significant advances in cancer therapy there is still little progress in the treatment of advanced disease. Successful drug treatment of prostate cancer requires the use of therapeutics with specific effects on target cells while maintaining minimal clinical effects on the host. The goal of cancer therapy is to trigger tumor-selective cell death. Therefore, understanding the mechanisms in such death is critical in determining the efficacy of a specific treatment.

The dependency of prostate cancer cell survival on PAX2 expression is shown here. In order to distinguish between death observed in the p53-expressing cell line LNCaP, the p53-mutated line DU145, and the p53-null line PC3 downstream events that follow p53 activation as a result of PAX2 knock-down were examined. Caspase activity was detected in all three lines indicative of the initiation of programmed cell death. With this, changes in the expression of pro-apoptotic genes were examined. Here, BAX expression was upregulated in all three cell lines independent of p53 status. The expression of pro-apoptotic factor BAD was increased in all three lines following PAX2 inhibition. Following treatment with PAX2 siRNA, BID expression was increased in LNCaP and DU145, but actually decreased in PC3. This indicates that cell death observed in prostate cancer is influenced by but is not dependent on p53 expression. The initiation of apoptosis in prostate cancer cells through different cell death pathways irrespective of p53 status indicates that PAX2 inhibits other tumor suppressors Example 3

Inhibition of PAX2 Oncogene Results in DEFB1-Mediated Death of Prostate Cancer Cells Abstract The identification of tumor-specific molecules that serve as targets for the development of new cancer drugs is considered to be a major goal in cancer research. Example I demonstrated that there is a high frequency of DEFB1 expression loss in prostate cancer, and that induction of DEFB1 expression results in rapid apoptosis in androgen receptor negative-stage prostate cancer. These data show that DEFB1 plays a role in prostate tumor suppression. In addition, given that it is a naturally occurring component of the immune system of normal prostate epithelium, DEFB1 is expected to be a viable therapeutic agent with little to no side effects. Example II demonstrated that inhibition of PAX2 expression results in prostate cancer cell death independent of p53. These data indicate that there is an addition pro-apoptotic factor or tumor suppressor that is inhibited by PAX2. In addition, the data show that the oncogenic factor PAX2, which is over-expressed in prostate cancer, is a transcriptional repressor of DEFB1. The purpose of this study is to determine if DEFB1 loss of expression is due to aberrant expression of the PAX2 oncogene, and whether inhibiting PAX2 results in DEFB1-mediated cell death.

The data show that loss of DEFB1 expression occurs at the transcriptional level. Furthermore, computational analysis of the DEFB1 promoter revealed the presence of a GTTCC (SEQ ID NO: 2) DNA binding site for the PAX2 transcriptional repressor next to the DEFB1 TATA box (FIG. 1). The results presented here show that PAX2 and DEFB1 exhibit several attributes of suitable cancer targets, including a role in the suppression of cell death. Therefore, DEFB1 plays a role in tumor immunity and its expression is modulated through therapeutic down-regulation of the PAX2 oncogene.

Materials and Methods

RNA Isolation and Quantitative RT-PCR: In order to verify changes in DEFB1 expression levels RNA was collected after 4 days of PAX2 siRNA treatment. Briefly, total RNA was isolated using the SV Total RNA Isolation System (Promega, Madison, Wis.) from approximately $1 \times 10^6$ cells harvested by trypsinizing. Here, cells were lysed and total RNA was isolated by centrifugation through spin columns. Total RNA (0.5 µg per reaction) from both sources was reverse transcribed into cDNA utilizing random primers (Promega). AMV Reverse Transcriptase II enzyme (500 units per reaction; Promega) was used for first strand synthesis and Tfl DNA Polymerase for second strand synthesis (500 units per reaction; Promega) as per the manufacturer's protocol. In each case, 50 pg of cDNA was used per ensuing PCR reaction. Two-step QRT-PCR was performed on cDNA generated using the MultiScribe Reverse Transcripatase from the TaqMan Reverse Transcription System and the SYBR Green PCR Master Mix (Applied Biosystems).

The primer pair for DEFB1 was generated from the published DEFB1 sequence (Accession No. U50930). Forty cycles of PCR were performed under standard conditions using an annealing temperature of 56° C. In addition, GAPDH was amplified as a housekeeping gene to normalize the initial content of total cDNA. DEFB1 expression was calculated as the relative expression ratio between DEFB1 and GAPDH and was compared in cells lines before and after siRNA knock-down of PAX2 expression. All reactions were run three times in triplicate.

Generation of the DEFB1 Reporter Construct: The pGL3 luciferase reporter plasmid was used to monitor DEFB1 reporter activity. Here, a region 160 bases upstream of the DEFB1 transcription initiation site and included the DEFB1 TATA box. The region also included the GTTCC (SEQ ID NO: 2) sequence which is necessary for PAX2 binding. The PCR primers were designed to contain KpnI and NheI restriction sites. The DEFB1 promoter PCR products were restriction digested Kpn I and NheI and ligated into a similarly restriction digested pGL3 plasmid (FIG. 2). The constructs were transfected into E. coli and individual clones were selected and expanded. Plasmids were isolated and sequence integrity of the DEFB1/pGL3 construct was verified by automated sequencing.

Luciferase Reporter Assay: Here, 1 µg of the DEFB1 reporter construct or the control pGL3 plasmid was transfected into $1 \times 10^6$ DU145 cells. Next, $0.5 \times 10^3$ cells were seeded onto each well of a 96-well plate and allowed to grow overnight. Then fresh medium was added containing PAX2 siRNA or media only and the cells were incubated for 48 hours. Luciferase was detected by the BrightGlo kit according to the manufacturer's protocol (Promega) and the plates were read on a Veritas automated 96-well luminometer. Promoter activity was expressed as relative luminescence.

Analysis of Membrane Permeability: Acridine orange (AO)/ethidium bromide (EtBr) dual staining was performed to identify changes in cell membrane integrity, as well as apoptotic cells by staining the condensed chromatin. AO stains viable cells as well as early apoptotic cells, whereas EtBr stains late stage apoptotic cells that have lost membrane permeability. Briefly, cells were seeded into 2 chamber culture slides (BD Falcon, USA). Cells transfected with empty pIND plasmid/pvgRXR or pIND DEFB1/pvgRXR were induced for 24 or 48 h with media containing 10 µM Ponasterone A. Control cells were provided fresh media at 24 and 48 h. In order to determine the effect of PAX2 inhibition on membrane integrity, separate culture slides containing DU145, PC3 and LNCaP were treated with PAX2 siRNA and incubated for 4 days. Following this, cells were washed once with PBS and stained with 2 ml of a mixture (1:1) of AO (Sigma, USA) and EtBr (Promega, USA) (5 ug/ml) solution for 5 min. Following staining, the cells were again washed with PBS. Fluorescence was viewed by a Zeiss LSM 5 Pascal Vario 2 Laser Scanning Confocal Microscope (Carl Zeiss Jena, Germany). The excitation color wheel contain BS505-530 (green) and LP560 (red) filter blocks which allowed for the separation of emitted green light from AO into the green channel and red light from EtBr into the red channel. The laser power output and gain control settings within each individual experiment were identical between control and DEFB1 induced cells. The excitation was provided by a Kr/Ar mixed gas laser at wavelengths of 543 nm for AO and 488 nm for EtBr. Slides were analyzed under 40× magnification and digital images were stored as uncompressed TIFF files and exported into Photoshop CS software (Adobe Systems, San Jose, Calif.) for image processing and hard copy presentation.

ChIP Analysis of PAX2: Chromatin immunoprecipitation (ChIP) allows the identification of binding sites for DNA-binding proteins based upon in vivo occupancy of a promoter by a transcription factor and enrichment of transcription factor bound chromatin by immunoprecipitation. A modification of the protocol described by the Farnham laboratory was used; also on line at http://mcardle.oncology.wisc.edu/farnham/). The DU145 and PC3 cell lines over-expresses the PAX2 protein, but does not express DEFB1. Cells were incubated with PBS containing 1.0% formaldehyde for 10 minutes to crosslink proteins to DNA. Samples were then sonicated to yield DNA with an average length of 600 bp. Sonicated chromatin precleared with Protein A Dynabeads was incubated with PAX2-specific antibody or "no antibody" control [isotype-matched control antibodies]. Washed immunoprecipitates were then collected. After reversal of the crosslinks, DNA was analyzed by PCR using promoter-specific primers to determine whether DEFB1 is represented in the PAX2-immunoprecipitated samples. Primers were designed to amplify the 160 by region immediately upstream of the DEFB1 mRNA start site which contained the DEFB1 TATA box and the functional GTTCC (SEQ ID NO: 2) PAX2 recognition site. For these studies, positive controls included PCR of an aliquot of the input chromatin (prior to immunoprecipitation, but crosslinks reversed). All steps were performed in the presence of protease inhibitors.

Figure 13:
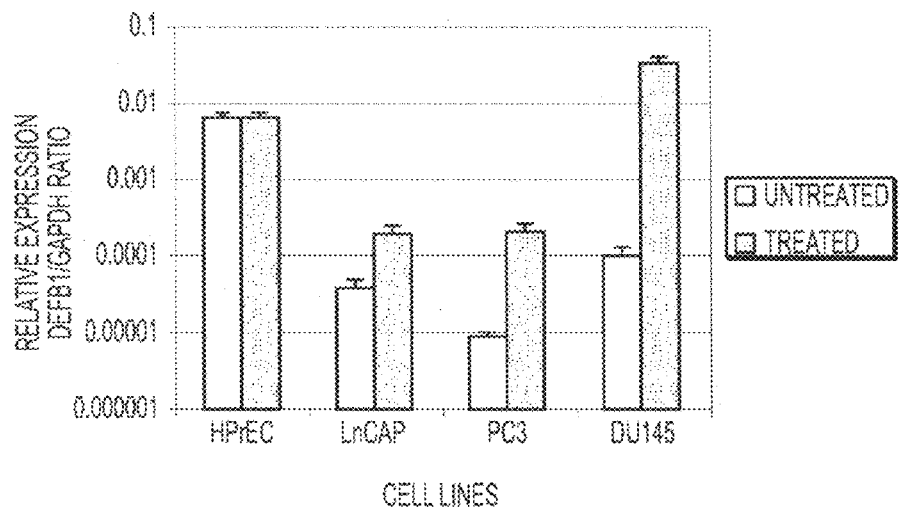
FIG. 13 shows inhibition of PAX2 results in DEFB1 Expression. DU145, PC3, LNCaP and HPrEC were treated for 48 hours with PAX2 siRNA. QRT-PCR analysis before treatment showed no DEFB1 expression in DU145, PC3 and LNCaP. However, DEFB1 expression was restored following treatment in all lines. There was no change in DEFB1 expression following siRNA treatment of PAX2-null HprEC.

Results siRNA Inhibition of PAX2 Increases DEFB1 Expression: QRT-PCR analysis of DEFB1 expression before siRNA treatment revealed relative expression levels of 0.00097 in DU145, 0.00001 in PC3, and 0.00004 LNCaP (FIG. 13). Following siRNA knock-down of PAX2, relative expression was 0.03294 (338-fold increase) in DU145, 0.00020 (22.2-fold increase) in PC3 and 0.00019 (4.92-fold increase) in LNCaP. As a negative control, the human prostate epithelial cell line (hPrEC) which is PAX2 null, revealed expression levels at 0.00687 before treatment and 0.00661 following siRNA treatment confirming no statistical change in DEFB1 expression.

Figure 14:
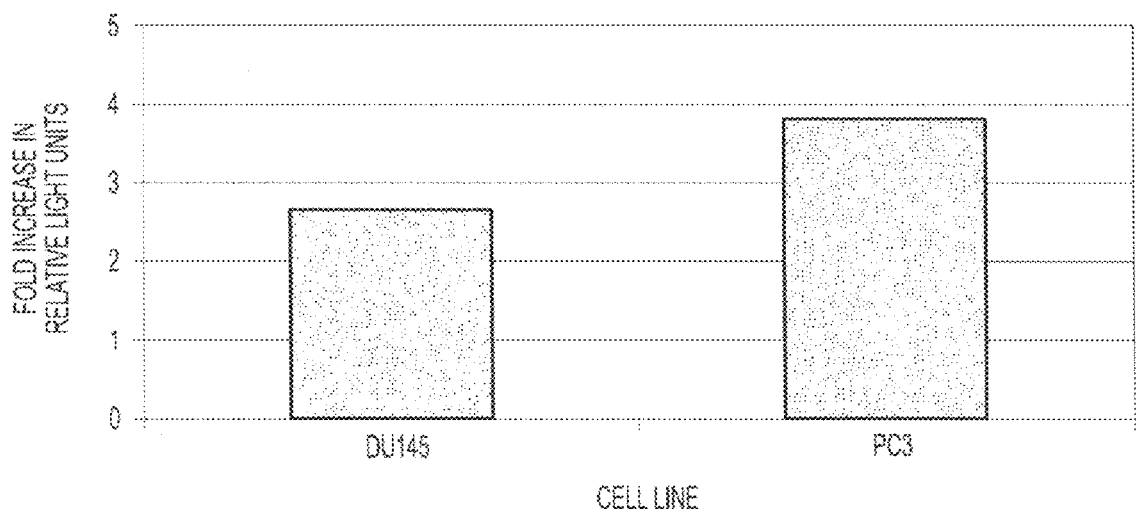
FIG. 14 shows inhibition of PAX2 results in increased DEFB1 promoter activity. PC3 promoter/pGL3 and DU145 promoter/pGL3 construct were generated and were transfected into PC3 and DU145 cells, respectively. Promoter activity was compared before and after PAX2 inhibition by siRNA treatment. DEFB1 promoter activity increased 2.65-fold in DU145 and 3.78 fold in PC3 following treatment.
Figure 16:
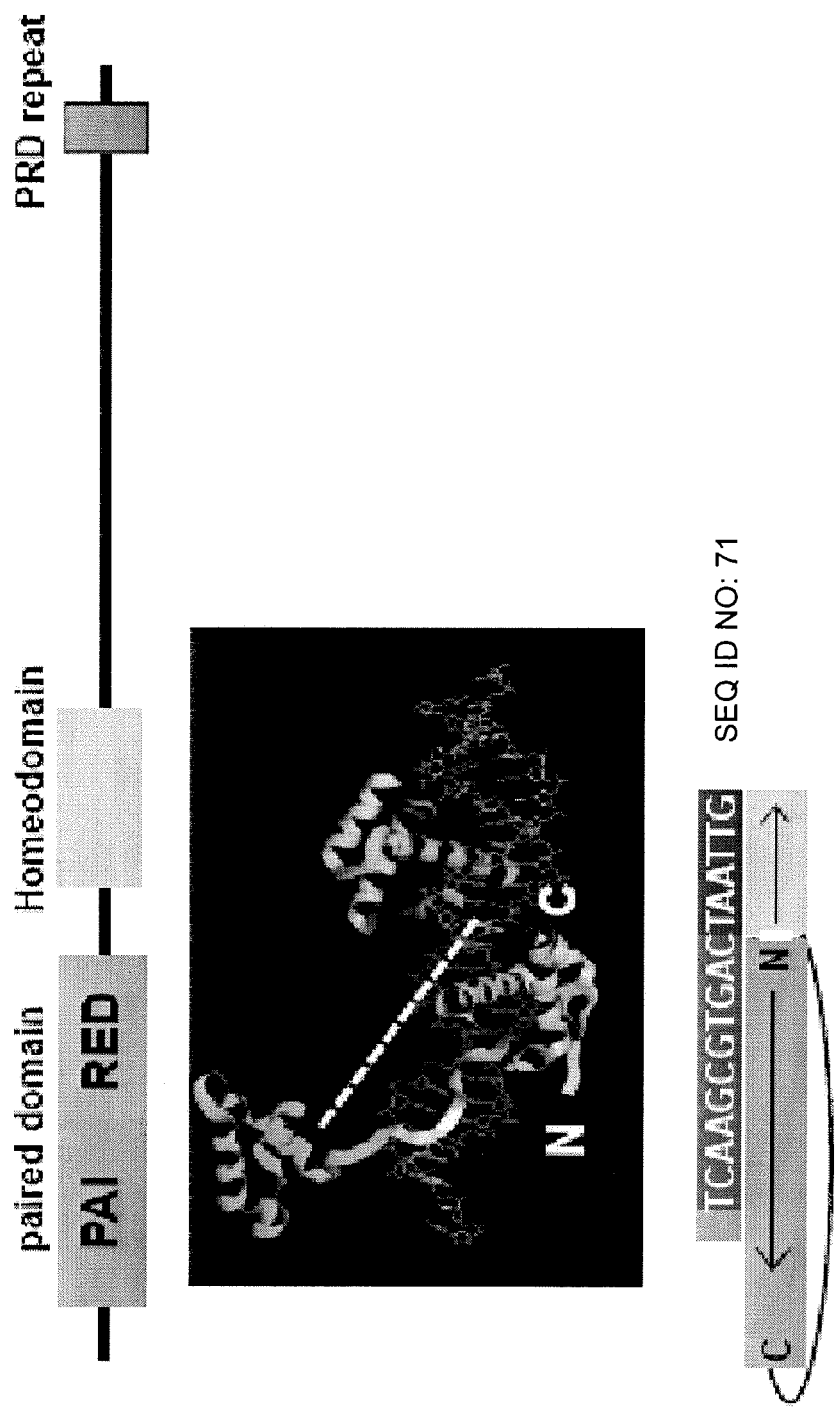
FIG. 16 shows predicted structure of the PrdPD and PrdHD with DNA. The coordinates of the structures of the PrdPD bound to DNA (Xu et al., 1995) and the PrdHD bound to DNA (Wilson et al., 1995) were used to construct a model of the two domains as they bound to a PH0 site (SEQ ID NO:71). The individual binding sites are abutted next to each other with a specific orientation as indicated. The PAI binding site is in red, the HD binding site is in blue, and the corresponding PAI domain is in turquoise, and HD is in yellow. The RED domain is oriented based on the PrdPD crystal structure.
Figure 17:
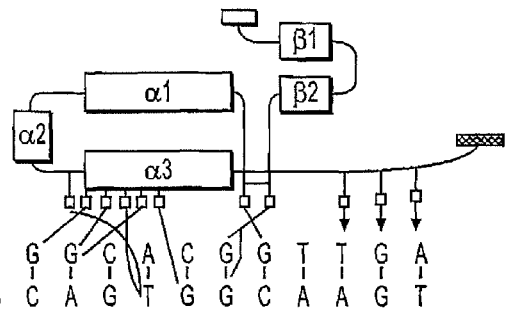
FIG. 17 shows comparison of consensus sequences of different paired domains. At the top of the Figure is drawn a schematic representation of protein±DNA contacts described in the crystallographic analysis of the Prd-paired-domain±DNA complex. Empty boxes indicate a-helices, shaded boxes indicates b-sheets and a thick line indicate a b-turn. Contacting amino acids are shown by single-letter code. Only direct amino acid±base contacts are shown. Empty circles indicate major groove contacts while red arrows indicate minor groove contacts. This scheme is aligned to all known consensus sequences for paired-domain proteins (top strands only are shown). Vertical lines between consensus sequences indicate conserved base-pairs. Numbering of the positions is shown at the bottom of the Figure.

DEFB1 Causes Cell Membrane Permeability: Membrane integrity was monitored by confocal analysis (FIG. 14). Here, intact cells stain green due to AO which is membrane permeable. In addition, cells with compromised plasma membranes would stain red by EtBr which is membrane impermeable. Here, uninduced DU145 (A) and PC3 (D) cells stained positively with AO and emitted green color, but did not stain with EtBr. However, DEFB1 induction in both DU145 (B) and PC3 (E) resulted in the accumulation of EtBr in the cytoplasm at 24 hours indicated by the red staining. By 48 hours, DU145 (C) and PC3 (F) possessed condensed nuclei and appeared yellow, which was due to the presence of both green and red staining resulting from the accumulation of AO and EtBr, respectively.

Inhibition of PAX2 Results in Membrane Permeability: Cells were treated with PAX2 siRNA for 4 days and membrane integrity was monitored again by confocal analysis. Here, both DU145 and PC3 possessed condensed nuclei and appeared yellow. However, LNCaP cells' cytoplasm and nuclei remained green following siRNA treatment. Also red staining at the cell periphery indicates the maintenance of cell membrane integrity. These findings indicate that the inhibition of PAX2 results in specifically DEFB1-mediated cell death in DU1145 and PC3, but not LNCaP cells. Death observed in LNCaP is due to the transactivation of the existing wild-type p53 in LNCap following PAX2 inhibition.

siRNA Inhibition of PAX2 Increases DEFB1 Promoter Activity: Analysis of DEFB1 promoter activity in DU145 cells containing the DEFB1/pGL3 construct revealed a 2.65 fold increase in relative light units following 48 hours of treatment compared to untreated cells. In PC3 cells, there was a 3.78-fold increase in relative light units compared to untreated cells.

PAX2 Binds to the DEFB1 Promoter: ChIP analysis was performed on DU145 and PC3 cells to determine if the PAX2 transcriptional repressor is bound to the DEFB1 promoter (FIG. 15). Lane 1 contains a 100 by molecular weight marker. Lane 2 is a positive control representing 160 by region of the DEFB1 promoter amplified from DU145 before cross-linking and immunoprecipitation. Lane 3 is a negative control representing PCR performed without DNA. Lane 4 and 5 are negative controls representing PCR from immunoprecipitations performed with IgG from cross-linked DU145 and PC3, respectively. PCR amplification of 25 pg of DNA (lane 6 and 8) and 50 pg of DNA (lane 7 and 9) immunoprecitipated with anti-PAX2 antibody after crosslinking show 160 by promoter fragment in DU145 and PC3, respectively.

Conclusion

The present novel data are the first to disclose the role of DEFB1 in prostate cancer tumor immunity. The data also show that the oncogenic factor PAX2 suppresses DEFB1 expression. One of the hallmarks of defensin cytotoxicity is the disruption of membrane integrity. The present results show that ectopic expression of DEFB1 in prostate cancer cells results in a loss of membrane potential due to compromised cell membranes. The same phenomenon is observed after inhibiting PAX2 protein expression. ChIP analysis was also performed and confirmed that PAX2 is bound to the DEFB1 promoter resulting in the repression of DEFB1 expression. Therefore, suppression of PAX2 expression or function, results in the re-establishment of DEFB1 expression and subsequently DEFB1-mediated cell death. Also, the present data establish the utility of DEFB1 as a directed therapy for prostate cancer treatment through innate immunity.

3. Example 4

Expression of DEFB1 Results in Tumor Shrinkage

The anti-tumoral ability of DEFB1 is evaluated by injecting tumor cells that overexpress DEFB1 into nude mice. DEFB1 is cloned into pBI-EGFP vector, which has a bidirectional tetracycline responsible promoter. Tet-Off Cell lines are generated by transfecting pTet-Off into DU145, PC3 and LNCaP cells and selecting with G418. The pBI-EGFP-DEFB1 plasmid is co-transfected with pTK-Hyg into the Tet-off cell lines and selected with hygromycin. Only single-cell suspensions with a viability of >90% are used. Each animal receives approximately 500,000 cells administered subcutaneously into the right flank of female nude mice. There are two groups, a control group injected with vector only clones and a group injected with the DEFB1 over-expressing clones. 35 mice are in each group as determined by a statistician. Animals are weighed twice weekly, tumor growth monitored by calipers and tumor volumes determined using the following formula: volume=0.5×(width)2×length. All animals are sacrificed by CO2 overdose when tumor size reaches 2 mm3 or 6 months following implantation; tumors are excised, weighed and stored in neutral buffered formalin for pathological examination. Differences in tumor growth between the groups are descriptively characterized through summary statistics and graphical displays. Statistical significance is evaluated with either the t-test or non-parametric equivalent.

4. Example 5

Expression of PAX2 siRNA Results in Up-Regulation of DEFB1 Expression and Tumor Shrinkage In Vivo Hairpin PAX2 siRNA template oligonucleotides utilized in the in vitro studies are utilized to examine the effect of the up-regulation of DEFB1 expression in vivo. The sense and antisense strand (see Table 3) are annealed and cloned into pSilencer 2.1 U6 hygro siRNA expression vector (Ambion) under the control of the human U6 RNA pol III promoter. The cloned plasmid is sequenced, verified and transfected into PC3, Du145, and LNCap cell lines. Scrambled shRNA is cloned and used as a negative control in this study. Hygromycin resistant colonies are selected, cells are introduced into the mice subcutaneously and tumor growth is monitored as described above.

5. Example 6

Small Molecule Inhibitors of PAX2 Binding Results in Up-Regulation of DEFB1 Expression and Tumor Shrinkage In Vivo The DNA recognition sequence for PAX2 binding resides in the DEFB1 promoter between nucleotides −75 and −71 [+1 refers to the transcriptional start site]. Short oligonucleotides complementary to the PAX2 DNA-binding domain are provided. Examples of such oligonucleotides include the 20-mer and 40-mer oligonucleotides containing the GTTCC (SEQ ID NO: 2) recognition sequence provided below. These lengths were randomly selected, and other lengths are expected to be effective as blockers of binding. As a negative control, oligonicleotides with a scrambled sequence (CTCTG)—(SEQ ID NO: 17) were designed to verify specificity. The oligonucleotides are transfected into the prostate cancer cells and the HPrEC cells with lipofectamine reagent or Codebreaker transfection reagent (Promega, Inc). In order to confirm DNA-protein interactions, double stranded oligonucleotides will be labeled with [$^{32}$P] dCTP and electrophoretic mobility shift assays are performed. In addition, DEFB1 expression is monitored by QRT-PCR and Western analysis following treatment with oligonucleotides. Finally, cell death is detected by MTT assay and flow cytometry as previously described.

```
Recognition Sequence #1:
                                       (SEQ ID NO: 13)
CTCCCTTCAGTTCCGTCGAC Recognition Sequence #2:
                                       (SEQ ID NO: 14)
CTCCCTTCACCTTGGTCGAC Scramble Sequence #1:
                                       (SEQ ID NO: 18)
CTCCCTTCACTCTGGTCGAC Recognition Sequence #3:
                                       (SEQ ID NO: 15)
ACTGTGGCACCTCCCTTCAGTTCCGTCGACGAGGTTGTGC Recognition Sequence #4:
                                       (SEQ ID NO: 16)
ACTGTGGCACCTCCCTTCACCTTGGTCGACGAGGTTGTGC Scramble Sequence #2:
                                       (SEQ ID NO: 19)
ACTGTGGCACCTCCCTTCACTCTGGTCGACGAGGTTGTGC
```

Further examples of oligonucleotides of the invention include:

```
Recognition Sequence #1:
                                       (SEQ ID NO: 20)
5'-AGAAGTTCACCCTTGACTGT-3'

Recognition Sequence #2:
                                       (SEQ ID NO: 21)
5'-AGAAGTTCACGTTCCACTGT-3'

Scramble Sequence #1:
                                       (SEQ ID NO: 22)
5'-AGAAGTTCACGCTCTACTGT-3'

Recognition Sequence #3:
                                       (SEQ ID NO: 23)
5'-TTAGCGATTAGAAGTTCACCCTTGACTGTGGCACCTCCC-3'

Recognition Sequence #4:
                                       (SEQ ID NO: 24)
5'-GTTAGCGATTAGAAGTTCACGTTCCACTGTGGCACCTCCC-3'

Scramble Sequence #2:
                                       (SEQ ID NO: 25)
5'-GTTAGCGATTAGAAGTTCACGCTCTACTGTGGCACCTCCC-3'
```

This set of alternative inhibitory oligonucleotides represents the recognition sequence (along with the CCTTG (SEQ ID NO: 1) core sequence) for the PAX2 binding domain and homeobox. These include actual sequences from the DEFB1 promoter.

The PAX2 gene is required for the growth and survival of various cancer cells including prostate. In addition, the inhibition of PAX2 expression results in cell death mediated by the innate immunity component DEFB1. Suppression of DEFB1 expression and activity is accomplished by binding of the PAX2 protein to a GTTCC (SEQ ID NO: 2) recognition site in the DEFB1 promoter. Therefore, this pathway provides a viable therapeutic target for the treatment of prostate cancer. In this method, the sequences bind to the PAX2 DNA binding site and block PAX2 binding to the DEFB I promoter thus allowing DEFB1 expression and activity. The oligonucleotide sequences and experiment described above are examples of and demonstrate a model for the design of additional PAX2 inhibitor drugs.

Given that the GTTCC (SEQ ID NO: 2) sequence exists in interleukin-3, interleukin-4, the insulin receptor and others, PAX2 regulates their expression and activity as well. Therefore the PAX2 inhibitors disclosed herein have utility in a number of other diseases including those directed related to inflammation including prostatitis and benign prostatic hypertrophy (BPH).

6. Example 7

Loss of DEFB1 Expression Results in Increased Tumorigenesis

Generation of Loss of Function Mice: The Cre/loxP system has been useful in elucidating the molecular mechanisms underlying prostate carcinogenesis. Here a DEFB1 Cre conditional KO is used for inducible disruption within the prostate. The DEFB1 Cre conditional KO involves the generation of a targeting vector containing loxP sites flanking DEFB1 coding exons, targeted ES cells with this vector and the generation of germline chimeric mice from these targeted ES cells. Heterozygotes are mated to prostate-specific Cre transgenics and heterozygous intercross is used to generate prostate-specific DEFB1 KO mice. Four genotoxic chemical compounds have been found to induce prostate carcinomas in rodents: N-methyl-N-nitrosourea (MNU), N-nitrosobis 2-oxopropyl. amine (BOP), 3,2α-dimethyl-4-amino-biphenyl (MAB) and 2-amino-1-methyl-6-phenylmidazow 4,5-bx-pyridine (PhIP). DEFB1-transgenic mice are treated with these carcinogenic compounds via intra-gastric administration or i.v. injection for prostate adenoma and adenocarcinoma induction studies. Prostate samples are studied for differences in tumor growth and changes gene expression though histological, immunohistological, mRNA and protein analyses.

Generation of GOF mice: For PAX2 inducible GOF mice, PAX2 GOF (bi-transgenic) and wild-type (mono-transgenic) littermates are administered doxycycline (Dox) from 5 weeks of age to induce prostate-specific PAX2 expression. Briefly, PROBASIN-rtTA mono-transgenic mice (prostate cell-specific expression of tet-dependent rtTA inducer) are crossed to our PAX2 transgenic responder lines. For induction, bi-transgenic mice are fed Dox via the drinking water (500 mg/L freshly prepared twice a week). Initial experiments verify low background levels, good inducibility and cell-type specific expression of PAX2 and the EGFP reporter using transgenic founder line in bi-transgenic mice. Regarding experimental group sizes, 5-7 age- and sex-matched individuals in each group (wild-type and GOF) allow for statistical significance. For all animals in this study, prostate tissues are collected initially at weekly intervals for analysis and comparison, to determine carcinogenic time parameters.

PCR Genotyping, RT-PCR and qPCR: PROBASIN-rtTA transgenic mice are genotyped using the following PCR primers and conditions:

```
                                        (SEQ ID NO: 26)
PROBASIN5 (forward)    5'-ACTGCCCATTGCCCAAACAC-3';

(SEQ ID NO: 27)
RTTA3 (reverse)        5'-AAAATCTTGCCAGCTTTCCCC-3';
```

95° C. denaturation for 5 min, followed by 30 cycles of 95° C. for 30 sec, 57° C. for 30 sec, 72° C. for 30 sec, followed by a 5 min extension at 72° C., yielding a 600 bp product. PAX2 inducible transgenic mice are genotyped using the following PCR primers and conditions: PAX2For 5'-GTCGGTTACG-GAGCGGACCGGAG-3' (SEQ ID NO: 28); Rev5'IRES 5'-TAACATATAGACAAACGCACACCG-3' (SEQ ID NO: 29);

95° C. denaturation for 5 min, followed by 34 cycles of 95° C. for 30 sec, 63° C. for 30 sec, 72° C. for 30 sec, followed by a 5 min extension at 72° C., yielding a 460 bp product.

Immortomouse hemizygotes are be genotyped using the following PCR primers and conditions: Immo11, 5'-GCGCT-TGTGTC GCCATTGTATTC-3' (SEQ ID NO: 30); Immo12, 5'-GTCACACCACAGAAGTAAGGTTCC-3' (SEQ ID NO: 31); 94° C. 30 sec, 58° C. 1 min, 72° C. 1 min 30 sec, 30 cycles to yield a 1 kb transgene band. For genotyping PAX2 knockout mice, the following PCR primers and conditions are used: PAX2 For 5'-GTCGGTTACGGAGCGGACCGGAG-3' (SEQ ID NO: 32);

PAX2Rev 5'-CACAGAGCATTGGCGATCTCGATGC-3' (SEQ ID NO: 33); 94° C. 1 min, 65° C. 1 min, 72° C. 30 sec, 36 cycles to yield a 280 by band.

DEFB1 Peptide Animal Studies: Six-week-old male athymic (nude) mice purchased from Charles River Laboratories are injected sub-cutaneously over the scapula with $10^6$ viable PC3 cells. One week after injection, the animals are randomly allocated to one of three groups—group I: control; group II: intraperitoneal injections of DEFB1, 100 μg/day, 5 days a week, for weeks 2-14; group III: intraperitoneal injections of DEFB1, 100 mg/day, 5 days a week, for weeks 8-14. Animals are maintained in sterile housing, four animals to a cage, and observed on a daily basis. At 10-day intervals, the tumors are measured by using calipers, and the volumes of the tumors are calculated by using V=(L×W2)/2.

TABLE 2

Sequences of QRT-PCR Primers.

| | Sense (5'-3') | |
|---|---|---|
| β-actin | 5'-CCTGGCACCCAGCACAAT-3' | SEQ ID NO: 34 |
| DEFB1 | 5'-GTTGCCTGCCAGTCGCCATGAGAACTTCCTAC-3' | SEQ ID NO: 35 |
| | Antisense (5'-3') | |
| β-actin | 5'-GCCGATCCACACGGAGTACT-3' | SEQ ID NO: 36 |
| DEFB1 | 5'-TGGCCTTCCCTCTGTAACAGGTGCCTTGAATT-3' | SEQ ID NO: 37 |

TABLE 3

PAX2 siRNA Sequences. A pool of four siRNA was utilized to inhibit PAX2 protein expression.

Sense (5'-3')

| | | |
|---|---|---|
| Sequence A | 5'-GAAGUCAAGUCGAGUCUAUUU-3' | SEQ ID NO: 38 |
| Sequence B | 5'-GAGGAAACGUGAUGAAGAUUU-3' | SEQ ID NO: 39 |
| Sequence C | 5'-GGACAAGAUUGCUGAAUACUU-3' | SEQ ID NO: 40 |
| Sequence D | 5'-CAUCAGAGCACAUCAAAUCUU-3' | SEQ ID NO: 41 |

Antisense (5'-3')

| | | |
|---|---|---|
| Sequence A | 5'-AUAGACUCGACUUGACUUCUU-3' | SEQ ID NO: 3 |
| Sequence B | 5'-AUCUUCAUCACGUUUCCUCUU-3' | SEQ ID NO: 4 |
| Sequence C | 5'-GUAUUCAGCAAUCUUGUCCUU-3' | SEQ ID NO: 5 |
| Sequence D | 5'-GAUUUGAUGUGCUCUGAUGUU-3' | SEQ ID NO: 6 |

TABLE 4

Quantitative RT-PCR Primers. Nucleotide sequences of primers used to amplify PAX2 and GAPDH.

Sense (5'-3')

| | | |
|---|---|---|
| GAPDH | 5'-CCACCCATGGCAAATTCCATGGCA-3' | SEQ ID NO: 42 |
| BAD | 5'-CTCAGGCCTATGCAAAAAGAGGA-3' | SEQ ID NO: 43 |
| BID | 5'-AACCTACGCACCTACGTGAGGAG-3' | SEQ ID NO: 44 |
| BAX | 5'-GACACCTGAGCTGACCTTGG-3' | SEQ ID NO: 45 |

Antisense (5'-3')

| | | |
|---|---|---|
| GAPDH | 5'-TCTAGACGGCAGGTCAGGTCAACC-3' | SEQ ID NO: 46 |
| BAD | 5'-GCCCTCCCTCCAAAGGAGAC-3' | SEQ ID NO: 47 |
| BID | 5'-CGTTCAGTCCATCCCATTTCTG-3' | SEQ ID NO: 48 |
| BAX | 5'-GAGGAAGTCCAGTGTCCAGC-3' | SEQ ID NO: 49 |

7. Example 8

Targeting PAX2 Expression for the Chemoprevention of Intraepithelial Neoplasia and Cancer

Abstract

The accumulation of mutations and the loss of cellular control functions cause progressive phenotypic changes from normal histology to early pre-cancer such as intraepithelial neoplasia (IEN) to increasingly severe IEN to superficial cancer and finally to invasive disease. Although this process can be relatively aggressive in some cases, it generally occurs relatively slowly over years and even decades. As described by Weinstein and others, oncogene addiction is the physiologic dependence of cancer cells on the continued activation or overexpression of single oncogenes for maintaining the malignant phenotype. This dependence occurs in the milieu of the other changes that mark neoplastic progression. The addiction and reliance of cancer cells on the PAX2 oncogene for growth and cell survival is one such example. Conversely, the absence of tumor suppressor genes such as DEFB1 which is transcriptionally repressed by PAX2, confers a similar pro-cancer addiction.

Cancer chemoprevention is defined as the prevention of cancer or treatment at the pre-cancer state or even earlier. The long period of progression to invasive cancer is a major scientific opportunity but also an economic obstacle to showing the clinical benefit of candidate chemopreventive drugs. Therefore, an important component of chemopreventive agent development research in recent years has been to identify earlier (than cancer) end points or biomarkers that accurately predict an agent's clinical benefit or cancer incidence-reducing effect. In many cancers, IEN is an early end point such as in prostate cancer. Given that the PAX2/DEFB1 pathway is deregulated during IEN and perhaps at even an earlier histopathological state makes it a powerful predictive biomarker and an excellent target for chemoprevention of cancer. Shown are a number of compounds that suppress PAX2 and increases DEFB1 expression that may have utility as chemoprevention agents for prostate cancer.

Background

Figure 18:
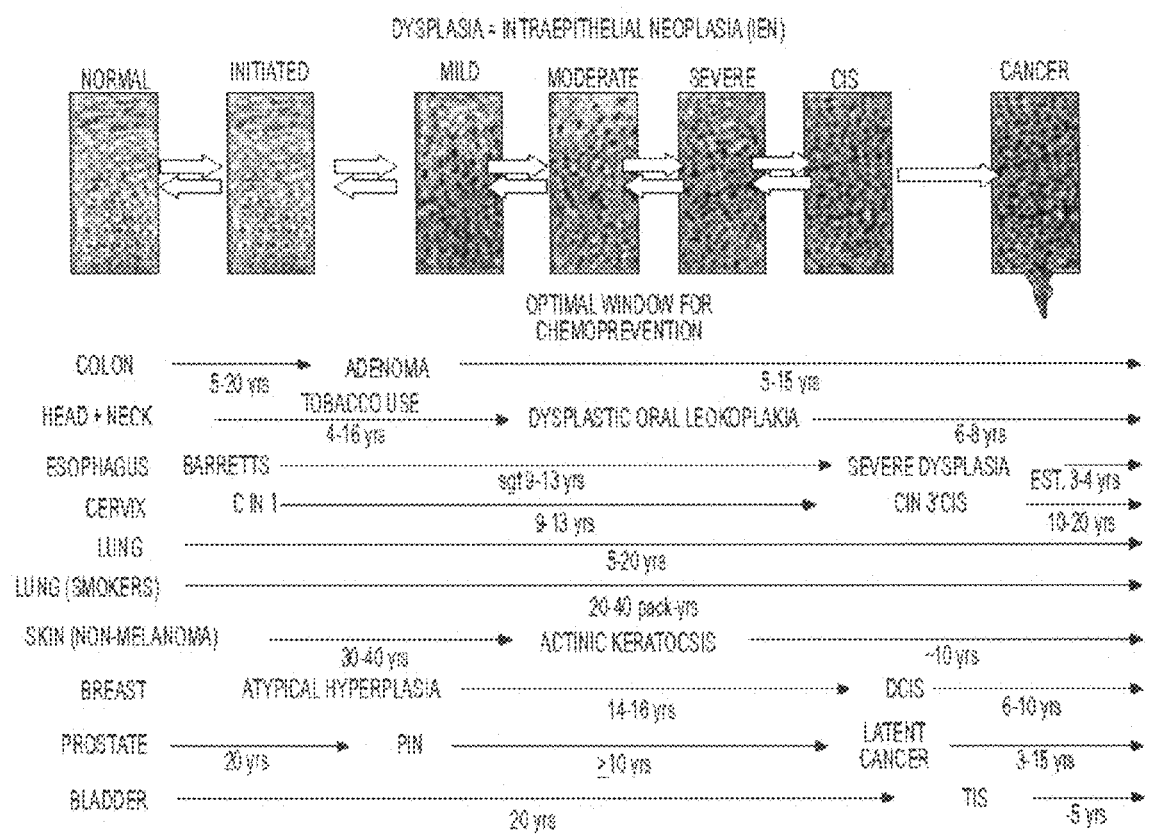
FIG. 18 shows targeting PAX2 as a chemopreventive strategy. Aberrant PAX2 expression is an early event in the initiation and progression of cancer. Inhibition of PAX2 during dysplasia or other precancerous stage can be used for cancer prevention.

PAX genes are capable of acting as proto-oncogenes through the structural alterations of transcription factors and genes that regulate cell growth and apoptosis resulting in a strong survival signal in prostate cancer. In addition, several cancers have been shown to have aberrant PAX2 expression (FIG. 18). Angiotensin II (AngII) is a major regulator of blood pressure and cardiovascular homeostasis and is recognized as a potent mitogen. AngII mediates its biological effects through binding to two subtypes of receptors, Angiotensin Type I receptor (AT1R) and Angiotensin Type II receptor (AT2R) which belong to the super-family of G-protein-coupled receptors but have different tissue distribution and intracellular signaling pathways. In addition to its effects on blood pressure, AngII has been shown to play a role in various pathological situations involving tissue remodeling, such as wound healing, cardiac hypertrophy and development. In fact, recent studies have revealed local expression of several components of the Renin-Angiotensin System (RAS) in various cancer cells and tissues including the prostate. Upregulation of AT1R provides a considerable advantage to cancer cells that have learn to evade apoptosis and growth regulatory elements.

This study demonstrates that the upregulation of the PAX2 oncogene in prostate cancer is due to deregulated RAS signaling. PAX2 expression is regulated by the ERK 1/2 signaling pathway which is mediated by the Angiotensin type I receptor. In addition, blocking the AT1R with Losartan (Los) suppresses PAX2 expression. In addition, AICAR which is an AMPK activator has also shown promise as a potential PAX2 inhibitor. Collectively, these studies strongly implicate these classes of drugs as potential suppressors of PAX2 expression and may ultimately serve as novels chemoprevention agents (Table 5).

TABLE 5

PAX2 Expressing Cancers as Candidates for Chemoprevention Strategies

| PAX2 Expressing Cancers | Estimated New Cases in US [22] | Estimated Deaths in US [22] | Estimated New Cases Global | Estimated Deaths Global |
|---|---|---|---|---|
| Prostate | 234,460 | 27,350 | 679,023 | 221,002 |
| Breast | 214,600 | 41,430 | 1,151,298 | 410,712 |

TABLE 5-continued

PAX2 Expressing Cancers as Candidates for Chemoprevention Strategies

| PAX2 Expressing Cancers | Estimated New Cases in US [22] | Estimated Deaths in US [22] | Estimated New Cases Global | Estimated Deaths Global |
|---|---|---|---|---|
| Ovarian | 20,180 | 15,310 | 204,500 | 124,860 |
| Renal | 38,890 | 12,840 | 208,479 | 101,895 |
| Brain | 12,820 | 18,820 | 189,485 | 141,650 |
| Cervical | 9,710 | 3,700 | 493,243 | 273,505 |
| Bladder | 61,420 | 13,060 | 356,556 | 145,009 |
| Leukemia | 35,020 | 22,280 | 300,522 | 222,506 |
| Kaposi Sarcoma | Data Not Available | Data Not Available | Data Not Available | Data Not Available |
| TOTAL (approx.) | 627,100 | 154,790 | 3,583,106 | 1,641,139 |

To date a number of cancers have been shown to aberrantly express PAX2. Chemoprevention via target PAX2 expression may have a significant impact on cancer related deaths.

Materials and Methods

Cell Culture: The cell lines DU145 were cultured in DMEM medium, and PC3 were grown in F12 medium (Life Technologies, Inc., Grand Island, N.Y.). Growth media for all three lines was supplemented with 10% (v/v) fetal bovine serum (Life Technologies). The hPrEC cells were cultured in prostate epithelium basal media (Cambrex Bio Science, Inc., Walkersville, Md.). All cell lines were maintained at 37° C. and 5% CO2.

Reagents and Treatments: Cells were treated with 5 or 10 uM of AngII, 5 uM of the ATR1 antagonist Los, 5 uM of the ATR2 antagonist PD123319, 25 uM of the MEK inhibitor U0126, 20 uM of the MEK/ERK inhibitor PD98059 or 250 µM of the AMP kinase inducer AICAR.

Western Analysis: Briefly, cells were harvested by trypsinization and washed twice with PBS. Lysis buffer was prepared according to the manufacturer's instructions (Sigma) and then added to the cells. Following a 15-minute incubation period at 4° C. on an orbital shaker, cell lysates were collected and centrifuged for 10 minutes at 12000×g to pellet cellular debris. The protein-containing supernatant were then collected and quantitated. Next, 25 ug protein extract was loaded onto an 8-16% gradient SDS-PAGE (Novex). Following electrophoresis, proteins were transferred to PVDF membranes, and then blocked with 5% nonfat dry milk in TTBS (0.05% Tween 20 and 100 mM Tris-Cl) for 1 hour. Blots were then probed with primary antibody (anti-PAX2, -phospho-PAX2, -JNK, -phospho-JNK, -ERK1/2, or -phospho-ERK1/2) (Zymed, San Francisco, Calif.) at 1:1000-2000 dilutions. After washing, the membranes were incubated with anti-rabbit antibody conjugated to horseradish peroxidase (HRP) (dilution 1:5000; Sigma), and signal detection was visualized using chemilluminescence reagents (Pierce) on an Alpha Innotech Fluorchem 8900. As a control, blots were stripped and re-probed with mouse anti-β-actin primary antibody (1:5000; Sigma-Aldrich) and HRP-conjugated anti-mouse secondary antibody (1:5000; Sigma-Aldrich), and signal detection was again visualized.

QRT-PCR Analysis: Quantitative real-time RT-PCR was performed to verify changes in gene expression following PAX2 knockdown in PC3 and DU145 prostate cancer cell lines and the hPrEC normal prostate epithelial cells. Approximately 1×10$^6$ cells were harvested by trypsinizing and the cells were rinsed in PBS. Cells were then lysed and total RNA was isolated by centrifugation through spin columns using the SV Total RNA Isolation System (Promega). cDNA was generated (0.5 µg per reaction) by reverse transcription by Oligo (dT) 15 primer (Promega) and AMV Reverse Transcriptase II enzyme (500 units per reaction; Promega) for first strand synthesis and Tfl DNA Polymerase for second strand synthesis (500 units per reaction; Promega) as per the manufacturer's protocol. Typically, 50 pg of each cDNA was used per ensuing PCR reaction. Two-step QRT-PCR was performed on cDNA generated using the MultiScribe Reverse Transcripatase from the TaqMan Reverse Transcription System and the SYBR Green PCR Master Mix (PE Biosystems). Reactions were performed in MicroAmp Optical 96-well Reaction Plate (PE Biosystems). Forty cycles of PCR were performed under standard conditions using an annealing temperature of 60° C. Quantification was determined by the cycle number where exponential amplification began (threshold value) and averaged from the values obtained from the triplicate repeats. There was an inverse relationship between message level and threshold value. In addition, GAPDH was used as a housekeeping gene to normalize the initial content of total cDNA. Relative expression was calculated as the ratio between each genes and GAPDH. All reactions were carried out in triplicate.

Thymidine Incorporation: Proliferation of cells was determined by [3H] thymidine ribotide ([3H] TdR) incorporation into DNA. 0.5×10$^6$ cells/well of suspension DU145 cells were plated in their appropriate media. Cells were incubated for 72 h with or without the presence of AngII at the indicated concentrations. Cells were exposed to 37 kBq/ml [methyl-3H] thymidine in the same medium for 6 h. The adherent cells were fixed by 5% trichloroacetic acid and lysed in SDS/NaOH lysis buffer overnight. Radioactivity was measured by Beckman LS3801 liquid scintillation counter (Canada). Suspension cell culture was harvested by cell harvester (Packard instrument Co., Meriden, Conn.), and radioactivity was measured by 1450 microbeta liquid scintillation counter (PerkinElmer Life Sciences).

Statistical Analysis: Statistical differences were evaluated using the Student's t-test for unpaired values. P values were determined by a two-sided calculation, and a P value of less than 0.05 was considered statistically significant.

Results

Figure 19:
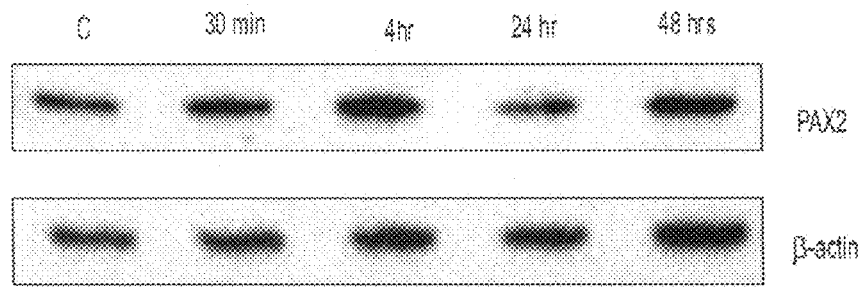
FIG. 19 shows effect of angiotensin II (Ang II) on PAX2 expression in DU145 Cells. In order to determine the effect of AngII on PAX2 expression, DEFB1 protein levels was monitored following treatment. Here PAX2 expression levels increased as early as 4 hours and persisted until 48 hours.
Figure 20A:
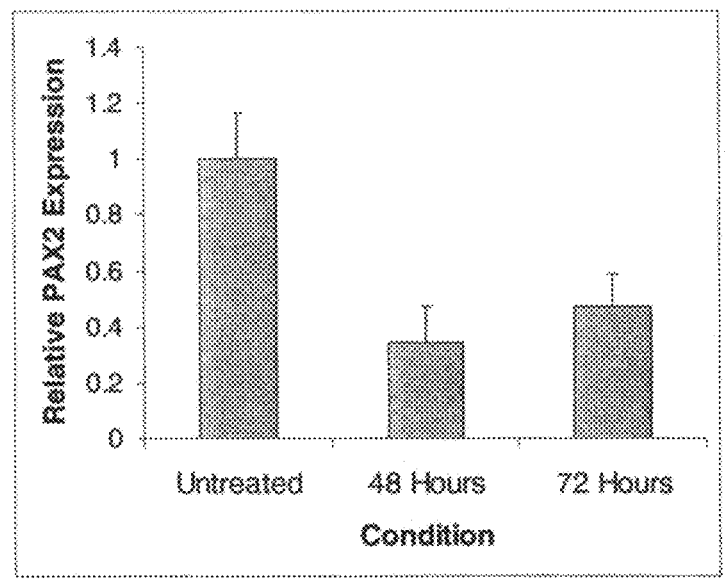
FIG. 20A shows effect of Losartan (Los) on PAX2 expression in DU145. DU145 cells were treated with the angiotensin II type 1 receptor (ATR1) blocker Losartan. QRT-PCR revealed that PAX2 message levels were decreased by at least half following treatment.
Figure 20B:
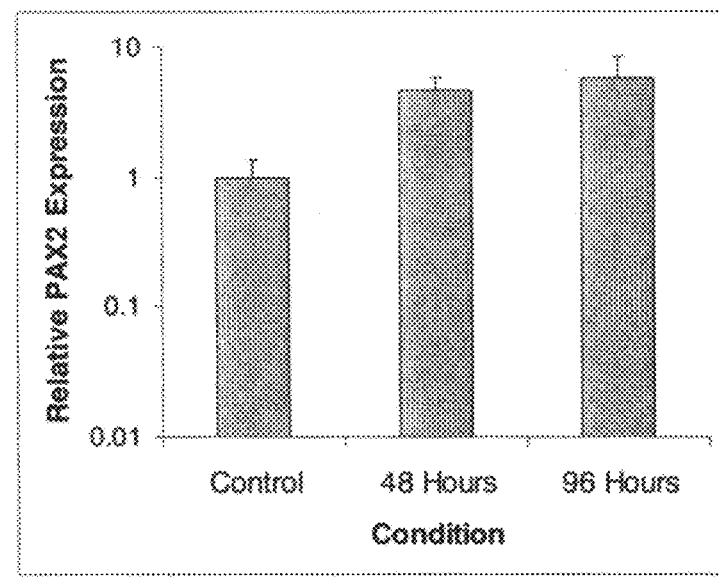
FIG. 20B shows effect of an angiotensin II type 2 receptor (ATR2) blocker on PAX2 Expression in DU145. To determine the effect of the ATR2 receptor on PAX2 expression, DU145 cells were treated with the ATR2 receptor blocker PD123319. Here, PAX2 expression was increased 7 to 8-fold.
Figure 21:
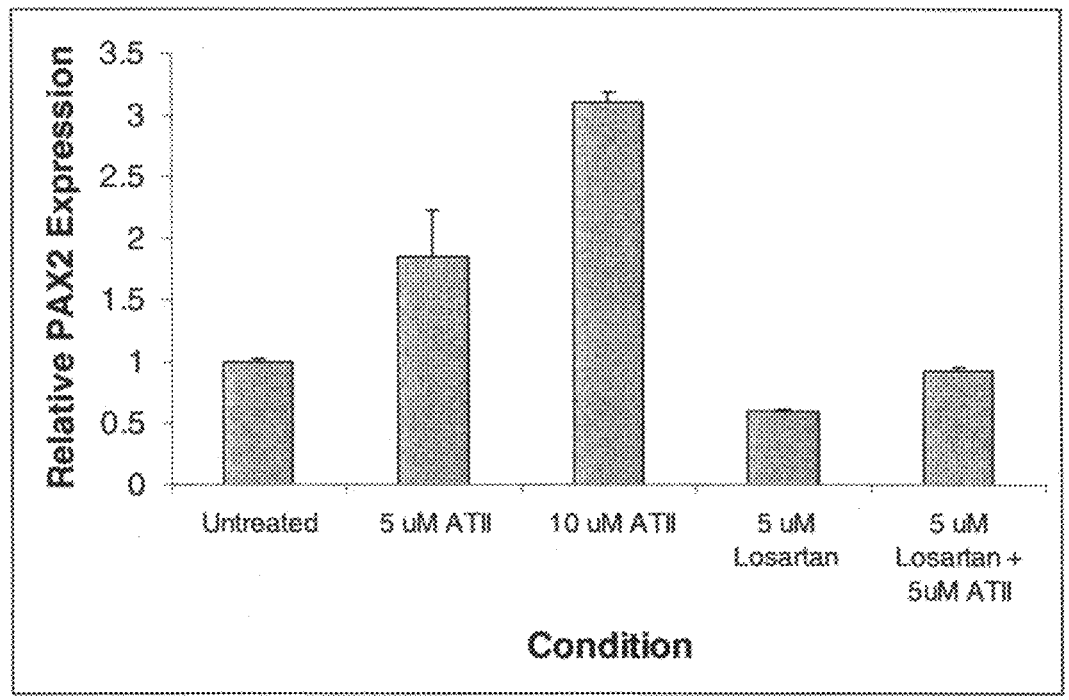
FIG. 21 shows Los blocks AngII effect on PAX2 expression in DU145. Treatment of DU145 cells with 5 μM of AngII for 72 hours resulted in a 2-fold increase in PAX2 expression. In addition, treatment with 10 μM for 72 hours resulted in more than a 3-fold increase in expression. Treatment of cells with 5 μM of Losartan suppressed proliferation by 50%. In addition, treatment with Losartan for 30 min prior to treatment with AngII blocked the effect of AngII on proliferation.

To investigate the effect of AngII on PAX2 expression in DU145 prostate cancer cells, PAX2 expression was examined following treatment with AngII over a 30 min to 48 hour period. As shown in FIG. 19, PAX2 expression progressively increased over time following AngII treatment. Blocking RAS signaling by treating DU145 with Los significantly reduced PAX2 expression (FIG. 20A). Here, PAX2 expression was 37% after 48 hours and was 50% after 72 hours of Los treatment compared to untreated control DU145 cells (FIG. 21). It is known that the AT2R receptor oppose the action of the AT1R. Therefore, the effect of blocking the AT2R receptor on PAX2 expression was examined. Treatment of DU145 with the AT2R blacker PD123319 resulted in a 7-fold increase in PAX2 expression after 48 hours and an 8-fold increase after 96 hours of treatment (FIG. 20B). Collectively, these findings demonstrate that PAX2 expression is regulated by the ATR1 receptor.

It is known that AngII directly affects the proliferation of prostate cancer cells through AT1R—mediated activation of MAPK and STAT3 phosphorylation. Treatment of DU145 with AngII resulted in a two- to three-fold increase in proliferation rate (FIG. 21). However, treatment with Los decreased proliferated rates by 50%. In addition, blocking the AT1R receptor by pre-treating with Los for 30 min suppressed the effect of AngII on proliferation.

Figure 22:
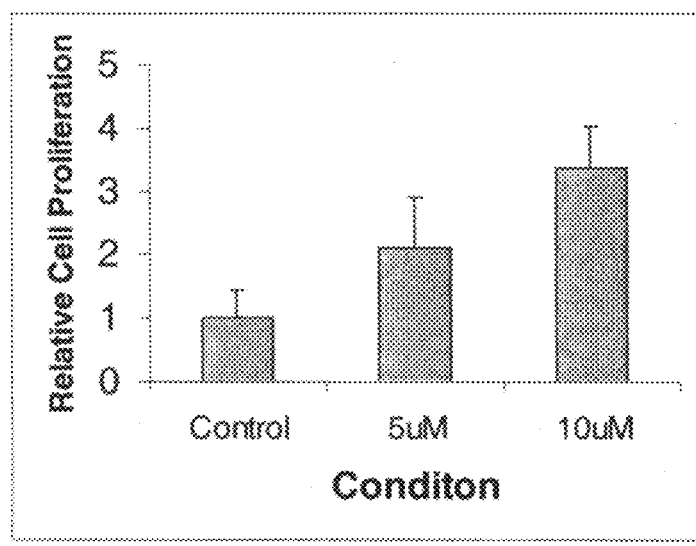
FIG. 22 shows AngII increases DU145 cell proliferation. Treatment of DU145 cells with 5 μM of AngII for 72 hours resulted in a 2-fold increase in proliferation. In addition, treatment with 10 μM for 72 hours resulted in more than a 3-fold increase in proliferation.
Figure 23A:
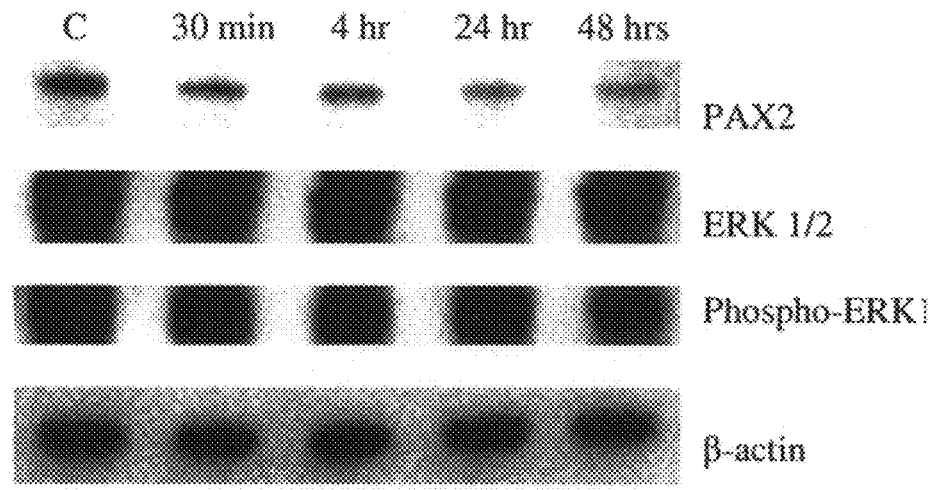
FIG. 23A shows treatment of DU145 cells with Losartan suppresses phosphor-ERK 1/2 and PAX2 expression.
Figure 23B:
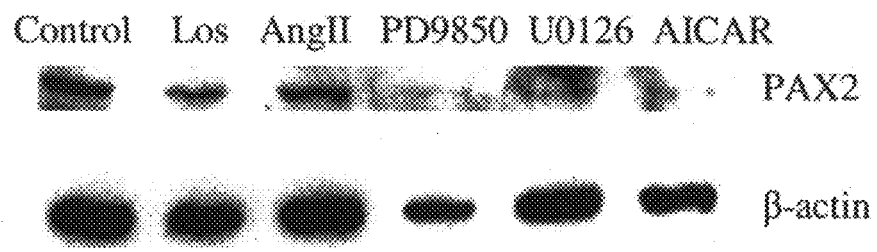
FIG. 23B shows MEK kinase inhibitors and AICAR suppresses PAX2 protein expression.
Figure 23C:
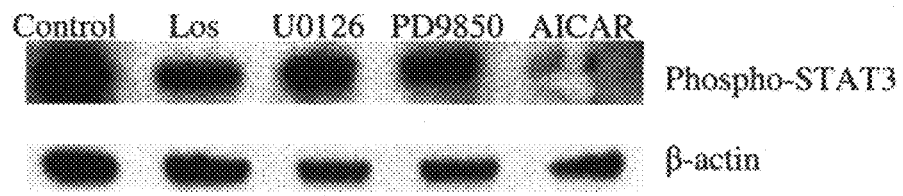
FIG. 23C shows MEK kinase inhibitors and Losartan suppresses phospho-STAT3 protein expression.

To further examine the role of the AT1R signaling in the regulation of PAX2 expression and activation, the effect of blocking various components of the MAP kinase signaling pathway on PAX2 expression was examined. Here, DU145 cells treated with the MEK inhibitor U0126 resulted in a significant reduction of PAX2 expression (FIG. 22). Furthermore, treatment with MEK/ERK inhibitor PD98059 also resulted in decreased PAX2. Treatment of DU145 cells with Los had no effect on ERK protein levels, but reduced the amount of phospho-ERK (FIG. 23A). However, treatment of DU145 with Los resulted in a significant reduction of PAX2 expression. Similar results were observed with U0126 and PD98059. It is also known that PAX2 expression is regulated by STAT3 which is a down-stream target of ERK. Treatment of DU145 with Los, U0126, and PD98059 reduced phospho-STAT3 protein levels (FIG. 23C). These results demonstrate that PAX2 is regulated via AT1R in prostate cancer cells.

Figure 24A:
FIG. 24A shows treatment of DU145 cells with inhibitors of AT1R signaling resulted in a decrease in phosphor-PAX2 protein levels which is the active form of PAX2. In addition, treatment with the AMP kinase inducer AICAR resulted in suppressed PAX2 expression.
Figure 24B:
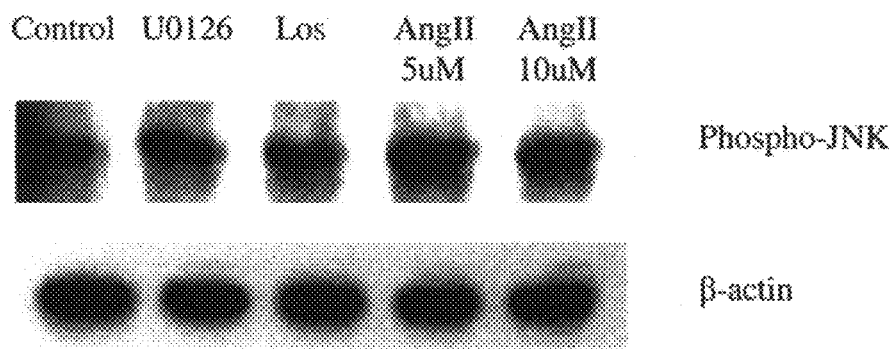
FIG. 24B shows inhibition of AT1R signaling with Los decreased phopho-JNK levels. However, AngII increased phosphor-JNK protein levels.
Figure 25:
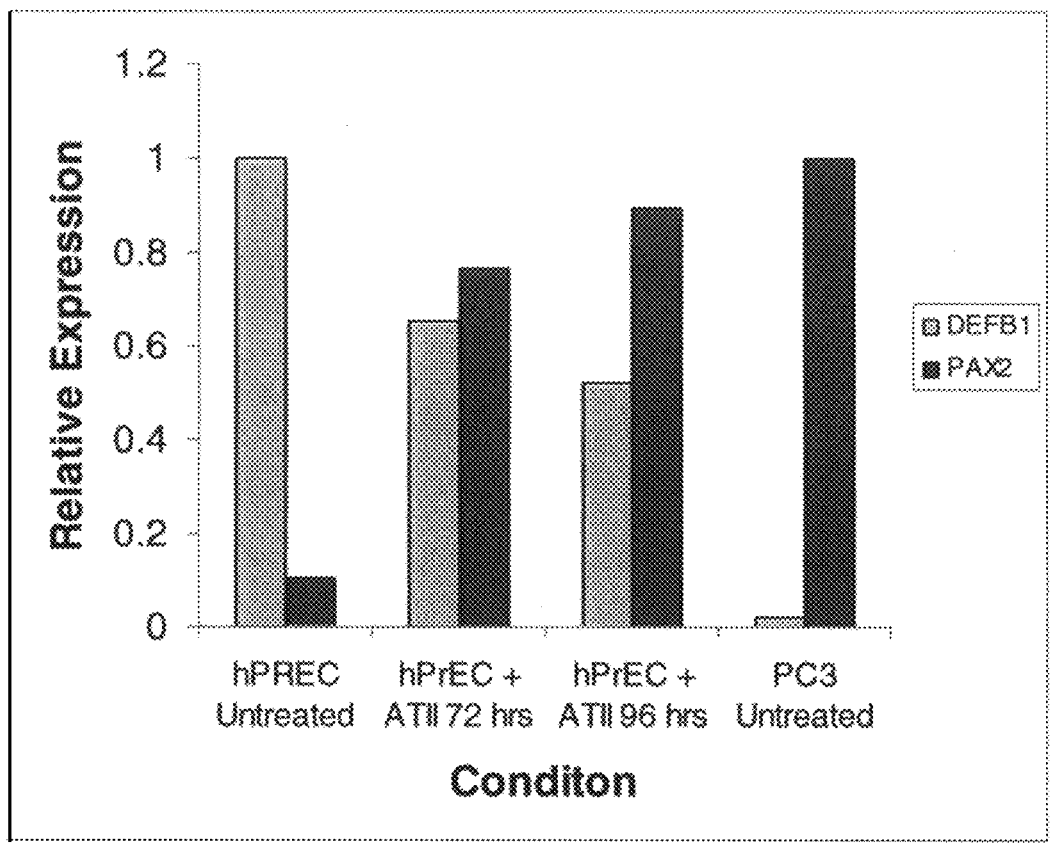
FIG. 25 shows AngII increases PAX2 and decreases DEFB1 expression in hPrEC cells. To determine the effect of AngII on PAX2 levels in hPrEC, cells were treated for 72 and 96 hours and PAX2 and DEFB1 expression was examined by QRT-PCR. Here, AngII treatment resulted in dramatic increases in PAX2 to levels similar to PC3 prostate cancer cells. Conversely, DEFB1 expression was reduced significantly after AngII treatment.

In addition, the effect of AT1R signaling on PAX2 activation by JNK was examined. Treatment of DU145 with Los, U0126, and PD98059 all resulted in a significant decrease or suppression of phospho-PAX2 protein levels (FIG. 24A). However, Los and U0126 did not decrease phospho-JNK protein levels (FIG. 24B). Therefore, the decrease in phospho-PAX2 appears to be due to decreased PAX2 levels, but not decreased phosphorylation.

5-Aminoimidazole-4-carboxamide-1-β-4-ribofuranoside (AICAR) is widely used as an AMP-kinase activator, which regulates energy homeostasis and response to metabolic stress. Recent reports have indicated anti-proliferative and pro-apoptotic action of activated AMPK using pharmacological agents or AMPK overexpression. AMPK activation has been shown to induce apoptosis in human gastric cancer cells, lung cancer cells, prostate cancer, pancreatic cells, and hepatic carcinoma cells and enhance oxidative stress induced apoptosis in mouse neuroblastoma cells, by various mechanisms that include inhibition of fatty acid synthase pathway and induction of stress kinases and caspase 3. In addition, treatment of PC3 prostate cancer cells increased expression of p21, p27, and p53 proteins and inhibition of PI3K-Akt pathway. All of these pathways are directly or indirectly regulated by PAX2. Treatment of prostate cancer cells with AICAR resulted in the suppression of PAX2 pression expression (FIG. 23B) as well as its activated form phosphor-PAX2 (FIG. 24A). In addition, phospho-STAT3 which regulated PAX2 expression was also suppressed (FIG. 23C).

Finally, it was hypothesized that aberrant RAS signaling which leads to upregulation and overexpression of PAX2 suppresses the expression of the DEFB1 tumor suppressor gene. To investigate this, the normal prostate epithelial primary culture hPrEC was treated with AngII and examined both PAX2 and DEFB1 expression levels. An inverse relationship between DEFB1 and PAX2 expression was discovered in normal prostate cells versus prostate cancer cells. Untreated hPrEC exhibited 10% relative PAX2 expression compared to expression in PC3 prostate cancer cells. Conversely, untreated PAX2 exhibited only 2% relative DEFB1 expression compared to expression in hPrEC. Following 72 hours of treatment with 10 uM of AngII, there was a 35% decrease in DEFB1 expression compared to untreated hPrEC, and by 96 hours there was a 50% decrease in DEFB1 expression compared to untreated hPrEC cells. However, there was 66% increase in PAX2 expression at 72 hours, and by 96 hours there was a 79% increase in PAX2 expression compared to untreated hPrEC cells. Furthermore, the increase in PAX2 expression in hPrEC after 72 hours was 77% of PAX2 levels observed in PC3 prostate cancer cells. After 96 hours of AngII treatment PAX2 expression was 89% of PAX2 expression in PC3. These results demonstrate that deregulated RAS signaling suppresses DEFB1 expression via the upregulation of PAX2 expression in prostate cells.

Discussion

The Renin-Angiotensin system AngII is a major regulator of blood pressure and cardiovascular homeostasis and is recognized as a potent mitogen. Ang II mediates its biological effects through binding to two subtypes of receptors, AT1R and AT2R which belong to the superfamily of G-protein-coupled receptors but have different tissue distribution and intracellular signaling pathways. Upregulation of AT1 provides a considerable advantage to cancer cells that have learned to evade apoptosis and growth regulatory elements. Furthermore, increased expression of AT1R has been detected in prostate cancer tissue compared to expression levels in normal human prostate.

It is now well established that AT1R induces cell proliferation in a variety of cellular models, including human cancer cells, by activating various intracellular cascades of protein kinases usually associated with growth factor stimulation. Most notably, AT1R transactivates the EGFR in prostate cancer cells, leading to extracellular-regulated kinase (ERK) activation, phosphorylation of signal transducer and activator of transcription 3 (STAT3). AT1R-mediated transactivation of EGFR is particularly relevant to cancer because EGFR amplification is frequently associated with tumor progression. In fact, efficient anticancer strategies are now being developed using monoclonal antibodies to the EGFR such as Herceptin® (Genentec, Inc.).

Recent interest has focused on the possible role of antihypertensive drugs in anticancer therapy. For example the use of ACE's in experimental animal models indicates a protective effect of these drugs against tumor development. Also, Los and Candesartan which are both AT1R antagonists, have been shown to reduce tumor growth and vascularization in xenograft models of human prostate cancer cells. In addition, upregulation of ACE has been detected in benign prostatic hypertrophy. PAX2 was upregulated in benign regions of patients with PIN and prostate cancer. Therefore, it is plausible that PAX2 is an initiating event in the pathobiology of prostate cancer and may be a viable chemoprevention target for the prevention of prostate cancer development.

Figure 26:
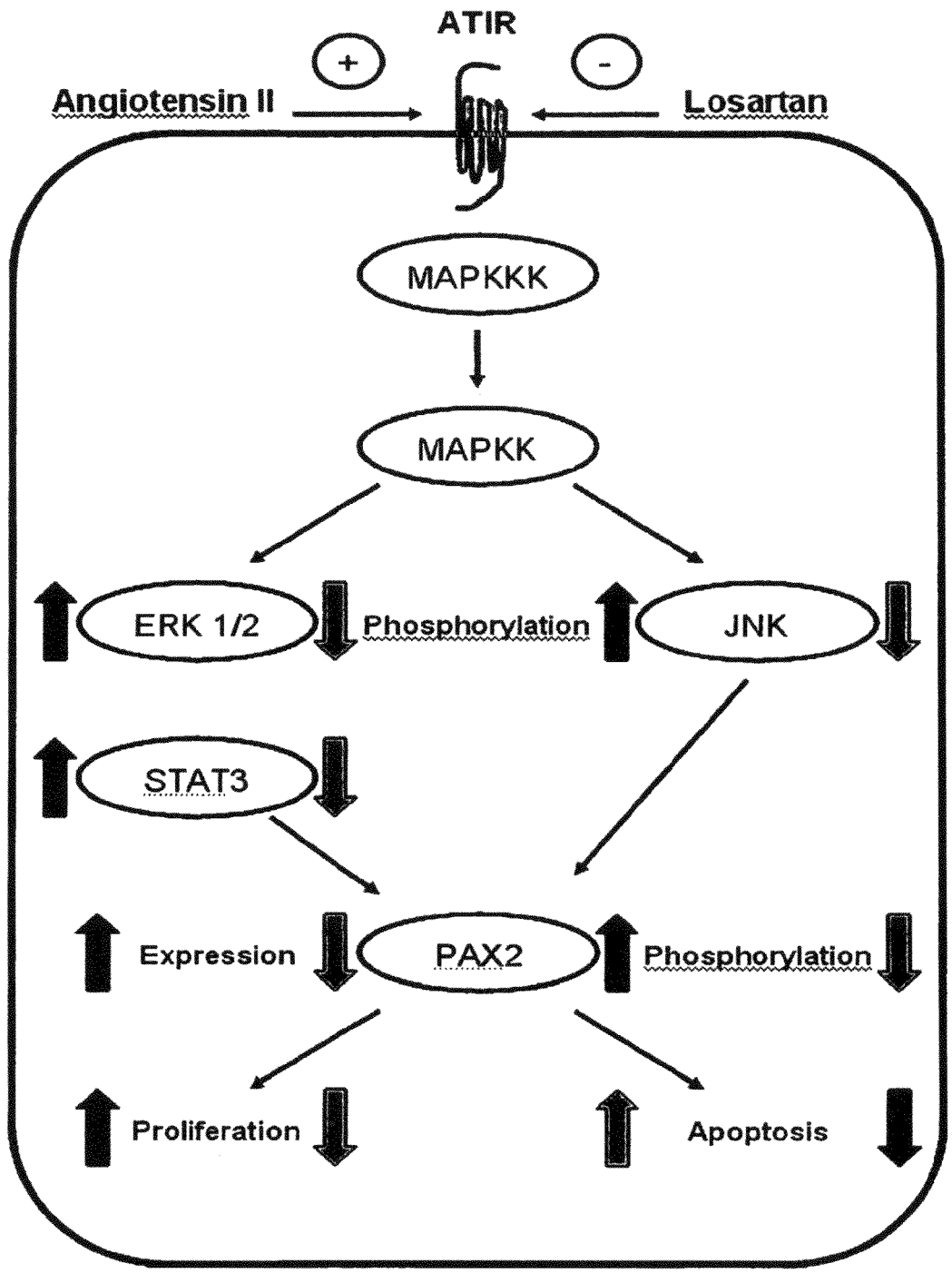
FIG. 26 shows schematic of AngII signaling and PAX2 prostate cancer. PAX2 expression in prostate cancer cells is regulated by the AT1R signaling pathway. Specifically, the MEK kinase signaling cascade leads to increased PAX2 expression. In addition, the AT1R and AngII upregulates PAX2 activation via JNK.
Figure 27:
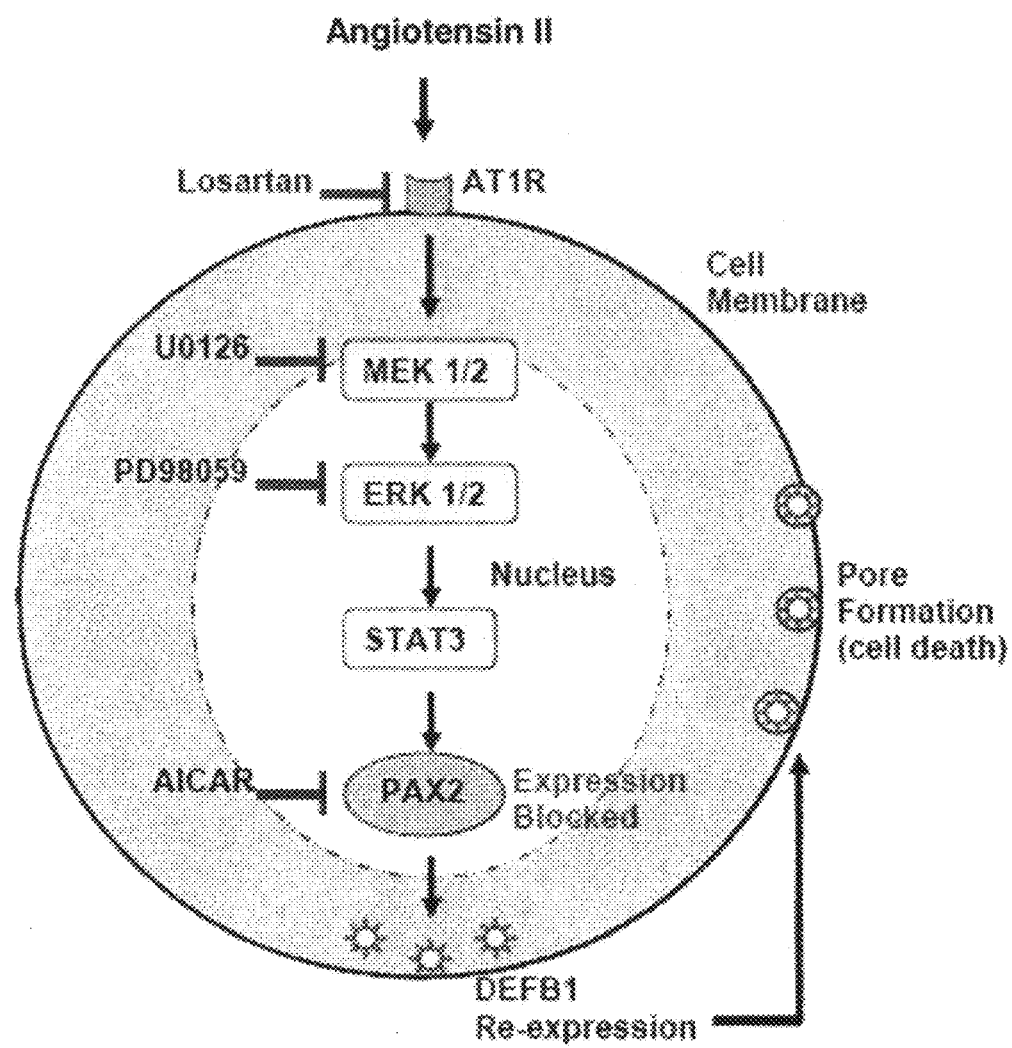
FIG. 27 shows schematic of blocking PAX2 expression as a therapy for prostate cancer.

Inhibition of apoptosis is a critical pathophysiological factor that contributes to the development of prostate cancer. Despite significant advances in cancer therapeutics, little progress has been made in the treatment of advanced disease. Given that carcinogenesis is a multiyear, multistep, multipath disease of progression, chemoprevention through the use of drug or other agents to inhibit, delay, or reverse this process has been recognized as a very promising area of cancer research. Successful drug treatment for the chemoprevention of prostate cancer requires the use of therapeutics with specific effects on target cells while maintaining minimal clinical effects on the host with the overall goal of suppressing cancer development. Therefore, understanding the mechanisms in early stage carcinogenesis is critical in determining the efficacy of a specific treatment. The significance of aberrant PAX2 expression and its abrogation of apoptosis, with subsequent contribution to tumor formation, suggest that it may be a suitable target for prostate cancer treatment. PAX2 was regulated by the AT1R in prostate cancer (FIG. 26). In this, deregulated RAS signaling resulted in increased PAX2 oncogene expression, and a decrease in the expression of DEFB1 tumor suppressor. Therefore, the use of AT1R antagonists decreases PAX2 expression and results in increased prostate cancer cell death via re-expression of DEFB1 (FIG. 27). These results offer a novel finding that targeting PAX2 expression via the Renin-Angiotensin signaling pathway, the AMP Kinase pathway, or other methods involving the inactivation of the PAX2 protein (i.e. anti-PAX2 antibody vaccination) may be a viable target for cancer prevention (Table 7).

TABLE 7

Compounds Utilized to Inhibit PAX2 Expression for Chemoprevention

| | NAME | Drug Class |
| --- | --- | --- |
| Drug 1 | Losartan | Angiotensin Type 1 Receptor blocker |
| Drug 2 | PD123319 | Angiotensin Type 2 Receptor blocker |
| Drug 3 | U0126 | MEK inhibitor |
| Drug 4 | PD98059 | MEK/ERK inhibitor |
| Drug 5 | AICAR | AMP kinase inducer |
| | Target | Drug Function |
| Drug A | Anti-PAX2 Antibody | PAX2 Vaccine |
| Drug B | Angiotensinogen | Renin-AngII pathway inhibitor |
| Drug C | Angiotensin Converting Enzyme | Renin-AngII pathway inhibitor |

8. Example 9

PAX2-DEFB1 Expression Level as a Grading Tool for Prostate Tissue and Predictor of Prostate Cancer Development Materials and Methods QRT-PCR Analysis: Prostate sections were collected from patients that underwent radical prostatectomies. Following pathological examination, laser capture microdisection was performed to isolate areas of Normal, Proliferative Intraepithelial Neoplasia (PIN) and Cancerous tissue. QRT-PCR was performed as previously described to assess expression. DEFB1 and PAX2 expression in each region and GAPDH was used as an internal control.

Blood collection and RNA isolation: For QRT-PCR, blood (2.5 ml) from each individual was colleted into a PAXgene™ Blood RNA tube (QIAGEN) following the manufacturer's protocol. Whole blood was thoroughly mixed with PAXgene stabilization reagent and stored at room temperature for 6 hours prior to RNA extraction. Total RNA was then extracted using the PAXgene™ Blood RNA kit according to the manufacturer's directions (QIAGEN). In order to remove contaminating genomic DNA, total RNA samples absorbed to the PAXgene™ Blood RNA System spin column was incubated with DNase I (QIAGEN) at 25° C. for 20 min to remove genomic DNA. Total RNA was eluted, quantitated, and QRT-PCR is performed as previously mentioned to compare PAX2 and DEFB1 expression ratios.

Results

Figure 28:
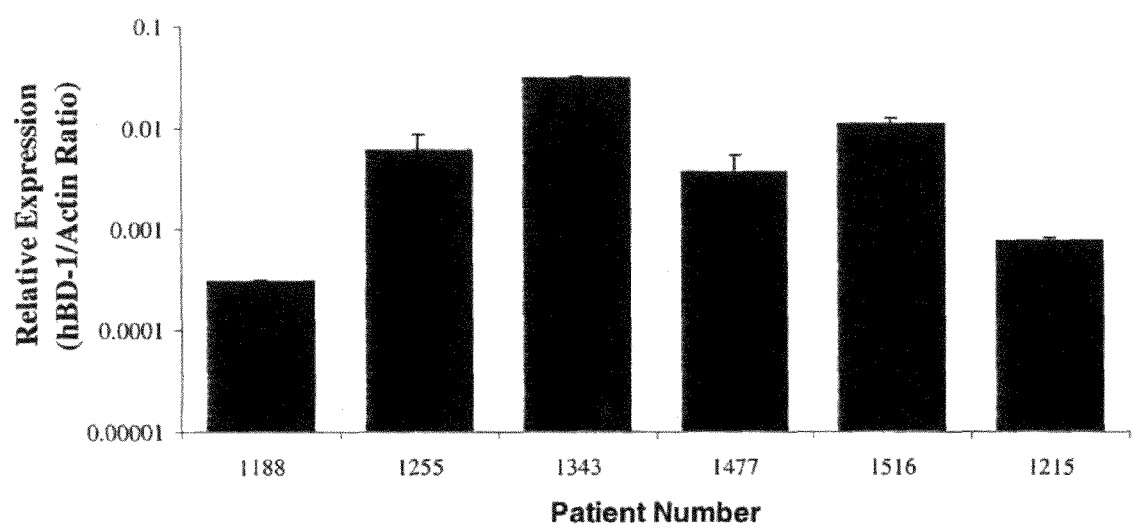
FIG. 28 shows comparison of DEFB1 and PAX2 expression with Gleason Score. DEFB1 relative expression levels were compared in benign clinical samples from 6 patients that underwent radical prostatectomies. Here Gleason score inversely correlated with DEFB1 expression levels in adjacent benign prostate tissue. Patients with relative DEFB1 expression levels higher than 0.005 had Gleason sores of 6. However, those with expression levels less than 0.005 had Gleason scores of 7.

QRT-PCR analysis of LCM normal tissue demonstrated that patients with relative DEFB1 expression levels greater than 0.005 have a lower Gleason Score compared to those with expression levels lower than 0.005 (FIG. 28A). Thus, there is an inverse relationship between DEFB1 expression and Gleason score. Conversely, there was a positive correlation between PAX2 expression and Gleason score in malignant prostate tissue and PIN (FIG. 28B).

Figure 29:
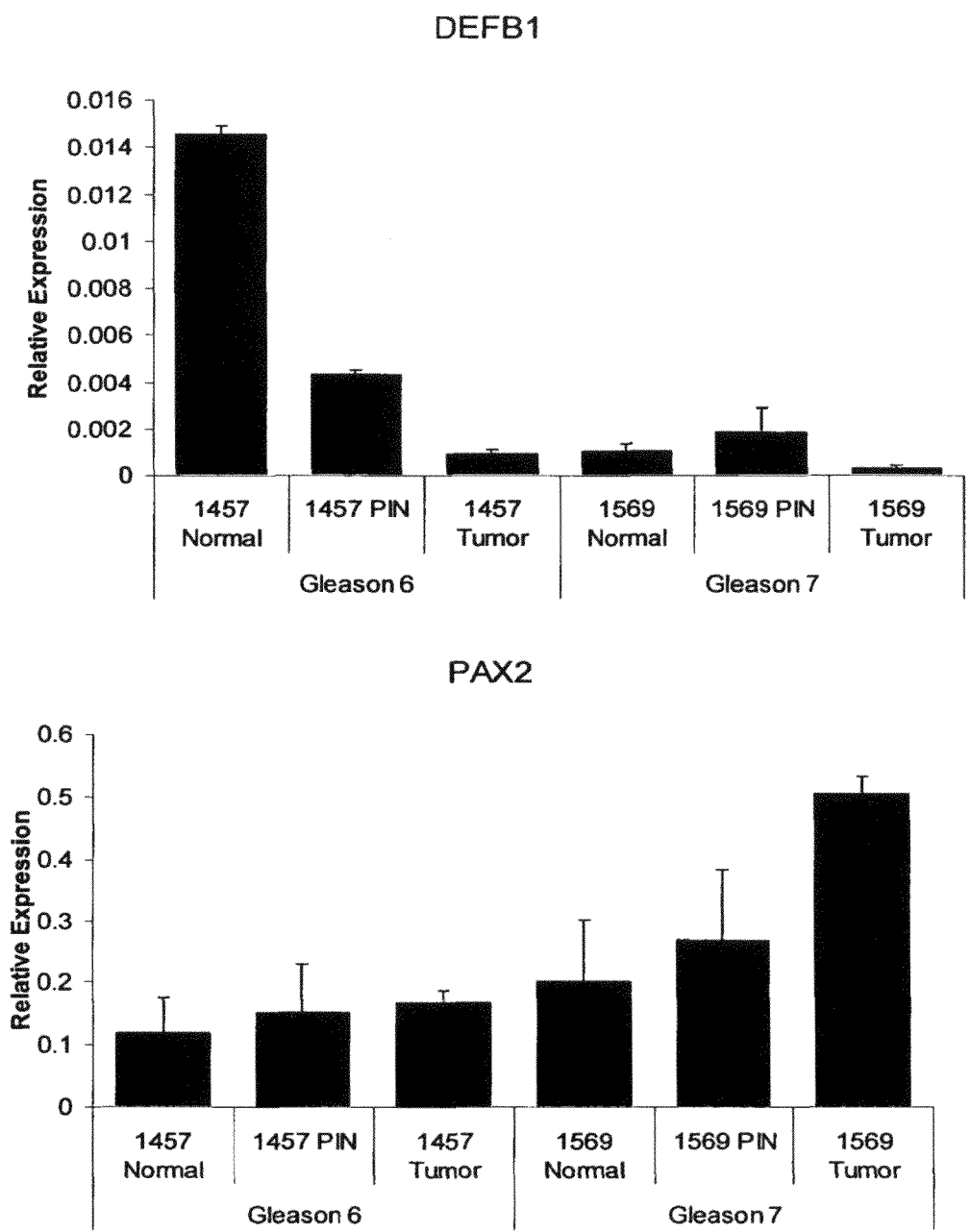
FIG. 29 shows PAX2-DEFB1 ratio as a predictive factor for prostate cancer development. QRT-PCR was performed on laser capture microdissection (LCM) prostate tissue sections to determine relative DEFB1 and PAX2 expression levels. DEFB1 expression levels decreased from Normal to EN to cancer. However, PAX2 expression increased from normal to PIN to cancer. In addition, patient #1457 with Gleason score 6 cancer had more DEFB1 in normal tissue and PIN compared to patient #1569 with Gleason score 7 cancer. Conversely, patient #1569 had higher PAX2 levels in cancerous regions compared to patient #1457.
Figure 30:
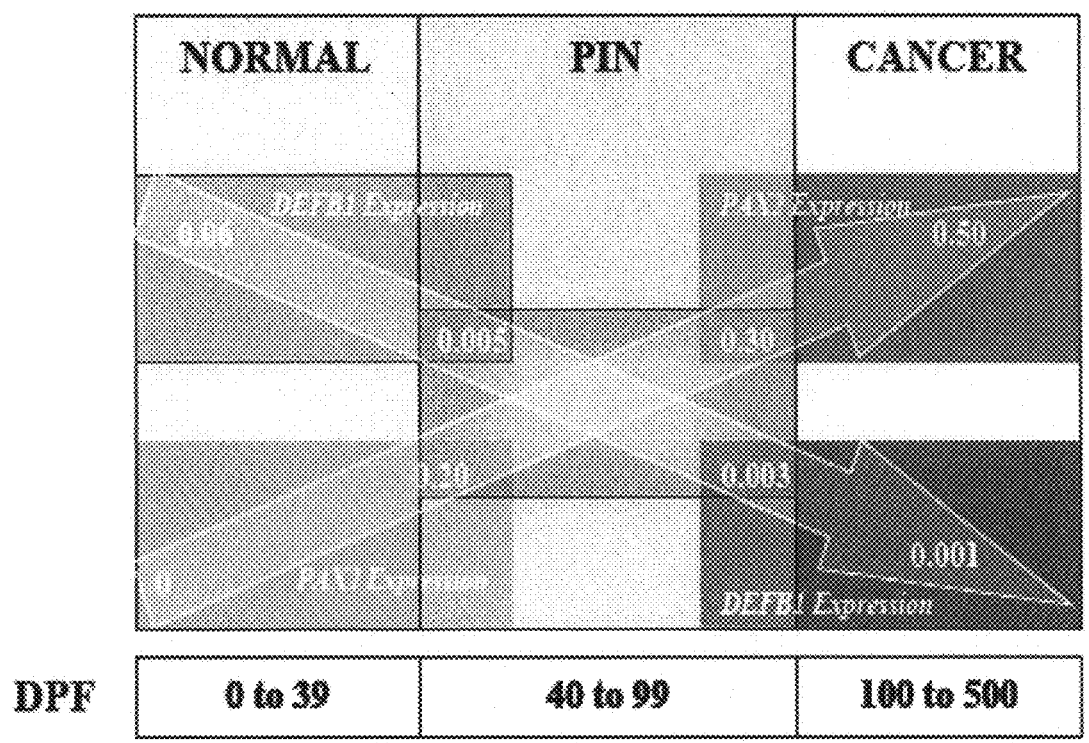
FIG. 30 shows the Donald Predictive Factor (DPF) is based on the relative PAX2-DEFB1 expression ratio. An increase in the DPF of prostate tissue increases the chance of developing prostate cancer. Tissue with a PAX2-DEFB1 ratio between 0 and 39 based on the DPF was normal (benign). Tissue with a PAX2-DEFB1 ratio between 40 and 99 represented PIN (precancerous) based on the DPF scale. Finally, tissue with a PAX2-DEFB1 ratio between 100 and 500 was malignant (low to high grade cancer).

The PAX2 and DEFB1 expression levels in normal, PIN and cancerous tissues from separate patients were calculated and compared (FIG. 29). Overall, PAX2 expression levels relative to GAPDH internal control ranged between 0 and 0.2 in normal (benign) tissue, 0.2 and 0.3 in PIN, and between 0.3 and 0.5 in cancerous (malignant) tissue (FIG. 30). For DEFB1 there was an inverse relationship compared to PAX2. Here, DEFB1 expression levels relative to GAPDH internal control ranged between 0.06 and 0.005 in normal (benign) tissue, 0.005 and 0.003 in PIN, and between 0.003 and 0.001 in cancerous (malignant) tissue. Therefore, disclosed is a predictive scale (DPF) which utilizes the PAX2-DEFB1 expression ratio as a prognosticator of benign, precancerous (PIN) and malignant prostate tissue. Tissues with PAX2-DEFB1 ratios between 0 and 39 based on the DPF will represent normal (pathologically benign). Tissue with a PAX2-DEFB1 ratio between 40 and 99 will represent PIN (pre-cancerous) based on the DPF scale. Finally, tissue with a PAX2-DEFB1 ratio between 100 and 500 will be malignant (low to high grade cancer).

Conclusion

There currently is a critical need for predictive biomarkers for prostate cancer development. It is known that the onset of prostate cancer occurs long before the disease is detectable by current screening methods such as the PSA test or the digital rectal exam. It is thought that a reliable test which could monitor the progression and early onset of prostate cancer would greatly reduce the mortality rate through more effective disease management. Disclosed herein is a predictive index to allow physicians to know well in advance the pathological state of the prostate. The DPF measures the decrease in the PAX2-DEFB1 expression ratio associated with prostate disease progression. This powerful measure can not only predict the likelihood of a patient developing prostate cancer, but also may pinpoint the early onset of pre-malignant cancer. Ultimately, this tool can allow physicians to segregate which patients have more aggressive disease from those which do not.

The identification of cancer-specific markers has been utilized to help identify circulating tumor cells (CTCs). There is also emerging evidence which demonstrates that detection of tumor cells disseminated in peripheral blood can provide clinically important data for tumor staging, prognostication, and identification of surrogate markers for early assessment of the effectiveness of adjuvant therapy. Furthermore, by comparing gene expression profiling of all circulating cells, one can examine the expression of the DEFB1 and PAX2 genes which play a role in "immunosurveillance" and "cancer survival", respectively as a prognosticator for the early detection of prostate cancer.

9. Example 10

Functional Analysis of the Host Defense Peptide Human Beta Defensin-1: New Insight into its Potential Role in Cancer Materials and Methods Cell culture: The prostate cancer cell lines were obtained from the American Type Culture Collection (Manassas, Va.). DU145 cells were cultured in DMEM medium, PC3 and PC3/AR+ were grown in F12 medium, and LNCaP were grown in RPMI medium (Life Technologies, Inc., Grand Island, N.Y.). Growth media for all three lines was supplemented with 10% (v/v) fetal bovine serum (Life Technologies). The hPrEC primary culture was obtained from Cambrex Bio Science, Inc. (Walkersville, Md.) and cells were grown in prostate epithelium basal media. All cells were maintained at 37° C. and 5% CO2.

Tissue samples and laser capture microdissection: Prostate tissues were obtained from patients who provided informed consent prior to undergoing radical prostatectomy. Samples were acquired through the Hollings Cancer Center tumor bank in accordance with an Institutional Review Board-approved protocol. This included guidelines for the processing, sectioning, histological characterization, RNA purification and PCR amplification of samples. Prostate specimens received from the surgeons and pathologists were immediately frozen in OCT compound. Each OCT block was cut to produce serial sections which were stained and examined. Areas containing benign cells, prostatic intraepithelial neoplasia (PIN), and cancer were identified and used to guide our selection of regions from unstained slides using the Arcturus PixCell II System (Sunnyvale, Calif.). Caps containing captured material were exposed to 20 µl of lysate from the Arcturus Pico Pure RNA Isolation Kit and processed immediately. RNA quantity and quality was evaluated using sets of primers that produce 5' amplicons. The sets include those for the ribosomal protein L32 (the 3' amplicon and the 5' amplicon are 298 bases apart), for the glucose phosphate isomerase (391 bases apart), and for the glucose phosphate isomerase (842 bases apart). Ratios of 0.95 to 0.80 were routinely obtained for these primer sets using samples from a variety of prepared tissues. Additional tumor and normal samples were grossly dissected by pathologists, snap frozen in liquid nitrogen and evaluated for hBD-1 and cMYC expression.

Cloning of hBD-1 gene: hBD-1 cDNA was generated from RNA by reverse transcription-PCR using primers generated from the published hBD-1 sequence (accession no. U50930) (Ganz, 2004). The PCR primers were designed to contain ClaI and KpnI restriction sites. hBD-1 PCR products were restriction digested with ClaI and KpnI and ligated into a TA cloning vector. The TA/hBD1 vector was then transfected into the XL-1 Blue strain of E. coli by heat shock and individual clones were selected and expanded. Plasmids were isolated by Cell Culture DNA Midiprep (Qiagen, Valencia, Calif.) and sequence integrity verified by automated sequencing. The hBD-1 gene fragment was then ligated into the pTRE2 digested with ClaI and KpnI, which served as an intermediate vector for orientation purposes. The pTRE2/hBD-1 construct was digested with ApaI and KpnI to excise the hBD-1 insert. The insert was ligated into pIND vector of the Ecdysone Inducible Expression System (Invitrogen, Carlsbad, Calif.) also double digested with ApaI and KpnI. The construct was transfected into E. coli and individual clones were selected and expanded. Plasmids were isolated and sequence integrity of pIND/hBD-1 was again verified by automated sequencing.

Transfection: Cells (1×10$^6$) were seeded onto 100-mm Petri dishes and grown overnight. Next, the cells were co-transfected using Lipofectamine 2000 (Invitrogen) with 1 µg of pvgRXR plasmid, which expresses the heterodimeric ecdysone receptor, and 1 µg of the pIND/hBD-1 vector construct or pIND/β-galactosidase (β-gal) control vector in Opti-MEM media (Life Technologies, Inc.). Transfection efficiency was determined by inducing β-gal expression with Ponasterone A (PonA) and staining cells with a β-galactosidase detection kit (Invitrogen). Assessment of transfection efficiency by counting positive staining (blue) colonies which demonstrated that 60-85% of cells expressed β-galactosidase for the cell lines.

Immunocytochemistry: In order to verify hBD-1 protein expression, DU145 and hPrEC cells were seeded onto 2-chamber culture slides (BD Falcon, USA) at 1.5-2×10$^4$ cells per chamber. DU145 cells transfected with pvgRXR alone (control) or with the hBD-1 plasmid were induced for 18 h with media containing 10 µM Pon A, while untransfected cells received fresh growth media. Following induction, cells were washed in 1×PBS and fixed for 1 h at room temperature with 4% paraformaldehyde. Cells were then washed six times with 1×PBS and blocked in 1×PBS supplemented with 2% BSA, 0.8% normal goat serum (Vector Laboratories, Inc., Burlingame, Calif.) and 0.4% Triton-X 100 for 1 h at room temperature. Next, cells were incubated overnight in primary rabbit anti-human BD-1 polyclonal antibody (PeproTech Inc., Rocky Hill, N.J.) diluted 1:1000 in blocking solution. Following this, cells were washed six times with blocking solution and incubated for 1 h at room temperature in Alexa Fluor 488 goat anti-rabbit IgG (H+L) secondary antibody at a dilution of 1:1000 in blocking solution. After washing cells with blocking solution six times, coverslips were mounted with Gel Mount (Biomeda, Foster City, Calif.). Finally, cells were viewed under differential interference contrast (DIC) and under laser excitation at 488 nm. The fluorescent signal was analyzed by confocal microscopy (Zeiss LSM 5 Pascal) using a 63×DIC oil lens with a Vario 2 RGB Laser Scanning Module. The digital images were exported into Photoshop CS Software (Adobe Systems) for image processing and hard copy presentation.

RNA isolation and quantitative RT-PCR: QRT-PCR was performed as previously described (Gibson et al., 2007). Briefly, total RNA (0.5 µg per reaction) from tissue sections were reverse transcribed into cDNA utilizing random primers (Promega). Two-step QRT-PCR was performed on cDNA generated using the MultiScribe Reverse Transcriptase from the TaqMan Reverse Transcription System and the SYBR Green PCR Master Mix (Applied Biosystems, Foster City, Calif.). The primer pairs for hBD-1 and c-MYC were generated from the published sequences (Table 7). Forty cycles of PCR were performed under standard conditions using an annealing temperature of 56.4° C. for hBD-1 and c-MYC and 55° C. for PAX2. In addition, β-actin (Table 7) was amplified as a housekeeping gene to normalize the initial content of total cDNA. Gene expression in benign prostate tissue samples was calculated as the expression ratio compared to β-actin. Levels of hBD-1 expression in malignant prostate tissue, hPREC prostate primary culture, and prostate cancer cell lines before and after induction were calculated relative to the average level of hBD-1 expression in hPrEC cells. As a negative control, QRT-PCR reactions without cDNA template were also performed. All reactions were run a minimum of three times.

MTT cell viability assay: To examine the effects of hBD-1 on cell growth, metabolic 3-[4,5-dimethylthiazol-2-yl]-2,5-diphenyl tetrazolium bromide (MTT) assay was performed. DU145, LNCaP, PC3 and PC3/AR+ cells co-transfected with pvgRXR plasmid and pIND/hBD-1 construct or control pvgRXR plasmid were seeded onto a 96-well plate at 1-5×10$^3$ cells per well. Twenty-four hours after seeding, fresh growth medium was added containing 10 µM Pon A daily to induce hBD-1 expression for 24, 48 and 72 h after which the MTT assay was performed according to the manufacturer's instructions (Promega). Reactions were performed three times in triplicate.

Analysis of membrane integrity: Acridine orange (AO)/ethidium bromide (EtBr) dual staining was performed to identify changes in cell membrane integrity, as well as apoptotic cells by staining the condensed chromatin. AO stains viable cells and early apoptotic cells, whereas EtBr stains late stage apoptotic cells that have compromised membranes. Briefly, PC3, DU145 and LNCaP cells were seeded into 2-chamber culture slides (BD Falcon). Cells transfected with empty plasmid or hBD-1 plasmid were induced for 24 or 48 h with media containing 10 µM Pon A, while control cells received fresh growth media at each time point. After induction, cells were washed once with PBS and stained with 2 ml of a mixture (1:1) of AO (Sigma, St. Louis, Mo.) and EtBr (Promega) (5 µg/ml) solution for 5 min and were again washed with PBS.

Fluorescence was viewed by a Zeiss LSM 5 Pascal Vario 2 Laser Scanning Confocal Microscope (Carl Zeiss). The excitation color wheel contains BS505-530 (green) and LP560 (red) filter blocks which allowed for the separation of emitted green light from AO into the green channel and red light from EtBr into the red channel. The laser power output and gain control settings within each individual experiment were identical between control and hBD-1 induced cells. The excitation was provided by a Kr/Ar mixed gas laser at wavelengths of 543 nm for AO and 488 nm for EtBr. Slides were analyzed under 40× magnification and digital images were stored as uncompressed TIFF files and exported into Photoshop CS software (Adobe Systems) for image processing and hard copy presentation.

TABLE 7

Sequences of QRT-PCR primers

| | Sense (5'-3') | Antisense (5'-3') |
|---|---|---|
| β-Actin | CCTGGCACCCAGCACAAT (SEQ ID NO: 34) | GCCGATCCACACGGAGTACT (SEQ ID NO: 36) |
| hBD-1 | TCAGCAGTGGAGGGCAATG (SEQ ID NO: 50) | CCTCTGTAACAGGTGCCTTGAAT (SEQ ID NO: 51) |
| cMYC | ACAGCAAACCTCCTCACAGCC (SEQ ID NO: 52) | TGGAGACGTGGCACCTCTTG (SEQ ID NO: 53) |

Nucleotide sequences of primers used to amplify hBD-1, cMyc, PAX2, and β-actin.

Flow cytometry: PC3 and DU145 cells transfected with the hBD-1 expression system were grown in 60-mm dishes and induced for 12, 24, and 48 h with 10 µM Pon A. Following each incubation period, the medium was collected from the plates (to retain any detached cells) and combined with PBS used to wash the plates. The remaining attached cells were harvested by trypsinization and combined with the detached cells and PBS. The cells were then pelleted at 4° C. (500×g) for 5 min, washed twice in PBS, and resuspended in 100 µl of 1×Annexin binding buffer (0.1 M Hepes/NaOH at pH 7.4, 1.4 M NaCl, 25 mM $CaCl_2$) containing 5 of Annexin V-FITC and 5 µl of PI. The cells were incubated at RT for 15 min in the dark, then diluted with 400 µl of 1× Annexin binding buffer and analyzed by FACscan (Becton Dickinson, San Jose, Calif.). All reactions were performed three times.

Caspase detection: Detection of caspase activity in the prostate cancer cell lines was performed using an APO LOGIX™ Carboxyfluorescin Caspase detection kit (Cell Technology, Mountain View, Calif.). Active caspases were detected through the use of the carboxyfluorescein labeled peptide fluoromethyl ketone (FAMVAD-FMK) that irreversibly binds to active caspases. Briefly, DU145 and LNCaP cells ($1.5-3\times10^5$) containing the hBD-1 expression system were plated in 35 mm glass bottom dishes (Matek, Ashland, Mass.) and treated for 24 h with media only or with media containing Pon A as previously described. Next, 10 µl of a 30× working dilution of FAM-VAD-FMK was added to 300 µl of media and added to each 35 mm dish. Cells were then incubated for 1 h at 37° C. under 5% CO2. The medium was aspirated and the cells were washed twice with 2 ml of a 1× working dilution Wash Buffer. Cells were viewed under differential interference contrast (DIC) or under laser excitation at 488 nm. The fluorescent signal was analyzed by confocal microscopy as described above.

siRNA silencing of PAX2: SiRNA knock-down and verification was performed as previously described (Gibson et al., 2007). Briefly, a pool of four complementary siRNAs targeting human PAX2 mRNA (accession no. NM_003989.1) were synthesized (Dharmacon Research, Lafayette, Colo., USA). In addition, a second pool of four non-specific siRNAs was used as a negative control to test for the specificity of PAX2 siRNAs. SiRNA molecules were coated with Code-Breaker transfection reagent (Promega, Inc.) according to manufacturer's directions prior to treatment.

Statistical analysis: Statistical analysis was performed by using the Student's t-test for unpaired values. P values were determined by a two-sided calculation, and a P value of less than 0.05 was considered statistically significant. Statistical differences are indicated by asterisks.

Figure 31A:
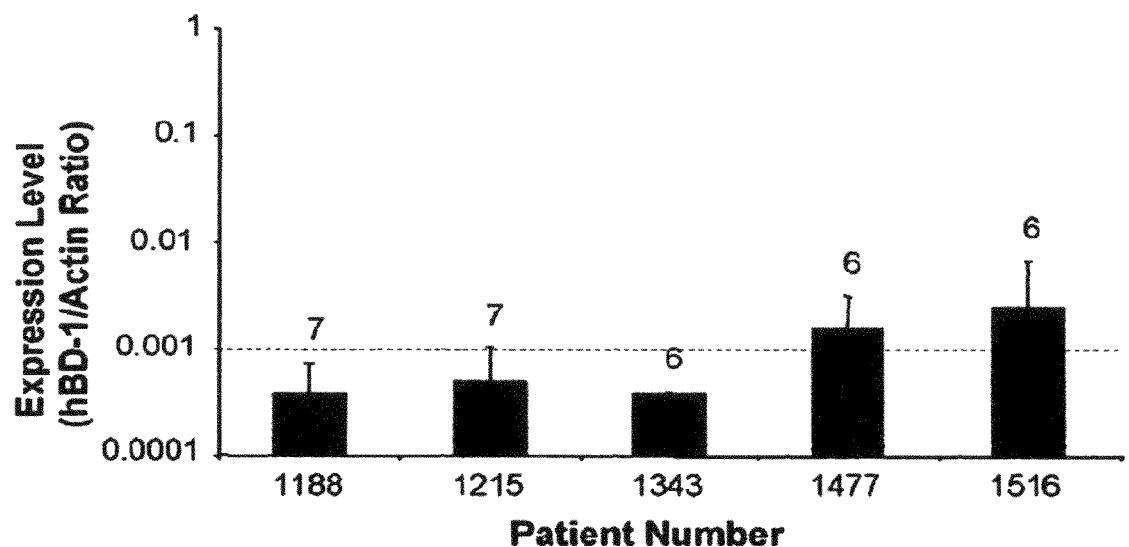
FIG. 31A shows hBD-1 expression levels compared in tissues obtained by gross dissection.
Figure 31B:
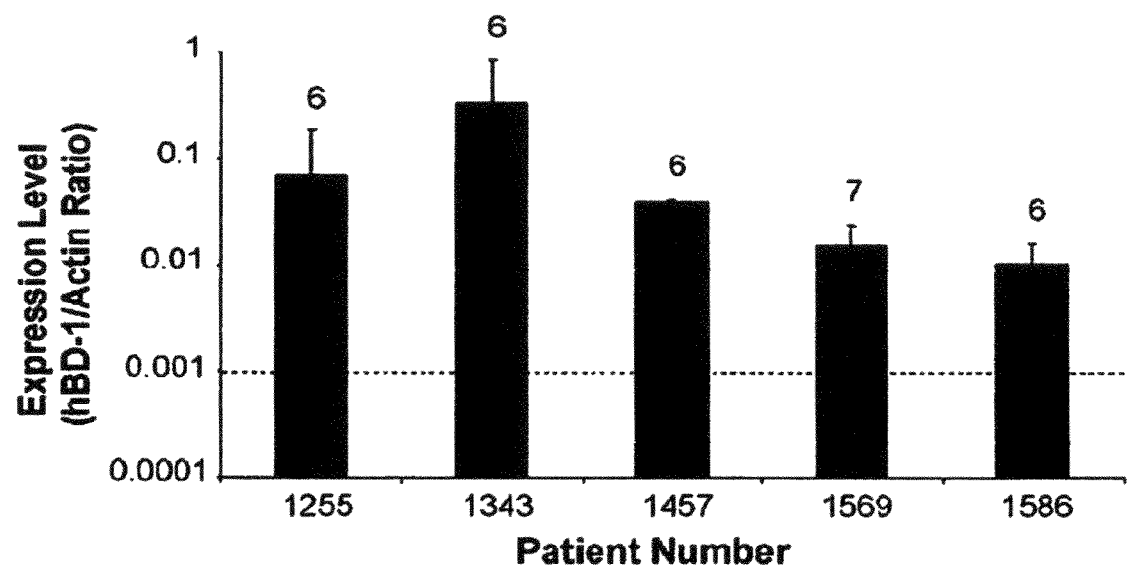
FIG. 31B shows hBD-1 expression levels compared in tissue obtained by Laser Capture Microdissection.
Figure 32A:
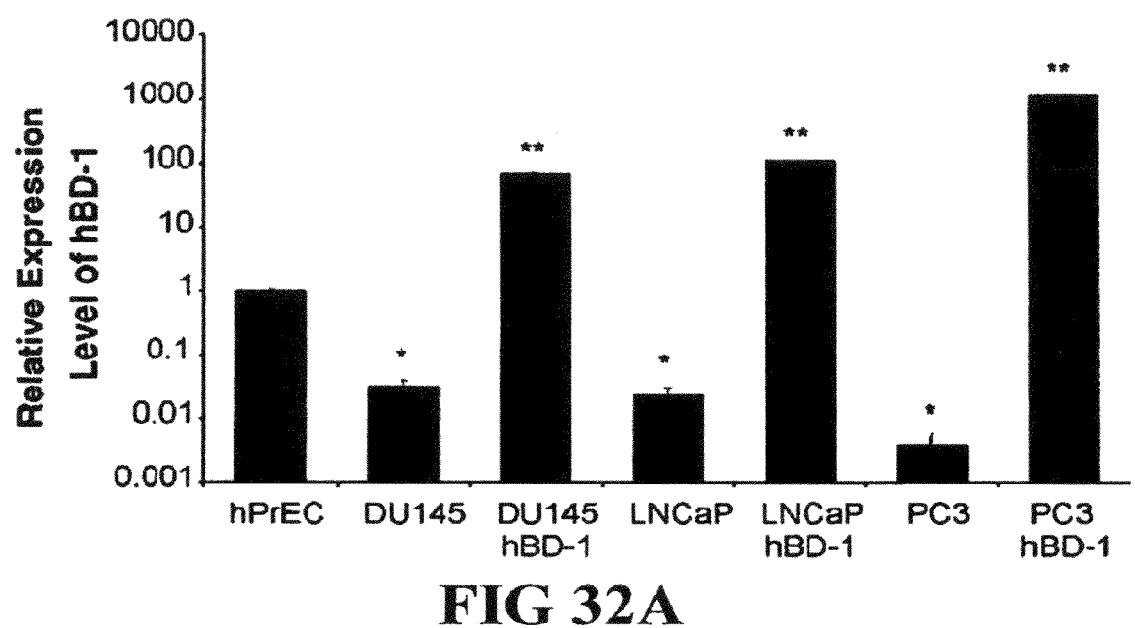
FIG. 32A shows hBD-1 expression levels compared relative to hPrEC cells in prostate cancer cell lines before and after hBD-1 induction. An asterisk represents statistically higher expression levels compared to hPrEC. Double asterisks represent statistically significant levels of expression compared to the cell line before hBD-1 induction (Student's t-test, p<0.05).

Results hBD-1 expression in prostate tissue: 82% of prostate cancer frozen tissue sections analyzed exhibited little or no expression of hBD-1 (Donald et al., 2003). To compare hBD-1 expression levels, QRTPCR analysis was performed on normal prostate tissue obtained by gross dissection or LCM of normal prostate tissue adjacent to malignant regions which were randomly chosen. Here, hBD-1 was detected in all of the gross dissected normal clinical samples with a range of expression that represents approximately a 6.6-fold difference in expression levels (FIG. 31A). LCM captured normal tissue samples expressed hBD-1 at levels in a range that represents a 32-fold difference in expression (FIG. 31B). Matching sample numbers to corresponding patient profiles revealed that in most cases, the hBD-1 expression level was higher in patient samples with a Gleason score of 6 than in patient samples with a Gleason score of 7. In addition, a comparison of hBD-1 expression levels in tissue obtained by gross dissection and LCM from the same patient, #1343, demonstrated an 854-fold difference in expression between the two isolation techniques. Therefore, these results indicate that LCM provides a more sensitive technique to assess hBD-1 expression in prostate tissue.

hBD-1 expression in prostate cell lines: To verify upregulation of hBD-1 in the prostate cancer cell lines after transfection with the hBD-1 expression system, QRTPCR was performed. In addition, no template negative controls were also performed, and amplification products were verified by gel electrophoresis. Here, hBD-1 expression was significantly lower in the prostate cancer cell lines compared to hPrEC cells. Following a 24 h induction period, relative expression levels of hBD-1 significantly increased in DU145, PC3 and LNCaP as compared to the cell lines prior to hBD-1 induction (FIG. 32A).

Next, protein expression of hBD-1 in was verified DU145 cells transfected with the hBD-1 expression system after induction with Pon A by immunocytochemistry. As a positive control, hBD-1 expressing hPrEC prostate epithelial cells were also examined. Cells were stained with primary antibody against hBD-1 and protein expression was monitored based on the green fluorescence of the secondary antibody (FIG. 32B). Analysis of cells under DIC verify the presence of hPrEC cells and DU145 cells induced for hBD-1 expression at 18 h. Excitation by the confocal laser at 488 nm produced revealed green fluorescence indicating the presence of hBD-1 protein in hPrEC as a positive control. However, there was no detectable green fluorescence in control DU145 cells and empty plasmid induced DU145 cells demonstrating no hBD-1 expression. Confocal analysis of DU145 cells induced for hBD-1 expression revealed green fluorescence indicating the presence of hBD-1 protein following induction with Pon A.

Figure 33:
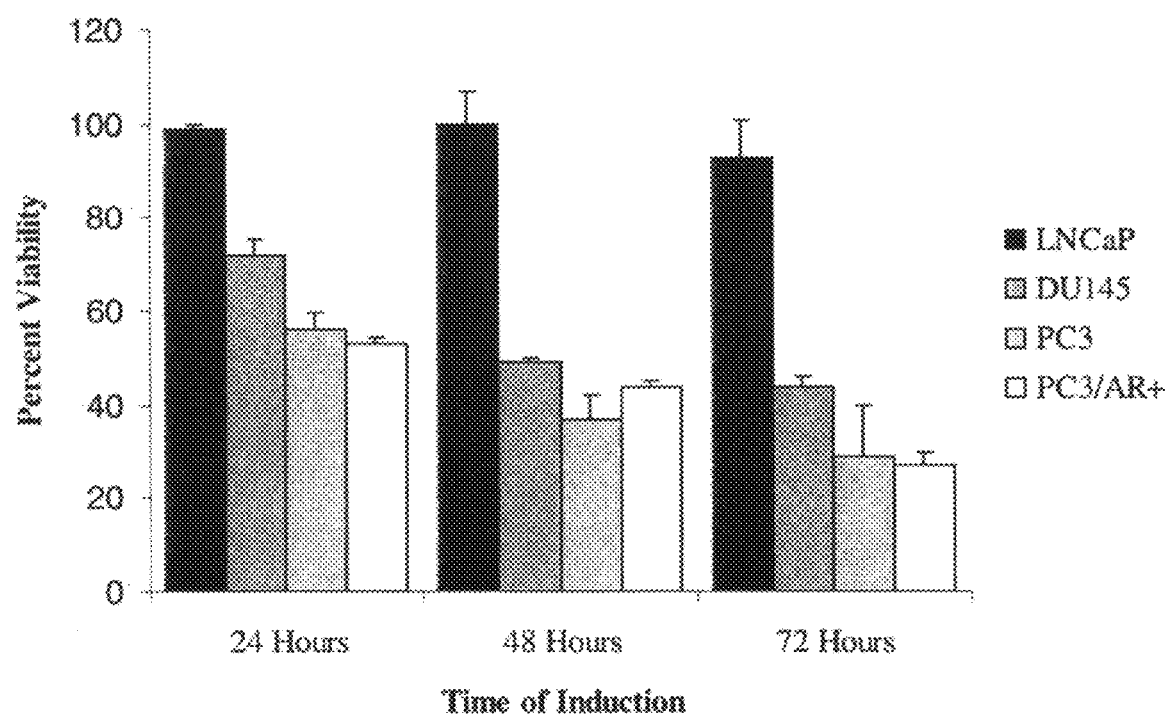
FIG. 33 shows analysis of hBD-1 cytotoxicity in prostate cancer cells. The prostate cell lines DU145, PC3, PC3/AR+ and LNCaP were treated with Pon A to induce hBD-1 expression for 1-3 days after which MTT assay was performed to determine cell viability. Each bar represents the mean±S.E.M. of three independent experiments performed in triplicate.

Expression of hBD-1 results in decreased cell viability: MTT assay was performed to assess the effect of hBD-1 expression on relative cell viability in DU145, PC3, PC3/AR+ and LNCaP prostate cancer cell lines. MTT analysis with empty vector exhibited no statistical significant change in cell viability. Twenty-four hours following hBD-1 induction, relative cell viability was 72% in DU145 and 56% in PC3 cells, and after 48 h cell viability was reduced to 49% in DU145 and 37% in PC3 cells (FIG. 33A). Following 72 h of hBD-1 induction, relative cell viability decreased further to 44% in DU145 and 29% PC3 cells. Conversely, there was no significant effect on the viability of LNCaP cells. In order to assess whether the resistance to hBD-1 cytotoxicity observed in LNCaP was due to the presence of the androgen receptor (AR), the hBD-1 cytotoxicity in PC3 cells was examined with ectopic AR expression (PC3/AR+). Here, there was no difference between PC3/AR+ and PC3 cells. Therefore, the data indicates that that hBD-1 is cytotoxic specifically to late-stage prostate cancer cells.

In order to determine whether the effects of hBD-1 on PC3 and DU145 were cytostatic or cytotoxic, FACS analysis was performed to measure cell death. Under normal growth conditions, more than 90% of PC3 and DU145 cultures were viable and non-apoptotic (lower left quadrant) and did not stain with annexin V or PI (FIG. 4). After inducing hBD-1 expression in PC3 cells, the number of cells undergoing early apoptosis and late apoptosis/necrosis (lower and upper right quadrants, respectively) totaled 10% at 12 h, 20% at 24 h, and 44% at 48 h. For DU145 cells, the number of cells undergoing early apoptosis and late apoptosis/necrosis totaled 12% after 12 h, 34% at 24 h, and 59% after 48 h of induction. No increase in apoptosis was observed in cells containing empty plasmid following induction with Pon A. Annexin V and propidium iodide uptake studies have demonstrated that hBD-1 has cytotoxic activity against DU145 and PC3 prostate cancer cells and results indicate apoptosis as a mechanism of cell death.

hBD-1 causes alterations in membrane integrity and caspase activation: It was investigated whether the cell death observed in prostate cancer cells after hBD-1 induction is caspase-mediated apoptosis. To better understand the cellular mechanisms involved in hBD-1 expression, confocal laser microscopic analysis was performed (FIG. 5) on DU145 and LNCaP cells induced for hBD-1 expression. Pan-caspase activation was monitored based on the binding and cleavage of green fluorescing FAM-VAD-FMK to caspases in cells actively undergoing apoptosis. Analysis of cells under DIC showed the presence of viable control DU145 (FIG. 5A) and LNCaP (FIG. 5E) cells at 0 h. Excitation by the confocal laser at 488 nm produced no detectable green staining which indicates no caspase activity in DU145 (FIG. 5B) or LNCaP (FIG. 5F) control cells. Following induction for 24 h, DU145 (FIG. 5C) and LNCaP (FIG. 5G) cells were again visible under DIC. Confocal analysis under fluorescence revealed green staining in DU145 (FIG. 5D) cells indicating pan-caspase activity after the induction of hBD-1 expression. However, there was no green staining in LNCaP (FIG. 5H) cells induced for hBD-1 expression. Therefore, cell death observed following induction of hBD-1 is caspase-mediated apoptosis.

The proposed mechanism of antimicrobial activity of defensin peptides is the disruption of the microbial membrane due to pore formation (Papo and Shai, 2005). In order to determine if hBD-1 expression altered membrane integrity EtBr uptake was examined by confocal analysis. Intact cells were stained green due to AO which is membrane permeable, while only cells with compromised plasma membranes stained red due to incorporation of membrane impermeable EtBr. Control DU145 and PC3 cells stained positively with AO and emitted green color, but did not stain with EtBr. However, hBD-1 induction in both DU145 and PC3 resulted in the accumulation of EtBr in the cytoplasm at 24 as indicated by the red staining. By 48 h, DU145 and PC3 possessed condensed nuclei and appeared yellow due to the colocalization of green and red staining from AO and EtBr, respectively. Conversely, there were no observable alterations to membrane integrity in LNCaP cells after 48 h of induction as indicated by positive green fluorescence with AO, but lack of red EtBr fluorescence. This finding indicates that alterations to membrane integrity and permeabilization in response to hBD-1 expression differ between early- and late-stage prostate cancer cells.

Figure 34A:
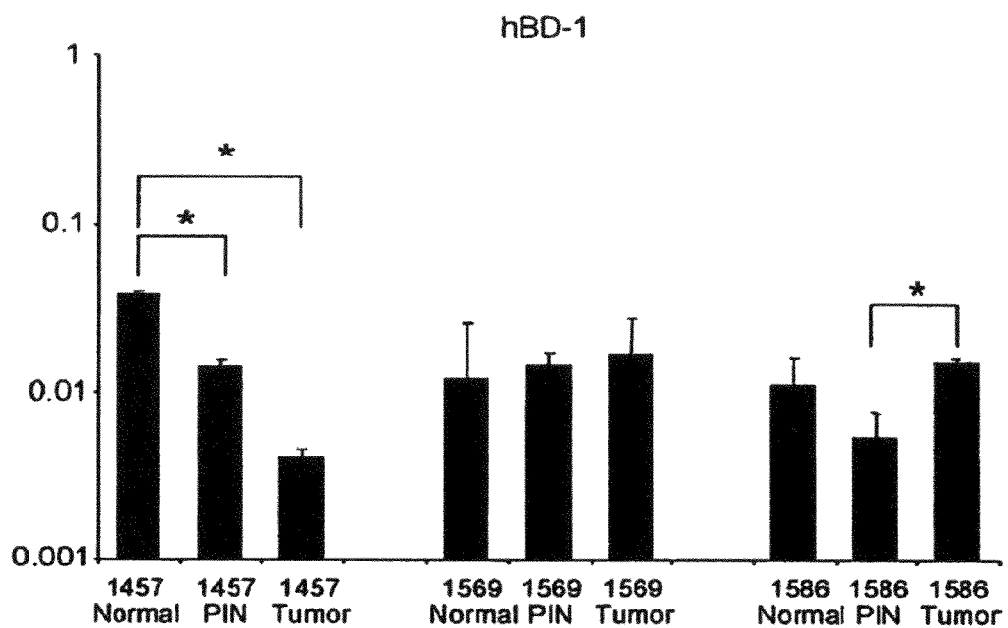
FIG. 34 shows QRT-PCR analysis of hBD-1 and cMYC expression in LCM human prostate tissue sections of normal, PIN and tumor. Expression for each gene is presented as expression ratios compared to β-actin.
Figure 34B:
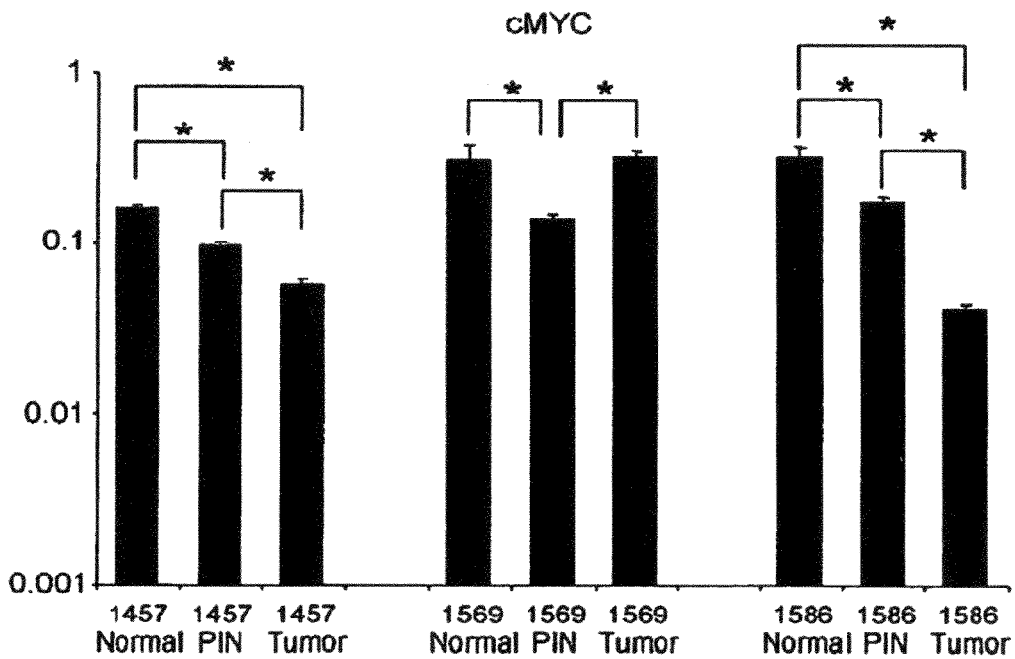

Comparison of hBD-1 and cMYC expression levels: QRT-PCR analysis was performed on LCM prostate tissue sections from three patients (FIG. 34). In patient #1457, hBD-1 expression exhibited a 2.7-fold decrease from normal to PIN, a 3.5-fold decrease from PIN to tumor and a 9.3-fold decrease from normal to tumor (FIG. 34A). Likewise, cMYC expression followed a similar expression pattern in patient #1457 where expression decreased by 1.7-fold from normal to PIN, 1.7-fold from PIN to tumor and 2.8-fold from normal to tumor (FIG. 34B). In addition, there was a statistically significant decrease in cMYC expression in the other two patients. Patient #1569 had a 2.3-fold decrease from normal to PIN, while in patient #1586 there was a 1.8-fold decrease from normal to PIN, a 4.3-fold decrease from PIN to tumor and a 7.9-fold decrease from normal to tumor.

Figure 35:
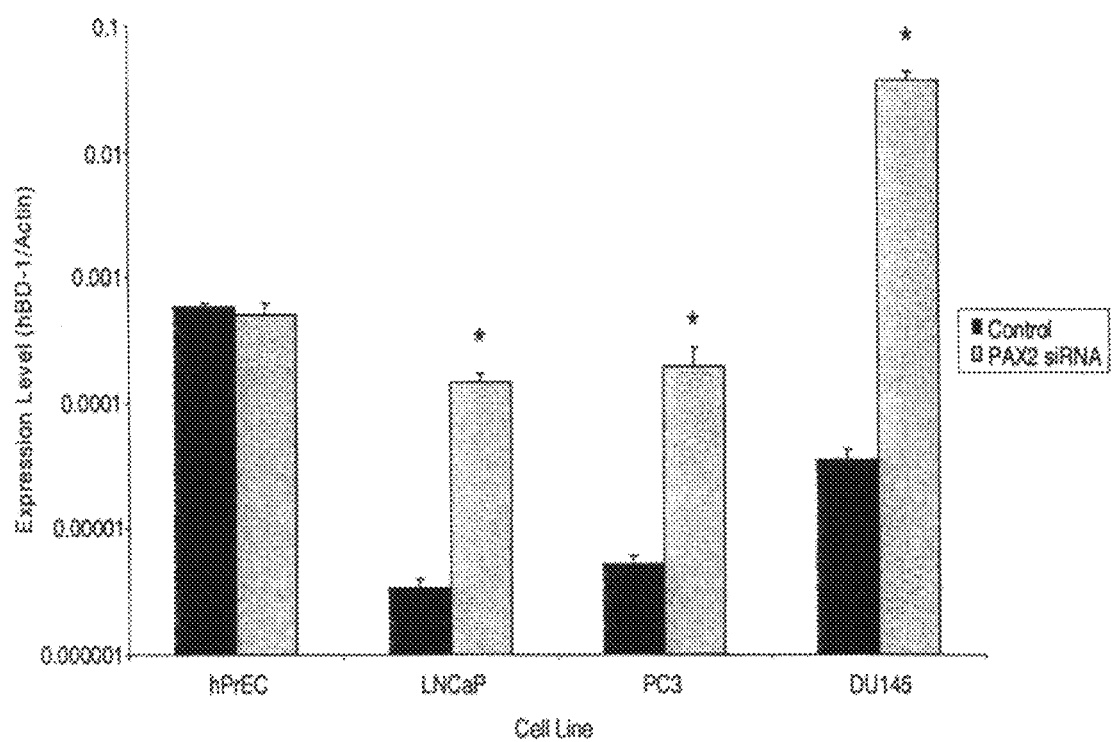
FIG. 35 shows QRT-PCR analysis of hBD1 expression following PAX2 knockdown with siRNA. hBD-1 expression levels are presented as expression ratios compared to β-actin. An asterisk represents statistically higher expression levels compared to the cell line before PAX2 siRNA treatment (Student's t-test, p<0.05).

Induction of hBD-1 expression following PAX2 inhibition: To further examine the role of PAX2 in regulating hBD-1 expression, siRNA was utilized to knockdown PAX2 expression and QRT-PCR performed to monitor hBD-1 expression. Treatment of hPrEC cells with PAX2 siRNA exhibited no effect on hBD-1 expression (FIG. 35). However, PAX2 knockdown resulted in a 42-fold increase in LNCaP, a 37-fold increase in PC3 and a 1026-fold increase in DU145 expression of hBD-1 compared to untreated cells. As a negative control, cells were treated with non-specific siRNA which had no significant effect on hBD-1 expression.

10. Example 11

Inhibition of PAX2 Expression Results in Alternate Cell Death Pathways in Prostate Cancer Cells Differing in p53 Status Materials and Methods Cell lines: The cancer cell lines PC3, DU145 and LNCaP, which all differ in p53 mutational status, were obtained from the American Type Culture Collection (Rockville, Md., USA). PC3 cells were grown in F-12 media, DU145 in DMEM, and LNCaP in RPMI all supplemented with 10% (v/v) fetal bovine serum. The prostate epithelial cell line HPrEC was obtained from Cambrex Bio Science, Inc., (Walkersville, Md.) and were cultured in prostate epithelium basal media. Cells were maintained at 37° C. in 5% CO2.

siRNA silencing of PAX2: To achieve efficient gene silencing, a pool of four complementary short interfering ribonucleotides (siRNAs) targeting human PAX2 mRNA (Accession No. NM_003989.1) were synthesized (Dharmacon Research, Lafayette, Colo., USA). To ensure specificity, siRNAs were designed to target regions unique to the PAX2 sequence to prevent subsequent knockdown of other members of the PAX family. In addition, a second pool of four siRNAs was used as an internal control to test for the specificity of PAX2 siRNAs. Two of the sequences that were synthesized targeted the GL2 luciferase mRNA (Accession No. X65324), and the other two targeted a scrambled PAX2 mRNA (Table 9).

Western analysis: Briefly, cells were harvested by trypsinization and washed twice with PBS. Lysis buffer was prepared according to the manufacturer's instructions (Sigma) and then added to the cells. Following a 15-min incubation period at 4° C. on an orbital shaker, cell lysates were collected and centrifuged for 10 min at 12,000 g to pellet cellular debris. The protein-containing supernatant were then collected and quantitated. Next, 25 µg protein extract was loaded onto an 8-16% gradient SDS-PAGE (Novex). Following electrophoresis, proteins were transferred to PVDF membranes, and then blocked with 5% non-fat dry milk in TTBS (0.05% Tween 20 and 100 mM Tris-Cl) for 1 h. Blots were then probed with rabbit anti-PAX2 primary antibody (Zymed, San Francisco, Calif.) at a 1:1000 dilution. After washing, the membranes were incubated with anti-rabbit antibody conjugated to horseradish peroxidase (HRP) (dilution 1:5000; Sigma), and signal detection was visualized using chemiluminescence reagents (Pierce) on an Alpha Innotech Fluorchem 8900. As a control, blots were stripped and reprobed with mouse anti-β-actin primary antibody (1:5000; Sigma-Aldrich) and HRP-conjugated anti-mouse secondary antibody (1:5000; Sigma-Aldrich), and signal detection was again visualized.

TABLE 8 p53 gene mutation in prostate cancer cell lines

| Cell line | Nucleotide change | Amino acid change | Gene status | Reference |
|---|---|---|---|---|
| DU145 | CCT-CTT | Pro-Leu | Gain/loss-of-function | Tepper et al. 2005; Bodhoven et al. 2003 |
| PC3 | GTT-TTT Deleted a C, GCC-GC | Val-Phe Frame-shift | No activity | Isaacs et al. 1991 |
| LNCaP | No deletion, wild-type | — | Normal function | Carroll et al. 1993 |

TABLE 9

PAX2 siRNA sequences

| Sequence | Sense (5'-3') | Antisense (5'-3') |
|---|---|---|
| A | GAAGUCAAGUCGAGUCUAUUU (SEQ ID NO: 38) | AUAGACUCGACUUGACUUCUU (SEQ ID NO: 3) |
| B | GAGGAAACGUGAUGAAGAUUU (SEQ ID NO: 39) | AUCUUCAUCACGUUUCCUCUU (SEQ ID NO: 4) |
| C | GGACAAGAUUGCUGAAUACUU (SEQ ID NO: 40) | GUAUUCAGCAAUCUUGUCCUU (SEQ ID NO: 5) |
| D | CAUCAGAGCACAUCAAAUCUU (SEQ ID NO: 41) | GAUUUGAUGUGCUCUGAUGUU (SEQ ID NO: 6) |

Phase contrast microscopy: The effect of PAX2 knockdown on cell number was analyzed by phase contrast microscopy. Here, $1-2 \times 10^4$ cells were seeded overnight onto six-well culture plates (BD Falcon, USA). Next the cells were treated with media only, negative control non-specific siRNA or PAX2 siRNA and allowed to incubate for 6 days. The cells were then viewed under an inverted Zeiss IM 35 microscope (Carl Zeiss, Germany). Phase contrast pictures of a field of cells were obtained using the SPOT Insight Mosaic 4.2 camera (Diagnostic Instruments, USA).

MTT cytotoxicity assay: DU145, PC3 and LNCaP cell suspensions were diluted and seeded onto a 96-well plate at $1-5 \times 10^3$ cells per well. Next the cells were transfected, according to the manufacturer's protocol (Promega), with 5 pg/cell of the PAX2 siRNA pool, control siRNA pool, or the Codebreaker transfection reagent alone. All cells were allowed to grow for 2-, 4- or 6 days after treatment. Cell viability was then determined by measuring the conversion of 3-[4,5-dimethylthiazol-2-yl]-2,5 diphenyl tetrazolium bromide, MTT (Promega) to a colored formazan product. Absorbance was read at 540 nm on a scanning multi-well spectrophotometer.

Pan-caspase detection: Detection of caspase activity in the prostate cancer cell lines was performed using APO LOGIX™ Carboxyfluorescin Caspase detection kit (Cell Technology, Mountain View, Calif.). Active caspases were detected with a FAMVAD-FMK inhibitor which irreversibly binds to active caspases. Briefly, $1-2 \times 10^4$ cells were plated onto 35 mm glass bottom microwell dishes (Matek, Ashland, Mass.) and treated with media only or PAX2 siRNA as previously described. Next, 300 µl of carboxyfluorescein labeled peptide fluoromethyl ketone (FAM-VAD-FMK) was added to each 35 mm dish and incubated for 1 h at 37° C. under 5% $CO_2$. Finally, the cells were washed twice with 2 ml of wash buffer, and viewed under differential interference contrast (DIC) or under laser excitation at 488 nm. The fluorescent signal was analyzed using a Zeiss LSM 5 Pascal confocal microscope with a Vario 2 RGB Laser Scanning Module.

Quantitative real-time RT-PCR: To verify changes in gene expression following PAX2 knockdown in PC3, DU145 and LNCaP cell lines, quantitative real-time RT-PCR was performed. Approximately $1 \times 10^6$ cells were harvested by trypsinizing and the cells were rinsed in PBS. Cells were then lysed and total RNA was isolated by centrifugation through spin columns using the SV Total RNA Isolation System (Promega). cDNA was generated (0.5 µg per reaction) by reverse transcription by Oligo (dT) 15 primer (Promega) and AMV Reverse Transcriptase II enzyme (500 U per reaction; Promega) for first strand synthesis and Tfl DNA Polymerase for second strand synthesis (500 U per reaction; Promega) as per the manufacturer's protocol. Typically, 50 pg of each cDNA was used per ensuing PCR. Two-step QRT-PCR was performed on cDNA generated using the MultiScribe Reverse Transcriptase from the TaqMan Reverse Transcription System and the SYBR Green PCR Master Mix (PE Biosystems). The primer pairs for BAX, BID, BCL-2, AKT and BAD were generated from the published sequences (Table 10). Reactions were performed in MicroAmp Optical 96-well Reaction Plate (PE Biosystems). Forty cycles of PCR were performed under standard conditions using an annealing temperature of 60° C. Quantification was determined by the cycle number where exponential amplification began (threshold value) and averaged from the values obtained from the triplicate repeats. There was an inverse relationship between message level and threshold value. In addition, GAPDH was used as a housekeeping gene to normalize the initial content of total cDNA. Relative expression was calculated as the ratio between each genes and GAPDH. All reactions were carried out in triplicate.

TABLE 10

Quantitative RT-PCR primers

| | Sense (5'-3') | Antisense (5'-3') |
|---|---|---|
| GAPDH | CCACCCATGGCAAATTCCATGGCA (SEQ ID NO: 42) | TCTAGACGGCAGGTCAGGTCAACC (SEQ ID NO: 46) |
| BAD | CTCAGGCCTATGCAAAAAGAGGA (SEQ ID NO: 43) | GCCCTCCCTCCAAAGGAGAC (SEQ ID NO: 47) |
| BID | AACCTACGCACCTACGTGAGGAG (SEQ ID NO: 44) | CGTTCAGTCCATCCCATTTCTG (SEQ ID NO: 48) |
| BAX | GACACCTGAGCTGACCTTGG (SEQ ID NO: 45) | GAGGAAGTCCAGTGTCCAGC (SEQ ID NO: 49) |
| BCL-2 | TATGATACCCGGGAGATCGTGATC (SEQ ID NO: 54) | GTGCAGATGCCGGTTCAGGTACTC (SEQ ID NO: 55) |
| AKT | TCAGCCCTGGACTACCTGCA (SEQ ID NO: 56) | GAGGTCCCGGTACACCACGT (SEQ ID NO: 57) |

Membrane permeability assay: Acridine orange (AO)/ ethidium bromide (EtBr) dual staining was performed to identify changes in cell membrane integrity, as well as apoptotic cells by staining the condensed chromatin. AO stains viable cells, as well as early apoptotic cells, whereas EtBr stains late stage apoptotic cells that have compromised membrane integrity. Briefly, PC3 and LNCaP cells were seeded into two-chamber culture slides (BD Falcon) and cells were transfected with PAX2 siRNA, non-specific siRNA or media only. After treatment, cells were washed once with PBS and stained with 2 ml of a mixture (1:1) of AO (Sigma, St. Louis, Mo.) and EtBr (Promega) (5 µg/ml) solution for 5 min. Following staining, the cells were again washed with PBS. Fluorescence was viewed by a Zeiss LSM 5 Pascal Vario 2 Laser Scanning Confocal Microscope (Carl Zeiss). The excitation color wheel contain BS505-530 (green) and LP560 (red) filter blocks which allowed for the separation of emitted green light from AO into the green channel and red light from EtBr into the red channel. The laser power output and gain control settings within each individual experiment were identical between control and PAX2 siRNA treated cells. The excitation was provided by a Kr/Ar mixed gas laser at wavelengths of 543 nm for AO and 488 nm for EtBr. Slides were analyzed under 40× magnification and digital images were stored as uncompressed TIFF files and exported into Photoshop CS software (Adobe Systems) for image processing and hard copy presentation.

Statistical analysis: Statistical differences were evaluated using the Student's t-test for unpaired values. P values were determined by a two-sided calculation, and a P value of less than 0.05 was considered statistically significant.3.

Results

Figure 36A:
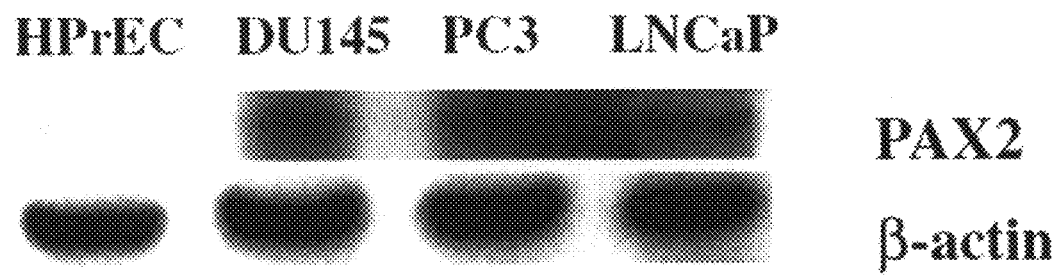
FIG. 36 shows silencing of PAX2 protein expression following PAX2 siRNA treatment.

Analysis of PAX2 protein expression in prostate cells: PAX2 protein expression was examined by Western analysis in HPrEC prostate primary culture and in LNCaP, DU145 and PC3 prostate cancer cell lines. Here, PAX2 protein was detected in all of the prostate cancer cell lines (FIG. 36A). However, no PAX2 protein was detectable in HPrEC. Blots were stripped and re-probed for β-actin as internal control to ensure equal loading. PAX2 protein expression was also monitored after selective targeting and inhibition by PAX2 specific siRNA in DU145, PC3 and LNCaP prostate cancer cell lines. Cells were given a single round of transfection with the pool of PAX2 siRNA over a 6-day treatment period. PAX2 protein was expressed in control cells treated with media only.

Figure 36B:
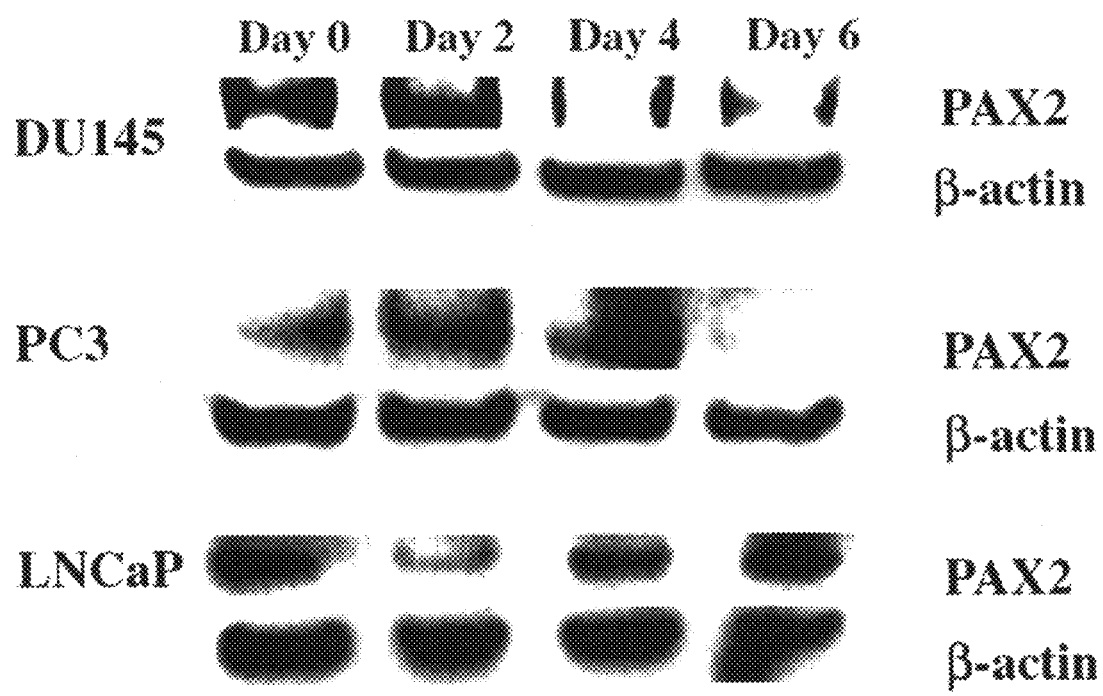

Specific targeting of PAX2 mRNA was confirmed by observing knockdown of PAX2 protein in all three cell lines (FIG. 36B).

Figure 37:
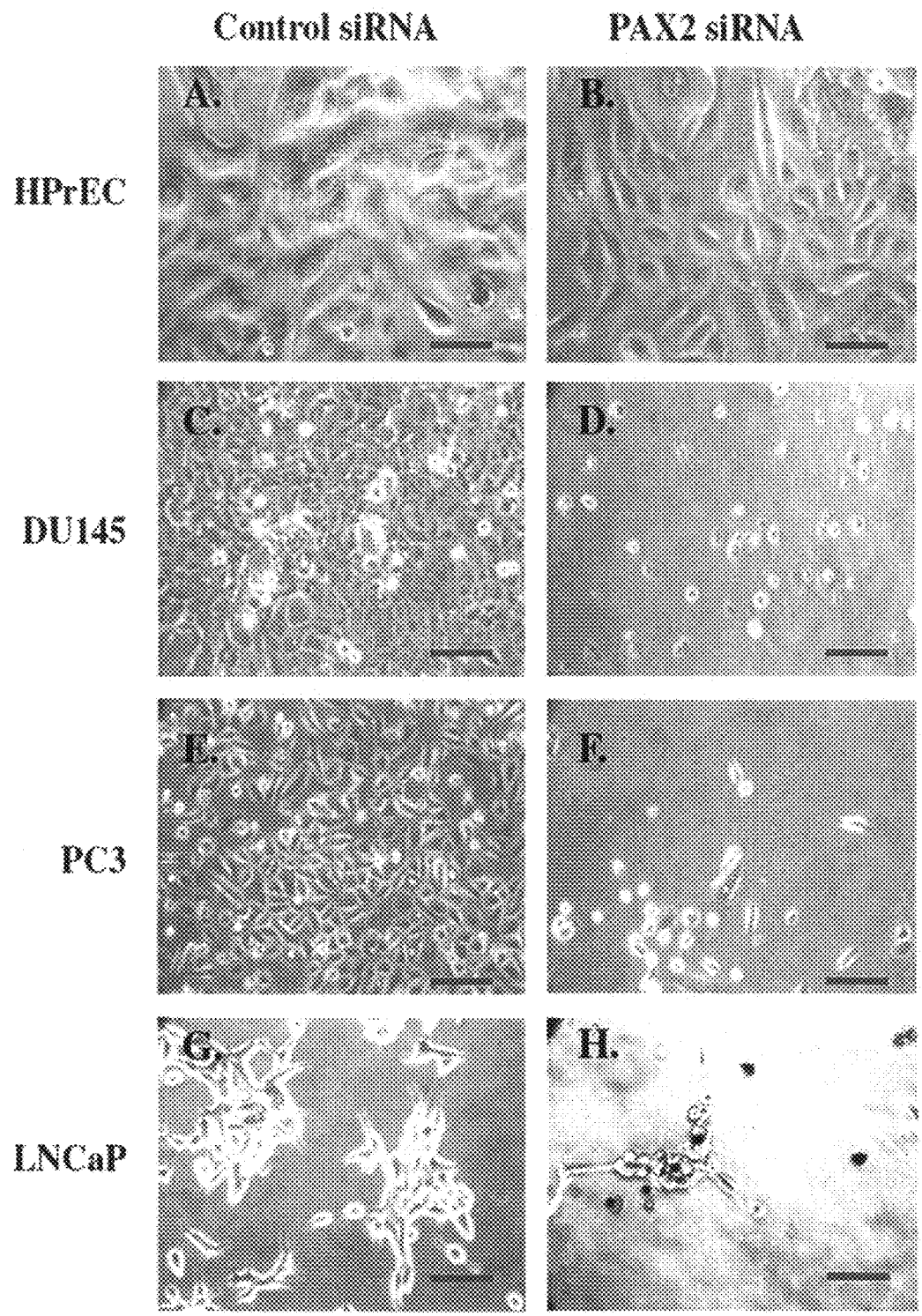
FIG. 37 shows analysis of prostate cancer cells growth after treatment with PAX2 siRNA. Phase contrast microscopic analysis of HPrEC (A), LNCaP (C), DU145 (E) and PC3 (G) at 6 days in the presence of negative control non-specific siRNA. There was a significant reduction in cell number in DU145 (D), PC3 (F) and LNCaP (H) following treatment with PAX2 siRNA. However, there appeared to be no effect in HPrEC (B). Bar=20 µm.

Effect of PAX2 knockdown on prostate cancer cell growth: The effect of PAX2 siRNA on cell number and cell viability was analyzed using light microscopy and MTT analysis. To examine the effect of PAX2 siRNA on cell number, PC3, DU145 and LNCaP cell lines were transfected with media only, non-specific siRNA or PAX2 siRNA over a period of 6 days. Each of the cell lines reached a confluency of 80-90% in 60 mm culture dishes containing media only. Treatment of HPrEC, DU145, PC3 and LNCaP cells with non-specific siRNA appeared to have little to no effect on cell growth compared to cell treated with media only (FIGS. 38A, 38C and 38E, respectively). Treatment of the PAX2-null cell line HPrEC with PAX2 siRNA appeared to have no significant effect on cell growth (FIG. 37B). However, treatment of the prostate cancer cell lines DU145, PC3 and LNCaP with PAX2 siRNA resulted in a significant decrease in cell number (FIGS. 38D, 38F and 38H, respectively).

Figure 38:
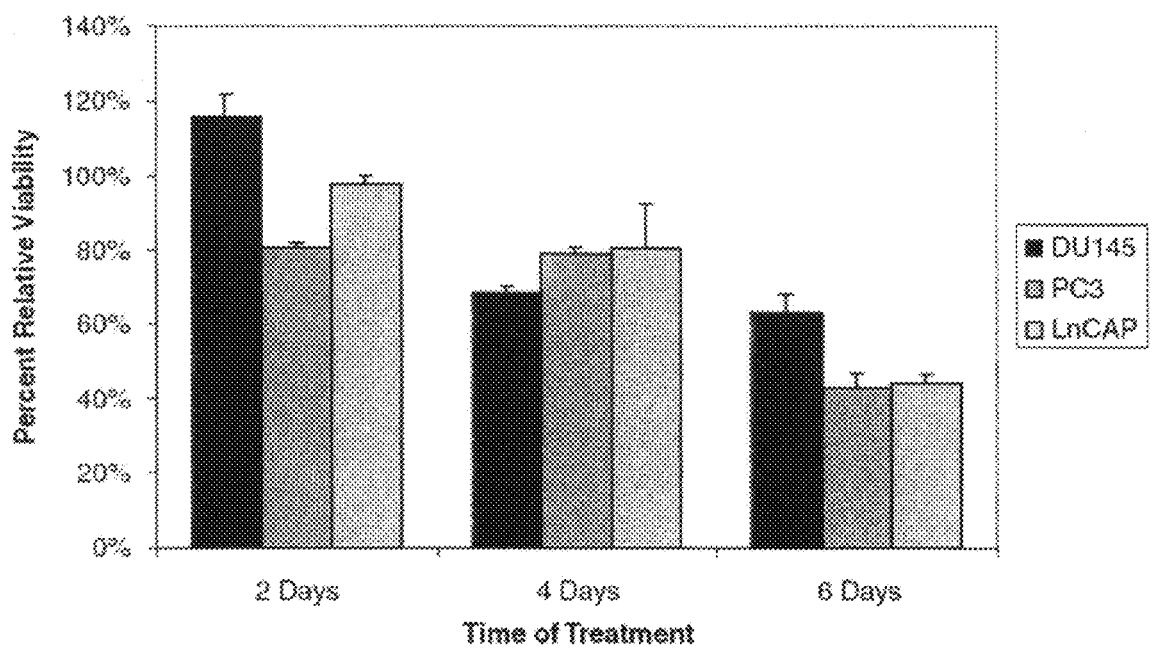
FIG. 38 shows analysis of cell death following siRNA silencing of PAX2. Prostate cancer cell lines PC3, DU145 and LNCaP were treated with PAX2 siRNA or non-specific negative control siRNAs for 2, 4 or 6 days after which MTT assay was performed. Knockdown of PAX2 resulted in a decrease in relative cell viability in all three lines. Results represent mean±SD, n=9.

Effect of PAX2 knockdown on prostate cancer cell viability: Cell viability was measured after 2-, 4-, and 6-day exposure times. Percent viability was calculated as the ratio of the 570-630 nm absorbance of cell treated with PAX2 siRNA divided by untreated control cells. As negative controls, cell viability was measured after each treatment period with negative control non-specific siRNA or transfection with reagent alone. Relative cell viability was calculated by dividing percent viability following PAX2 siRNA treatment by percent viability following treatment with non-specific siRNA (FIG. 38). After 2 days of treatment, relative viability was 116% in DU145, 81% in PC3 and 98% in LNCaP. After 4 days of treatment, relative cell viability decreased to 69% in DU145, 79% in PC3, and 80% in LNCaP. Finally, by 6 days relative viability was 63% in DU145, 43% in PC3 and 44% in LNCaP. In addition, cell viability was also measured following treatment with transfection reagent alone. Here, each cell line exhibited no significant decrease in cell viability.

Figure 39:
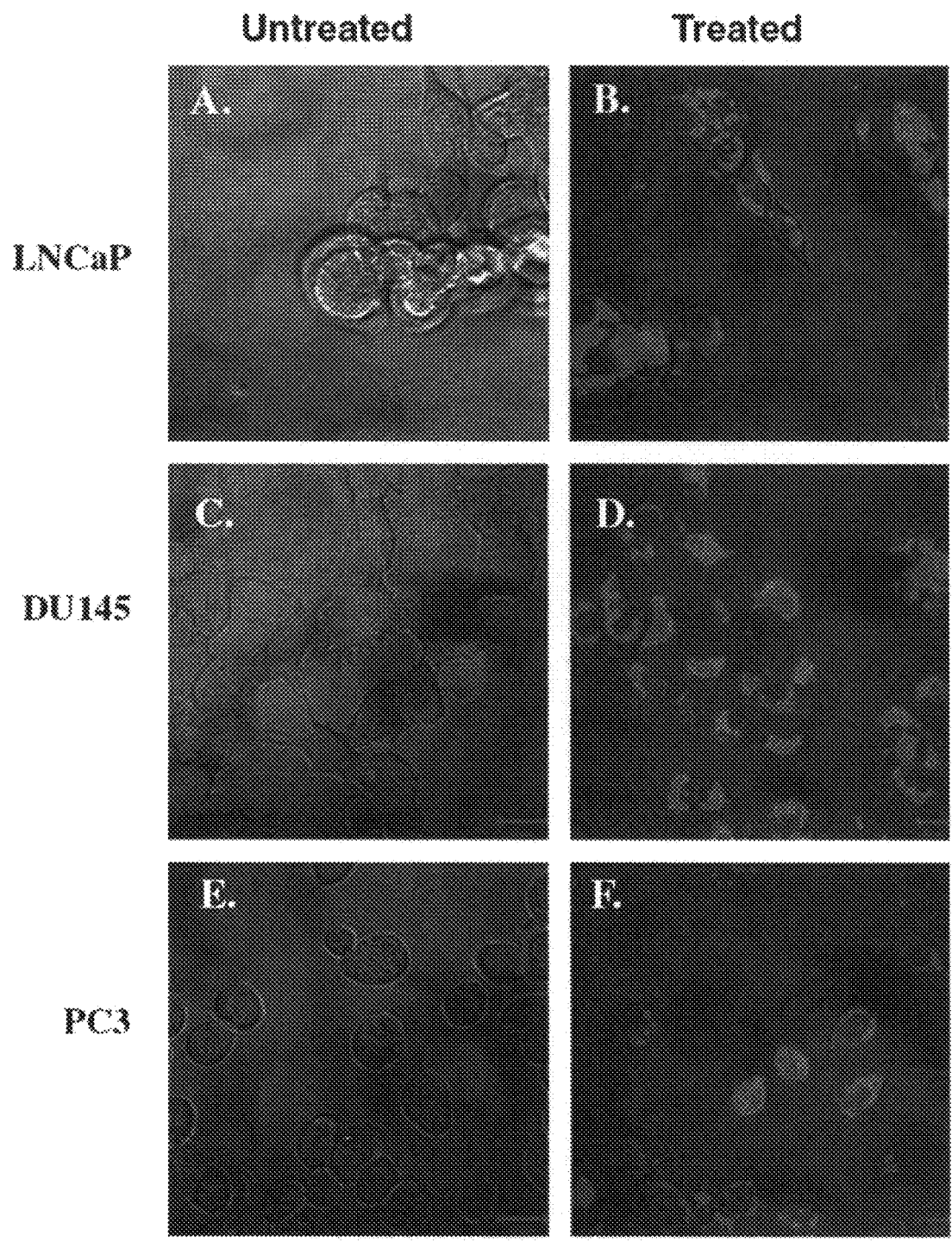
FIG. 39 shows analysis of caspase activity. DU145, PC3 and LNCaP cells were stained with carboxyfluorescein-labeled fluoromethyl ketone to detected caspase activity following treatment with PAX2 siRNA. Analysis under fluorescence revealed no caspase staining in control DU145 (A), PC3 cells (C) and LNCaP cells (E). However, cell treated with PAX2 siRNA induced caspase activity in DU145 (B), PC3 (D) and LNCaP (F). Bar=20 µm.

Detection of pan-caspase activity: Caspase activity was detected by confocal laser microscopic analysis. LNCaP, DU145 and PC3 cells were treated with PAX2 siRNA and activity was monitored based on the binding of FAM-labeled peptide to caspases in cells actively undergoing apoptosis which will fluoresce green. Analysis of cells with media only shows the presence of viable LNCaP, DU145 and PC3 cells, respectively. Excitation by the confocal laser at 488 nm produced no detectable green staining which indicates no caspase activity in the untreated cells (FIGS. 39A, 39C and 39E, respectively). Following 4 days of treatment with PAX2 siRNA, LNCaP, DU145 and PC3 cells under fluorescence presented green staining indicating caspase activity (FIGS. 39B, 39D and 39F, respectively).

Figure 40A:
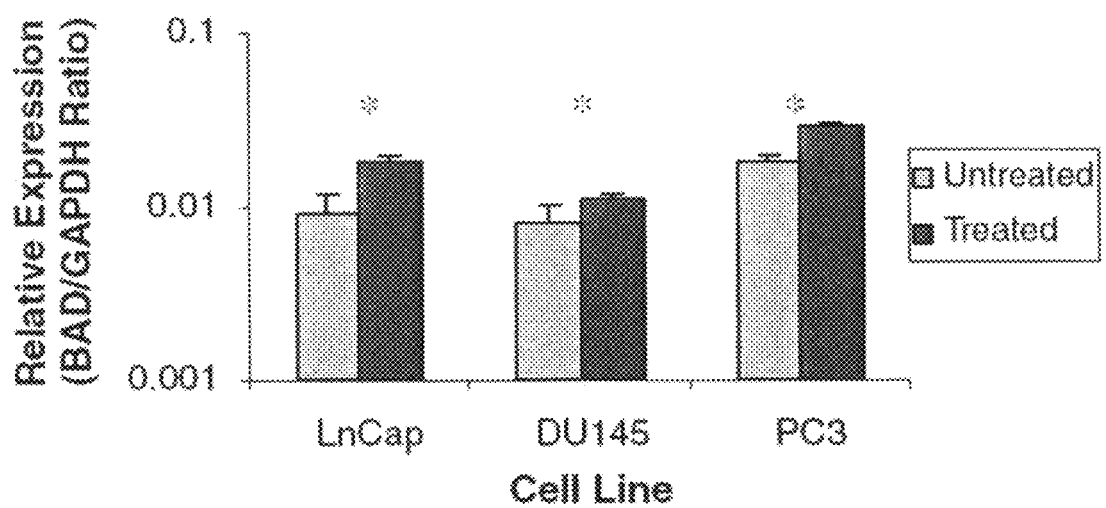
FIG. 40 shows analysis of apoptotic factors following PAX2 siRNA treatment. Changes in expression of pro-apoptotic factors were compared in untreated control cells and in cells treated for 6 days with PAX2 siRNA.
Figure 40B:
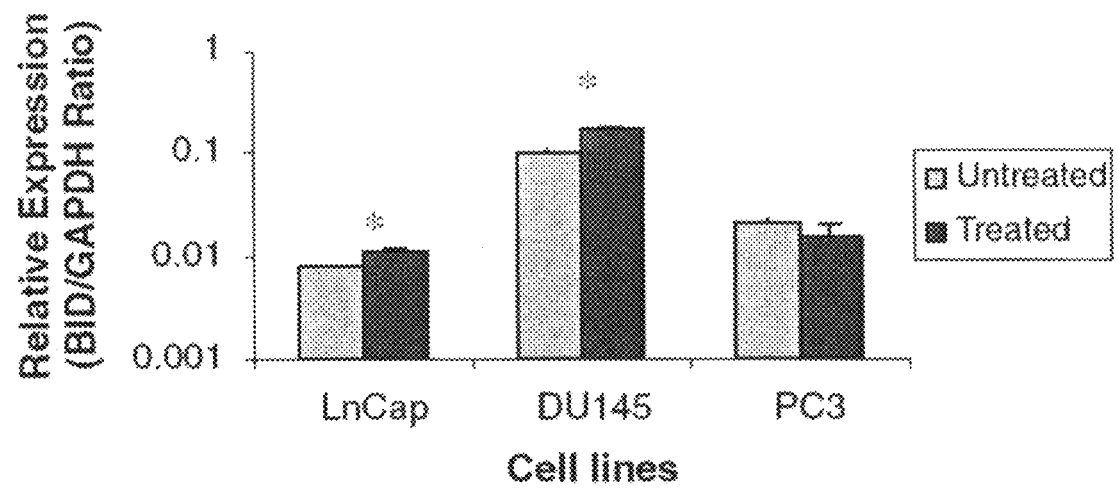
Figure 40C:
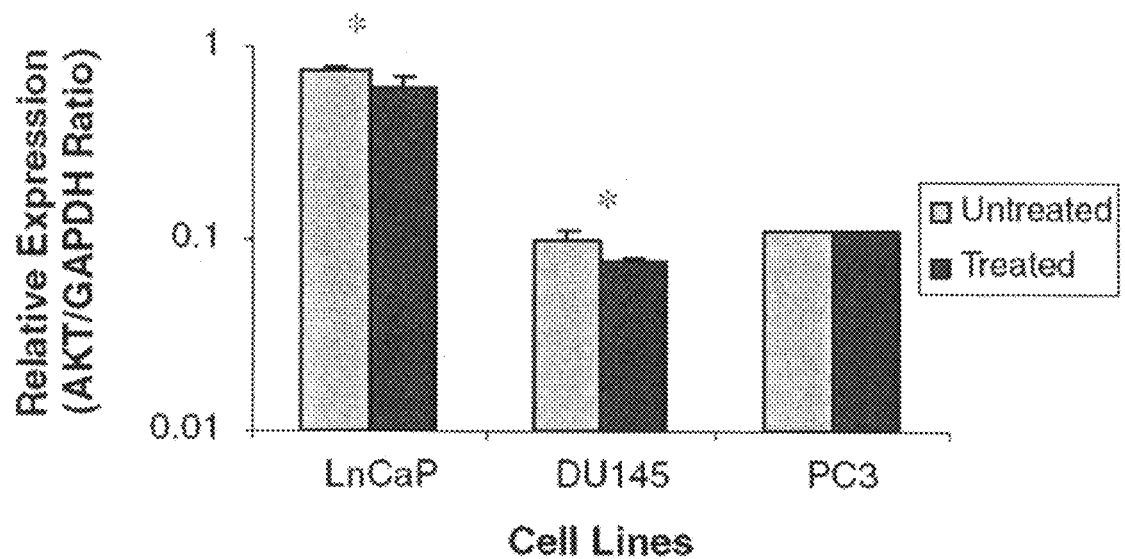

Effect of PAX2 inhibition on apoptotic factors: LNCaP, DU145 and PC3 cells were treated with siRNA against PAX2 for 4 days and expression of both pro- and anti-apoptotic factors were measured by QRTPCR. Following PAX2 knockdown, analysis of BAD revealed a 2-fold in LNCaP, 1.58-fold in DU145 and 1.375 in PC3 (FIG. 40A). Expression levels of BID increased by 1.38-fold in LNCaP and a 1.78-fold increase in DU145, but there was no statistically significant difference in BID observed in PC3 after suppressing PAX2 expression (FIG. 40B). Analysis of the anti-apoptotic factor AKT revealed a 1.25-fold decrease in expression in LNCaP and a 1.28-fold decrease in DU145 following treatment, but no change was observed in PC3 (FIG. 40C).

Analysis of membrane integrity and necrosis: Membrane integrity was monitored by confocal analysis in LNCaP, DU145 and PC3 cells. Here, intact cells stained green due to AO which is membrane permeable, while cells with compromised plasma membranes would stained red due to incorporation of membrane impermeable EtBr into the cytoplasm, and yellow due to co-localization of AO and EtBr in the nuclei. Untreated LNCaP, DU145 and PC3 cells stained positively with AO and emitted green color, but did not stain with EtBr. Following PAX2 knockdown, there were no observable alterations to membrane integrity in LNCaP cells as indicated by positive green fluorescence with AO and absence of red EtBr fluorescence. These finding further indicate that LNCaP cells can be undergoing apoptotic, but not necrotic cell death following PAX2 knockdown. Conversely, PAX2 knockdown in DU145 and PC3 resulted in the accumulation of EtBr in the cytoplasm as indicated by the red staining. In addition, both DU145 and PC3 possessed condensed nuclei which appeared yellow due to the co-localization of green and red staining from AO and EtBr, respectively. These results indicate that DU145 and PC3 are undergoing an alternate cell death pathway involving necrotic cell death compared to LNCaP.

F. References

Ady N, Morat L, Fizazi K, Soria J C, Mathieu M C, Prapotnich D, Sabatier L, Chauveinc L: Detection of HER-2/neupositive circulating epithelial cells in prostate cancer patients. Br J Cancer 2004, 90:443-448.

Bals R, Goldman M J, Wilson J M. Mouse beta-defensin 1 is a salt-sensitive antimicrobial peptide present in epithelia of the lung and urogenital tract. Infect Immun. 1998 March; 66(3):1225-32.

Banchereau, J.; Palucka, A. K.; Dhodapkar, M.; Burkeholder, S.; Taquet, N.; Rolland, A.; Taquet, S.; Coquery, S.; Wittkowski, K. M.; Bhardwaj, N.; Pineiro, L.; Steinman, R.; Fay, J., Immune and Clinical Responses in Patients with Metastatic Melanoma to CD34+ Progenitor-derived Dendritic Cell Vaccine. Cancer Res 2001, 61, (17), 6451-6458.

Bensch K W, Raida M, Magert H J, Schulz-Knappe P, Forssmann W G. hBD-1: a novel beta-defensin from human plasma. FEBS Lett. 1995 Jul. 17; 368(2):331-5.

Benson & Olsson (1989) "The staging and grading of prostatic cancer" in The Prostate, ed Fitzpatrick, J. M. and Krane R. J. pp 261-272, Edinburgh, Churchill Livingstone.

Bockmuhl, U.; Ishwad, C. S.; Ferrell, R. E.; Gollin, S. M., Association of 8p23 deletions with poor survival in head and neck cancer. Otolaryngol Head Neck Surg 2001, 124, (4), 451-5.

Bodhoven, A. V. et al. Molecular characterization of Human Prostate Carcinoma Cell Lines, Prostate 57 (2003) 205-225.

Boyd, K. E. and Farnham, P. J. Coexamination of site-specific transcription factor binding and promoter activity in living cells. Mol Cell Biol, 19: 8393-8399., 1999.

Braida, L., Boniotto, M., Pontillo, A., Tovo, P. A., Amoroso, A., Crovella, S., 2004. A singlenucleotide polymorphism in the human beta-defensin 1 gene is associated with HIV-1 infection in Italian children. Aids 18, 1598-1600. Discenza, M. T., He, S., Lee, T. H., Chu, L. L., Bolan, B., Goodyer, P., Eccles, Buttiglieri, S.; Deregibus, M. C.; Bravo, S.; Cassoni, P.; Chiarle, R.; Bussolati, B.; Camussi, G., Role of PAX2 in apoptosis resistance and proinvasive phenotype of Kaposi's sarcoma cells. J Biol Chem 2004, 279, (6), 4136-43.

Carroll, A. G. et al. p53 oncogene mutations in three human prostate cancer cell lines, Prostate 23 (2) (1993) 123-134.

Catalano, M. G.; Pfeffer, U.; Raineri, M.; Ferro, P.; Curto, A.; Capuzzi, P.; Como, F.; Berta, L.; Fortunati, N., Altered expression of androgen-receptor isoforms in human colon-cancer tissues. Int J Cancer 2000, 86, (3), 325-30.

Chaib, H.; MacDonald, J. W.; Vessella, R. L.; Washburn, J. G.; Quinn, J. E.; Odman, A.; Rubin, M. A.; Macoska, J. A., Haploinsufficiency and reduced expression of genes localized to the 8p chromosomal region in human prostate tumors. Genes Chromosomes Cancer 2003, 37, (3), 306-13.

Coultas, L.; Strasser, A., The role of the Bcl-2 protein family in cancer. Semin Cancer Biol 2003, 13, (2), 115-23.

Davies et al., Hum. Mol. Gen Jan. 15, 13 (2); 235.

Dearnaley D P, Sloane J P, Oimerod M G, Steele K, Coombes R C, Clink H M, Powles T J, Ford H T, Gazet J C, Neville A M: Increased detection of mammary carcinoma cells in marrow smearsusing antisera to epithelial membrane antigen. Br J Cancer 1981, 44:85-90.

Dhebi, M. et al. The paired-box transcription factor, PAX2, positively modulates expression of the Wilms' tumor suppressor gene (WT1), Oncogene 13 (1996) 447-453.

Discenza, M. T.; He, S.; Lee, T. H.; Chu, L. L.; Bolan, B.; Goodyer, P.; Eccles, M.; Pelletier, J., WT1 is a modifier of the PAX2 mutant phenotype: cooperation and interaction between WT1 and PAX2. Oncogene 2003, 22, (50), 8145-55.

Donald, C. D.; Sun, C. Q.; Lim, S. D.; Macoska, J.; Cohen, C.; Amin, M. B.; Young, A. N.; Ganz, T. A.; Marshall, F. F.; Petros, J. A., Cancer-specific loss of beta-defensin 1 in renal and prostatic carcinomas. Lab Invest 2003, 83, (4), 501-5.

Dorfler, P. et al. C-terminal activating and inhibitory domains determine the transactivation potential of BSAP (PAX-5), PAX-2 and PAX-8, EMBO J. 15 (8) (1996) 1971-1982.

Dressler et al (1990) Development 109, 787-795

Dressler G R, Douglass E C. Pax-2 is a DNA-binding protein expressed in embryonic kidney and Wilms tumor. Proc Natl Acad Sci USA 1992; 89(4):1179-1183.

Dressler G R, Woolf A S. PAX2 in development and renal disease. Int J Dev Biol 1999; 43(5):463-468.

Dressler G R. Pax-2, kidney development, and oncogenesis. Med Pediatr Oncol 1996; 27(5):440-444.

Dunn G P, Bruce A T, Ikeda H, Old L J, Schreiber R D: Cancer immunoediting: from immunosurveillance to tumor escape. Nat Immunol 2002, 3:991-998.

Eccles M R, He S, Legge M, Kumar R, Fox J, Zhou C, French M, Tsai R W. PAX genes in development and disease: the role of PAX2 in urogenital tract development. Int J Dev Biol 2002; 46(4):535-544.

Eccles M R, Wallis L J, Fidler A E, Spurr N K, Goodfellow P J, Reeve A E. Expression of the PAX2 gene in human fetal kidney and Wilms' tumor. Cell Growth Differ 1992; 3(5): 279-289.

Eccles, M. R., HE, S., Legge, M., Kumar, R., Fox, J., Zhou, C., French, M., Tsai, R. W., 2002. PAX genes in development and disease: the role of PAX2 in urogenital tract development. Int. J. Dev. Biol. 46 (4), 535-544. Ganz, T., 1999. Defensins and host defense. Science 286, 420-421. Ganz, T., 2002. Immunology. Versatile defensins. Science 298, 977-979. Ganz, T., 2004. Defensins: antimicrobial peptides of vertebrates. CR Biol. 327, 539-549.

Eccleset M. R. et al. FAX genes in development and disease: the role of PAX2 in urogenital tract development, Int. J. Dev. Biol. 46 (4) (2002) 535-544.

Fong, L.; Brockstedt, D.; Benike, C.; Breen, J. K.; Strang, G.; Ruegg, C. L.; Engleman, E. G., Dendritic Cell-Based Xenoantigen Vaccination for Prostate Cancer Immunotherapy. J Immunol 2001, 167, (12), 7150-7156.

Fonsato V. et al. Expression of Pax2 in human renal tumor-derived endothelial cells sustains apoptosis resistance and angiogenesis, Am J Pathol. 2006 February; 168(2):706-1.

Fromont, G.; Joulin, V.; Chantrel-Groussard, K.; Vallancien, G.; Guillonneau, B.; Validire, P.; Latil, A.; Cussenot, O., Allelic losses in localized prostate cancer: association with prognostic factors. J Urol 2003, 170, (4 Pt 1), 1394-7.

Fujii Y, Kageyama Y, Kawakami S, Kihara K, Oshima H: Detection of disseminated urothelial cancer cells in peripheral venous blood by a cytokeratin 20-specific nested reverse transcriptase-polymerase chain reaction. Jpn J Cancer Res 1999, 90:753-757.

Gann et al (1995) JAMA 273, 289-294

Ganz T, Weiss J. Antimicrobial peptides of phagocytes and epithelia.Semin Hematol. 1997 October; 34(4):343-54

Ganz, T., Defensins and host defense. Science 1999, 286, (5439), 420-1.

Ganz, T., Defensins: antimicrobial peptides of vertebrates. C R Biol 2004, 327, (6), 539-49.

Ganz, T., Immunology. Versatile defensins. Science 2002, 298, (5595), 977-9.

Gerhard M, Juhl H, Kalthoff H, Schreiber H W, Wagener C, Neumaier M: Specific detection of carcinoembryonic antigen-expressing tumor cells in bone marrow aspirates by polymerase chain reaction. J Clin Oncol 1994, 12:725-729.

Ghossein R A, Bhattacharya S, Rosai J: Molecular detection of micrometastases and circulating tumor cells in solid tumors. Clin Cancer Res 1999, 5:1950-1960.

Ghossein R A, Scher H I, Gerald W L, Kelly W K, Curley T, Amsterdam A, Zhang Z F, Rosai J: Detection of circulating tumor cells in patients with localized and metastatic prostatic carcinoma: clinical implications. J Clin Oncol 1995, 13:1195-1200.

Gibson, W., Green, A., Bullard, R. S., Eaddy, A. R., Donald, C. D., 2007. Inhibition of PAX2 expression results in alternate cell death pathways in prostate cancer cells differing in p53 status. Cancer Lett. 248 (2), 251-261.

Gilbey A M, Burnett D, Coleman R E, Holen I: The detection of circulating breast cancer cells in blood. J Clin Pathol 2004, 57:903-911.

Gleason (1966) "Classification of prostatic carcinomas" Cancer Chemother Rep 50, 125-128

Gnarra, J. R.; Dressler, G. R., Expression of Pax-2 in human renal cell carcinoma and growth inhibition by antisense oligonucleotides. Cancer Res 1995, 55, (18), 4092-8.

Goldman M J, Anderson G M, Stolzenberg E D, Kari U P, Zasloff M, Wilson J M. Human beta-defensin-1 is a salt-sensitive antibiotic in lung that is inactivated in cystic fibrosis. Cell. 1997 Feb. 21; 88(4):553-60.

Gropp, R.; Frye, M.; Wagner, T. O.; Bargon, J., Epithelial defensins impair adenoviral infection: implication for adenovirus-mediated gene therapy. Hum Gene Ther 1999, 10, (6), 957-64.

Gunther, M.; Wagner, E.; Ogris, M., Specific targets in tumor tissue for the delivery of therapeutic genes. Curr Med Chem Anti-Canc Agents 2005, 5, (2), 157-71.

Guseva, N. V. et al. Death receptor-induced cell death in prostate cancer, J. Cell Biochem. 91 (2004) 70-99.

Harder J, Bartels J, Christophers E, Schroder J M. A peptide antibiotic from human skin. Nature. 1997 Jun. 26; 387 (6636):861.

Harder J, Bartels J, Christophers E, Schroder J M. Isolation and characterization of human beta-defensin-3, a novel human inducible peptide antibiotic. Biol Chem. 2001 Feb. 23; 276(8):5707-13.

Harder J, Siebert R, Zhang Y, Matthiesen P, Christophers E, Schlegelberger B, Schroder J M. Mapping of the gene encoding human beta-defensin-2 (DEFB2) to chromosome region 8p22-p23.1. Genomics. 1997 Dec. 15; 46(3):472-5.

Havik B, Ragnhildstveit E, Lorens J B, Saelemyr K, Fauske O, Knudsen L K, Fjose A. A novel paired domain DNA recognition motif can mediate PAX2 repression of gene transcription. Biochem Biophys Res Commun 1999; 266(2): 532-541.

Hildebrandt M, Mapara M Y, Korner I J, Bargou R C, Moldenhauer G, Dorken B: Reverse transcriptase-polymerase chain reaction (RT-PCR)-controlled immunomagnetic purging of breast cancer cells using the magnetic cell separation (MACS) system: a sensitive method for monitoring purging efficiency. Exp Hematol 1997, 25:57-65.

Hoon D S, Sarantou T, Doi F, Chi D D, Kuo C, Conrad A J, Schmid P, Turner R, Guiliano A: Detection of metastatic breast cancer by b-hCG polymerase chain reaction. Int J Cancer 1996, 69:369-374.

Hueber et al. PAX2 inactivation enhances cisplatin-induced apoptosis in renal carcinoma cells, Kidney Int. 2006 April; 69(7):1139-45.

Hugel, A.; Wernert, N., Loss of heterozygosity (LOH), malignancy grade and clonality in microdissected prostate cancer. Br J Cancer 1999, 79, (3-4), 551-7.

Ino K, Shibata K, Kajiyama H, Yamamoto E, Nagasaka T, Nawa A, Nomura S, Kikkawa F. Angiotensin II type 1 receptor expression in ovarian cancer and its correlation with tumor angiogenesis and patient survival. Br J Cancer 2006; 94(4): 552-560.

Isaacs, W. B. et al. Wild-type p53 suppresses growth of human prostate cancer cells containing mutant p53 alleles, Cancer Res. 51 (1991) 4716-4720.

Jackers, P., Szalai, G., and Watson, D. K. Ets-dependent regulation of target gene expression during megakaryopoiesis. in preparation, 2003.

Jemal, A., Siegel, R., Ward, E., Murray, T., Xu, J., Smigal, C., Thun, M. J., 2006. Cancer statistics, 2006. CA Cancer J. Clin. 56, 106-130, Jemal, A.; Tiwari, R. C.; Murray, T.; Ghafoor, A.; Samuels, A.; Ward, E.; Feuer, E. J.; Thun, M. J., Cancer statistics, 2004. CA Cancer J Clin 2004, 54, (1), 8-29.

Jia H P, Schutte B C, Schudy A, Linzmeier R, Guthmiller J M, Johnson G K, Tack B F, Mitros J P, Rosenthal A, Ganz T, McCray P B Jr. Discovery of new human beta-defensins using a genomics-based approach. Gene. 2001 Jan. 24; 263(1-2): 211-8.

Jia H P, Wowk S A, Schutte B C, Lee S K, Vivado A, Tack B F, Bevins C L, McCray P B Jr. A novel murine beta-defensin expressed in tongue, esophagus, and trachea. J Biol Chem. 2000 Oct. 27; 275(43):33314-20.

Johnson P W, Burchill S A, Selby P J: The molecular detection of circulating tumor cells. Br J Cancer 1995, 72:268-276.

Jotsuka T, Okumura Y, Nakano S, Nitta H, Sato T, Miyachi M, Suzumura K, Yamashita J: Persistent evidence of circulating tumor cells detected by means of RT-PCR for CEA mRNA predicts early relapse: a prospective study in node-negative breast cancer. Surgery 2004, 135:419-426.

Juin, P., Hunt, A., Littlewood, T., Griffiths, B., Brown-Swigart, L., Korsmeyer, S., Evan, G., 2002. c-Myc functionally cooperates with Bax to induce apoptosis. Mol. Cell. Biol. 22, 6158-6169.

Jung, J. E., Lee, J., Ha, J., Kim, S. S., Cho, Y. H., Baik, H. H., and Kang, I. 5-Aminoimidazole-4-carboxamide-ribonucleoside enhances oxidative stress-induced apoptosis through activation of nuclear factor-κB in mouse Neuro 2a neuroblastoma cells. (2004) Neurosci. Lett. 354, 197-200

Jurevic, R. J., Chrisman, P., Mancl, L., Livingston, R., Dale, B. A., 2002. Single-nucleotide polymorphisms and haplotype analysis in beta-defensin genes in different ethnic populations. Genet. Test 6, 26 1-269.

Kasahara, K. et al. Detection of genetic alterations in advanced prostate cancer by comparitive genomic hybridization, Cancer Genet. Cytogenet. 137 (1) (2002) 59-63.

Kefas, B. A., Cai, Y., Ling, Z., Heimberg, H., Hue, L., Pipeleers, D., and Van de Casteele, M. AMP-activated protein kinase can induce apoptosis of insulin-producing MIN6 cells through stimulation of c-Jun-N-terminal kinase. (2003) J. Mol. Endocrinol. 30, 151-161

Kelloff, G. J., Lippman, S. M., Dannenberg, A. J., et al. Progress in chemoprevention drug development: the promise of molecular biomarkers for prevention of intraepithelial neoplasia and cancer—a plan to move forward. Clin Cancer Res. 2006 Jun. 15; 12(12):3661-97.

Khoubehi B, Kessling A M, Adshead J M, Smith G L, Smith R D, Ogden C W. Expression of the developmental and oncogenic PAX2 gene in human prostate cancer. J Urol 2001; 165(6 Pt 1):2115-2120.

Krisanaprakornkit S, Weinberg A, Perez C N, Dale B A. Expression of the peptide antibiotic human beta-defensin 1 in cultured gingival epithelial cells and gingival tissue. Infect Immun. 1998 September; 66(9):4222-8.

Lang D, Powell S K, Plummer R S, Young K P, Ruggeri B A. PAX genes: Roles in development, pathophysiology, and cancer. Biochem Pharmacol 2006.

Lehrer, R. I., Ganz, T., 1996. Endogenous vertebrate antibiotics. Defensins, protegrins, and other cysteine-rich antimicrobial peptides. Ann. N.Y. Acad. Sci. 797, 228-239.

Li, J., Jiang, P., Robinson, M., Lawrence, T. S., and Sun, Y. (2003) AMPK-β1 subunit is a p53-independent stress responsive protein that inhibits tumor cell growth upon forced expression Carcinogenesis 24, 827-834

Lin, S.; Ying, S. Y., Differentially expressed genes in activin-induced apoptotic LNCaP cells. Biochem Biophys Res Commun 1999, 257, (1), 187-92.

Linzmeier, R.; Ho, C. H.; Hoang, B. V.; Ganz, T., A 450-kb contig of defensin genes on human chromosome 8p23. Gene 1999, 233, (1-2), 205-11.

Liu, J., Wilson, T. E., Milbrandt, J., and Johnsen, M. Identifying DNA-binding sites and analyzing DNA-binding domains using a yeast selection system. METHODS: A companion to Methods in Enzymology, 5: 125-137, 1993.

Discenza M T, He S, Lee T H, Chu L L, Bolon B, Goodyer P. Eccles M, Pelletier J., 2003. WT1 is a modifier of the Pax2 mutant phenotype: cooperation and interaction between WT1 and Pax2. Oncogene 22 (50), 8145-8155.

Macoska, J. A.; Paris, P.; Collins, C.; Andaya, A.; Beheshti, B.; Chaib, H.; Kant, R.; Begley, L.; MacDonald, J. W.; Squire, J. A., Evolution of 8p loss in transformed human prostate epithelial cells. Cancer Genet Cytogenet 2004, 154, (1), 36-43.

Mansouri, A. et al. Pax genes and their roles in cell differentiation and development, Cur. Opin. Cell Biol. 8 (1996) 851-857.

Margue, C. M.; Bernasconi, M.; Barr, F. G.; Schafer, B. W., Transcriptional modulation of the anti-apoptotic protein BCL-XL by the paired box transcription factors PAX3 and PAX3/FKHR. Oncogene 2000, 19, (25), 2921-9.

Margue, C. M. et al. Transcriptional modulation of the anti-apoptotic protein BCL-XL by the paired box transcription factors PAX3 and PAX3/FKHR, Oncogene 19 (25) (2003) 2921-2929.

Margure, C. M. et al. Transcriptional modulation of the anti-apoptotic protein BCL-XL by the paired box transcription factors PAX3 and PAX3/FKHR, Oncogene 19 (2000) 2921-2929.

Mathews M, Jia H P, Guthmiller J M, Losh G, Graham S, Johnson G K, Tack B F, McCray P B Jr. Production of beta-defensin antimicrobial peptides by the oral mucosa and salivary glands. Infect Immun. 1999 June; 67(6):2740-5.

Matsumura M, Niwa Y, Kato N, Komatsu Y, Shiina S, Kawabe T, Kawase T, Toyoshima H, Ihori M, Shiratori Y: Detection of a-fetoprotein mRNA, an indicator of hematogenous spreading hepatocellular carcinoma, in the circulation: a possible predictor of metastatic hepatocellular carcinoma. Hepatology 1994, 20:1418-1425.

Maulbecker C C, Gruss P. The oncogenetic potential of Pax genes. Embo J 1993; 12(6):2361-7

Mazal, P. R.; Stichenwirth, M.; Koller, A.; Blach, S.; Haitel, A.; Susani, M., Expression of aquaporins and PAX-2 compared to CD10 and cytokeratin 7 in renal neoplasms: a tissue microarray study. Mod Pathol 2005, 18, (4), 535-40.

Mazzucchelli, R.; Barbisan, F.; Tarquini, L. M.; Galosi, A. B.; Stramazzotti, D., Molecular mechanisms in prostate cancer. A review. Anal Quant Cytol Histol 2004, 26, (3), 127-33.

McConnell, M. J.; Cunliffe, H. E.; Chua, L. J.; Ward, T. A.; Eccles, M. R., Differential regulation of the human Wilms tumor suppressor gene (WT1) promoter by two isoforms of PAX2. Oncogene 1997, 14, (22), 2689-700.

McCray P B Jr, Bentley L. Human airway epithelia express a beta-defensin. Am J Respir Cell Mol Biol. 1997 March; 16(3):343-9.

McNamara N A, Van R, Tuchin O S, Fleiszig S M. lar surface epithelia express mRNA for human beta defensin-2Exp Eye Res. 1999 November; 69(5):483-90.

McNeel, D. G., Malkovsky, M., 2005. Immune-based therapies for prostate cancer. Immunol. Lett. 96, 3-9.

Meisse, D., Van de Casteele, M., Beauloye, C., Hainault, I., Kefas, B. A., Rider, M. H., Foufelle, F., and Hue, L. Sustained activation of AMP-activated protein kinase induces c-Jun N-terminal kinase activation and apoptosis in liver cells. (2002) FEBS Lett. 526, 38-42

Michalak, E.; Villunger, A.; Erlacher, M.; Strasser, A., Death squads enlisted by the tumor suppressor p53. Biochem Biophys Res Commun 2005, 331, (3), 786-98.

Muratovska A, Zhou C, He S, Goodyer P, Eccles M R. Paired-Box genes are frequently expressed in cancer and often required for cancer cell survival. Oncogene 2003; 22(39):7989-7997.

Murer, L.; Caridi, G.; Della Vella, M.; Montini, G.; Carasi, C.; Ghiggeri, G.; Zacchello, G., Expression of nuclear transcription factor PAX2 in renal biopsies of juvenile nephronophthisis. Nephron 2002, 91, (4), 588-93.

Nakamura, Y. Isolation of p53-target genes and their functional analysis, Cancer Sci. 95 (1) (2004) 7-11.

Nelson, W. G., De Marzo, A. M., DeWeese, T. L., Isaacs, W. B., 2004. The role of inflammation in the pathogenesis of prostate cancer. J. Urol. 172, S6-S11 (discussion S11-S12).

Nigro, J. M., Sikorski, R., Reed, S. I., and Vogelstein, B. Human p53 and CDC2Hs genes combine to inhibit the proliferation of Saccharomyces cerevisiae. Mol Cell Biol, 12: 1357-1365., 1992.

Nishimura, M.; Abiko, Y.; Kurashige, Y.; Takeshima, M.; Yamazaki, M.; Kusano, K.; Saitoh, M.; Nakashima, K.; Inoue, T.; Kaku, T., Effect of defensin peptides on eukaryotic cells: primary epithelial cells, fibroblasts and squamous cell carcinoma cell lines. Journal of Dermatological Science 2004, 36, (2), 87.

Noguchi S, Aihara T, Motomura K, Inaji H, Imaoka S, Koyama H: Detection of breast cancer micrometastases in axillary lymph nodes by means of reverse transcriptase-polymerase chain reaction. Comparison between MUC1 mRNA and keratin 19 mRNA amplification. Am J Pathol 1996, 148: 649-656.

O'Hara S M, Moreno J G, Zweitzig D R, Gross S, Gomella L G, Terstappen L W: Multigene reverse transcription-PCR profiling of circulating tumor cells in hormone-refractory prostate cancer. Clin Chem 2004, 50:826-835.

Ogata, T.; Muroya, K.; Sasagawa, I.; Kosho, T.; Wakui, K.; Sakazume, S.; Ito, K.; Matsuo, N.; Ohashi, H.; Nagai, T., Genetic evidence for a novel gene(s) involved in urogenital development on 10q26. Kidney Int 2000, 58, (6), 2281-90.

O'Neil D A, Porter E M, Elewaut D, Anderson G M, Eckmann L, Ganz T, Kagnoff M F. Expression and regulation of the human beta-defensins hBD-1 and hBD-2 in intestinal epithelium. J Immunol. 1999 Dec. 15; 163(12):6718-24.

Orlando, V. Mapping chromosomal proteins in vivo by formaldehyde-crosslinked-chromatin immunoprecipitation. Trends Biochem Sci, 25: 99-104., 2000.

Ostrom, L.; Tang, M. J.; Gruss, P.; Dressler, G. R., Reduced PAX2 gene dosage increases apoptosis and slows the progression of renal cystic disease. Dev Biol 2000, 219, (2), 250-8.

Palapattu, G. S., Sutciffe, S., Bastian, P. J., Platz, E. A., De Marzo, A. M., Isaacs, W. B., Nelson, W. G., 2005. Prostate carcinogenesis and inflammation: emerging insights. Carcinogenesis 26, 1170-1181.

Pantel K, Riethmuller G: Micrometastasis detection and treatment with monoclonal antibodies. Curr Top Microbiol Immunol 1996, 213:1-18.

Papo, N., Shai, Y., 2005. Host defense peptides as new weapons in cancer treatment. Cell Mol. Life Sci. 62, 784-790.

Perfettini, J. L.; Kroemer, R. T.; Kroemer, G., Fatal liaisons of p53 with Bax and Bak. Nat Cell Biol 2004, 6, (5), 386-8.

Perfettini, J. L.; Roumier, T.; Kroemer, G., Mitochondrial fusion and fission in the control of apoptosis. Trends Cell Biol 2005, 15, (4), 179-83.

Perfettini, J. L. et al. Fatal liaisons of p53 with Bax and Bak, Nat. Cell Biol. 6 (5) (2004) 386-388.

Perfettini, J. L. et al. Mitochondrial fusion and fission in the control of apoptosis, Trends Cell Biol. 15 (4) (2005) 179-183.

Prasad, M. A., Trybus, T. M., Wojno, K. J., Macoska, J. A., 1998. Homozygous and frequent deletion of proximal 8p sequences in human prostate cancers: identification of a potential tumor suppressor gene site. Genes Chromosomes Cancer 23, 255-262.

Raj G V, Moreno J G, Gomella L G: Utilization of polymerase chain reaction technology in the detection of solid tumors. Cancer 1998, 82:1419-1442.

Reiger, K. M. et al. Human bladder carcinoma lines as indicators of oncogenic change relevant to urothelial neoplastic progression, Br. J. Cancer 72 (3) (1995) 683-690.

Robson, E. J. et al. PANorama of PAX genes in cancer and development, Nat. Rev. Cancer 6 (1) (2006) 52-62.

Saitoh, M., Nagai, K., Nakagawa, K., Yamamura, T., Yamamoto, S., and Nishizaki, T. Adenosine induces apoptosis in the human gastric cancer cells via an intrinsic pathway relevant to activation of AMP-activated protein kinase. (2004) Biochem. Pharmacol. 67, 2005-2011

Sanyanusin P et al (1996) Genomic structure of the PAX2 gene Genomics 35(1), 258-261

Schmidt B, Anastasiadis A G, Seifert H H, Franke K H, Oya M, Ackermann R: Detection of circulating prostate cells during radical prostatectomy by standardized PSMA RT-PCR: association with positive lymph nodes and high malignant grade. Anticancer Res 2003, 23:3991-3999.

Seiden M V, Kantoff P W, Krithivas K, Propert K, Bryant M, Haltom E, aynes L, Kaplan I, Bubley G, DeWolf W, Sklar J: Detection of circulating tumor cells in men with localized prostate cancer. J Clio Oncol 1994, 12:2634-2639.

Shariat S F, Kattan M W, Song W, Bernard D, Gottenger E, Wheeler T M, Slawin K M: Early postoperative peripheral blood reverse transcription PCR assay for prostate-specific antigen is associated with prostate cancer progression in patients undergoing radical prostatectomy. Cancer Res 2003, 63:5874-5878.

Sherman, H., Chapnik, N., Froy, O., 2006. Albumin and amino acids upregulate the expression of human beta-defensin 1. Mol. Immunol. 43, 1617-1623.

Sikorski, R. S, and Hieter, P. A system of shuttle vectors and yeast host strains designed for efficient manipulation of DNA in Saccharomyces cerevisiae. Genetics, 122: 19-27., 1989.

Soeth E, Vogel I, Roder C, Juhl H, Marxsen J, Kruger U, Henne-Bruns D, Kremer B, Kalthoff H: Comparative analysis of bone marrow and venous blood isolates from gastrointestinal cancer patients for the detection of disseminated tumor cells using reverse transcription PCR. Cancer Res 1997, 57:3106-3110.

Stambolic, V. et al. Negative regulation of PKB/Aktdependent cell survival by the tumor suppressor PTEN, Cell Oct 2 95 (1) (1998) 29-39.

Strasser, A. The role of BH3-only proteins in the immune system, Nat. Rev. Immunol. 5 (3) (2005) 189-200.

Stuart E T et al Mammalian Pax genes. Annual Review of Genetics 1994; 28(219):219-36

Stuart E T et al. PAX and HOX in neoplasia. Advances in Genetics 1995; 33(255):255-74.

Stuart E T, Haffner R, Oren M, Gruss P. Loss of p53 function through PAX-mediated transcriptional repression. Embo J 1995; 14(22):5638-5645.

Tagge, E. P.; Hanson, P.; Re, G. G.; Othersen, H. B., Jr.; Smith, C. D.; Garvin, A. J., Paired box gene expression in Wilms' tumor. J Pediatr Surg 1994, 29, (2), 134-41.

Takeuchi, S.; Iida, M.; Kobayashi, S.; Jin, K.; Matsuda, T.; Kojima, H., Differential effects of phthalate esters on transcriptional activities via human estrogen receptors alpha and beta, and androgen receptor. Toxicology 2005, 210, (2-3), 223-33.

Teixeira, M. R.; Ribeiro, F. R.; Eknaes, M.; Waehre, H.; Stenwig, A. E.; Giercksky, K. E.; Heim, S.; Lothe, R. A., Genomic analysis of prostate carcinoma specimens obtained via ultrasound-guided needle biopsy may be of use in preoperative decision-making. Cancer 2004, 101, (8), 1786-93.

Tepper, C. G. et al. Profiling of gene expression changes caused by p53 gain-offunction mutant alleles in prostate cancer cells, Prostate 65 (4) (2005) 375-389.

Tien, A. H., Xu, L., Helgason, C. D., 2005. Altered immunity accompanies disease progression in a mouse model of prostate dysplasia. Cancer Res. 65, 2947-2955.

Tokino, T.; Nakamura, Y., The role of p53-target genes in human cancer. Crit. Rev Oncol Hematol 2000, 33, (1), 1-6.

Torres, M. et al. PAX-2 controls multiple steps of urogenital development, Development 121 (1995) 4057-4065.

Uemura H, Hasumi H, Ishiguro H, Teranishi J, Miyoshi Y, Kubota Y. Renin-angiotensin system is an important factor in hormone refractory prostate cancer. Prostate 2006; 66(8): 822-830.

Uemura H, Ishiguro H, Kubota Y. Angiotensin II receptor blocker: possibility of antitumor agent for prostate cancer. Mini Rev Med Chem 2006; 6(7):835-844.

Valore E V, Park C H, Quayle A J, Wiles K R, McCray P B Jr, Ganz T. Human beta-defensin-1: an antimicrobial peptide of urogenital tissues. J Clin Invest. 1998 Apr. 15; 101(8): 1633-42.

Vecchione, A.; Ishii, H.; Baldassarre, G.; Bassi, P.; Trapasso, F.; Alder, H.; Pagano, F.; Gomella, L. G.; Croce, C. M.; Baffa, R., FEZ1/LZTS1 is down-regulated in high-grade bladder cancer, and its restoration suppresses tumorigenicity in transitional cell carcinoma cells. Am J Pathol 2002, 160, (4), 1345-52.

Vogelstein, B. et al. The multi-step nature of cancer, Trends Genet. 9 (4) (1993) 138-141.

Wallin, J. J. et al. Dependence of BSAP repressor and activator functions on BSAP concentration, Science 279 (1998) 1961-1964.

Wang Z P, Eisenberger M A, Carducci M A, Partin A W, Scher H I, Ts'o P O: Identification and characterization of circulating prostate carcinoma cells. Cancer 2000, 88:2787-2795.

Wang, Z.; Lai, F. M., [Analysis of loss of heterozygosity on chromosome 8 in human prostate carcinoma and high grade prostatic intraepithelial neoplasia]. Zhonghua Nan Ke Xue 2004, 10, (1), 26-8, 31.

Wells, J. and Farnham, P. J. Characterizing transcription factor binding sites using formaldehyde crosslinking and immunoprecipitation. Methods, 26: 48-56., 2002.

Wilson, T. E., Fahrner, T. J., Johnston, M., and Milbrandt, J. Identification of the DNA binding site for NGFI-B by genetic selection in yeast. Science, 252: 1296-1300., 1991.

Xiang, X., Saha, A. K., Wen, R., Ruderman, N. B., and Luo, Z. AMP-activated protein kinase activators can inhibit the growth of prostate cancer cells by multiple mechanisms. (2004) Biochem. Biophys. Res. Commun. 321, 161-167

Xu, Rould, Jun, Desplan and Pabo (1995) Cell 80, 639-650.

Yang, D.; Biragyn, A.; Hoover, D. M.; Lubkowski, J.; Oppenheim, J. J., Multiple Roles of Antimicrobial Defensins, Cathelicidins, and Eosinophil-Derived Neurotoxin in Host Defense. Annual Review of Immunology 2004, 22, (1), 181-215.

Ylikoski A, Pettersson K, Nurmi J, Irjala K, Karp M, Lilja H, Lovgren T, Nurmi M: Simultaneous quantification of prostate-specific antigen and human glandular kallikrein 2 mRNA in bloodsamples from patients with prostate cancer and benign disease. Clin Chem 2002, 48:1265-1271.

Yuan S S, Yeh Y T, Lee E Y. Pax-2 interacts with RB and reverses its repression on the promoter of Rig-1, a Robo member. Biochem Biophys Res Commun 2002; 296(4): 1019-1025.

Zucht H D, Grabowsky J, Schrader M, Liepke C, Jurgens M, Schulz-Knappe P, Forssmann W G. Human beta-defensin-1: A urinary peptide present in variant molecular forms and its putative functional implication. Eur J Med Res. 1998 Jul. 20; 3(7):315-23.

G. Sequences

What is claimed is:

1. A method for treating prostate intraepithelial neoplasia (PIN) in a subject, comprising:
    administering to the subject an effective amount of a composition comprising an anti-PAX2 antibody.

2. The method of claim 1, wherein the subject is diagnosed with prostate intraepithelial neoplasia (PIN).

3. The method of claim 1, wherein the subject has a ratio of PAX2 to DEFB1 of at least about 40:1 and less than about 100:1.

* * * * *